US009828346B2

(12) United States Patent
Brand et al.

(10) Patent No.: US 9,828,346 B2
(45) Date of Patent: *Nov. 28, 2017

(54) N-MYRISTOYL TRANSFERASE INHIBITORS

(71) Applicant: University of Dundee, Dundee (GB)

(72) Inventors: Stephen Brand, Dundee (GB); Paul Wyatt, Dundee (GB); Stephen Thompson, Dundee (GB); Victoria Smith, Dundee (GB); Tracy Bayliss, Dundee (GB); Justin Harrison, Dundee (GB); Neil Norcross, Dundee (GB); Laura Cleghorn, Dundee (GB); Ian Gilbert, Dundee (GB); Ruth Brenk, Dundee (GB)

(73) Assignee: University of Dundee, Dundee (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/840,660

(22) Filed: Aug. 31, 2015

(65) Prior Publication Data

US 2016/0060224 A1 Mar. 3, 2016

Related U.S. Application Data

(63) Continuation of application No. 13/061,811, filed as application No. PCT/GB2009/002084 on Aug. 29, 2009, now Pat. No. 9,156,811.

(30) Foreign Application Priority Data

Sep. 2, 2008 (GB) .................................. 0815947.7

(51) Int. Cl.
| | | |
|---|---|---|
| C07D 231/42 | (2006.01) |
| C07D 213/75 | (2006.01) |
| C07D 239/69 | (2006.01) |
| C07D 263/50 | (2006.01) |
| C07D 401/04 | (2006.01) |
| C07D 403/12 | (2006.01) |
| C07D 407/12 | (2006.01) |
| C07D 409/12 | (2006.01) |
| C07D 413/12 | (2006.01) |
| C07D 413/14 | (2006.01) |
| C07D 417/12 | (2006.01) |
| C07D 471/04 | (2006.01) |
| C07D 487/04 | (2006.01) |
| C07D 401/12 | (2006.01) |
| C07D 401/14 | (2006.01) |
| A61K 31/415 | (2006.01) |

(52) U.S. Cl.
CPC .......... *C07D 231/42* (2013.01); *A61K 31/415* (2013.01); *C07D 213/75* (2013.01); *C07D 239/69* (2013.01); *C07D 263/50* (2013.01); *C07D 401/04* (2013.01); *C07D 401/12* (2013.01); *C07D 401/14* (2013.01); *C07D 403/12* (2013.01); *C07D 407/12* (2013.01); *C07D 409/12* (2013.01); *C07D 413/12* (2013.01); *C07D 413/14* (2013.01); *C07D 417/12* (2013.01); *C07D 471/04* (2013.01); *C07D 487/04* (2013.01)

(58) Field of Classification Search
None
See application file for complete search history.

(56) References Cited

U.S. PATENT DOCUMENTS

| | | | |
|---|---|---|---|
| 5,266,576 A | 11/1993 | Vincent et al. |
| 2009/0163545 A1 | 6/2009 | Goldfarb |
| 2010/0075947 A1 | 3/2010 | Aftab et al. |

FOREIGN PATENT DOCUMENTS

| | | |
|---|---|---|
| JP | 2006070014 | 3/2006 |
| WO | 00/37464 | 6/2000 |
| WO | 01/44239 | 6/2001 |
| WO | 2004/074288 | 9/2004 |
| WO | 2007/076055 | 7/2007 |
| WO | 2008/118758 | 10/2008 |
| WO | 2009013348 | 1/2009 |

OTHER PUBLICATIONS

Database Registry Chemical Abstracts Service, Columbus, Ohio, Accession No. RN 877963-74-1, Entered STN: Mar. 24, 2006.*
Database Registry Chemical Abstracts Service, Columbus, Ohio, Accession No. RN 956632-97-6, Entered STN: Dec. 4, 2007.*
Lindley et al., "The Crystal and Molecular Structure of N-(1,2,3,5-Tetramethyl-r-pyrazolio)toluene-p-sulphonamidate, $C_{14}H_{19}N_2O_2S$, a Mesoionic Pyrazole," *Acta Cryst*, B33(7):2160 (1977).
International Preliminary Report on Patentability of International Application No. PCT/GB2009/002084 dated Mar. 8, 2011.
Golub et al., "Molecular Classification of Cancer: Class Discovery and Class Prediction by Gene Expression Monitoring," *Science*, 286:531-537 (1999).
Lala et al., "Role of nitric oxide in tumor progression: Lessons from experimental tumors," *Cancer and Metastasis Review*, 17(1):91-106 (1998).

* cited by examiner

*Primary Examiner* — Samantha Shterengarts
(74) *Attorney, Agent, or Firm* — Goodwin Procter LLP

(57) ABSTRACT

The present invention relates to N-heterocyclic sulphonamide compounds, in particular pyrazole sulphonamide compounds, and their use as N-myristoyl transferase inhibitors.

12 Claims, 1 Drawing Sheet

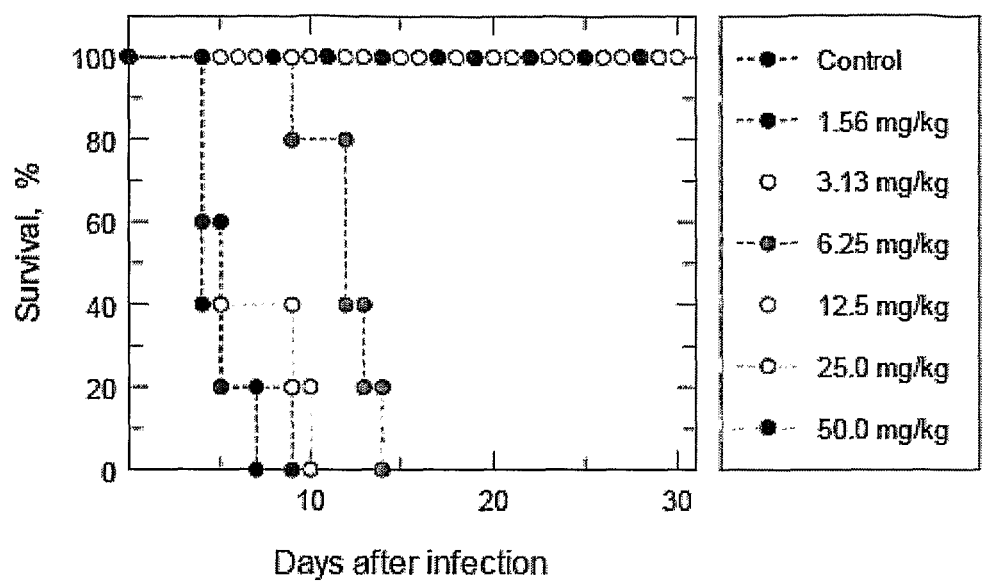

N-MYRISTOYL TRANSFERASE INHIBITORS

CROSS-REFERENCE TO RELATED APPLICATIONS

This application is a continuation patent application under 35 U.S.C. §120 of U.S. patent application Ser. No. 13/061,811, filed on Apr. 29, 2011, which application is the national phase of International (PCT) Patent Application Serial No. PCT/GB2009/002084, filed on Aug. 29, 2009, and entitled, "N-Myristoyl Transferase Inhibitors," which in turn claims priority to and the benefit of United Kingdom Patent Application No. 0815947.7, filed on Sep. 2, 2008, the entire disclosure of each of which is incorporated by reference herein.

FIELD OF THE INVENTION

The present invention relates to compounds and their use as N-myristoyl transferase inhibitors.

BACKGROUND TO THE INVENTION

The modification of proteins by myristoylation is required for the subcellular targeting, protein conformation and biological activity of many important proteins in eukaryotic cells, including those required for signal transduction and regulatory functions important in cell growth (Towler et al. J Biol Chem 1987; 262:1030-6. 20: Wolven et al. Mol Biol Cell 1997; 8:1159-73). The myristoylation reaction, the transfer of myristic acid from myristoyl-coenzyme A (CoA) to the amino groups of terminal glycine residues, is catalysed by the ubiquitously distributed enzyme N-myristoyl-CoA:protein, N-myristoyl transferase (NMT). The reaction requires only myristoyl-CoA and a protein containing a suitable peptide sequence, and occurs through an ordered Bi Bi mechanism. This modification occurs primarily as a cotranslational process (Wilcox et al. Science 1987, 238: 1275-8. 22; Deichaite et al. Mol Cell Biol 1988; 8:4295-301), although myristoylation can also occur post-translationally (Pillai et al. Proc Natl Acad Sci USA 1987; 84:7654-8. 24: King et al. J Biol Chem 1989; 264:7772-5).

N-myristoyltransferase (NMT) has been shown to be essential in the kinetoplastid protozoan parasites, *Leishmania, Trypanosoma brucei* and *Plasmodium falciparum*. The demonstration of essentiality by genetic studies in these parasites has been supported by limited chemical validation. Non-specific myristoyl CoA inhibitors inhibit *T. brucei* and *Leishmania* growth in culture. A screen of compounds developed as inhibitors of fungal NMT identified a number of inhibitors of both *T. brucei* NMT and *T. brucei* in culture. Screening of recombinant *Plasmodium falciparum* NMT has identified a series of benzothiazole analogues with $IC_{50}$ values <50 µM, with selectivity over human NMT1. Two of compounds of the series when tested at a concentration of 10 µM against cultured parasites in vitro reduced parasitemia by >80%. (Bowyer et al., Biochemical Journal (2007), 408(2), 173-180.)

Two isozymes of the mammalian NMT enzymes, NMT1 and NMT2, have been cloned and share ~77% identity (Giang D K, Cravatt B F. A second mammalian N-myristoyltransferase. J Biol Chem 1998; 273:6595-8.) with the majority of divergence occurring in the amino-terminal domains. Splice variants of NMT1 have also been observed in some cells. Possibly these amino-terminal variations allow differential cellular localization of the isozymes, thereby allowing either cotranslational ribosome-based or post-translational cytosol-based protein myristoylation. NMT1 and NMT2 have similar, but distinguishable, relative selectivity, as shown by an in vitro comparison of the activity of the isozymes on a limited panel of substrate peptides. (Giang and Cravatt, J Biol Chem 1998; 273:6595-8. 27; Aitken A, Biochem Soc Trans 1989; 17:871-5.).

The role of myristoylation is still being elucidated; however evidence of its involvement in many disease states, such as cancer (Selvakumar, P. et al., Progress in Lipid Res., 2006, (46), 1-36), epilepsy (Selvakhumar, P. et al., Biochem. Biophys Res. Comm. 2005, (335), 1132-1139), Alzheimer's disease, ischemia, diabetes, HIV (Shoji, S. et al., JP2006223173) and osteoporosis is growing. Cellular myristoylated proteins have diverse biological functions in oncogenesis and signal transduction. Examples include the catalytic subunit of cAMP4-dependent protein kinase, various tyrosine kinases (pp60src, pp60yes, pp56lck, pp59fyn/syn, and c-Abl), the α-subunit of calcineurin (Lakshmikuttyamma, A et al., Progress in Neurobiol. 2008, 84 (1), 77-84) the myristoylated alanine-rich C kinase substrate, and the α-subunit of several guanine nucleotide binding proteins and ADP ribosylation factors.

An increase in NMT activity and expression has been shown in a number of tumour types, suggesting inhibitors of NMT would be potential anti-cancer agents. In addition the Src family of tyrosine kinases (e.g., c-Src, Yes, and Fyn) are oncogenic proteins which require myristoylation in order for them to function in cells.

Functionally characterization of the two NMT isozymes in human cells using unique small interfering RNAs (siRNA) for each isozyme were shown to decrease NMT1 or NMT2 protein levels by at least 90%. Knockdown of NMT1 inhibited cell replication associated with a loss of activation of c-Src and its target FAK. Depletion of either NMT isozyme induced apoptosis, with NMT2 having a 2.5-fold greater effect than NMT1. Intratumoral injection of siRNA for NMT1 or for both NMT1 and NMT2 inhibited tumour growth in vivo, whereas the same treatment with siRNA for NMT2 or negative control siRNA did not. Overall, the data indicate that NMT1 and NMT2 have only partially overlapping functions and that NMT1 is critical for tumour cell proliferation. (Ducker et al., Mol Cancer Res 2005; 3(8). August 2005).

Viruses and bacteria usually lack N-myristoyltransferases so consequently their proteins are processed by NMTs of their eukaryotic hosts. (Maurer-Stroh et al., Trends in Microbiology (2004), 12(4), 178-185.) For example, human N-myristoyltransferase (hNMT) catalyzes N-myristoylation of several HIV-1 proteins, including Pr160gag-pol, Pr55gag, the capsid protein p17 derived from proteolytic processing of gag, and neg. factor (nef). N-myristoylation of Pr160gag-pol and Pr55gag is required for viral replication. Reduction in the mRNA levels of human NMT isoforms and NMT activities have been shown in the course of HIV-1 infection in the human T-cell line, CEM. In consequence, novel synthetic NMT inhibitors were significantly more cytotoxic to chronically HIV-1 infected T-cell line, CEM/LAV-1, compared to uninfected CEM cells. (Takamune et al., FEBS Letters (2002), 527(1-3), 138-142.)

Myristic acid analogues designed as alternative substrates for NMT have shown to inhibit the proliferation of HIV-1 (Bryant et al., Perspectives in Drug Discovery and Design (1993), 1(1), 193-209.; Devadas et al., Bioorganic & Medicinal Chemistry Letters (1993), 3(4), 779-84.) and Hepatitis B (Parang et al., Antiviral Research (1997), 34(3), 75-90.) In addition myristic acid analogues have been shown to inhibit HIV-1 (Adams et al., Eur. Pat. Appl. (1992), 20 pp.

EP 480901 A1) and Varicella Zoster virus replication (Gilbert et al., Antiviral Chemistry & Chemotherapy (1994), 5(3), 182-6.).

NMT has been shown genetically to be essential for a number of fungal strains, such as *Candida albicans* (Weinberg et al., Molecular Microbiology (1995), 16(2), 241-50.), *Saccharomyces cerevisiae, Cryptococcus neoformans* (Lodge et al., PNAS USA (1994), 91(25), 12008-12.) and *Aspergillus fumigatus* (Cook, W J et al., US Patent 20020025524 (2002), both in culture and animal models of infection.

Given the diverse role of myristoyl transferases and their association with a large variety of diseases and disorders, there is a need to find further myristoyl transferase inhibitors.

The present inventors have provided sulphonamide compounds which are inhibitors of N-myristoyl transferases.

STATEMENTS OF THE INVENTION

The present invention relates to a class of N-heterocyclic sulphonamides and to their use in therapy. More particularly, the invention provides a family of N-heteroarylsulphonamides which are substituted [in the meta- or para-position] by an optionally substituted amine-bearing moiety.

According to a first aspect of the invention there is provided a sulphonamide derivative comprising a sulphonamide group linking a N-heterocyclic head group and tail group via an aryl or heteroaryl linker attached to the tail wherein the tail includes a protonatable moiety such as a primary, secondary or tertiary alkylamine (or a protonatable heterocycle such as imidazole).

In a preferred aspect of the invention there is provided a compound of formula (I)

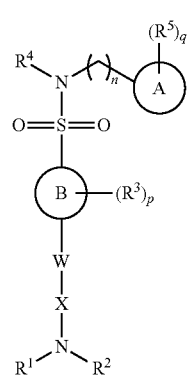

(I)

wherein
n is 0, 1, 2, 3, 4, 5 or 6;
ring A, herein referred to as a "head" group, is an optionally substituted nitrogen containing aryl group wherein each substitutable carbon or nitrogen in Ring A is optionally and independently substituted by one or more $R^5$ and wherein if Ring A contains an —NH— moiety that nitrogen may be optionally substituted by $C_{1-6}$ alkyl (e.g. methyl); and wherein $R^4$ and ring A together with the atoms to which they are attached may form a cyclic group.
ring B is an optionally substituted aryl or heteroaryl group wherein each substitutable carbon or heteroatom in Ring B is optionally and independently substituted by one or more $R^3$;

W and X, one of which may be absent, are independently selected from $R^{11}$, hydrocarbyl (e.g. $C_{1-8}$ alkyl, alkenyl, alkynyl, or haloalkyl) optionally substituted with $R^{11}$, and —$(CH_2)_k$-heterocyclyl optionally substituted with $R^{12}$; k is 0, 1, 2, 3, 4, 5 or 6;
$R^1$, $R^2$, $R^3$, $R^4$ and $R^5$ are independently selected from hydrogen, $R^{12}$, hydrocarbyl (e.g. $C_{1-6}$ alkyl, alkenyl, alkynyl, or haloalkyl) optionally substituted with $R^{12}$, and —$(CH_2)_l$-heterocyclyl optionally substituted with $R^{12}$; wherein $R^1$ and $R^2$ taken together with the atoms to which they are attached may form a heterocycle, optionally substituted with one or more $R^{12}$; wherein $R^1$ and/or $R^2$ taken together with W or X may form a heterocycle optionally substituted with one or more $R^{12}$; and wherein one or more of $R^3$ and $R^5$ taken together with the atoms to which they are attached may form a carbocycle, for example heterocyclyl, optionally substituted with $R^{12}$; l is 0, 1, 2, 3, 4, 5 or 6;
wherein each $R^{11}$ and $R^{12}$ is independently selected from halogen, trifluoromethyl, cyano, thio, nitro, oxo, =$NR^{13}$, —$OR^{13}$, —$SR^{13}$, —$C(O)R^{13}$, —$C(O)OR^{13}$, —$OC(O)R^{13}$, —$NR^{13}COR^{14}$, —$NR^{13}CONR^{13}{}_2$, —$NR^{13}COR^{14}$, —$NR^{13}CO_2R^{14}$, —$S(O)R^{13}$, —$S(O)_2R^{13}$, —$SONR^{13}{}_2$, —$NR^{13}S(O)_2R^{14}$; —$CSR^{13}$, —$N(R^{13})R^{14}$, —$C(O)N(R^{13})R^{14}$, —$SO_2N(R^{13})R^{14}$ and $R^{15}$;
wherein $R^{13}$ and $R^{14}$ are each independently selected from hydrogen or $R^{15}$;
wherein $R^{15}$ is selected from hydrocarbyl (e.g. $C_{1-6}$ alkyl, alkenyl, alkynyl, or haloalkyl), carbocyclyl and —$(CH_2)_m$-heterocyclyl, and each $R^{15}$ is optionally and independently substituted with one or more of halogen, cyano, amino, hydroxy, $C_{1-6}$ alkyl or cycloalkyl and $C_{1-6}$ alkoxy;
m is 0, 1, 2, 3, 4, 5 or 6;
p is 0, 1, 2, 3 or 4; wherein the values of $R^4$ may be the same or different;
q is 0, 1, 2, 3 or 4; wherein the values of $R^5$ may be the same or different;
or a pharmaceutically acceptable salt or pro-drug thereof.

According to a further aspect of the invention there is provided a sulphonamide derivative comprising a sulphonamide group linking a heteroaryl head group and an aryl or heteroaryl central group for use as a medicament.

In a second aspect of the invention there is provided a compound of formula (II) for use as a medicament:

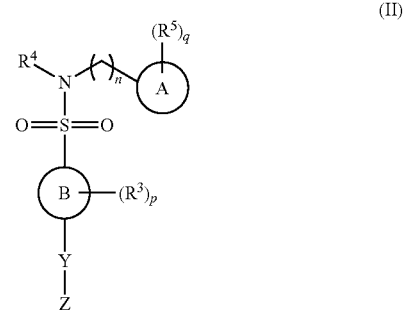

(II)

wherein n, ring A, ring B, $R^3$, $R^4$, $R^5$, p and q are as defined herein;
Y and Z, one or both of which may be absent, are independently selected from hydrogen, $R^{16}$, hydrocarbyl (e.g. $C_{1-6}$ alkyl, alkenyl, alkynyl, or haloalkyl) optionally substituted with $R^{16}$, and —$(CH_2)_r$-heterocyclyl optionally substituted with $R^{16}$, wherein each $R^{16}$ is independently selected from halogen, trifluoromethyl, cyano, thio, nitro, oxo, $=NR^{17}$, $-OR^{17}$, $-SR^{17}$, $-C(O)R^{17}$, $-C(O)OR^{17}$, $-OC(O)R^{17}$, $-NR^{17}COR^{18}$, $-NR^{17}CONR^{18}{}_2$, $-NR^{17}COR^{18}$, $-NR^{17}CO_2R^{18}$, $-S(O)R^{17}$, $-S(O)_2R^{17}$, $-SONR^{17}{}_2$, $-NR^{17}S(O)_2R^{18}$; $-CSR^{17}$, $-N(R^{17})R^{18}$, $-C(O)N(R^{17})R^{18}$, $-SO_2N(R^{17})R^{18}$ and $R^{19}$; r is 0, 1, 2, 3, 4, 5 or 6;

wherein $R^{17}$ and $R^{18}$ are each independently selected from hydrogen or $R^{19}$;

wherein $R^{19}$ is selected from hydrocarbyl (e.g. $C_{1-6}$ alkyl, alkenyl, alkynyl, or haloalkyl), carbocyclyl and $-(CH_2)_s$-heterocyclyl, and each $R^{19}$ is optionally and independently substituted with one or more of halogen, cyano, amino, hydroxy, $C_{1-6}$ alkyl and $C_{1-6}$ alkoxy;

s is 0, 1, 2, 3, 4, 5 or 6;

or a pharmaceutically acceptable salt or pro-drug thereof.

Preferably Y is absent and Z is halogen e.g. Br or Cl. Preferably still, ring B is aryl e.g. a 6-membered aromatic ring including benzene.

n may be 0 or 1. Preferably n is 0.

The compounds of the invention can exist in different forms, such as free acids, free bases, esters and other prodrugs, salts and tautomers, for example, and the invention includes all variant forms of the compounds.

Hydrocarbyl

The term "hydrocarbyl" as used herein includes reference to moieties consisting exclusively of hydrogen and carbon atoms; such a moiety may comprise an aliphatic and/or an aromatic moiety. The moiety may comprise 1, 2, 3, 4, 5, 6, 7, 8, 9, 10, 11, 12, 13, 14, 15, 16, 17, 18, 19 or 20 carbon atoms. Examples of hydrocarbyl groups include $C_{1-6}$ alkyl (e.g. $C_1$, $C_2$, $C_3$ or $C_4$ alkyl, for example methyl, ethyl, propyl, isopropyl, n-butyl, sec-butyl or tert-butyl); $C_{1-6}$ alkyl substituted by aryl (e.g. benzyl) or by cycloalkyl (e.g cyclopropylmethyl); cycloalkyl (e.g. cyclopropyl, cyclobutyl, cyclopentyl or cyclohexyl); alkenyl (e.g. 2-butenyl); alkynyl (e.g. 2-butynyl); aryl (e.g. phenyl, benzyl, naphthyl or fluorenyl) and the like.

Alkyl

The terms "alkyl" and "$C_{1-6}$ alkyl" as used herein can be used interchangeably and include reference to a straight or branched chain alkyl moiety having 1, 2, 3, 4, 5 or 6 carbon atoms. This term includes reference to groups such as methyl, ethyl, propyl (n-propyl or isopropyl), butyl (n-butyl, iso-butyl, sec-butyl or tert-butyl), pentyl, hexyl and the like. In particular, alkyl may have 1, 2, 3 or 4 carbon atoms. Haloalkyl relates to an alkyl radical preferably having 1 to 8 carbon atoms, preferably 1 to 4 carbon atoms, substituted with one or more halide atoms for example $CH_2CH_2Br$, $CF_3$ or $CCl_3$.

Alkenyl

The terms "alkenyl" and "$C_{2-6}$ alkenyl" as used herein can be used interchangeably and include reference to a straight or branched chain alkyl moiety having 2, 3, 4, 5 or 6 carbon atoms and having, in addition, at least one double bond, of either E or Z stereochemistry where applicable. This term, includes reference to groups such as ethenyl, 2-propenyl, 1-butenyl, 2-butenyl, 3-butenyl, 1-pentenyl, 2-pentenyl, 3-pentenyl, 1-hexenyl, 2-hexenyl and 3-hexenyl and the like.

Alkynyl

The terms "alkynyl" and "$C_{2-6}$ alkynyl" as used herein can be used interchangeably and include reference to a straight or branched chain alkyl moiety having 2, 3, 4, 5 or 6 carbon atoms and having, in addition, at least one triple bond. This term includes reference to groups such as ethynyl, 1-propynyl, 2-propynyl, 1-butynyl, 2-butynyl, 3-butynyl, 1-pentynyl, 2-pentynyl, 3-pentynyl, 1-hexynyl, 2-hexynyl and 3-hexynyl and the like.

Alkoxy

The terms "alkoxy" and "$C_{1-6}$ alkoxy" as used herein can be used interchangeably and include reference to —O-alkyl, wherein alkyl is straight or branched chain and comprises 1, 2, 3, 4, 5 or 6 carbon atoms. In one class of embodiments, alkoxy has 1, 2, 3 or 4 carbon atoms. This term includes reference to groups such as methoxy, ethoxy, propoxy, isopropoxy, butoxy, tert-butoxy, pentoxy, hexoxy and the like.

Cycloalkyl

The term "cycloalkyl" as used herein includes reference to an alicyclic moiety having 3, 4, 5, 6, 7 or 8 carbon atoms. The group may be a bridged or polycyclic ring system. More often cycloalkyl groups are monocyclic. This term includes reference to groups such as cyclopropyl, cyclobutyl, cyclopentyl, cyclohexyl, norbornyl, bicyclo[2.2.2]octyl and the like.

Aryl

The term "aryl" as used herein includes reference to an aromatic ring system comprising 6, 7, 8, 9, 10, 11, 12, 13, 14, 15 or 16 ring carbon atoms. Aryl is often phenyl but may be a polycyclic ring system, having two or more rings, at least one of which is aromatic. This term includes reference to groups such as phenyl, naphthyl, fluorenyl, azulenyl, indenyl, anthryl and the like.

Carbocyclyl

The term "carbocyclyl" as used herein includes reference to a saturated (e.g. cycloalkyl) or unsaturated (e.g. aryl) ring moiety having 3, 4, 5, 6, 7, 8, 9, 10, 11, 12, 13, 14, 15 or 16 carbon ring atoms. In particular, carbocyclyl includes a 3- to 10-membered ring or ring system and, in particular, a 5- or 6-membered ring, which may be saturated or unsaturated. A carbocyclic moiety is, for example, selected from cyclopropyl, cyclobutyl, cyclopentyl, cyclohexyl, norbornyl, bicyclo[2.2.2]octyl, phenyl, benzyl, naphthyl, fluorenyl, azulenyl, indenyl, anthryl and the like.

Heterocyclyl

The term "heterocyclyl" as used herein includes reference to a saturated (e.g. heterocycloalkyl) or unsaturated (e.g. heteroaryl) heterocyclic ring moiety having from 3, 4, 5, 6, 7, 8, 9, 10, 11, 12, 13, 14, 15 or 16 ring atoms, at least one of which is selected from nitrogen, oxygen, phosphorus, silicon and sulphur. In particular, heterocyclyl includes a 3- to 10-membered ring or ring system and more particularly a 5- or 6- or 7-membered ring, which may be saturated or unsaturated.

A heterocyclic moiety is, for example, selected from oxiranyl, azirinyl, 1,2-oxathiolanyl, imidazolyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, especially thiomorpholino, indolizinyl, isoindolyl, 3H-indolyl, indolyl, benzimidazolyl, cumaryl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, β-carbolinyl, phenanthridinyl, acridinyl, perimidinyl, phenanthrolinyl, furazanyl, phenazinyl, phenothiazinyl, phenoxazinyl, chromenyl, isochromanyl, chromanyl and the like.

Heterocycloalkyl

The term "heterocycloalkyl" as used herein includes reference to a saturated heterocyclic moiety having 3, 4, 5, 6 or 7 ring carbon atoms and 1, 2, 3, 4 or 5 ring heteroatoms selected from nitrogen, oxygen, phosphorus and sulphur. The group may be a polycyclic ring system but more often is monocyclic. This term includes reference to groups such as azetidinyl, pyrrolidinyl, tetrahydrofuranyl, piperidinyl, oxiranyl, pyrazolidinyl, imidazolyl, indolizidinyl, piperazinyl, thiazolidinyl, morpholinyl, thiomorpholinyl, quinolinidinyl and the like.

Heteroaryl

The term "heteroaryl" as used herein includes reference to an aromatic heterocyclic ring system having 5, 6, 7, 8, 9, 10, 11, 12, 13, 14, 15 or 16 ring atoms, at least one of which is selected from nitrogen, oxygen and sulphur. The group may be a polycyclic ring system, having two or more rings, at least one of which is aromatic, but is more often monocyclic. This term includes reference to groups such as pyrimidinyl, furanyl, benzo[b]thiophenyl, thiophenyl, pyrrolyl, imidazolyl, pyrrolidinyl, pyridinyl, benzo[b]furanyl, pyrazinyl, purinyl, indolyl, benzimidazolyl, quinolinyl, phenothiazinyl, triazinyl, phthalazinyl, 2H-chromenyl, oxazolyl, isoxazolyl, thiazolyl, isoindolyl, indazolyl, purinyl, isoquinolinyl, quinazolinyl, pteridinyl and the like.

Halogen

The term "halogen" as used herein includes reference to F, Cl, Br or I. In particular, halogen may be F or Cl.

Substituted

The term "substituted" as used herein in reference to a moiety means that one or more, especially up to 5, more especially 1, 2 or 3, of the hydrogen atoms in said moiety are replaced independently of each other by the corresponding number of the described substituents. The term "optionally substituted" as used herein means substituted or unsubstituted.

It will, of course, be understood that substituents are only at positions where they are chemically possible, the person skilled in the art being able to decide (either experimentally or theoretically) without inappropriate effort whether a particular substitution is possible. For example, amino or hydroxy groups with free hydrogen may be unstable if bound to carbon atoms with unsaturated (e.g. olefinic) bonds. Additionally, it will of course be understood that the substituents described herein may themselves be substituted by any substituent, subject to the aforementioned restriction to appropriate substitutions as recognised by the skilled man.

Independently

Where two or more moieties are described as being "each independently" selected from a list of atoms or groups, this means that the moieties may be the same or different. The identity of each moiety is therefore independent of the identities of the one or more other moieties.

Ring A is preferably an optionally substituted 5 or 6 membered nitrogen containing heteroaryl. For example, ring A may be an optionally substituted 5 membered nitrogen-containing heteroaryl including, but not limited to, optionally substituted pyrazole, imidazole, imidazoline, triazole or tetrazole. Alternatively ring A may be an optionally substituted 6 membered nitrogen-containing heteroaryl including, but not limited to, optionally substituted pyridine, 3 amino pyridine, 4 amino pyridine, pyridazine, pyrimidine, pyrazine, triazine and tetrazine.

Ring A may be Comprise other ring heteroatoms in addition to N for example O or S. For example ring A may be optionally substituted isoxazole.

Preferably ring A is selected from optionally substituted pyrazole, pyridine or isoxazole.

Preferably still ring A is optionally substituted pyrazole. Thus in a preferred aspect of the invention there is provided a compound of formula (III)

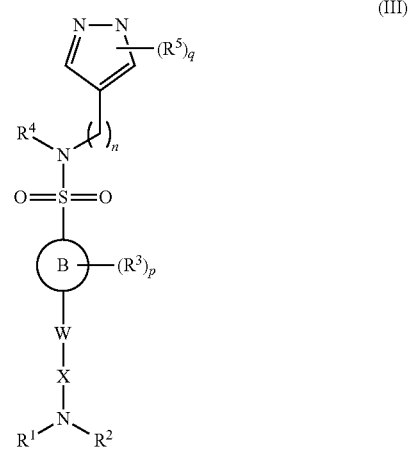

(III)

wherein n, ring B, W, X, $R^1$, $R^2$, $R^3$, $R^4$, $R^5$, p and q are as defined herein.

In a further preferred aspect of the invention there is provided a compound of formula (III)(i)

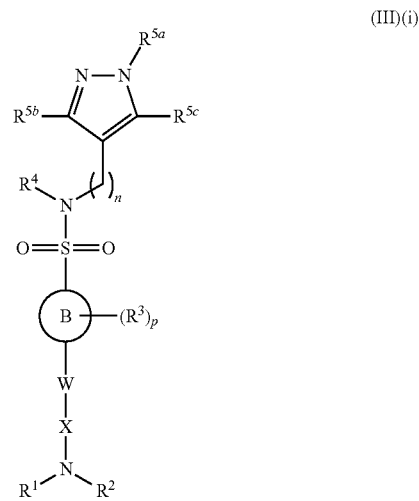

(III)(i)

wherein n, ring B, W, X, $R^1$, $R^2$, $R^3$, $R^4$, p and q are as defined herein and $R^{5a}$, $R^{5b}$ and $R^{5c}$ are independently selected from hydrogen, $R^{12}$, hydrocarbyl (e.g. $C_{1-6}$ alkyl, alkenyl, alkynyl, or haloalkyl) optionally substituted with $R^{12}$, and $—(CH_2)_t$-heterocyclyl optionally substituted with $R^{12}$.

In one embodiment, there is provided a compound of formula (III)(i) wherein $R^{5a}$ is $C_{1-6}$ alkyl (e.g. methyl).

Preferably ring B is an optionally substituted 5 or 6 membered aryl (e.g. benzene) or heteroaryl wherein each substitutable carbon or heteroatom in ring B may be optionally and independently substituted by halogen for example selected from one or more of F, Cl and Br. Ring B may be a 5 membered aryl containing one or more heteroatoms selected from N, S and O. By way of example ring B may be thiophene. Alternatively ring B may be a 6 membered aryl containing one or more heteratoms selected from N, S and O. By way of example ring B may be a 6 membered nitrogen containing heteroaryl, for example pyridine.

Thus there may be provided a compound of formula IV

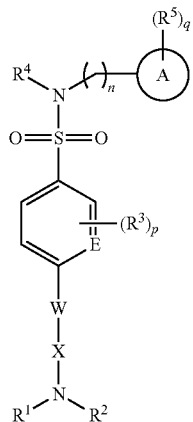

(IV)

wherein n, ring A, W, X, $R^1$, $R^2$, $R^3$, $R^4$, $R^5$, p and q are as defined herein; and E is independently selected from C and N.

In one embodiment the invention provides a compound of formula (IV) wherein E is N.

In another embodiment the invention provides a compound of formula (IV) wherein E is C.

In a preferred aspect of the invention there is provided a compound of formula (IV)(i)

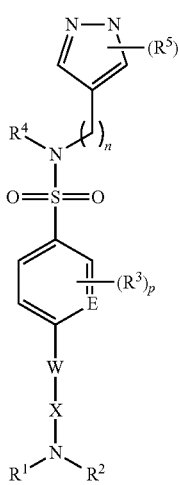

(IV)(i)

wherein n, W, X, $R^1$, $R^2$, $R^3$, $R^4$, $R^5$, p and q are as defined herein; and E is independently selected from C and N.

In a further preferred aspect of the invention there is provided a compound of formula (IV)(ii)

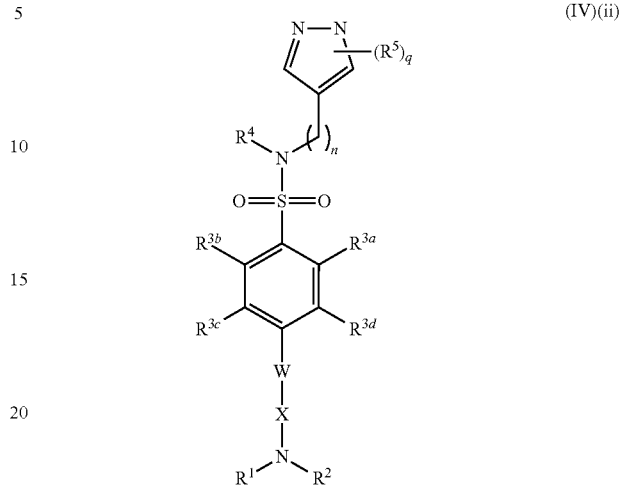

(IV)(ii)

wherein n, W, X, $R^1$, $R^2$, $R^4$, $R^5$, p and q are as defined herein; and wherein $R^{3a}$, $R^{3b}$, $R^{3c}$ and $R^{3d}$ are independently selected from hydrogen, $R^{12}$, hydrocarbyl (e.g. $C_{1-6}$ alkyl, alkenyl, alkynyl, or haloalkyl) optionally substituted with $R^{12}$, and $-(CH_2)_t$-heterocyclyl optionally substituted with $R^{12}$.

Preferably, $R^{3a}$, $R^{3b}$, $R^{3c}$ and $R^{3d}$ are independently selected from hydrogen, halogen (e.g. Cl or F) and $C_{1-6}$ alkyl or haloalkyl.

In a further preferred aspect of the invention there is provided a compound of formula (IV)(iii)

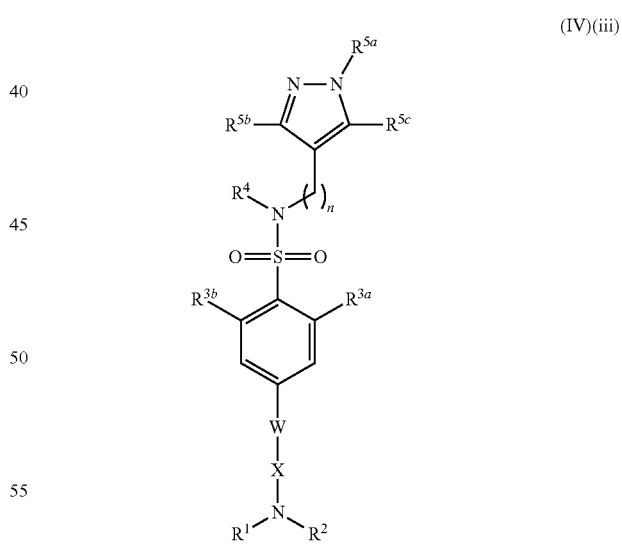

(IV)(iii)

Preferably $R^{3a}$ and/or $R^{3b}$ is halogen for example Cl or F.

In a preferred aspect of the invention W is absent and X is carbocyclyl e.g. heterocyclyl optionally substituted with $R^{11}$. Preferably X is aryl, for example heteroaryl, or heterocyclyl optionally substituted with $R^{11}$.

In one embodiment of the invention, W is aryl optionally substituted with $R^{11}$ and X is $C_{1-6}$ alkyl, e.g. $CH_2$.

Preferably $R^1$ and $R^2$ are joined with N to form a saturated five to seven membered protonatable N-containing heterocycle, for example piperidine, azepane or azocane, optionally substituted with one or more $R^{12}$.

Preferably at least one of $R^1$ or $R^2$ is an amine. Preferably still $R^1$ and $R^2$, wherein one of $R^1$ or $R^2$ is an amine, are joined with N to form a protonatable N containing heterocycle for example piperazine, optionally substituted with one or more $R^{12}$.

Preferably $R^4$ is selected from hydrogen or $C_{1-6}$ alkyl optionally substituted with halogen, cyano, amino, hydroxy, $C_{1-6}$ alkyl and $C_{1-6}$ alkoxy or carbocyclyl, for example cycloalkyl or aryl. The inventors have found that substitution of the sulphonamide nitrogen atom enhances penetration of the compounds into the mouse CNS. Thus, preferably still $R^4$ is $C_{1-6}$ alkyl e.g. methyl or $C_{1-6}$ alkyl substituted with fluoro e.g. monofluoroalkyl, difluoroalkyl or trifluoroalkyl.

Preferably $R^5$ is selected from hydrogen and $C_{1-6}$ alkyl e.g. methyl.

The invention further provides a compound of formula V

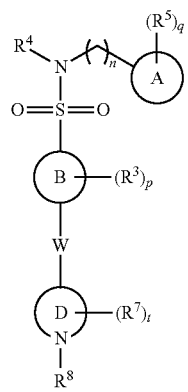

(V)

wherein n, ring A, W, ring B, $R^3$, $R^4$, $R^5$, p and q are as defined herein; t is 0, 1, 2, 3, 4, 5 or 6; ring D is an optionally substituted nitrogen containing 6 or 7 membered heterocycle, for example piperidine, wherein each substitutable carbon or nitrogen in Ring D is optionally and independently substituted by one or more $R^7$; $R^7$ is independently selected from hydrogen, $R^{20}$, hydrocarbyl (e.g. $C_{1-6}$ alkyl, alkenyl, alkynyl, or haloalkyl) optionally substituted with $R^{20}$, and —$(CH_2)_v$-heterocyclyl optionally substituted with $R^{20}$; v is 0, 1, 2, 3, 4, 5 or 6;
  wherein each $R^{20}$ is independently selected from halogen, trifluoromethyl, cyano, thio, nitro, oxo, =$NR^{21}$, —$OR^{21}$, —$SR^{21}$, —$C(O)R^{21}$, —$C(O)OR^{21}$, —$OC(O)R^{21}$, —$NR^{21}COR^{22}$, —$NR^{21}CONR^{22}_2$, —$NR^{21}COR^{22}$, —$NR^{21}CO_2R^{22}$, —$S(O)R^{21}$, —$S(O)_2R^{21}$, —$SONR^{21}_2$, —$NR^{21}S(O)_2R^{22}$; —$CSR^{21}$, —$N(R^{21})R^{22}$, —$C(O)N(R^{21})R^{22}$, —$SO_2N(R^{21})R^{22}$ and $R^{23}$;
  wherein $R^{21}$ and $R^{22}$ are each independently selected from hydrogen or $R^{23}$;
  wherein $R^{23}$ is selected from hydrocarbyl (e.g. $C_{1-6}$ alkyl, alkenyl, alkynyl, or haloalkyl), carbocyclyl and —$(CH_2)_w$-heterocyclyl, and each $R^{23}$ is optionally and independently substituted with one or more of halogen, cyano, amino, hydroxy, $C_{1-6}$ alkyl and $C_{1-6}$ alkoxy;
  w is 0, 1, 2, 3, 4, 5 or 6;
$R^8$ is selected from the list of optional substituents represented by the group $R^4$.

Preferably $R^8$ is hydrogen or methyl. Preferably still $R^8$ is methyl.

Preferably W is $C_{1-8}$ alkyl, in particular $C_{1-6}$ alkyl, optionally substituted with oxo.

In a preferred aspect of the invention there is provided a compound of formula (V)(i)

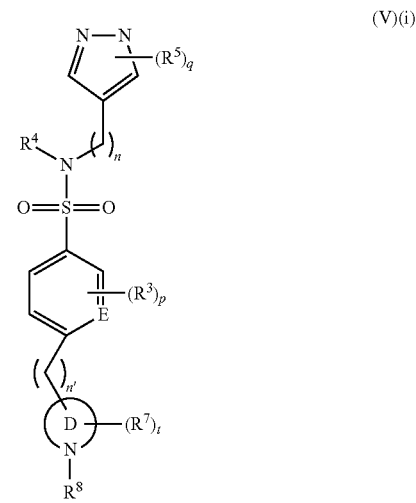

(V)(i)

wherein ring D, E, n, $R^3$, $R^4$, $R^5$, $R^7$, $R^8$, p, q and t are as defined herein; n' is 0, 1, 2, 3, 4, 5, 6, 7 or 8. Preferably E is C.

The invention further provides a compound of formula VI

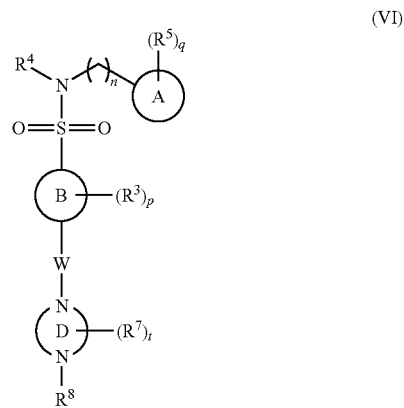

(VI)

wherein n, ring A, W, ring B, $R^3$, $R^4$, $R^5$, $R^7$, $R^8$, p, q and t are as defined herein; ring D is an optionally substituted nitrogen containing 6 or 7 membered heterocycle, for example 1,4-piperazine, wherein each substitutable carbon or nitrogen in Ring D is optionally and independently substituted by one or more $R^7$.

In one embodiment the invention provides a compound of formula (VI) wherein W is cycloalkyl, for example heterocycloalkyl such as piperidinyl.

In one embodiment of the invention there is provided a compound of formula VI wherein W is $C_{1-6}$ alkyl for example propyl.

Preferably ring B is a benzene ring or pyridinyl. Thus, in a preferred aspect the invention provides a compound of formula (VI)(i)

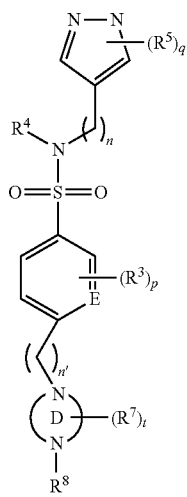

(VI)(i)

wherein n, n', ring D, E, $R^3$, $R^4$, $R^5$, $R^7$, $R^8$, p, q and t are as defined herein. Preferably E is C.

In a preferred compound of the invention W is an optionally substituted aryl or heteroaryl group. Thus in a further preferred aspect of the invention there is provided a compound of formula VII

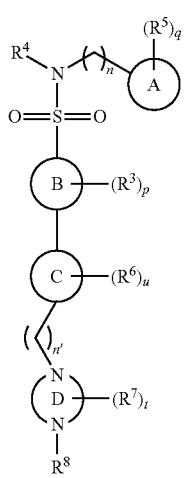

(VII)

wherein n, ring A, ring B, ring D, $R^3$, $R^4$, $R^5$, $R^7$, $R^8$, p, q and t are as defined herein; u is 0, 1, 2, 3, 4, 5 or 6; ring C is an optionally substituted cyclic group wherein each substitutable carbon or heteroatom in Ring C is optionally and independently substituted by one or more $R^6$; $R^6$ is independently selected from hydrogen, $R^{20}$, hydrocarbyl (e.g. $C_{1-6}$ alkyl, alkenyl, alkynyl, or haloalkyl) optionally substituted with $R^{20}$, and $-(CH_2)_v$-heterocyclyl optionally substituted with $R^{20}$; v is 0, 1, 2, 3, 4, 5 or 6;

wherein each $R^{20}$ is independently selected from halogen, trifluoromethyl, cyano, thio, nitro, oxo, $=NR^{21}$, $-OR^{21}$, $-SR^{21}$, $-C(O)R^{21}$, $-C(O)OR^{21}$, $-OC(O)R^{21}$, $-S(O)R^{21}$, $-S(O)_2R^{21}$, $-N(R^{21})R^{22}$, $-C(O)N(R^{21})R^{22}$, $-SO_2N(R^{21})R^{22}$ and $R^{23}$;

wherein $R^{21}$ and $R^{22}$ are each independently selected from hydrogen or $R^{23}$;

wherein $R^{23}$ is selected from hydrocarbyl (e.g. $C_{1-6}$ alkyl, alkenyl, alkynyl, or haloalkyl), carbocyclyl and $-(CH_2)_w$-heterocyclyl, and each $R^{23}$ is optionally and independently substituted with one or more of halogen, cyano, amino, hydroxy, $C_{1-6}$ alkyl and $C_{1-6}$ alkoxy;

w is 0, 1, 2, 3, 4, 5 or 6;

n' is 0, 1, 2, 3, 4, 5, 6, 7 or 8.

In one embodiment of the invention there is provided a compound of formula VII wherein ring B and Ring C are aryl.

In a preferred aspect, the invention provides a compound of formula VII(i)

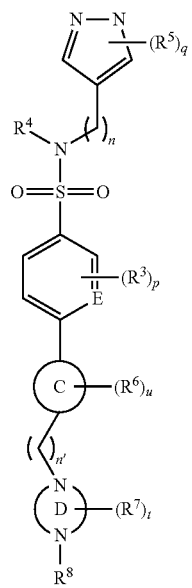

(VII)(i)

wherein n, n', ring C, ring D, E, $R^3$, $R^4$, $R^5$, $R^6$, $R^7$, $R^8$, p, q, t and u are as defined herein. Preferably E is C.

Ring C may be a carbocycle, for example aryl. Alternatively ring C may be a heterocycle for example heterocycloalkyl (e.g. piperidinyl) or heteroaryl. Preferably ring C is aryl (e.g. phenyl) or heteroaryl (pyridinyl).

Preferably ring D is 6 or 7 membered heterocycle, for example, a 6 membered heterocycle. Preferably ring D is a saturated heterocycle. By way of example, ring D may be an optionally substituted pyrrolidine, pyrazolidine, imidazolidine, piperidine or piperazine (e.g. 1,4-piperazine). Alternatively, ring D may be an unsaturated heterocycle for example an optionally substituted pyyrole, pyrazole, imidazole, imidazoline, pyridine, pyrazine, pyrimidine or triazine. Preferably still, ring D is an optionally substituted imidazole.

Thus in a further preferred aspect of the invention there is provided a compound of formula VIII

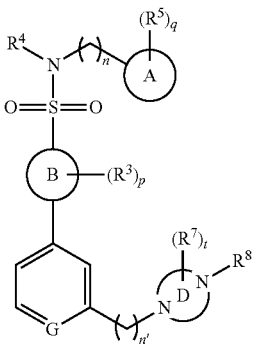

(VIII)

wherein n, n', ring A, ring B, ring D, $R^3$, $R^4$, $R^5$, $R^7$, $R^8$, p, q and t are as defined herein; G is independently selected from C and N.

In one embodiment there is provided a compound of formula VIII wherein G is C. In an alternative embodiment there is provided a compound of formula VIII wherein G is N.

In a preferred aspect of the invention, ring D is selected from piperidin-4-yl, 1-methyl piperidin-4-yl, piperidin-3-yl, 1-methyl piperidin-3-yl, piperidin-2-yl, 1-methyl piperidin-2-yl, piperazine-4-yl, 1-methyl piperazine-4-yl, 1,4-homopiperazine-4-yl, 1-methy-1,4-homopiperazin-4-yl, 1-methyl pyrolidin-3-yl, 1-methyl pyrolidin-2-yl, imidazol-1-yl, imidazol-2-yl, quinuclidin-3-yl, quinuclidin-4-yl.

The invention further provides a compound of formula IX(a)

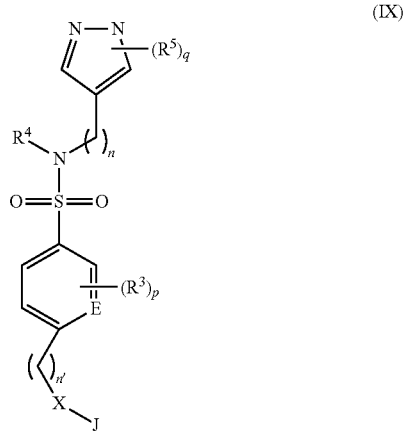

(IX)

wherein n, n', E, X, $R^3$, $R^4$, $R^5$, p and q are as defined herein and wherein J is independently a nitrogen containing heterocycle, for example heteroaryl, or an amine. Preferably E is C.

J may be selected from piperidin-4-yl, 1-methyl piperidin-4-yl, piperidin-3-yl, 1-methyl piperidin-3-yl, piperidin-2-yl, 1-methyl piperidin-2-yl, piperazine-4-yl, 1-methyl piperazine-4-yl, 1,4-homopiperazine-4-yl, 1-methy-1,4-homopiperazin-4-yl, 1-methyl pyrolidin-3-yl, 1-methyl pyrolidin-2-yl, imidazol-1-yl, imidazol-2-yl, quinuclidin-3-yl, quinuclidin-4-yl. Alternatively J may be selected from —$NH_2$, a secondary amine of formula —NHR and a tertiary amine of formula —NRR', where R and R' are independently $C_{1-6}$ alkyl optionally substituted with halogen, cyano, amino, hydroxy, $C_{1-6}$ alkyl and $C_{1-6}$ alkoxy or carbocyclyl, for example cycloalkyl or aryl Preferably $R^4$ is $C_{1-6}$ alkyl optionally substituted with halogen, cyano, amino, hydroxy, $C_{1-6}$ alkyl and $C_{1-6}$ alkoxy or carbocyclyl, for example cycloalkyl or aryl. Preferably $R^3$ is chloro, fluoro or methyl. Preferably n' is 0, 1 or 2. Preferably X is oxygen or $C_{1-6}$ alkyl e.g. $CH_2$.

The present invention further provides a compound according to the invention which comprises the racemate, the S or the R enantiomer or a mixture thereof, of a compound according to the invention. Preferably, the compound is the S-enantiomer or the R-enantiomer.

Illustrative, but non-limiting, examples of the compounds, including pharmaceutically acceptable salts thereof, of the present invention are shown in Table 1.

Preferred examples of compounds of the invention include DDD85646, DDD86481, DD99742, DDD99837, DDD100097, DDD100144, DDD100153, DDD100156, DDD100159, DDD100160, DDD100161 and DDD100868 as shown in Table 1.

Further preferred examples of compounds of the invention include DD99742, DDD100097, DDD100144, DDD100153 as shown in Table 1. An alternative preferred example of a compound of the invention is DDD85646.

Several methods for preparing the compounds of the invention are illustrated in the Schemes shown in the Examples (starting materials are made according to procedures known in the art or as illustrated herein). Thus in a further aspect of the invention there is provided a process for the manufacture of any one or more of the compounds according to the first aspect of the invention. Thus the invention provides a process for the preparation of a compound of formula I comprising the reaction steps of Example 1.

Any mixtures of final products or intermediates obtained can be separated on the basis of the physico-chemical differences of the constituents, in a known manner, into the pure final products or intermediates, for example by chromatography, distillation, fractional crystallisation, or by the formation of a salt if appropriate or possible under the circumstances.

Compounds of the invention may be in the form of salts. In particular, the salts may be pharmaceutically acceptable salts. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., US, 1985, p. 1418, the disclosure of which is hereby incorporated by reference; see also Stahl et al, Eds, *"Handbook of Pharmaceutical Salts Properties Selection and Use"*, Verlag Helvetica Chimica Acta and Wiley-VCH, 2002.

The disclosure thus includes pharmaceutically-acceptable salts of the disclosed compounds wherein the parent compound is modified by making acid or base salts thereof. For example the conventional non-toxic salts or the quaternary ammonium salts which are formed, e.g. from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The invention includes prodrugs for the active pharmaceutical species of the invention, for example in which one or more functional groups are protected or derivatised but can be converted in vivo to the functional group, as in the case of esters of carboxylic acids convertible in vivo to the free acid, or in the case of protected amines, to the free amino group. The term "prodrug," as used herein, represents in particular compounds which are rapidly transformed in vivo to the parent compound, for example, by hydrolysis in blood. A thorough discussion is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987; H Bundgaard, ed, Design of Prodrugs, Elsevier, 1985; and Judkins, et al. Synthetic Communications, 26(23), 4351-4367 (1996), each of which is incorporated herein by reference.

Also to be mentioned as metabolic activations of prodrugs are nucleotide activation, phosphorylation activation and decarboxylation activation. For additional information, see "The Organic Chemistry of Drug Design and Drug Action", R B Silverman (particularly Chapter 8, pages 497 to 546), incorporated herein by reference.

The use of protecting groups is fully described in 'Protective Groups in Organic Chemistry', edited by J W F McOmie, Plenum Press (1973), and 'Protective Groups in Organic Synthesis', 2nd edition, T W Greene & P G M Wutz, Wiley-Interscience (1991).

Thus, it will be appreciated by those skilled in the art that, although protected derivatives of compounds of the disclosure may not possess pharmacological activity as such, they may be administered, for example parenterally or orally, and thereafter metabolised in the body to form compounds of the invention which are pharmacologically active. Such derivatives are therefore examples of "prodrugs". All prodrugs of the described compounds are included within the scope of the disclosure.

Some groups mentioned herein (especially those containing heteroatoms and conjugated bonds) may exist in tautomeric forms and all these tautomers are included in the scope of the disclosure. More generally, many species may exist in equilibrium, as for example in the case of organic acids and their counterpart anions; a reference herein to a species accordingly includes reference to all equilibrium forms thereof.

The compounds of the invention may also contain one or more asymmetric carbon atoms and may therefore exhibit optical and/or diastereoisomerism. All diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric derivatives by conventional means (e.g. HPLC, chromatography over silica). All stereoisomers are included within the scope of the disclosure. Where a single enantiomer or diastereomer is disclosed, the disclosure also covers the other enantiomers or diastereomers, and also racemates; in this regard, particular reference is made to the specific compounds listed herein.

Geometric isomers may also exist in the compounds of the present disclosure. The present disclosure contemplates the various geometric isomers and mixtures thereof resulting from the arrangement of substituents around a carbon-carbon double bond and designates such isomers as of the Z or E configuration, wherein the term "Z" represents substituents on the same side of the carbon-carbon double bond and the term "E" represents substituents on opposite sides of the carbon-carbon double bond.

The disclosure therefore includes all variant forms of the defined compounds, for example any tautomer or any pharmaceutically acceptable salt, ester, acid or other variant of the defined compounds and their tautomers as well as substances which, upon administration, are capable of providing directly or indirectly a compound as defined above or providing a species which is capable of existing in equilibrium with such a compound.

Pharmaceutical Formulations and Use

The compounds of the invention in free form or in pharmaceutically acceptable salt form possess pharmacological activity. They are therefore intended for use as a pharmaceutical. In particular they inhibit N-myristoyl transferase activity.

Where used in therapy, the compounds of the invention will normally be administered orally, intravenously, subcutaneously, buccally, rectally, dermally, nasally, tracheally, bronchially, by any other parenteral route, as an oral or nasal spray or via inhalation. The compounds may be administered in the form of pharmaceutical preparations comprising prodrug or active compound either as a free compound or, for example, a pharmaceutically acceptable non-toxic organic or inorganic acid or base addition salt, in a pharmaceutically acceptable dosage form. Depending upon the disorder and patient to be treated and the route of administration, the compositions may be administered at varying doses.

Typically, therefore, the pharmaceutical compounds of the invention may be administered orally or parenterally ("parenterally" as used herein, refers to modes of administration which include intravenous, intramuscular, intraperitoneal, intrasternal, subcutaneous and intraarticular injection and infusion) to a host to obtain an inhibitory effect. In the case of larger animals, such as humans, the compounds may be administered alone or as compositions in combination with pharmaceutically acceptable diluents, excipients or carriers.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated and the condition and prior medical history of the patient being treated. However, it is within the skill of the art to start doses of the compound at levels lower than required for to achieve the desired therapeutic effect and to gradually increase the dosage until the desired effect is achieved.

In the treatment, prevention, control, amelioration, or reduction of risk of conditions which require inhibition of kinase activity, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0 and 1000.0 milligrams of the active ingredient for the symptomatic adjustment of the dosage to the patient to be treated. The compounds may be administered on a regimen of 1 to 4 times per day, preferably once or twice per day. The dosage regimen may be adjusted to provide the optimal therapeutic response.

According to a further aspect of the invention there is thus provided a pharmaceutical composition including a compound of the invention, in admixture with a pharmaceutically acceptable adjuvant, diluent or carrier.

Pharmaceutical compositions of this invention for parenteral injection suitably comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and non-aqueous carriers, diluents, solvents or vehicles include water, ethanol, polyols (such as glycerol, propylene glycol, polyethylene glycol and the like), and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants.

These compositions may also contain adjuvants such as preservative, wetting agents, emulsifying agents and dispersing agents. Prevention of the action of microorganisms may be ensured by the inclusion of various antibacterial and antifungal agents, for example, paraben, chlorobutanol or phenol sorbic acid. It may also be desirable to include isotonic agents such as sugars or sodium chloride, for example. Prolonged absorption of the injectable pharmaceutical form may be brought about by the inclusion of agents (for example aluminum monostearate and gelatin) which delay absorption.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are suitably made by forming microencapsule matrices of the drug in biodegradable polymers, for example polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations may also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use.

Solid dosage forms for oral administration include capsules, tablets, pills, powders and granules. In such solid dosage forms, the active compound is typically mixed with at least one inert, pharmaceutically acceptable excipient or carrier such as sodium citrate or dicalcium phosphate and/or one or more: a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycol, for example.

Suitably, oral formulations contain a dissolution aid. The dissolution aid is not limited as to its identity so long as it is pharmaceutically acceptable. Examples include nonionic surface active agents, such as sucrose fatty acid esters, glycerol fatty acid esters, sorbitan fatty acid esters (e.g. sorbitan trioleate), polyethylene glycol, polyoxyethylene hydrogenated castor oil, polyoxyethylene sorbitan fatty acid esters, polyoxyethylene alkyl ethers, methoxypolyoxyethylene alkyl ethers, polyoxyethylene alkylphenyl ethers, polyethylene glycol fatty acid esters, polyoxyethylene alkylamines, polyoxyethylene alkyl thioethers, polyoxyethylene polyoxypropylene copolymers, polyoxyethylene glycerol fatty acid esters, pentaerythritol fatty acid esters, propylene glycol monofatty acid esters, polyoxyethylene propylene glycol monofatty acid esters, polyoxyethylene sorbitol fatty acid esters, fatty acid alkylolamides, and alkylamine oxides; bile acid and salts thereof (e.g. chenodeoxycholic acid, cholic acid, deoxycholic acid, dehydrocholic acid and salts thereof, and glycine or taurine conjugate thereof); ionic surface active agents, such as sodium laurylsulfate, fatty acid soaps, alkylsulfonates, alkylphosphates, ether phosphates, fatty acid salts of basic amino acids; triethanolamine soap, and alkyl quaternary ammonium salts; and amphoteric surface active agents, such as betaines and aminocarboxylic acid salts.

The solid dosage forms of tablets, dragees, capsules, pills, and granules can be prepared with coatings and shells such as enteric coatings and other coatings well known in the pharmaceutical formulating art. They may optionally contain opacifying agents and may also be of a composition such that they release the active ingredient(s) only, or preferentially, in a certain part of the intestinal tract, and/or in delayed fashion. Examples of embedding compositions include polymeric substances and waxes.

The active compounds may also be in micro-encapsulated form, if appropriate, with one or more of the above-mentioned excipients.

The active compounds may be in finely divided form, for example it may be micronised.

Liquid dosage forms for oral administration include pharmaceutically acceptable emulsions, solutions, suspensions, syrups and elixirs. In addition to the active compounds, the liquid dosage forms may contain inert diluents commonly used in the art such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan and mixtures thereof. Besides inert diluents, the oral compositions may also include adjuvants such as wetting agents, emulsifying and suspending agents, sweetening, flavoring and perfuming agents. Suspensions, in addition to the active compounds, may contain suspending agents such as ethoxylated isostearyl alcohols, polyoxyethylene sorbitol and sorbitan esters, microcrystalline cellulose, aluminum metahydroxide, bentonite, agar-agar, and tragacanth and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolisable lipid capable of forming liposomes can be used. The present compositions in liposome form can contain, in addition to a compound of the present invention, stabilisers, preservatives, excipients and the like. The preferred lipids are the phospholipids and the phosphatidyl cholines (lecithins), both natural and synthetic. Methods to form liposomes are known in the art, for example, Prescott, Ed., Methods in Cell Biology, Volume XIV, Academic Press, New York, N.Y. (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants which may be required. Ophthalmic formulations, eye ointments, powders and solutions are also contemplated as being within the scope of this invention.

Advantageously, the compounds of the invention may be orally active, have rapid onset of activity and low toxicity.

The compounds of the invention may have the advantage that they are more efficacious, less toxic, longer acting, have a broader range of activity, more potent, produce fewer side effects, more easily absorbed than, or have other useful pharmacological properties over, compounds known in the prior art.

Compounds of the invention may be useful in the therapy of a variety of diseases and conditions. In particular, compounds of the invention may be useful in the treatment or prevention of diseases or disorders which can be prevented, alleviated or treated by modulation/inhibition of N-myristoyl transferase (NMT) activity (referred to herein as NMT related diseases or disorders). Such NMT related diseases or disorders include but are not limited to hyperproliferative disorders, for example cancer, microbial infections, neurological diseases/disorders and diabetes and associated conditions.

As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "cancer" includes malignancies of the various organ systems, such as those affecting, for example, lung, breast, thyroid, lymphoid, gastrointestinal, and genito-urinary tract, as well as adenocarcinomas which include malignancies such as most colon cancers, renal-cell carcinoma, prostate cancer and/or testicular tumours, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary.

The term "carcinoma" also includes carcinosarcomas, e.g., which include malignant tumours composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation. Further types of cancer include leukaemia, skin, intracranial and brain cancer.

By "microbial infection" is meant an infection caused by a bacterium, parasite, protozoa, virus or fungus including yeast. A "pathogen" is generally defined as any disease-causing organism.

A parasitic pathogen may be derived from a parasite selected from, but not limited to, the group consisting of *Trypanosoma* spp. (e.g. *T. cruzi*, *T. brucei*, *T. congolense*), *Leishmania* spp. (e.g. *L. major*, *L. donovani*, *L. braziliensis*), *Giardia* spp., *Trichomonas* spp. (e.g. *Tr. vaginalis*), *Entamoeba* spp. (e.g. *E. histolytica*), *Naegleria* spp., *Acanthamoeba* spp. (e.g. *A. castelleni*), *Schistosoma* spp. (e.g. *S. mansoni, S. japonicam*), *Plasmodium* spp. (e.g. *P. falciparum*), *Crytosporidium* spp., *Isospora* spp., *Balantidium* spp., *Loa Loa*, *Ascaris lumbricoides*, *Dirofilaria immitis*, *Toxoplasma* ssp. (e.g *To. gondii*), *Onchocerca* spp. (e.g. *O. volualno*).

A viral pathogen may be derived from a virus selected from, but not limited to, the group consisting of: Human Immunodeficiency Virus (HIV1 & 2); Human T Cell Leukaemia Virus (HTLV 1 & 2); Ebola virus; human papilloma virus (e.g. HPV-2, HPV-5, HPV-8 HPV-16, HPV-18, HPV-31, HPV-33, HPV-52, HPV-54 and HPV-56); papovavirus; rhinovirus; poliovirus; herpesvirus; adenovirus; Epstein Barr virus; influenza virus, hepatitis B and C viruses, Variola virus, rotavirus or SARS coronavirus.

A fungal pathogen may be derived from a fungus (including yeast) selected from, but not limited to, the genera *Candida* spp., (e.g. *C. albicans, C. tropicalis*), *Aspergillus* spp. (e.g. *A. fumigatus*), *Cryptococcus* spp. (e.g. *Cryptococcus neoformans*), and *Saccharomyces* spp. (e.g. *Saccharomyces cerevisiae*), *Pneumocystis* spp. (e.g. *Pneumocystis carinii*).

As used herein the "neurological diseases/disorder" may include neuropsychiatric disorders, including Parkinson's Disease, Attention Deficit Hyperactivity Disorder (ADHD), depression (bipolar disorder) and schizophrenia and addiction; neurodegenerative disorders (e.g. Alzheimer's disease, Tourette Syndrome, Parkinson's disease, Huntington's disease, Amyotrophic Lateral Sclerosis, senile chorea, Sydenham's chorea, autism, head and spinal cord trauma, acute and chromic pain, epilepsy and seizures, dementia, distonia, tremor, autism, cerebral ischemia and neuronal cell death) and disorders linked to apoptosis (particularly neuronal apoptosis).

Thus the invention provides the use of a compound of the invention, or pharmaceutically acceptable salt thereof, in the manufacture of a medicament for the treatment or prevention of a NMT related disease or disorder.

In a preferred use according to the invention the NMT related disease or disorder is cancer. The compounds of the invention may be useful in the therapy of a variety of cancer including, but not limited to, prostate, breast, brain (e.g. glioma), gallbladder, colon, ovarian and oral (e.g. squamous cell) cancer or leukaemia.

In a further preferred use according to the invention the NMT related disease or disorder is a microbial infection for example a parasite, viral or fungal infection. By way of example the parasite infection may be caused by *Trypanosoma* spp. (e.g. *Trypanosoma cruzi, Trypansosoma brucei*) or *Leishmania* spp. (e.g. *L. major, L. donovani*) or *Plasmodium* spp. (e.g. *P. falciparum*). The viral infection may be caused by HIV e.g. HIV1 or HIV2 or hepatitis B. The fungal infection may be caused by a fungus selected from the group consisting of *Candida albicans, Aspergillus Fumigatus, Pneumocystis carinii* and *Cryptococcus neoformans*. The microbial infection may include Leishmaniasis, Trypanosomiasis, Malaria, (Invasive) Aspergillosis, Candidiasis, *Pneumocystis* pneumonia and Cryptococcosis.

In a further use according to the invention the NMT related disease or disorder is a neurological disease or disorder for example epilepsy or Alzheimer's disease.

In a yet further use according to the invention the NMT related disease or disorder is diabetes, ischemia or osteoporosis.

The invention further provides a method of treating a NMT related disease or disorder in a subject which method comprises administering to said subject a therapeutically effective amount of a compound, or pharmaceutically acceptable salt thereof, or composition of the invention. Preferably the subject is a mammal for example a human.

The compounds of the invention, or pharmaceutically acceptable salts thereof, may be administered in combination with a chemotherapeutic agent. Thus in a further aspect the invention provides a method of increasing the efficacy of a chemotherapeutic agent in a mammal having cancer, said method comprising administering to said mammal an effective amount of a compound of the invention or pharmaceutically acceptable salt thereof.

In a further aspect the invention provides a method of inhibiting the activity of one or more NMT (NMT1 and NMT2), said method comprising contacting one or more NMT with an effective amount of the compound of the invention. The method may be an in vitro method. Alternatively the method may be an in vivo method.

As used herein, "treatment" refers to clinical intervention in an attempt to alter the natural course of the individual or cell being treated, and may be performed either for prophylaxis or during the course of clinical pathology. Desirable effects include preventing occurrence or recurrence of disease, alleviation of symptoms, diminishment of any direct or indirect pathological consequences of the disease, lowering the rate of disease progression, amelioration or palliation of the disease state, and remission or improved prognosis. The term, "treatment" as used herein is intended to include the treatment and prevention of the indicated conditions/disorders There is further provided a package or kit of parts comprising:
(1) a compound, or pharmaceutically acceptable salt thereof, as described herein; together with
(2) instructions to use said compound or salt in a method described herein.

The package defined herein may comprise more than one dosage unit, in order to provide for repeat dosing. If more than one dosage unit is present, such units may be the same, or may be different in terms of the dose of active agent composition and/or physical form.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

EXAMPLE 1

Materials and Methods

The following abbreviations are used:
Pd(dppf)Cl$_2$.DCM—[1,1'-Bis(diphenylphosphino)ferrocene]dichloropalladium (II)-dichloromethane complex;
THF—tetrahydrofuran,
EtOAc—ethyl acetate; DMF—N,N-dimethylformamide;
MeOH—methanol; Boc—t-butoxycarbonyl;
EtOH—ethanol; CHCl$_3$—chloroform;
DCM—dichloromethane; AcOH—acetic acid;

DIPEA—diisopropylethylamine; EtOH—ethanol;
Pyr—pyridine; Ar—aryl;
DMSO—dimethylsulphoxide; iPr—isopropyl;
Et$_2$O—diethylether; Me—methyl;

All NMR's were obtained either at 500 MHz on a Bruker Avance II spectrometer or at 300 MHz on a Bruker DPX 300 spectrometer.

All LCMS's were obtained using a Bruker Daltonics mass spectrometer in combination with an Agilent 1100 series high pressure liquid chromatograph.

All Intermediates and Examples were named with the aid of Beilstein Autonom or were given names that seemed consistent with IUPAC convention.

General Methods of Synthesis of Compounds

The following is a description of a process for preparing a compound of the invention or a pharmaceutically acceptable salt thereof:

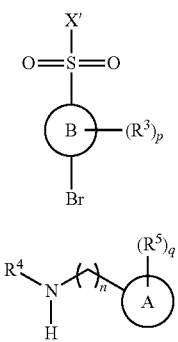

(X)

(XI)

a) reacting a sulfonyl compound of formula (X) with an intermediate compound of formula (XI) in which X' represents a leaving group for example halo, e.g. chloro, in the presence or absence of a diluent for example an organic solvent e.g. dichloromethane or chloroform and optionally in the presence of a base, for example an organic amine e.g. DIPEA, triethylamine etc. but preferentially pyridine, at a temperature in the range of 0-150° C.

Where they are not commercially available, the starting materials of formula (XI), being derived from amine-bearing heterocycles such as pyridine, isoxazole and pyrazole, may be prepared by methods analogous to those described in the accompanying examples or by standard methods well known in the art (Labeeuw, O. et al. Tett. Asymm., 2004, 15, 1899-1908 and Blay, G. et al. Tetrahedron, 2006, 62, 8069-8076).

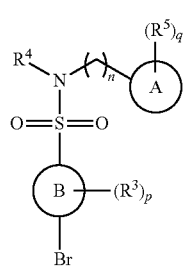

(XII)

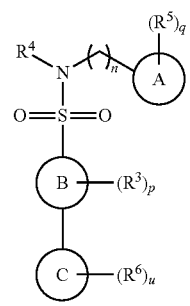

(XIII)

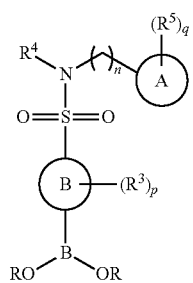

(XIV)

b) reacting an intermediate sulphonamide compound of formula (XII) with an appropriately substituted aryl or heteroaryl boronic acid or a suitably reactive analogue therein, such as an aryl or heteroaryl pinacolboronic ester, in the presence of a metal catalyst. e.g. Pd or derivatives thereof, such as Pd(dppf)Cl$_2$.DCM or Pd(PPh$_3$)$_4$, and in a solvent such as DMF or THF, optionally with water as a co-solvent, and an organic or inorganic base such as triethylamine or potassium phosphate, and in the temperature range 0-170° C., to provide a compound of formula (XIII).

Where the appropriate boronic acids or boronic esters are not commercially available, compounds of formula (XIII) may be prepared by reacting an appropriately substituted aryl or heteroaryl halide with intermediate (XIV), where B(OR)$_2$ is typically —B(OH)$_2$ or any suitably reactive ester derivative thereof, which itself can be prepared from intermediate (XII) by an appropriate boronation reaction with a boronating reagent e.g. bispinacolatodiboron or pinacolborane, according to the method of Murata et al. (Murata, M; Oyama, T.; Watanabe, S; Masuda, Y., *J. Org. Chem.* 2000, 65, 164-168).

c) reacting an intermediate compound of formula (XII) with an appropriately substituted alkyne of formula (XV) in the presence of a copper(I) halide e.g. copper(I) iodide, a metal catalyst e.g. Pd or derivatives thereof, such as Pd(PPh3)$_2$Cl$_2$ or Pd(PPh$_3$)$_4$, and in a solvent such as DMF or THF, with an organic or inorganic base such as triethylamine, diisopropylamine or sodium acetate, and in the temperature range 0-170° C.

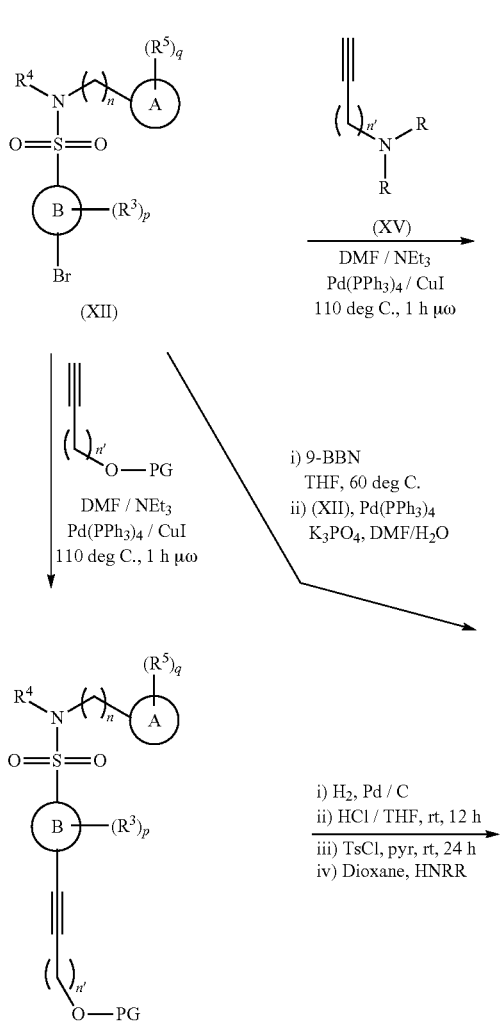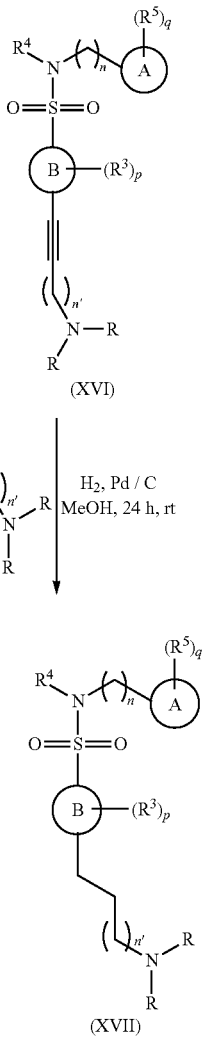

d) reacting an intermediate compound of formula (XII) with an appropriately substituted alkene in the presence of 9-borabicyclo[3.3.1]nonane and a metal catalyst e.g. tetrakis-triphenylphosphine palladium (0) or Pd(dppf)Cl$_2$.DCM and in a solvent such as DMF or THF, with an organic or inorganic base such as triethylamine, diisopropylamine or potassium phosphate, and in the temperature range 0-170° C., according to the methods described by Suzuki et al. (Miyaura, M.; Ishiyama, T.; Sasaki, H.; Ishikawa, M.; Satoh, M.; Suzuki, A., *J. Am. Chem. Soc.,* 1989, 111, 314-321) and Lynch et al. (Lynch, C. L. *Bioorg. Med. Chem. Letts.,* 2003, 13, 119-123).

It will be understood that certain compounds of the invention initially obtained from any of the above processes may, where appropriate, be elaborated into certain other compounds of the invention by techniques known to those skilled in the art. By way of example, the conversion of a compound of formula (XVI) to a compound of formula (XVII), where n'=1 or 2, can be effected by the use of a reducing agent, for example, hydrogen gas, in combination with a heterogeneous or homogeneous transition metal catalyst, such as Pd on charcoal, or Wilkinson's catalyst. Alternatively, transfer hydrogenation conditions can be employed to effect the same transformation, e.g. using tosylhydrazone or formic acid, or the use of a dissolving metal in a protic solvent i.e. lithium in liquid ammonia.

It will be understood that the conversion of a compound of formula (XIII) to a compound of formula (XVII) can also be effected via a five step process which comprises (i) reaction of intermediate (XII) with a suitably protected alcohol-bearing alkyne, for example tetrahydro-2-(2-propynyloxy)-2H-pyran; (ii) catalytic reduction of the alkyne with a suitable reducing agent; (iii) deprotection of the alcohol by treatment with HCl in a suitable protic solvent, such as methanol; (iv) conversion of the alcohol to a suitably reactive leaving group such as halo, e.g. chloro or bromo, or sulfonyl group, e.g. p-toluenesulfonyl or methanesulfonyl; and (v) displacement of the intermediate thereof obtained by an appropriately substituted amine e.g. piperazine or homopiperazine or a suitably substituted analogue thereof, in a solvent such as DMF or THF.

A compound of formula (XII), wherein $R^4$=H, can be converted into the corresponding compound of formula (XII), wherein $R^4$=(alkyl or substituted alkyl or substituted alkaryl etc. . . . ) by reaction with an appropriate alkyl or alkaryl halide, such as methyl iodide or benzyl bromide in the presence of a strong base, typically sodium hydride, in a solvent such as DMF. Alternatively a base such as sodium carbonate, potassium carbonate or caesium carbonate may be used, in which case the reaction may be performed in DMF at elevated temperature. A compound of formula (XII), wherein $R^4$=H, can be converted into the corresponding compound of formula (XII), wherein $R^4$=$CF_3CH_2$— or $CHF_2CH_2$—, by reaction with the appropriate fluoroalkyl trifluoromethanesulfonate in the presence of a base, typically potassium carbonate, in a solvent such as acetonitrile. A compound of formula (XII), wherein $R^4$=H, can be converted into the corresponding compound of formula (XII), wherein $R^4$=$CHF_2$ by reaction with sodium chlorodifluoroacetate and potassium carbonate in acetonitrile.

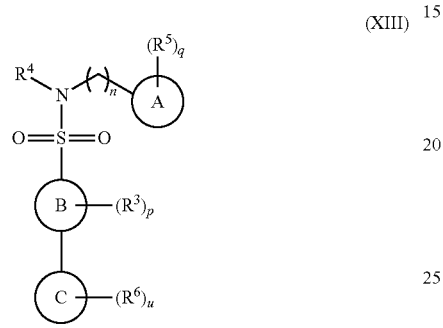

(XIII)

A compound of formula (XIII), wherein $(R^6)_u$ represents a —$(CH_2)_n$-formyl group in the ortho-, meta-, or para-position and n=0, 1 or 2, may be converted to the corresponding compound wherein $(R^6)_u$ represents a —$(CH_2)_n$—NRR' moiety in the ortho-, meta-, or para-position and n=0, 1 or 2, wherein NRR' represents a substituted amine moiety such as dimethylamino-, diethylamino-, pyrolidine-1-yl-, piperazine-1-yl-, 4-methylpiperazine-1-yl- or related substituted analogues of piperazine, by reaction with an appropriate amine of formula HNRR' e.g. N-methylpiperazine in the presence of a reducing agent such as sodium cyanoborohydride or sodium triacetoxyborohydride.

A compound of formula (XIII) wherein $(R^6)_u$ represents a —$(CH_2)_n$-alcohol group in the ortho-, meta-, or para-position and n=0, 1 or 2 may be converted to the corresponding compound wherein $(R^6)_u$ represents a —$(CH_2)_n$—R in the ortho-, meta-, or para-position and n=1 or 2, where R is imidaz-1-yl or analogue thereof, e.g. 2-methyl-imidazol-1-yl, via a two step process which comprises; (i) conversion of the alcohol to a suitable leaving group, such as halo e.g. chloro, or sulfonyl e.g. methanesulfonyl or para-toluenesulfonyl; (ii) displacement of the intermediate thereof obtained by an appropriately substituted imidazole e.g. 2-methylimidazole or a suitably substituted analogue thereof, in a solvent such as DMF or THF, with a base such as potassium carbonate.

A compound of formula (XIII) wherein $(R^6)_u$ represents a hydroxyl group in the ortho-, meta-, or para-position may be converted to the corresponding compound wherein $(R^6)_u$ represents an imidazole or substituted imidazole, e.g. 1H-imidazol-2-yl, 1H-imidazol-4-yl, 1-methyl-imidazol-2-yl, 1-methyl-imidazol-4-yl and 1-methyl-imidazol-5-yl via a two step process which comprises; (i) conversion of the phenol to a trifluoromethanesulfonate by reaction with trifluoromethanesulphonic acid anhydride and triethylamine, in DCM at 0 deg C., followed by (ii) Suzuki reaction of the intermediate thereof obtained with an appropriately substituted bromo- or iodo-imidazole e.g. 1-methyl-2-bromoimidazole under conditions previously described herein.

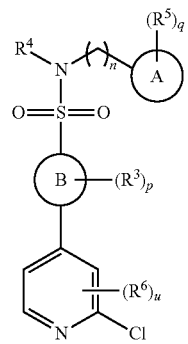

(XVIII)

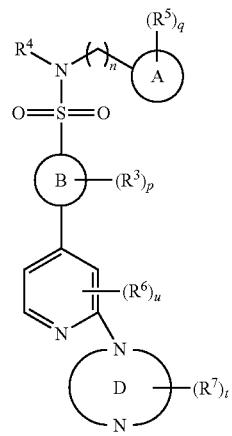

(XIX)

A compound of formula (XVIII) may be converted to a compound of formula (XIX), by treatment with a primary or secondary cyclic or acyclic amine in a solvent such as ethanol at elevated temperature, such as 150° C. Alternatively the transformation can be effected by reaction of an amine in the presence of a transition metal catalyst, e.g. palladium, and a strong base according to the methods described by Buchwald et al. (Wolf, J. P.; Buchwald, S. L. i *J. Org. Chem.*, 2000, 65, 1158).

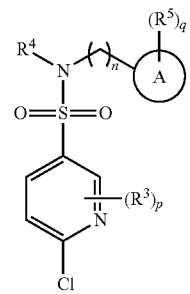

(XX)

Likewise, a compound of formula (XX) may be converted to a compound of the invention, under analogous conditions.

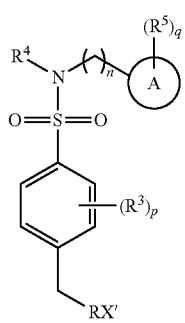

(XXI)

A compound of formula (XXI), wherein RX' represents a suitable leaving group, such as chloro or bromo or methanesulphonyl or para-toluenesulphonyl, may be converted to a compound of formula (XXI), wherein RX' represents —NRaRb, by treatment with an amine of formula HNRaRb under conditions which employ a solvent e.g. DMF, DMSO or ethanol, and an inorganic or organic base e.g. NEt$_3$, DIPEA, potassium carbonate or sodium carbonate, as examples, at a temperature in the range of 0 to 170° C.

Similarly, a compound of formula (XXI), wherein RX' represents a suitable leaving group, such as chloro or bromo or methanesulphonyl or para-toluenesulphonyl, may be converted to a compound of formula (XXI), wherein RX' represents —SRa, by treatment with a thiol-bearing compound of formula HSRa under analogous conditions as described.

Similarly, a compound of formula (XXI), wherein RX' represents a suitable leaving group, such as chloro or bromo or methanesulphonyl or para-toluenesulphonyl, may be converted to a compound of formula (XXI), wherein RX' represents —ORa, by treatment with an alcohol-bearing compound of formula HORa under analogous conditions as described. Similarly, a compound of formula (XXI), wherein RX' represents a suitable leaving group, such as chloro or bromo or methanesulphonyl or para-toluenesulphonyl, may be converted to a compound of formula (XXI), wherein RX' represents —C'HRaRb, by treatment with a compound of formula H$_2$C'RaRb, where Ra and/or Rb are functional groups capable of rendering the compound represented by H$_2$C'RaRb as a carbon-based nucleophile following deprotonation under basic conditions. Such compounds represented by H$_2$C'RaRb include, but are not limited to, dialkylmalonate and thiazolidine-1,3-dione, for example.

The compounds in accordance with this invention potently inhibit the activity of human, fungal and parasite NMT-1 and/or NMT-2.

Enzyme Inhibition Assay

Measurement of the ability of compounds to inhibit the NMT-1 and/or NMT-2 enzyme isoforms of human, trypanosome (*T. brucei*), leishmanial (*L. major*) and fungal (*A. fumigatus*) species was performed using a modification of the scintillation proximity assay platform described previously by Georgopapadakou, N. H. et al. (22$^{nd}$ International Congress on Chemotherapy, 2001, Abstract P16.001), as follows;

N-myristoyl transferase is an enzyme that catalyses the addition of myristic acid from myristoyl coenzyme A to the N-terminal glycine residue of numerous substrate proteins and peptides with the subsequent release of coenzyme A. $^3$H-labelled myristoyl coenzyme A (GE Healthcare) can be used in the reaction to transfer $^3$H-myristic acid to a biotinylated substrate peptide (GCGGSKVKPQPPQAK[SEQ. ID:1](Biotin)-Amide, Pepceuticals Inc). The reaction can be measured by the subsequent binding of the labelled peptide to streptavidin-coated scintillation proximity assay (SPA) beads (GE Healthcare) and monitoring of β-particle excitation of the embedded scintillant, Compounds were solubilised in DMSO at a top concentration of 10 mM and serially diluted in half log steps to achieve a range of final assay concentrations of 100 µM to 1 nM. Compound at each concentration (100-fold final) was added to white 384 well plates in a volume of 0.5 ml. Human, *A. fumigatus*, *T. brucei* or *L. major* N-myristoyl transferase enzyme, dissolved to a working concentration of 10 nM in assay buffer (30 mM Tris/HCl pH 7.4, 0.5 mM EGTA, 0.5 mM EDTA, 1.25 mM DTT, 0.1% Triton X-100), was then added to columns 1 to 11 and 13 to 23 of the plates in a volume of 20 ml. To columns 12 and 24, 20 ml assay buffer was added to provide a no enzyme control, Following a 5 minute incubation at room temperature the substrates (GCGGSKVKPQPPQAK [SEQ. ID:1](Biotin)-Amide and myristoyl coenzyme A), dissolved in assay buffer, were added to all wells in a volume of 20 ml to start the reaction. The final concentrations of peptide and $^3$H-myristoyl coenzyme A were 0.5 mM and 125 nM respectively and the specific activity of the radiolabel was 8 Ci/mmol. Plates were then incubated at room temperature for up to 50 minutes (dependant upon the period of linearity for the different enzyme species) before SPA beads, suspended to 1 mg/ml in a stop solution (200 mM Phosphoric Acid/NaOH pH 4, 750 mM MgCl$_2$), were added in a volume of 40 ml. Plates were then read on a TopCount microplate luminometer and data analysed by calculating the percentage inhibition compared to the maximum and minimum assay controls. Concentration effect curves were fitted using non linear regression using XLFit 4.2 and IC$_{50}$ values determined.

In-Vitro Antitrypanosomal Efficacy Assay

Measurement of the ability of the compounds to inhibit Trypanosome (*T. brucei brucei*) and Human (MRC5, human lung fibroblast cells) cell growth was performed using a modification of the cell viability assay previously described by Raz, B. et al. (Acta. Trop. 68:139-14, 1997);

Compounds were solubilised in DMSO at a top concentration of 10 mM and serially diluted in half log steps to achieve a range of final assay concentrations of 50 µM to 0.5 nM. Compound at each concentration (200-fold final) was added to clear 96 well tissue culture plates in a volume of 1 µl. 2000 cells per well in relevant growth media (HMI-9 for *T. brucei* as described by Hurumi, H. et al. J. Parasitol. 75(6):985-989, 1989; MEM with 10% FBS for MRC5) were then added to columns 1 to 11 of the plates in a volume of 1994 To column 12, 200 µl media was added to provide a no cells control. Plates were then incubated at 37° C. in an atmosphere of 5% CO$_2$ for 69 hours, before the addition of 20 µl of 500 µM rezasurin solution, and a further incubation period of 4 hours. Plates were then read on a BioTek flx800 fluorescent plate reader and percentage inhibition compared to the maximum and minimum assay controls. Concentration effect curves were fitted using non-linear regression using XLFit 4.2 and EC$_{50}$ values determined.

In-Vitro Antiproliferative Assay

The ability of test compounds to inhibit the proliferation of a panel of human cancer cell lines was determined using the following protocol; i) cells were seeded in 96-well plates at a cell density of 3000/well, and allowed to adhere overnight prior to addition of compound or vehicle control. ii) Test compounds were prepared from 10 mM DMSO stocks to give a final concentration range of 100 µM, 30 µM, 10 µM, 3 µM, 1 µM, 0.3 µM, 0.1 µM, 0.03 µM and 0.01 µM, with DMSO content constant at 1%. iii) Test compounds were incubated with the cells for 72 h at 37° C., 5% $CO_2$ in a humidified atmosphere. iv) Alamar blue 10% (v/v) was then added and incubated for a further 6 h, and fluorescent product detected using the BMG FLUOstar plate reader. v) Paclitaxel was used as a standard control inhibitor. vi) Data was analysed using a 4-parameter logistic equation in GraphPad Prism.

The following Intermediates and Examples illustrate the preparation and properties of compounds according to the invention with reference to the following FIGURE:

FIG. 1 shows a Kaplan Meier survival plot for DDD85646 in an acute model of trypanosomiasis infection

INTERMEDIATE 1

4-Bromo-N-(1,3,5-trimethyl-1H-pyrazol-4-yl)-benzenesulfonamide

Prototypical Procedure for Preparation of a Sulphonamide from an Amine and a Sulfonyl Chloride;

4-Bromobenzene sulfonyl chloride (5.0 g, 19.6 mmol) was added portionwise to a stirred solution of 4-amino-1,3,5-trimethyl-1H-pyrazole (2.45 g, 19.6 mmol) in pyridine (50 ml) at rt. The reaction was stirred for 24 h then concentrated to dryness in vacuo. The resulting residue was diluted with DCM (100 ml), washed with aqueous sodium hydroxide solution (0.5M, 100 ml), organic phase separated, dried ($MgSO_4$), filtered and concentrated to dryness in vacuo. Trituration from $Et_2O$ and collection by vacuum filtration gave the title compound as a fine off-white solid (5.1 g, 14.8 mmol, 79%). δH (D-6 DMSO, 300K). m/z ($ES^+$, 70V) 344.1 ($MH^+$)

INTERMEDIATE 2 (DDD73234)

4-Bromo-2,6-dichloro-N-(1,3,5-trimethyl-1H-pyrazol-4-yl)-benzenesulfonamide

Prepared from 4-bromo-2,6-dichlorobenzenesulfonyl chloride (5.0 g, 15.4 mmol) and 4-amino-1,3,5-trimethyl-1H-pyrazole (1.93 g, 15.4 mmol) in pyridine (35 ml) according to the method of intermediate 1, to give the title compound as an orange solid (5.64 g, 13.7 mmol, 89%). δH (D-6 DMSO, 300K) 9.75 (1H, s), 8.00 (2H, s), 3.57 (3H, s), 1.93 (3H, s), 1.72 (3H, s). m/z ($ES^+$, 70V) 413.9 ($MH^+$).

INTERMEDIATE 3 (DDD86208)

4-Bromo-2-chloro-N-(1,3,5-trimethyl-1H-pyrazol-4-yl)-benzenesulfonamide

Prepared from 4-bromo-6-chlorobenzene sulfonyl chloride (5.0 g, 17.3 mmol) and 4-amino-1,3,5-trimethyl-1H-pyrazole (2.16 g, 17.3 mmol) in pyridine (35 ml) according to the method of intermediate 1, to give the title compound as an off-white solid (4.1 g, 10.8 mmol, 62%). δH (D-6 DMSO, 300K) 9.52 (1H, s), 8.05 (1H, d J 1.6 Hz), 7.72-7.63 (3H, m), 3.54 (3H, s), 1.89 (3H, s), 1.69 (3H, s). m/z ($ES^+$, 70V) 379.9 ($MH^+$).

INTERMEDIATE 4 (DDD88004)

4-Bromo-3,6-difluoro-N-(1,3,5-trimethyl-1H-pyrazol-4-yl)-benzenesulfonamide

Prepared from 2,5-difluoro-4-bromobenzenesulfonyl chloride (2 g, 6.9 mmol) and 4-amino-1,3,5-trimethyl-1H-pyrazole (858 mg, 6.9 mmol) in pyridine (30 ml) according to the method of intermediate 1, to give the title compound as a pale yellow solid (1.9 g, 5.0 mmol, 73%). δH (D-6 DMSO, 300K) 9.77 (1H, s), 8.12 (1H, dd, J 5.5 Hz 9.0 Hz), 7.55 (1H, dd J 6. Hz 7.5 Hz), 3.58 (3H, s), 1.92 (3H, s), 1.74 (3H, s). m/z ($ES^+$, 70V) 380.0 ($MH^+$).

INTERMEDIATE 5 (DDD73235)

6-Chloro-pyridine-3-sulfonic acid (1,3,5-trimethyl-1H-pyrazol-4-yl)-amide

Prepared from 6-chloropyridine-3-sulfonyl chloride (4.8 g, 22.7 mmol) and 4-amino-1,3,5-trimethyl-1H-pyrazole (2.84 g, 22.7 mmol) in pyridine (35 ml) according to the method of intermediate 1, to give the title compound as a white solid (5.13 g, 17.1 mmol, 75%). δH (D-6 DMSO, 300K) 9.51 (1H, s), 8.59 (1H, d J 2.3 Hz), 8.03 (1H, dd J 7.6 Hz 2.3 Hz), 7.77 (1H, d J 7.6 Hz), 3.58 (3H, s), 1.84 (3H, s), 1.63 (3H, s). m/z ($ES^+$, 70V) 301.1 ($MH^+$).

INTERMEDIATE 6

4-Bromo-N-(3,5-dimethyl-isoxazol-4-yl)-benzenesulfonamide

Prepared from 4-bromobenzenesulfonyl chloride (4.56 g, 17.9 mmol) and 4-amino-3,5-dimethylisoxazole (2.02 g, 18.0 mmol) in pyridine (36 ml) according to the method of intermediate 1, to give the title compound as a white solid (5.15 g, 15.5 mmol, 87%). δH ($CDCl_3$, 300K) 7.69 (2H, dd, J 6.9 Hz 1.7 Hz), 7.65 (2H, dd, J 6.9 Hz 1.7 Hz), 6.11 (1H, s), 2.12 (3H, s), 1.91 (3H, s). m/z ($ES^+$, 70V) 333.0 ($MH^+$).

INTERMEDIATE 7

4-Bromo-2,6-dichloro-N-(3,5-dimethyl-isoxazol-4-yl)-benzenesulfonamide

Prepared from 4-bromo-2,6-dichlorobenzenesulfonyl chloride (1.00 g, 3.19 mmol) and 4-amino-3,5-dimethylisoxazole (0.346 g, 3.1 mmol) in pyridine (6 ml) according to the method of intermediate 1, to give the title compound as a tan solid (606 mg, 1.51 mmol, 49%). δH ($CDCl_3$, 300K) 7.70 (2H, s), 6.66 (1H, s), 2.23 (3H, s), 2.05 (3H, s). m/z ($ES^+$, 70V) 400.9 ($MH^+$).

INTERMEDIATE 8

4-Bromo-N-(2-methyl-pyridin-3-yl)-benzenesulfonamide

Prepared from 4-bromobenzenesulfonyl chloride (4.73 g, 18.5 mmol) and 2-methyl-3-aminopyridine (2.04 g, 18.9 mmol) in pyridine (36 ml) according to the method of intermediate 1, to give the title compound as a white solid (3.81 g, 11.6 mmol, 63%). δH ($CDCl_3$, 300K) 8.36 (1H, dd J 4.8 Hz 1.5 Hz), 7.70 (1H, dd J 8.1 Hz 1.5 Hz), 7.63 (2H, dd J 6.6 Hz 2.3 Hz), 7.60 (2H, dd J 6.6 Hz 2.3 Hz), 7.17 (1H, dd J 8.1 Hz 4.8 Hz), 6.89 (1H, s), 2.25 (3H, s). m/z ($ES^+$, 70V) 329.0 ($MH^+$).

INTERMEDIATE 9

4-Bromo-2,6-dichloro-N-(2-methyl-pyridin-3-yl)-benzenesulfonamide

Prepared from 4-bromo-2,6-dichlorobenzenesulfonyl chloride (1.00 g, 3.1 mmol) and 2-methyl-3-aminopyridine (0.33 g, 3.1 mmol) in pyridine (6 ml) according to the method of intermediate 1, to give the title compound as a yellow solid (0.80 g, 2.0 mmol, 65%). δH (CDCl$_3$, 300K) 8.31 (1H, dd J 4.8 Hz 1.4 Hz), 7.65 (1H, d J 1.4 Hz), 7.64 (2H, s), 7.10 (2H, m), 2.52 (3H, s). m/z (ES$^+$, 70V) 396.9 (MH$^+$).

INTERMEDIATE 10

4-Bromo-2-fluoro-N-(1,3,5-trimethyl-1H-pyrazol-4-yl)-benzenesulfonamide

Prepared from 4-bromo-2-fluorobenzenesulfonyl chloride (0.75 g, 2.7 mmol) and 4-amino-1,3,5-trimethyl-1H-pyrazole (0.35 g, 2.8 mmol) in pyridine (4.5 ml) according to the method of intermediate 1, to give the title compound as an orange solid (0.59 g, 1.6 mmol, 60%). δH (D-6 DMSO, 300K) 9.60 (1H, s), 7.90 (1H, d J 9.4 Hz), 7.56 (1H, d J 8.2 Hz), 7.51 (1H, d J 7.7 Hz), 3.56 (3H, s), 1.89 (3H, s), 1.69 (3H, s). m/z (ES$^+$, 70V) 364.0 (MH$^+$).

INTERMEDIATE 11

4-(2-Chloro-pyridin-4-yl)-N-(1,3,5-trimethyl-1H-pyrazol-4-yl)-benzenesulfonamide Prototypical Procedure for Suzuki Coupling of a Boronic Ester or Boronic Acid with an Aryl Halide;

METHOD 1: A solution of the compound of intermediate 1 (1.5 g, 4.36 mmol), 2-chloropyridine-4-boronic acid (684 mg, 4.35 mmol), tribasic potassium phosphate (924 mg, 4.35 mmol) and Pd(dppf)Cl$_2$.DCM (100 mg, 0.12 mmol) and water (1.5 ml) in oxygen-free DMF (8 ml) was heated in a microwave at 130° C. for 1 h. The reaction was concentrated to dryness in vacuo, diluted with DCM (100 ml), washed with saturated aqueous sodium hydrogencarbonate solution (2×25 ml), dried (MgSO$_4$) and concentrated in vacuo to give a residual oil. Chromatography (SiO$_2$, EtOAc) gave the title compound as a fine white solid (1.13 g, 2.66 mmol, 61%). δH (D-6 DMSO, 300K) 8.52 (1H, d J 5.2 Hz 7.88 (2H, d J 8.4 Hz), 7.74 (2H, d J 8.4 Hz), 7.58 (1H, s), 7.46 (1H, dd J 1.5 Hz 5.2 Hz), 6.36 (1H, s), 3.71 (3H, s), 2.12 (3H, s), 1.62 (3H, s). m/z (ES$^+$, 70V) 377.1 (MH$^+$).

INTERMEDIATE 12 (DDD86209)

2,6-Dichloro-4-(2-chloro-pyridin-4-yl)-N-(1,3,5-trimethyl-1H-pyrazol-4-yl)-benzenesulfonamide Prepared from the sulphonamide of intermediate 2 (250 mg, 0.6 mmol), 2-chloropyridine-4-boronic acid (108 g, 0.67 mmol), tribasic potassium phosphate (145 mg, 0.68 mmol), Pd(dppf)Cl$_2$.DCM (20 mg, 0.024 mmol) and water (0.3 ml) in oxygen-free DMF (2.5 ml) at 110° C. for 1 h according to the method of intermediate 11, to give the title compound as a white solid (212 mg, 0.47 mmol, 79%). δH (CDCl$_3$, 300K) 8.38 (1H, dd J 0.5 Hz 5.2 Hz), 7.54 (2H, s), 7.37 (1H, dd J 1.6 Hz 5.2 Hz), 6.56 (1H, s), 3.65 (3H, s), 2.09 (3H, s), 1.69 (3H, s). m/z (ES$^+$, 70V) 447.0 (MH$^+$).

INTERMEDIATE 13

4-Bromomethyl-N-(1,3,5-trimethyl-1H-pyrazol-4-yl)-benzenesulfonamide

4-Bromomethylbenzene sulfonyl chloride (3.72 g, 13.8 mmol) was added portionwise to a solution of 4-amino-1, 3,5-trimethyl-1H-pyrazole (1.73 g, 13.8 mmol) and pyridine (1.5 ml) in DCM (100 ml) at rt. Concentration in vacuo gave a solid which was collected by vacuum filtration and washed with water (2×25 ml) then Et2O (100 ml) to give the title compound as a white solid (2.71 g, 7.59 mmol, 55%). δH (D-6 DMSO, 300K) 9.13 (1H, s), 7.64-7.55 (4H, m), 4.77 (2H, s), 3.55 (3H, s), 1.80 (3H, s), 1.54 (3H, s). m/z (ES$^+$, 70V) 358.1 (MH$^+$).

INTERMEDIATE 14

3'-Formyl-biphenyl-4-sulfonic acid (1,3,5-trimethyl-1H-pyrazol-4-yl)-amide

Prepared from the sulphonamide of intermediate 1 (1.54 g, 4.48 mmol), 3-formylphenylboronic acid (1.40 g, 10.0 mmol), tribasic potassium phosphate (1.98 g, 9.0 mmol), Pd(dppf)Cl$_2$.DCM (100 mg, 0.12 mmol) and water (2 ml) in oxygen-free DMF (12 ml) at 130° C. for 1 h according to the method of intermediate 11, to give the title compound as a white solid (1.61 g, 4.36 mmol, 97%). δH (D-6 DMSO, 300K) 10.13 (1H, s), 9.19 (1H, s), 8.29 (1H, t J 1.6 Hz), 8.12-8.09 (1H, m), 8.0-7.96 (3H, m), 7.77-7.73 (3H, m), 3.56 (3H, s), 1.84 (3H, s), 1.61 (3H, s). m/z (ES$^+$, 70V) 370.1 (MH$^+$).

INTERMEDIATE 15

3,5-Dichloro-3'-formyl-biphenyl-4-sulfonic acid (1,3,5-trimethyl-1H-pyrazol-4-yl)-amide Prepared from the sulphonamide of intermediate 2 (1.0 g, 2.43 mmol), 3-formylphenylboronic acid (440 mg, 2.91 mmol), tribasic potassium phosphate (620 mg, 2.91 mmol), Pd(dppf)Cl$_2$.DCM (100 mg, 0.12 mmol) and water (0.5 ml) in oxygen-free DMF (6.0 ml) at 130° C. for 1 h according to the method of intermediate 11, to give the title compound as a white solid (870 mg, 2.0 mmol, 82%). δH (D-6 DMSO, 300K) 10.12 (1H, s), 9.68 (1H, s), 8.42 (1H, s), 8.21 (1H, d J 7.9 Hz), 8.07 (2H, s), 8.01 (1H, d J 7.5 Hz), 7.74 (1H dd J 7.5 Hz 7.9 Hz), 3.58 (3H, s), 1.50 (3H, s), 1.75 (3H, s). m/z (ES$^+$, 70V) 439.2 (MH$^+$).

INTERMEDIATE 16

3,5-Dichloro-4'-formyl-biphenyl-4-sulfonic acid (1,3,5-trimethyl-1H-pyrazol-4-yl)-amide Prepared from the sulphonamide of intermediate 2 (1.0 g, 2.43 mmol), 4-formylphenylboronic acid (440 mg, 2.91 mmol), tribasic potassium phosphate (620 mg, 2.91 mmol), Pd(dppf)Cl$_2$.DCM (100 mg, 0.12 mmol) and water (0.5 ml) in oxygen-free DMF (6.0 ml) at 130° C. for 1 h according to the method of intermediate 11, to give the title compound as a white solid (791 mg, 1.83 mmol, 75%). δH (D-6 DMSO, 300K) 10.12 (1H, s), 9.68 (1H, s), 8.31 (2H, d 7.1 Hz), 8.07 (2H, s), 8.01 (2H, d J 7.1 Hz), 3.58 (3H, s), 1.50 (3H, s), 1.75 (3H, s). m/z (ES$^+$, 70V) 439.2 (MH$^+$).

INTERMEDIATE 17

2'-Formyl-biphenyl-4-sulfonic acid (1,3,5-trimethyl-1H-pyrazol-4-yl)-amide

Prepared from the sulphonamide of intermediate 1 (1.0 g, 2.91 mmol), 2-formylphenyl boronic acid (524 mg, 3.49 mmol), tribasic potassium phosphate (740 mg, 3.49 mmol), Pd(dppf)Cl$_2$.DCM (119 mg, 0.146 mmol) and water (2.0 ml) in oxygen-free DMF (10.0 ml) at 130 degC for 1 h according to the method of intermediate 10, to give the title compound as a white solid (700 mg, 1.90 mmol, 65%). δH (CDCl$_3$, 300K) 9.93 (1H, s), 8.05 (1H, d J 7.7 Hz), 7.85 (2 h, d J 8.5 Hz), 7.68 (1H, dt J 1.5 Hz 7.6 Hz), 7.58 (1H, t J 1.5 Hz), 7.50 (1H, d J 8.5 Hz), 7.39 (1H, d J 7.7 Hz), 3.69 (3H, s), 2.12 (3H, s), 1.66 (3H, s). m/z (ES$^+$, 70V) 370.1 (M+H$^+$)

INTERMEDIATE 18 (DDD87766)

4-Bromo-N-methyl-N-(1,3,5-trimethyl-1H-pyrazol-4-yl)-benzenesulfonamide

Prototypical Procedure for N-Alkylation of a Sulphonamide with an Alkyl Halide;

Sodium hydride (88 mg, 95% w/w, 3.48 mmol) was added portionwise to a solution of Intermediate 1 (1.0 g, 2.91 mmol) in DMF (10 ml) at 0° C. When effervescence had ceased, methyl iodide (217 µl, 3.48 mmol) was added dropwise and the reaction was allowed to warm to rt over 4 h. The reaction was concentrated to dryness in vacuo, diluted by addition of DCM (30 ml), washed with water (2×15 ml), dried (MgSO$_4$) and concentrated in vacuo. The residue was triturated from Et$_2$O and collected by vacuum filtration to give the title compound as a fine off-white solid (557 mg, 1.56, 54%). δH (D-6 DMSO, 300K) 9.67 (1H, s), 8.78 (1H, d J 5.7 Hz), 8.51 (1H, d J 8.6 Hz), 8.09 (1H, d J 5.8 Hz), 7.86 (1H, d J 5.6 Hz), 7.50 (1H, d J 5.7 Hz), 7.21 (2H, d J 8.4 Hz), 4.17 (2H, d J 8.4 Hz), 4.34 (1H, s), 4.18-4.14 (1H, m), 3.21 (1H, dd J 4.9 Hz 13.9 Hz) 2.98 (1H, dd J 9.3 Hz 13.9 Hz), 1.06 (3H, s), 0.99 (3H, s). m/z (ES$^+$, 70V) 404.1 (MH$^+$).

INTERMEDIATE 19 (DDD73490)

4-Bromo-2,6-dichloro-N-methyl-N-(1,3,5-trimethyl-1H-pyrazol-4-yl)-benzenesulfonamide Was prepared from the sulphonamide of intermediate 2 (5.0 g, 12.2 mmol), sodium hydride (95% w/w, 380 mg, 15.2 mmol) according to the method of intermediate 18 to give the title compound as a brown solid (4.56 g, 10.7 mmol, 88%). δH (CDCl$_3$, 300K) 7.60 (2H, s), 3.71 (3H, s), 3.40 (3H, s), 2.12 (3H, s), 1.84 (3H, s). m/z (ES$^+$, 70V) 427.9 (MH$^+$)

INTERMEDIATE 20

4-Bromo-2-methyl-N-(1,3,5-trimethyl-1H-pyrazol-4-yl)-benzenesulfonamide

Prepared from 4-bromo-2-methylbenzenesulfonyl chloride (0.736 g, 2.7 mmol) and 4-amino-1,3,5-trimethyl-1H-pyrazole (0.35 g, 2.8 mmol) in pyridine (4.5 ml) according to the method of intermediate 1, to give the title compound as an orange solid (906 m, 2.52 mmol, 93%). δH (D-6 DMSO, 300K) 9.24 (1H, s), 7.70 (1H, d, J 1.5 Hz), 7.54 (1H, dd, J 8.5 Hz 1.5 Hz), 7.48 (1H, d 8.5 Hz), 3.55 (3H, s), 2.57 (3H, s), 1.82 (3H, s), 1.59 (3H, s). m/z (ES$^+$, 70V) 360.0 (MH$^+$).

INTERMEDIATE 21 (DDD85593)

4-Bromo-2,6-dichloro-N-(3-hydroxy-propyl)-N-(1,3,5-trimethyl-1H-pyrazol-4-yl)-benzenesulfonamide Prepared from the sulphonamide of intermediate 2 (230 mg, 0.56 mmol), 3-bromopropanol (500 mg, 3.6 mmol) and caesium carbonate (325 mg, 1.0 mmol) in DMF (1.5 ml) according to the method of intermediate 18, to give the title compound as a tan solid (211 mg, 0.45 mmol, 80%). δH (CDCl$_3$, 300K) 7.58 (2H, s), 4.17-4.11 (2H, m), 3.86-3.75 (2H, m), 3.68 (3H, s), 2.09 (3H, s), 1.79 (3H, s), 1.76-1.69 (2H, m). m/z (ES$^+$, 70V) 472.1 (MH$^+$).

INTERMEDIATE 22

3'-Formyl-biphenyl-4-sulfonic acid methyl-(1,3,5-trimethyl-1H-pyrazol-4-yl)-amide Prepared from Intermediate 18 (285 mg, 0.8 mmol), 3-formylphenylboronic acid (143 mg, 1.0 mmol), tribasic potassium phosphate (169 mg, 0.8 mmol), Pd(dppf)Cl$_2$.DCM (33 mg, 0.04 mmol) and water (0.5 ml) in oxygen-free DMF (2 ml) at 130° C. for 1 h, according to the method of intermediate 11, to give the title compound as a white solid (170 mg, 0.4 mmol, 56%). δH (CDCl$_3$, 300K) 10.12 (1H, s), 8.13 (1H, s), 7.94 (1H, d J 7.2 Hz), 7.88 (1H, d J 6.6 Hz), 7.83 (2H, d J 7.7 Hz), 7.76 (2H, d J 6.7 Hz), 7.65-7.70 (1H, m), 3.70 (3H, s), 3.22 (3H, s), 2.13 (3H, s), 1.59 (3H, s). m/z (ES$^+$, 70V) 384.0 (MH$^+$).

INTERMEDIATE 23A (DDD88198)

4-Bromo-2,6-dichloro-N-(3-isobutyl-1,5-dimethyl-1H-pyrazol-4-yl)-benzenesulfonamide Prepared from 4-bromo-2,6-dichlorobenzenesulfonyl chloride (0.68 g, 2.1 mmol) and 4-amino-1,5-dimethyl-3-isobutyl-1H-pyrazole (0.35 g, 2.1 mmol) in pyridine (5 ml) according to the method of intermediate 1, to give the title compound as a white solid (120 mg, 0.26 mmol, 12%). δH (D-6 DMSO, 300K) 7.65 (2H, s), 6.54 (1H, s), 3.70 (3H, s), 2.17 (3H, s), 1.96 (2H, d J 7.9 Hz), 1.74 (1H, m), 0.78 (6H, d J 6.6 Hz). m/z (ES$^+$, 70V) 456.0 (MH$^+$).

INTERMEDIATE 23B (DDD88197)

4-Bromo-2,6-dichloro-N-(5-isobutyl-1,3-dimethyl-1H-pyrazol-4-yl)-benzenesulfonamide Prepared from 4-bromo-2,6-dichlorobenzenesulfonyl chloride (0.35 g, 1.1 mmol) and 4-amino-1,3-dimethyl-5-isobutyl-1H-pyrazole (0.18 g, 1.1 mmol) in pyridine (4 ml) according to the method of intermediate 1, to give the title compound as an orange solid (118 mg, 0.26 mmol, 24%). δH (D-6 DMSO, 300K) 7.67 (2H, s), 6.69 (1H, s), 3.71 (3H, s), 2.45 (2H, d J 7.8 Hz), 1.90 (1H, m), 1.84 (3H, s), 0.91 (6H, d J 6.8 Hz). m/z (ES$^+$, 70V) 456.0 (MH$^+$).

INTERMEDIATE 24

5'-Formyl-3'-propoxy-biphenyl-4-sulfonic acid (1,3,5-trimethyl-1H-pyrazol-4-yl)-amide Prepared from the sulphonamide of intermediate 1 (1.0 g, 2.91 mmol), 3-formyl-5 propoxyphenyl boronic acid (726 mg, 3.49 mmol), tribasic potassium phosphate (740 mg, 3.49 mmol), Pd(dppf)Cl$_2$.DCM (119 mg, 0.146 mmol) and water (2.0 ml) in oxygen-free DMF (10.0 ml) at 130° C. for 1 h according to the method of intermediate 10, to give the title compound as a colourless solid (424 mg, 0.99 mmol, 34%). δH (CDCl$_3$, 300K) 10.04 (1H, s), 7.82 (2H, d J 8.5 Hz), 7.67 (2H, d J 8.5 Hz), 7.67 (1H, t J 1.4 Hz), 7.43 (1H, s br), 7.39 (1H, t J 2.4 Hz), 5.81 (1H, s), 4.05 (2H, t J 6.6 Hz), 3.69 (3H, s), 2.10 (3H, s), 1.87 (2H, h), 1.61 (3H, s), 1.08 (3H, t J 7.5 Hz). m/z (ES$^+$, 70V) 428.1 (M+H$^+$).

INTERMEDIATE 25

5'-Formyl-3'-isopropoxy-biphenyl-4-sulfonic acid (1,3,5-trimethyl-1H-pyrazol-4-yl)-amide Prepared from the sulphonamide of intermediate 1 (1.0 g, 2.91 mmol), 3-formyl-5 isopropoxyphenyl boronic acid (726 mg, 3.49 mmol), tribasic potassium phosphate (740 mg, 3.49 mmol), Pd(dppf)Cl$_2$.DCM (119 mg, 0.146 mmol) and water (2.0 ml) in oxygen-free DMF (10.0 ml) at 130° C. for 1 h according to the method of intermediate 10, to give the title compound as a white solid (469 mg, 1.10 mmol, 38%). δH (CDCl$_3$, 300K) 10.04 (1H, s), 7.82 (2H, d J 8.4 Hz), 7.71 (2H, d J 8.3 Hz), 7.65 (1H, s br), 7.41 (1H, s br), 7.37 (1H, t J 2.1 Hz), 5.88 (1H, s), 4.71 (1H, d J 6.1 Hz), 3.69 (3H, s), 2.10 (3H, s), 1.61 (3H, s), 1.40 (6H, d J 6.1 Hz). m/z (ES$^+$, 70V) 428.2 (M+H$^+$).

INTERMEDIATE 26

4-Bromo-N-(1,5-dimethyl-1H-pyrazol-4-yl)-benzenesulfonamide

Prepared from 4-bromobenzenesulfonyl chloride (0.396 g, 1.55 mmol) and 4-amino-1,5-dimethyl-1H-pyrazole (0.172 g, 1.55 mmol) in pyridine (3 ml) according to the method of intermediate 1, to give the title compound as a yellow solid (0.362 g, 1.10 mmol, 71%). δH (D-6 DMSO, 300K) 9.43 (1H, s), 7.80 (2H, d J 8.7 Hz), 7.58 (2H, d J 8.7 Hz), 3.63 (3H, s), 1.89 (3H, s). m/z (ES$^+$, 70V) 332.0 (MH$^+$).

INTERMEDIATE 27

4-Bromo-2,6-dichloro-N-(1,5-dimethyl-1H-pyrazol-4-yl)-benzenesulfonamide

Prepared from 4-bromo-2,6-dichlorobenzenesulfonyl chloride (500 mg, 1.54 mmol) and 4-amino-1,5-dimethyl-1H-pyrazole (172 mg, 1.55 mmol) in pyridine (3 ml) according to the method of intermediate 1, to give the title compound as a cream solid (392 mg, 0.99 mmol, 64%). δH (D-6 DMSO, 300K) 9.91 (1H, s), 7.97 (2H, s), 3.64 (3H, s), 2.04 (3H, s). m/z (ES$^+$, 70V) 399.9 (MH$^+$).

INTERMEDIATE 28

4-Bromo-N-(1,3-dimethyl-1H-pyrazol-4-yl)-benzenesulfonamide

Prepared from 4-bromobenzenesulfonyl chloride (396 mg, 1.55 mmol) and 4-amino-1,3-dimethyl-1H-pyrazole (228 mg, 1.55 mmol) in pyridine (3 ml) according to the method of intermediate 1, to give the title compound as a white solid (469 mg, 1.42 mmol, 92%). δH (D-6 DMSO, 300K) 9.44 (1H, s), 7.79 (2H, d J 8.7 Hz), 7.57 (2H, d J 8.7 Hz), 7.39 (1H, s), 3.65 (3H, s), 1.70 (3H, s). m/z (ES$^+$, 70V) 332.0 (MH$^+$).

INTERMEDIATE 29

4-Bromo-2,6-dichloro-N-(1,3-dimethyl-1H-pyrazol-4-yl)-benzenesulfonamide

Prepared from 4-bromo-2,6-dichlorobenzenesulfonyl chloride (500 mg, 1.54 mmol) and 4-amino-1,3-dimethyl-1H-pyrazole (228 mg, 1.55 mmol) in pyridine (3 ml) according to the method of intermediate 1, to give the title compound as a pale pink solid (501 mg, 1.26 mmol, 82%). δH (CDCl$_3$, 300K) 7.65 (2H, s), 7.31 (1H, s), 6.77 (1H, s), 3.78 (3H, s), 2.04 (3H, s). m/z (ES$^+$, 70V) 399.9 (MH$^+$).

INTERMEDIATE 30

4-Bromo-N-(1-methyl-1H-pyrazol-4-yl)-benzenesulfonamide

Prepared from 4-bromobenzenesulfonyl chloride (m396 g, 1.55 mmol) and 4-amino-1-methyl-1H-pyrazole (206 mg, 1.54 mmol) in pyridine (3 ml) according to the method of intermediate 1, to give the title compound as a white solid (424 mg, 1.34 mmol, 87%). δH (D-6 DMSO, 300K) 9.80 (1H, s), 7.79 (2H, d J 8.7 Hz), 7.61 (2H, d J 8.7 Hz), 7.48 (1H, s), 7.05 (1H, s), 3.71 (3H, s). m/z (ES$^+$, 70V) 318.0 (MH$^+$).

INTERMEDIATE 31

4-Bromo-2,6-dichloro-N-(1-methyl-1H-pyrazol-4-yl)-benzenesulfonamide

Prepared from 4-bromo-2,6-dichlorobenzenesulfonyl chloride (500 mg, 1.54 mmol) and 4-amino-1-methyl-1H-pyrazole (206 mg, 1.54 mmol) in pyridine (3 ml) according to the method of intermediate 1, to give the title compound as a white solid (496 mg, 1.29 mmol, 84%). δH (D-6 DMSO, 300K) 7.64 (2H, s), 7.45 (1H, s), 7.18 (1H, s), 7.01 (1H, s), 3.85 (3H, s). m/z (ES$^+$, 70V) 385.9 (MH$^+$).

INTERMEDIATE 32

4-(4,4,5,5-Tetramethyl-[1,3,2]dioxaborolan-2-yl)-N-(1,3,5-trimethyl-1H-pyrazol-4-yl)-benzenesulfonamide Prototypical Procedure for Conversion of an Aryl Halide to an Aryl Boronic Ester;

The sulphonamide of intermediate 1 (2.22 g, 7.5 mmol), bis-pinacolatodiboron (2.27 g, 8.97 mmol), potassium acetate (880 mg, 15.0 mmol) and Pd(dppf)Cl$_2$.DCM (110 mg) in oxygen-free dioxane (10 ml) was heated to 120° C. for 1 h in a microwave. Concentration in vacuo, dilution with DCM (100 ml), washing with water (2×20 ml), drying (MgSO$_4$) and concentration in vacuo gave a residue which was triturated with Et$_2$O and collected by vacuum filtration to give the title compound as a pale red solid (1.97 g, 5.04 mmol, 67%). δH (D-6 DMSO, 300K) 9.18 (1H, s), 7.86 (2H, d J 7.7 Hz), 7.68 (2H, d J 7.7 Hz), 3.59 (3H, s), 1.82 (3H, s), 1.68 (3H, s), 1.36 (12H, s). m/z (ES$^+$, 70V) 392.1 (MH$^+$).

INTERMEDIATE 33

N-(2-Methyl-pyridin-3-yl)-4-(4,4,5,5-tetramethyl-[1,3,2]dioxaborolan-2-yl)-benzenesulfonamide Prepared from the sulphonamide of intermediate 1 (720 mg, 2.91 mmol), bis-pinacolatodiboron (880 mg, 3.49 mmol), potassium acetate (342 mg) and Pd(dppf)Cl$_2$.DCM (50 mg) in oxygen-free dioxane (4 ml) at 120° C. for 1 h according to the method of intermediate 32, to give the title compound as a tan coloured solid (497 mg, 1.33 mmol, 46%). δH (D-6 DMSO, 300K) 10.03 (1H, s), 8.30 (1H, d J 4.4 Hz), 7.86 (2H, d J 8.0 Hz), 7.71 (2H, d J 8.0 Hz), 7.40 (1H, d J 8.0 Hz), 7.20 (1H, dd J 4.4 Hz 8.0 Hz), 2.18 (3H, s), 1.35 (12H, s).

INTERMEDIATE 34

N-(3,5-Dimethyl-isoxazol-4-yl)-4-(4,4,5,5-tetramethyl-[1,3,2]dioxaborolan-2-yl)-benzenesulfonamide Prepared from the sulphonamide of intermediate 6 (1.01 g, 3.06 mmol) and bis-pinacolatodiboron (851 mg, 3.35 mmol), potassium acetate (881 mg) and Pd(dppf)Cl$_2$.DCM (72 mg) in oxygen-free dioxane (15 ml) at 120° C. for 2 h according to the method of intermediate 32, to give the title compound as a tan coloured solid (661 mg, 1.75 mmol, 57%). $\delta$H (CDCl$_3$, 300K) 7.93 (2H, d J 8.3 Hz), 7.75 (2H, d J 8.3 Hz), 5.86 (1H, s), 2.06 (3H, s), 1.86 (3H, s), 1.38 (12H, s). m/z (ES$^+$, 70V) 379.1 (MH$^+$).

INTERMEDIATE 35

2,6-Dichloro-4-(4,4,5,5-tetramethyl-[1,3,2]dioxaborolan-2-yl)-N-(1,3,5-trimethyl-1H-pyrazol-4-yl)-benzenesulfonamide Prepared from the sulphonamide of intermediate 2 (1.0 g, 2.42 mmol) and bis-pinacolatodiboron (700 mg, 2.76 mmol), potassium acetate (750 mg) and Pd(dppf)Cl$_2$.DCM (60 mg) in oxygen-free dioxane (12 ml) at 120° C. for 2 h according to the method of intermediate 32, to give the title compound as an orange-brown solid (1.0 g, 2.17 mmol, 90%). $\delta$H (CDCl$_3$, 300K) 7.83 (2H, s), 6.70 (1H, s), 3.70 (3H, s), 2.14 (3H, s), 1.79 (3H, s), 1.35 (12H, s). m/z (ES$^+$, 70V) 378.0 ([M minus pinacol]H$^+$).

INTERMEDIATE 36

4-[3-(Tetrahydro-pyran-2-yloxy)-prop-1-ynyl]-N-(1,3,5-trimethyl-1H-pyrazol-4-yl)-benzenesulfonamide Prototypical Procedure for Sonogashira Coupling of an Aryl Halide to an Alkyne;

The sulphonamide of intermediate 1 (1.95 g, 6.76 mmol), tetrahydro-2-(2-propynyloxy)-2H-pyran (3.5 ml, 25.0 mmol), CuI (25 mg, 0.13 mmol) and Pd(PPh$_3$)$_4$ (100 mg, 0.08 mmol), in DMF (15 ml) and NEt$_3$ (10 ml) under argon, was heated at 110° C. for 1 h. The reaction was concentrated in vacuo, diluted with DCM (100 ml), washed with brine (2×25 ml), dried (MgSO4) and concentrated in vacuo to give a crude oil. Chromatography (SiO$_2$, EtOAc) gave the title compound as a white solid (1.95 g, 4.83 mmol, 71%). (D-6 DMSO, 300K) 9.71 (1H, s), 8.15 (2H, d J 8.3 Hz), 7.91 (2H, d J 8.3 Hz), 4.88 (1H, s), 4.58 (1H, d J 16.5 Hz), 4.49 (1H, d J 16.5 Hz), 3.85-3.75 (1H, m), 3.61 (3H, s), 3.57-3.51 (1H, m), 1.95 (3H, s), 1.78-1.67 (2H, m), 1.75 (3H, s), 1.61-1.45 (4H, m br).

INTERMEDIATE 37

4-(3-Hydroxy-propyl)-N-(1,3,5-trimethyl-1H-pyrazol-4-yl)-benzenesulfonamide

The sulphonamide of intermediate 36 (2.0 g, 4.96 mmol) and palladium on charcoal (500 mg, 10% w/w) in methanol (40 ml) under hydrogen was stirred at rt for 24 h. The reaction was filtered through celite and the resulting clear solution was treated with 2M HCl in THF (5 ml) and stirred for a further 3 h. Concentration in vacuo and purification by chromatography (SiO$_2$, EtOAc:MeOH 5:1) gave the title compound as a white powder (1.29 g, 3.99 mmol, 87%). $\delta$H (D-6 DMSO, 300K) 8.99 (1H, s), 7.52 (2H, d J 8.3 Hz), 7.38 (2H, d J 8.3 Hz), 4.55 (1H, s br), 3.55 (3H, s), 3.39 (2H, t J 6.4 Hz), 2.69 (2H, m), 1.80 (3H, s), 1.72 (2H, p J 6.4 Hz), 1.53 (3H, s). m/z (ES$^+$, 70V) 324.1 (MH$^+$).

INTERMEDIATE 38

2,6-Dichloro-4-[3-(tetrahydro-pyran-2-yloxy)-prop-1-ynyl]-N-(1,3,5-trimethyl-1H-pyrazol-4-yl)-benzenesulfonamide Prepared from the sulphonamide of intermediate 2 (3.4 g, 8.23 mmol), tetrahydro-2-(2-propynyloxy)-2H-pyran (3.5 ml, 25.0 mmol), CuI (50 mg, 0.26 mmol) and Pd(PPh$_3$)$_4$ (250 mg, 0.2 mmol), in DMF (25 ml) and NEt$_3$ (10 ml) according to the method of intermediate 35, to give the title compound as a white solid (2.81 g, 5.97 mmol, 73%). $\delta$H (D-6 DMSO, 300K) 9.71 (1H, s), 7.79 (2H, s), 4.88 (1H, s), 4.58 (1H, d J 16.5 Hz), 4.49 (1H, d J 16.5 Hz), 3.85-3.75 (1H, m), 3.61 (3H, s), 3.57-3.51 (1H, m), 1.95 (3H, s), 1.78-1.67 (2H, m), 1.75 (3H, s), 1.61-1.45 (4H, m br).

INTERMEDIATE 39

4-Piperidin-3-yl-piperazine-1-carboxylic acid tert-butyl ester

1-Benzyl-3-piperidone hydrochloride (700 mg, 2.7 mmol), triethylamine (270 mg, 2.7 mmol) and 1-(tert-butoxycarbonyl)-piperizine (500 mg, 2.7 mmol) in DCM, was stirred at rt for 1 h, then heated to 50° C. for 40 min. Sodium triacetoxyborohydride (1.12 g, 5.3 mmol) was added and the reaction mixture allowed to cool, with stirring, over 12 h then concentrated to dryness in vacuo. The residue was partioned between DCM/water, the organics dried (MgSO4) and concentrated to dryness in vacuo. The resulting residue in EtOH (10 ml) was hydrogenated with 10% w/w palladium on carbon (200 mg) under hydrogen at rt for 18 h. The reaction was filtered through celite and concentrated to dryness in vacuo to give 3-piperazine-1-yl-piperidine as a pale yellow gum (700 mg, 2.6 mmol, 97%). $\delta$H (CDCl$_3$, 300K) 3.43-3.37 (4H, m br), 3.21 (1H, d br, J 11.6 Hz), 3.01 (1H, d br, J 12.2 Hz) 2.59-2.47 (6H, m br), 2.45-2.38 (1H, m), 1.99-1.92 (1H, m br), 1.82-1.75 (1H, m), 1.58-1.48 (1H, m), 1.45 (9H, s), 1.42-1.33 (1H, m). m/z (ES$^+$, 70V) 270.3 (MH$^+$).

INTERMEDIATE 40 (DDD100805)

4-bromo-2,6-dichloro-N-(difluoromethyl)-N-(1,3,5-trimethyl-1H-pyrazol-4-yl)benzenesulfonamide A well-stirred slurry containing the compound of intermediate 2 (3.0 g, 7.2 mmol), potassium carbonate (3.0 g, 21 mmol) and sodium chlorodifluoroacetate (3.3 g, 21 mmol) in acetonitrile (100 ml) was heated to 60° C. for 48 h. The resulting slurry was then concentrated in vacuo, diluted with DCM (100 ml) and water (100 ml), the organic phase separated, dried (MgSO$_4$) and concentrated in vacuo. Trituration of the residue with diethyl ether gave a precipitate which was collected by vacuum filtration and dried to give the title compound as a fine white powder (2.05 g, 4.43 mmol, 62%). $\delta$H (CDCl$_3$, 300K) 7.61 (2H, s), 7.34 (1H, dd J 59.4 Hz 61.2 Hz), 3.67 (3H, s), 2.01 (3H, s), 1.71 (3H, s). m/z (ES+, 70V) 464.1 (MH+).

INTERMEDIATE 41

4-Bromo-N-(3-isobutyl-1,5-dimethyl-1H-pyrazol-4-yl)-benzenesulfonamide

Prepared from 4-bromobenzenesulfonyl chloride (8.41 g, 32.9 mmol) and the amine of intermediate 46 (5.23 g, 31.3 mmol) in pyridine (80 ml) according to the method of intermediate 1, to give the title compound as a pale yellow solid (9.57 g, 24.8 mmol, 79%). δH (CDCl$_3$, 300K) 7.61 (4H, m), 5.74 (1H, bs), 3.69 (3H, s), 2.07 (3H, s), 1.78 (2H, d J 7.0 Hz), 1.69 (1H, m), 0.75 (6H, d J 6.5 Hz). m/z (ES+, 70V) 386.1 (MH+).

INTERMEDIATE 42

4-(4,4,5,5-Tetramethyl-[1,3,2]dioxaborolan-2-yl)-N-(3-isobutyl-1,5-dimethyl-1H-pyrazol-4-yl)-benzenesulfonamide Prepared from the sulphonamide of intermediate 41 (1.00 g, 2.59 mmol) and bis-pinacolatodiboron (780 mg, 3.07 mmol), potassium acetate (5601 mg, 5.70 mmol) and Pd(dppf)Cl$_2$.DCM (80 mg) in oxygen-free dioxane (8 ml) at 120° C. for 40 min according to the method of intermediate 32, to give the title compound as a grey coloured solid (919 mg, 2.12 mmol, 82%). δH (D-6 DMSO, 300K) 323K, 50° C. 8.97 (1H, s), 7.82 (2H, d, J 8.2 Hz), 7.67 (2H, d J 8.2 Hz), 3.56 (3H, s), 1.90 (2H, d J 7.1 Hz), 1.75 (3H, s), 1.72 (1H, m), 1.32 (12H, s), 0.72 (6H, d J 6.6 Hz). m/z (ES+, 70V) 434.2 (MH+).

INTERMEDIATE 43

1,5-Dimethyl-3-(2-methylprop-1-enyl)-1H-pyrazole

A suspension of isopropyltriphenylphosphonium iodide (5.23 g, 12.1 mmol) in THF (35 ml) at −20° C. was treated dropwise with a 1.6 M solution of butyllithium in hexanes (7.5 ml, 12 mmol). The mixture was stirred at −20° C. for 45 minutes before a solution of 1,5-dimethyl-1H-pyrazole-3-carboxaldehyde (1.20 g, 9.68 mmol) in THF (50 ml) was added. The thick suspension was allowed to warm to room temperature and stirred for 24 hours. The reaction mixture was treated with saturated aqueous ammonium chloride (150 ml) and the phases separated. The aqueous phase was back-extracted with ethyl acetate (3×50 ml) and the combined organic phases were dried (Na$_2$SO$_4$) and concentrated. The residue was extracted with petroleum ether (2×100 ml) and the combined extracts were concentrated to afford a yellow oil which was purified by chromatography (SiO$_2$, 0-100% EtOAc-petroleum ether) to give the title compound as a colourless solid (1.56 g, 9.68 mmol). δH (CDCl$_3$, 300K) 6.15 (1H, m), 6.01 (1H, s), 3.75 (3H, s), 2.26 (3H, s), 1.96 (3H, d J 0.8 Hz), 1.89 (3H, d J 1.2 Hz). m/z (ES+, 70V) 151.1 (MH+).

INTERMEDIATE 44

3-Isobutyl-1,5-dimethyl-1H-pyrazole

A solution of the compound of intermediate 43 (1.56 g, 9.68 mmol) in methanol (50 ml) was purged with argon and treated with 10% palladium on carbon (0.291 g). The reaction vessel was purged with hydrogen and stirred at room temperature overnight. The reaction vessel was purged with argon and further 10% palladium on carbon (0.498 g) was added. The mixture stirred under hydrogen for a further 24 hours, then filtered through celite and concentrated. The residue was resuspended in petroleum ether 40-60 (100 ml), filtered and concentrated. The resulting residue was again suspended in petroleum ether (50 ml), re-filtered and concentrated to give the title compound (1.064 g, 6.99 mmol, 72%) as a pale yellow oil. δH (CDCl$_3$, 300K) 5.78 (3H, s), 3.71 (3H, s), 2.40 (2H, d J 7.1 Hz), 2.22 (31-1, s), 1.87 (1H, m), 0.92 (6H, d J 6.6 Hz). m/z (ES+, 70V) 153.1 (MH+).

INTERMEDIATE 45

3-Isobutyl-1,5-dimethyl-4-nitro-1H-pyrazole

The compound of intermediate 44 (1.049 g, 6.89 mmol) at 0° C. was treated with concentrated sulphuric acid (3.5 ml, 66 mmol). Nitric acid (90%, 2.8 ml, 67 mmol) was added dropwise at the same temperature. The cooling bath was removed and the mixture heated at 100° C. for 2 h. The mixture was then cooled, poured onto ice (150 ml), basified with aqueous sodium hydroxide (2M, 100 ml) and extracted with diethyl ether (3×100 ml). The combined organic extracts were washed with brine, dried (Na$_2$SO$_4$) and concentrated to give the title compound as a yellow oil (1.082 g, 5.49 mmol, 80%). δH (CDCl$_3$, 300K) 3.79 (3H, s), 2.77 (2H, d J 7.1 Hz), 2.60 (3H, s), 2.04 (1H, m), 0.94 (6H, d J 6.7 Hz). m/z (ES+, 70V) 198.1 (MH+).

INTERMEDIATE 46

3-Isobutyl-1,5-dimethyl-1H-pyrazol-4-amine

The compound of intermediate 45 (1.072 g, 5.44 mmol) in methanol (25 ml) under argon was treated with 10% palladium on carbon (0.174 g). The reaction vessel was purged with hydrogen and stirred at room temperature for 23 hours. The reaction mixture was filtered through a plug of celite and concentrated. The residue was dissolved in dichloromethane, re-filtered and concentrated to give the title compound as a red oil (0.886 g, 5.30 mmol, 97%). δH (CDCl$_3$, 300K) 3.67 (3H, s), 2.48 (2H, br.s), 2.39 (2H, d J 7.2 Hz), 2.13 (3H, s), 1.92 (1H, m), 0.94 (6H, d J 6.7 Hz). m/z (ES+, 70V) 168.2 (MH+).

INTERMEDIATE 47

4-bromo-2,6-dichloro-N-(2,2,2-trifluoroethyl)-N-(1,3,5-trimethyl-1H-pyrazol-4-yl)benzenesulfonamide The compound of intermediate 2 (200 mg, 0.48 mmol) and K$_2$CO$_3$ (127 mg, 0.96 mmol) in acetonitrile (2.0 mL) was, treated dropwise with 2,2,2-trifluoroethyl methanesulphonate (0.139 mL, 223 mg, 0.139 mmol) and the mixture heated in a microwave at 100° C. for 30 min. The mixture was then diluted with ethyl acetate (30.0 mL) and the organic layer washed with water (2×10 mL), brine (10 mL), dried over MgSO$_4$ and concentrated in vacuo. The crude material was purified by column chromatography (SiO$_2$, 6:4 Hexanes:EtOAc) to give the title compound as a colourless solid (217 mg, 0.44 mmol, 91%). δH (CDCl$_3$, 300K) 7.58 (2H, s), 4.82-4.68 (1H, m), 3.97-3.68 (1H, m), 3.68 (3H, s), 2.17 (3H, s), 1.68 (3H, s). m/z (ES+, 70V) 496.2 (M+H+).

EXAMPLE DDD73498

6-(8-Amino-3,4-dihydro-1H-isoquinolin-2-yl)-pyridine-3-sulfonic acid (1,3,5-trimethyl-1H-pyrazol-4-yl)-amide Prepared from the sulphonamide of intermediate 5 (1.33 gmg, 4.43 mmol) and 5-amino-1,2,3,4-tetrahydroisoquinoline (1.31 g, 8.8 mmol) in ethanol (0.75 ml), according to the method of example DDD86213, to give the title compound as a white powder (1.21 g, 2.94 mmol, 66%). $\delta$H (CDCl$_3$, 300K) 8.41 (1H, d J 2.5 Hz), 7.64 (1H, dd J 2.5 Hz 9.1 Hz), 7.36 (1H, s), 7.03 (1H, t J 7.8 Hz), 6.69 (2H, t J 7.8 Hz), 6.58 (1H, d J 9.1 Hz), 4.70 (2H, s), 3.95 (2H, t J 6.0 Hz), 3.62 (3H, s), 2.72 (2H, t J 6.0 Hz), 2.01 (3H, s), 1.74 (3H, s). m/z (ES$^+$, 70V) 413.2 (MH$^+$).

EXAMPLE DDD85602

6-[2-(4-Methyl-piperazin-1-yl)-ethylamino]-pyridine-3-sulfonic acid (1,3,5-trimethyl-1H-pyrazol-4-yl)-amide Prepared from the sulphonamide of intermediate 5 (225 mg, 0.75 mmol) and 4-(2-aminoethyl)-methylpiperazine (0.5 ml) in ethanol (0.75 ml), according to the method of example DDD86213, to give the title compound as a white powder (198 mg, 0.49 mmol, 65%). $\delta$H (D-6 DMSO, 300K) 8.77 (1H, s), 8.07 (1H, d J 2.4 Hz), 7.45 (1H, dd J 2.2 Hz 8.9 Hz), 7.28 (1H, s br), 6.54 (1H, d J 8.9 Hz), 3.57 (3H, s), 3.44-3.39 (2H, m), 2.41 (2H, t J 6.1 Hz), 2.41 (4H, s br), 2.36-2.31 (4H and 3H, s br), 2.16 (3H, s), 1.89 (3H, s), 1.67 (3H, s). m/z (ES$^+$, 70V) 408.2 (MH$^+$).

EXAMPLE DDD85646

2,6-Dichloro-4-(2-piperazin-1-yl-pyridin-4-yl)-N-(1,3,5-trimethyl-1H-pyrazol-4-yl)-benzenesulfonamide Prepared from the sulphonamide of intermediate 2 (250 mg, 0.61 mmol), 2-(1-piperazinyl)pyridine-4-boronic acid pinacol ester (211 mg, 0.73 mmol), tribasic potassium phosphate (155 mg, 0.73 mmol), and Pd(dppf)Cl$_2$.DCM (30 mg, 0.36 mmol) in DMF (2.5 ml) and water (0.50 ml), according to the method of intermediate 11, to give the title compound as an off-white powder (150 mg, 0.30 mmol, 50%). $\delta$H (D-6 DMSO, 300K) 9.79 (1H, s), 8.25 (1H, d J 5.9 Hz), 8.20 (2H, s), 7.61 (1H, s), 7.40 (1H, d J 5.9 Hz), 4.08 (4H, s br), 3.63 (3H, s), 3.28 (4H, s br), 2.00 (3H, s), 1.77 (3H, s). m/z (ES$^+$, 70V) 496.1 (MH$^+$).

EXAMPLE DDD86206

2-Chloro-4-(2-piperazin-1-yl-pyridin-4-yl)-N-(1,3,5-trimethyl-1H-pyrazol-4-yl)-benzenesulfonamide Prepared from the sulphonamide of intermediate 3 (500 mg, 1.3 mmol), 2-(1-piperazinyl)pyridine-4-boronic acid pinacol ester (580 mg, 2.0 mmol), tribasic potassium phosphate (427 mg, 2.0 mmol), and Pd(dppf)Cl$_2$.DCM (50 mg, 0.06 mmol) in DMF (3.0 ml) and water (0.75 ml), according to the method of intermediate 11, to give the title compound as an off-white powder (412 mg, 0.89 mmol, 68%). $\delta$H (D-6 DMSO, 300K) 8.20 (1H, d J 5.2 Hz), 8.14 (1H, d J 1.7 Hz), 7.84 (1H, dd J 1.75 Hz 8.3 Hz), 7.79 (1H, d J 8.3 Hz), 7.13 (1H, s), 6.99 (1H, dd J 1.15 Hz 5.2 Hz), 3.55 (3H, s), 3.51 (4H, s br), 2.79 (4H, s br), 1.90 (3H, s), 1.69 (3H, s). m/z (ES$^+$, 70V) 461.2 (MH$^+$).

EXAMPLE DDD86211

2,6-Dichloro-4-[2-(4-methyl-piperazin-1-yl)-pyridin-4-yl]-N-(1,3,5-trimethyl-1H-pyrazol-4-yl)-benzenesulfonamide Prepared by heating the chloropyridine of intermediate 12 (90 mg, 0.2 mmol) with N-methylpiperazine (100 µl) in EtOH (1.5 ml) at 150° C. for 1 h according to the method of DDD86213 to give the title compound as an off-white powder (45 mg, 0.08 mmol, 40%). $\delta$H (CDCl$_3$, 300K) 8.54 (1H, d J 5.1 Hz), 7.57 (1H, d J 1.8 Hz), 7.53 (1H, d J 0.95 Hz), 7.46 (1H, s), 7.42 (1H, dd J 1.6 Hz 5.1 Hz), 3.69 (3H, s), 3.29 (4H, s br), 2.66 (3H, s), 2.42 (4H, s br), 2.17 (3H, s), 1.80 (3H, s). m/z (ES$^+$, 70V) 509.1 (MH$^+$).

EXAMPLE DDD86212

3'-(4-Methyl-piperazin-1-ylmethyl)-biphenyl-4-sulfonic acid (1,3,6-trimethyl-1H-pyrazol-4-yl)-amide Prototypical Procedure for the Reductive Amination of an Aldehyde with an Alkylamine;

The aldehyde of intermediate 14 (200 mg, 0.54 mmol), N-methylpiperazine (100 mg, 1.0 mmol) and sodium triacetoxyborohydride (400 mg, 1.90 mmol) in CHCl$_3$ (15 ml) was heated at 50° C. for 24 h. Dilution with DCM (25 ml), washing with water (2×10 ml), drying (MgSO$_4$) and concentration in vacuo gave a gum which was subjected to chromatography (SiO$_2$, 50:10:1 EtOAc:MeOH:saturated aqueous ammonia solution) to give the title compound as a white powder (217 mg, 0.48 mmol, 89%). $\delta$H (D-6 DMSO, 300K) 9.20 (1H, s), 8.11 (1H, s br), 7.96 (2H, d J 8.4 Hz), 7.83 (1H, d J 6.95 Hz), 7.71 (2H, d J 8.4 Hz), 7.67 (1H, s br), 7.59 (1H, t J 7.6 Hz), 3.63 (2H, s), 3.57 (3H, s), 3.44 (4H, s br), 2.81 (4H, s br), 1.85 (3H, s), 1.58 (3H, s). m/z (ES$^+$, 70V) 453.1 (MH$^+$).

EXAMPLE DDD86213

4-(2-Piperazin-1-yl-pyridin-4-yl)-N-(1,3,6-trimethyl-1H-pyrazol-4-yl)-benzenesulfonamide Prototypical Procedure for Preparation of a 2-Aminopyridine by Displacement Reaction of a 2-Chloropyridine with an Alkylamine;

METHOD 1: The compound of intermediate 11 (250 mg, 0.66 mmol) and piperazine (500 mg, 5.8 mmol) in EtOH (0.75 ml) was heated at 155° C. for 2 h by microwave in a sealed vessel. Dilution with DCM (25 ml), washing with aqueous sodium hydrogencarbonate solution (2×5 ml), drying (MgSO$_4$) and concentration in vacuo gave a residual oil which was subjected to chromatography (SiO$_2$, 50:10:1 EtOAc:MeOH:saturated aqueous ammonia solution) to give the title compound as a white powder (189 mg, 0.44 mmol, 67%). $\delta$H (D-6 DMSO, 300K) 8.24 (1H, d J 5.2 Hz), 8.00 (2H, dd J 1.8 Hz 6.7 Hz), 7.74 (2H, dd J 1.8 Hz 6.7 Hz), 7.12 (1H, s), 7.00 (1H, dd J 5.2 Hz 1.4 Hz), 3.60 (3H, s), 3.54 (4H, s br), 2.84 (4H, s br), 1.87 (3H, s), 1.68 (3H, s). m/z (ES$^+$, 70V) 426.1 (MH$^+$).

METHOD 2: Alternatively this compound could be prepared by Suzuki reaction of the sulphonamide of intermediate 1 (500 mg, 1.68 mmol), 2-(1-piperazinyl)pyridine-4- boronic acid pinacol ester (581 mg, 2.0 mmol), tribasic potassium phosphate (427 mg, 2.0 mmol), and Pd(dppf)Cl$_2$.DCM (50 mg, 0.06 mmol) in DMF (3.0 ml) and water (0.75 ml), according to the method of intermediate 11, to give the title compound as an off-white powder (381 mg, 0.89 mmol, 53%).

EXAMPLE DDD86292

2,6-Dichloro-4-[2-(3-dimethylamino-pyrrolidin-1-yl)-pyridin-4-yl]-N-(1,3,5-trimethyl-1H-pyrazol-4-yl)-benzenesulfonamide Prepared by heating the chloropyridine of intermediate 12 (250 mg, 0.58 mmol) with 3-dimethylaminopiperidine (200 µl) in EtOH (1.5 ml) at 155° C. for 1 h according to the method of DDD86213 to give the title compound as a white powder (150 mg, 0.29 mmol, 49%). δH (CDCl3, 300K) 8.48 (1H, d J 5.1 Hz), 7.49 (2H, s), 7.39 (1H, d J 4.7 Hz), 7.32 (1H, s), 3.76-3.46 (6H, s br), 3.63 (3H, s), 3.46-3.39 (1H, m), 2.75 (2H, s br), 2.28 (2H, s br), 2.05 (3H, s), 1.85 (3H, s), 1.56 (2H, s br). m/z (ES$^+$, 70V) 523.2 (MH$^+$).

EXAMPLE DDD86297

2,6-Dichloro-4-[2-(2-methylamino-ethylamino)-pyridin-4-yl]N-(1,3,6-trimethyl-1H-pyrazol-4-yl)-benzenesulfonamide Prepared by heating the chloropyridine of intermediate 12 (250 mg, 0.58 mmol) with N-methylethylenediamine (200 µl) in EtOH (1.5 ml) at 155° C. for 1 h according to the method of DDD86213 to give the title compound as a white powder (134 mg, 0.28 mmol, 48%). δH (D-6 DMSO, 300K) 8.53 (1H, d J 5.2 Hz), 7.98 (1H, d J 0.9 Hz), 7.85 (1H, dd J 1.5 Hz 5.2 Hz), 7.28 (1H, s), 7.21 (1H, d J 1.5 Hz), 7.04 (1H, d J 1.5 Hz), 3.60 (3H, s), 3.24-3.20 (2H, m), 2.64-2.58 (2H, m), 2.29 (3H, s), 1.98 (3H, s), 1.82 (3H, s). m/z (ES$^+$, 70V) 483.1 (MH$^+$).

EXAMPLE DDD86302

2,6-Dichloro-4-{2-[2-(pyridin-2-ylamino)-ethyl-amino]-pyridin-4-yl}-N-(1,3,5-trimethyl-1H-pyrazol-4-yl)-benzenesulfonamide Prepared by heating the chloropyridine of intermediate 12 (250 mg, 0.58 mmol) with N-(2-pyridyl)ethylenediamine (200 µl) in EtOH (1.5 ml) at 155° C. for 1 h according to the method of DDD86213 to give the title compound as a white powder (111 mg, 0.2 mmol, 35%). δH (D-6 DMSO, 300K) 9.41 (1H, s), 8.51 (1H, d J 5.1 Hz), 7.93 (1H, d J 4.9 Hz), 7.91 (1H, s), 7.79 (1H, d J 5.2 Hz), 7.36 (1H, t J 7.1 Hz), 7.27 (1H, s), 7.20-7.18 (1H, m), 7.17 (1H, s), 6.60 (1H, s), 6.54-6.44 (2H, m), 3.55 (3H, s), 3.41-3.23 (4H, m), 1.92 (3H, s), 1.79 (3H, s). m/z (ES$^+$, 70V) 546.1 (MH$^+$).

EXAMPLE DDD86303

2,6-Dichloro-4-{2-[2-(pyridin-2-ylamino)-ethyl-amino]-pyridin-4-yl}-N-(1,3,5-trimethyl-1H-pyrazol-4-yl)-benzenesulfonamide Prepared by heating the chloropyridine of intermediate 12 (250 mg, 0.58 mmol) with ethylenediamine (200 µl) in EtOH (1.5 ml) at 155° C. for 1 h according to the method of DDD86213 to give the title compound as a white powder (137 mg, 0.29 mmol, 50%). δH (D-6 DMSO, 300K) 8.49 (1H, d J 4.1 Hz), 7.93 (1H, s), 7.80 (1H, d J 4.9 Hz), 7.22 (1H, s br), 7.17 (1H, s), 7.01 (1H, s), 4.03 (2H, s br), 3.55 (3H, s), 3.16 (2H, s br), 2.63 (2H, t J 7.1 Hz), 1.94 (3H, s), 1.78 (3H, s). m/z (ES$^+$, 70V) 469.2 (MH$^+$).

EXAMPLE DDD86308

2,6-Dichloro-4-[2-(3-imidazol-1-yl-propylamino)-pyridin-4-yl]-N-(1,3,5-trimethyl-1H-pyrazol-4-yl)-benzenesulfonamide Prepared by heating the chloropyridine of intermediate 12 (250 mg, 0.58 mmol) with N-(3-aminopropyl)imidazole (200 µl) in EtOH (1.5 ml) at 155° C. for 1 h according to the method of DDD86213 to give the title compound as a white powder (130 mg, 0.24 mmol, 41%). δH (CDCl$_3$, 300K) 8.46 (1H, dd J 0.5 Hz 5.1 Hz), 7.52 (1H, s), 7.46 (1H, dd J 0.5 Hz 1.5 Hz), 7.35 (1H, dd J 1.5 Hz 5.2 Hz), 7.24 (1H, t J 4.9 Hz), 7.1 Hz (1H, s), 7.00 (1H, d J 1.8 Hz), 6.83 (2H, s), 6.58 (1H, d J 1.8 Hz), 3.92 (2H, t J 6.1 Hz), 3.60 (3H, s), 3.04 (2H, q J 6.1 Hz), 2.13 (3H, s), 2.05 (2H, p J 6.1 Hz), 1.89 (3H, s). m/z (ES$^+$, 70V) 534.1 (MH$^+$).

EXAMPLE DDD86309

2,6-Dichloro-4-[2-(2-dimethylamino-ethylamino)-pyridin-4-yl]-N-(1,3,5-trimethyl-1H-pyrazol-4-yl)-benzenesulfonamide Prepared by heating the chloropyridine of intermediate 12 (250 mg, 0.58 mmol) with N,N-dimethylethylenediamine (200 µl) in EtOH (1.5 ml) at 155° C. for 1 h according to the method of DDD86213 to give the title compound as a white powder (70 mg, 0.14 mmol, 24%). δH (CDCl$_3$, 300K) 8.50 (1H, d J 5.1 Hz), 7.53 (1H, s), 7.44 (1H, d J 3.8 Hz), 7.39 (1H, t J 4.5 Hz), 7.02 (1H, s), 6.98 (1H, s), 6.76 (1H, s), 3.68 (3H, s), 3.27 ("h, s br), 2.60 (2H, s br), 2.31 (6H, s br), 2.14 (3H, s), 2.89 (3H, s). m/z (ES$^+$, 70V) 497.1 (MH$^+$).

EXAMPLE DDD86312

3'-Diethylaminomethyl-biphenyl-4-sulfonic acid (1,3,5-trimethyl-1H-pyrazol-4-yl)-amide Prepared from the aldehyde of intermediate 14 (80 mg, 0.23 mmol), diethylamine (0.088 ml, 50 mg, 0.069 mmol) and sodium triacetoxyborohydride (146 mg, 0.069 mmol) in CHCl$_3$ (5.0 ml) at 50° C. for 24 h according to the method of example DDD86212 to give the title compound as a white solid (55 mg, 0.13 mmol, 56%). δH (CDCl$_3$, 300K) 7.78 (2H, d J 8.6 Hz), 7.71 (2H, d J 8.5 Hz), 7.66 (1H, s br), 7.50 (1H, d J 6.8 Hz), 7.42 (2H, d J 5.8 Hz), 5.84 (1H, s), 3.71 (1H, s br), 3.68 (3H, s), 2.64 (3H, s br), 2.08 (3H, s), 1.62 (3H, s), 1.13 (6H, s br). m/z (ES$^+$, 70V) 427.2 (MH$^+$).

EXAMPLE DDD86314

3'-Morpholin-4-ylmethyl-biphenyl-4-sulfonic acid (1,3,5-trimethyl-1H-pyrazol-4-yl)-amide Prepared from the aldehyde intermediate 14 (150 mg, 0.41 mmol), morpholine (107 µl, 107 mg, 1.23 mmol) and sodium triacetoxyborohydride (261 mg, 1.23 mmol) in CHCl$_3$ (10.0 ml) at 50° C. for 24 h according to the method of example DDD86212 to give the title compound as a white solid (90 mg, 0.21 mmol, 50%). δH (CDCl$_3$, 300K) 7.79

(2H, d J 8.3 Hz), 7.69 (2H, d J 8.3 Hz), 7.57 (1H, s br), 7.50 (1H, d J 7.5 Hz), 7.43 (1H, t J 7.5 Hz), 7.39 (1H, d J 7.5 Hz), 5.74 (1H, s br), 3.73 (3H, t J 4.6 Hz), 3.69 (3H, s), 3.57 (2H, s), 2.49 (3H, s br), 2.11 (3H, s), 1.61 (3H, s), 1.55 (1H, s br). m/z (ES+, 70V) 441.1 (MH+).

EXAMPLE DDD86315

4-[4'-(1,3,5-Trimethyl-1H-pyrazol-4-ylsulfamoyl)-biphenyl-3-ylmethyl]-piperazine-1-carboxylic acid tert-butyl ester Prepared from the aldehyde of intermediate 14 (150 mg, 0.41 mmol), N-Boc piperazine (229 mg, 1.23 mmol) and sodium triacetoxyborohydride (261 mg, 1.23 mmol) in CHCl$_3$ (10.0 ml) at 50° C. for 24 h according to the method of example DDD86212 to give the title compound as a white solid (120 mg, 0.14 mmol, 54%). δH (CDCl$_3$, 300K) 7.79 (2H, d J 8.4 Hz), 7.69 (2H, d J 8.4 Hz), 7.56 (1H, s br), 7.50 (1H, d, J 7.7 Hz), 7.43 (1H, t J 7.6 Hz), 7.38 (1H, d, J 7.7 Hz), 5.74 (1H, s), 3.69 (3H, s), 3.58 (2H, s), 3.45 (4H, t J 5.0 Hz), 2.43 (4H, t J 4.5 Hz), 2.11 (3H, s), 1.54 (3H, s), 1.46 (9H, s). m/z (ES+, 70V) 540.1 (MH+).

EXAMPLE DDD86316

3'-[(2-Dimethylamino-ethylamino)-methyl]biphenyl-4-sulfonic acid (1,3,5-trimethyl-1H-pyrazol-4-yl)-amide Prepared from the aldehyde of intermediate 14 (150 mg, 0.41 mmol), NN'-dimethylethylenediamine (134 µl, 108 mg, 1.23 mmol) and sodium triacetoxyborohydride (261 mg, 1.23 mmol) in CHCl$_3$ (10.0 ml) at 50° C. for 18 h according to the method of example DDD86212 to give the title compound as a white solid (60 mg, 0.14 mmol, 33%). δH (CDCl$_3$, 300K) 7.78 (2H, d J 8.4 Hz), 7.69 (2H, d J 8.5 Hz), 7.59 (1H, s br), 7.48 (1H, d J 7.6 Hz), 7.43 (1H, t J 7.5 Hz), 7.38 (1H, d J 7.5 Hz), 5.75 (1H, s), 3.89 (2H, s), 3.68 (3H, s), 2.74 (2H, t J 5.9 Hz), 2.46 (2H, t J 6.2 Hz), 2.22 (6H, s), 2.08 (3H, s), 1.63 (3H, s). m/z (ES+, 70V) 442.1 (MH+).

EXAMPLE DDD86317

3'-Piperazin-1-ylmethyl-biphenyl-4-sulfonic acid (1,3,5-trimethyl-1H-pyrazol-4-yl)-amide Prepared from the aldehyde of intermediate 14 (150 mg, 0.41 mmol), piperazine (106 mg, 1.23 mmol) and sodium triacetoxyborohydride (261 mg, 1.23 mmol) in CHCl$_3$ (10.0 ml) at 50° C. for 24 h according to the method of example DDD86212 to give the title compound as a white solid (94 mg, 0.21 mmol, 52.0%). δH (CDCl$_3$, 300K) 7.79 (2H, d J 8.4 Hz), 7.69 (2H, d J 8.3 Hz), 7.56 (1H, s br), 7.49 (1H, d J 7.6 Hz), 7.42 (1H, t J 7.6 Hz), 7.38 (1H, d J 7.5 Hz), 5.87 (1H, s br), 3.68 (3H, s), 3.58 (2H, s), 2.96 (4H, t J 4.8 Hz), 2.51 (4H, s br), 2.10 (3H, s), 1.62 (3H, s). m/z (ES+, 70V) 440.1 (MH+).

EXAMPLE DDD86318

3'-Pyrrolidin-1-ylmethyl-biphenyl-4-sulfonic acid (1,3,5-trimethyl-1H-pyrazol-4-yl)-amide Prepared from the aldehyde of intermediate 14 (80 mg, 0.23 mmol), pyrrolidine (57.0 µl, 49 mg, 0.069 mmol) and sodium triacetoxyborohydride (146 mg, 0.069 mmol) in CHCl$_3$ (5.0 ml) at 50° C. for 24 h according to the method of example DDD86212 to give the title compound as a white solid (85 mg, 0.20 mmol, 87%). δH (CDCl$_3$, 300K) 7.78 (2H, d J 8.4 Hz), 7.71 (2H, d J 8.3 Hz), 7.51 (2H, s br), 7.43 (2H, d J 6.6 Hz), 5.76 (1H, s), 3.77 (2H, s br), 3.68 (3H, s), 2.64 (4 h, s br), 2.08 (3H, s), 1.86 (4H, s br), 1.64 (3H, s). m/z (ES+, 70V) 425.1 (MH+).

EXAMPLE DDD86467

2,6-Dichloro-N-(5-isobutyl-1,3-dimethyl-1H-pyrazol-4-yl)-4-(2-piperazin-1-yl-pyridin-4-yl)-benzenesulfonamide Prepared from the sulphonamide of intermediate 23B (115 mg, 0.25 mmol), 2-(1-piperazinyl)pyridine-4-boronic acid pinacol ester (80 mg, 0.28 mmol), tribasic potassium phosphate (60 mg, 0.28 mmol), and Pd(PPh$_3$)$_4$ (30 mg, 0.026 mmol) in DMF (1.6 ml) and water (0.4 ml), according to the method of intermediate 11, to give the title compound as a yellow solid (50 mg, 0.09 mmol, 37%). δH (D-6 DMSO, 300K) 8.20, (1H, d, J 5.3 Hz), 8.07 (2H, s), 7.16 (1H, s), 7.03 (1H, d, J 5.3 Hz), 3.59 (3H, s), 3.52 (4H, m), 2.80 (4H, m), 2.21 (2H, d J 7.5 Hz), 1.98 (1H, m), 1.77 (3H, s), 0.75 (6H, d J 6.6 Hz). m/z (ES+, 70V) 537.2 (MH+).

EXAMPLE DDD86468

2,6-Dichloro-N-(3,5-dimethyl-isoxazol-4-yl)-4-(2-piperazin-1-yl-pyridin-4-yl)-benzenesulfonamide Prepared from the sulphonamide of intermediate 7 (100 mg, 0.25 mmol), 2-(1-piperazinyl)pyridine-4-boronic acid pinacol ester (87 mg, 0.30 mmol), tribasic potassium phosphate (72 mg, 0.34 mmol), and Pd(PPh$_3$)$_4$ (30 mg, 0.026 mmol) in DMF (1.6 ml) and water (0.4 ml), according to the method of intermediate 11, to give the title compound as a yellow solid (12 mg, 0.025 mmol, 10%). δH (D-6 DMSO, 300K) 8.20, (1H, d J 5.3 Hz), 7.94 (2H, s), 7.21 (1H, s), 7.08 (1H, d J 5.3 Hz), 3.65 (4H, m), 2.97 (4H, m), 1.96 (3H, s), 1.91 (3H, s). m/z (ES+, 70V) 482.1 (MH+).

EXAMPLE DDD86469

2,6-Dichloro-4-[3-(4-methyl-piperazin-1-yl)-prop-1-ynyl]N-(1,3,5-trimethyl-1H-pyrazol-4-yl)-benzene-sulfonamide Prepared from the sulphonamide of intermediate 2 (355 mg, 0.86 mmol), 1-methyl-4-prop-2-ynyl-piperazine (142 mg, 1.03 mmol), CuI (8.2 mg, 0.043 mmol) and Pd(PPh$_3$)$_4$ (50 mg, 0.043 mmol), in DMF (3.0 ml) and NEt$_3$ (2.0 ml) according to the method of intermediate 36, to give the title compound as an off-white solid (150 mg, 0.32 mmol, 37%). δH (CDCl$_3$, 300K) 7.47 (2H, s), 6.58 (1H, s), 3.67 (3H, s), 3.56 (2H, s), 2.67 (4H, s br), 2.51 (4H, s br), 2.32 (3H, s br), 2.13 (3H, s), 1.78 (3H, s). m/z (ES+, 70V) 470.1 (MH+).

EXAMPLE DDD86470

2,6-Dichloro-N-(3,5-dimethyl-isoxazol-4-yl)-4-(2-piperazin-1-yl-pyridin-4-yl)-benzenesulfonamide Prepared from the boronic ester of intermediate 35 (184 mg, 0.4 mmol), 4-(3-bromophenyl)piperidine hydrochloride (133 mg, 0.48 mmol), tribasic potassium phosphate (144 mg, 0.68 mmol), and Pd(PPh$_3$)$_4$ (48 mg, 0.042 mmol) in DMF (3.2 ml) and water (0.8 ml), according to the method of intermediate 11, to give the title compound as a yellow solid (20 mg, 0.040 mmol, 16%). δH (CDCl$_3$, 300K) 7.63 (2H, s), 7.41 (3H, m), 7.33 (1H, d J 6.6 Hz), 3.68 (3H, s), 3.23 (2H, d J 12.0 Hz), 2.78 (2H, dt J 12.1 Hz 2.1 Hz), 2.71 (1H, tt J 12.1 Hz 3.6 Hz), 2.18 (3H, s), 1.88 (2H, d J 12.6 Hz), 1.73 (3H, s), 1.70 (2H, qd J 12.5 Hz 3.8 Hz). m/z (ES$^+$, 70V) 493.1 (MH$^+$).

EXAMPLE DDD86471

N-(1,3-Dimethyl-1H-pyrazol-4-yl)-4-(2-piperazin-1-yl-pyridin-4-yl)-benzenesulfonamide Prepared from the sulphonamide of intermediate 28 (83 mg, 0.25 mmol), 2-(1-piperazinyl)pyridine-4-boronic acid pinacol ester (80 mg, 0.28 mmol), tribasic potassium phosphate (60 mg, 0.28 mmol), and Pd(PPh$_3$)$_4$ (30 mg, 0.026 mmol) in DMF (1.6 ml) and water (0.6 ml), according to the method of intermediate 11, to give the title compound as a white solid (48 mg, 0.12 mmol, 47%). δH (D-6 DMSO, 300K) 8.20 (1H, d J 5.2 Hz), 7.95 (2H, d J 8.3 Hz), 7.74 (2H, d J 8.3 Hz), 7.41 (1H, s), 7.08 (1H, s), 6.97 (1H, d J 5.2 Hz), 3.65 (3H, s), 3.50 (4H, m), 2.80 (4H, m), 1.70 (3H, s). m/z (ES$^+$, 70V) 413.2 (MH$^+$).

EXAMPLE DDD86474

N-(1-Methyl-1H-pyrazol-4-yl)-4-(2-piperazin-1-yl-pyridin-4-yl)-benzenesulfonamide Prepared from the sulphonamide of intermediate 30 (79 mg, 0.25 mmol), 2-(1-piperazinyl)pyridine-4-boronic acid pinacol ester (80 mg, 0.28 mmol), tribasic potassium phosphate (60 mg, 0.28 mmol), and Pd(PPh$_3$)$_4$ (30 mg, 0.026 mmol) in DMF (1.6 ml) and water (0.6 ml), according to the method of intermediate 11, to give the title compound as a white solid (46 mg, 0.12 mmol, 47%). δH (D-6 DMSO, 300K) 8.19 (1H, d J 5.2 Hz), 7.93 (2H, d J 8.4 Hz), 7.78 (2H, d J 8.4 Hz), 7.49 (1H, s), 7.06 (2H, s), 6.95 (1H, d J 5.2 Hz), 3.71 (3H, s), 3.49 (4H, m), 2.79 (4H, m). m/z (ES$^+$, 70V) 399.2 (MH$^+$).

EXAMPLE DDD86475

2,6-Dichloro-N-(1,3-dimethyl-1H-pyrazol-4-yl)-4-(2-piperazin-1-yl-pyridin-4-yl)-benzenesulfonamide Prepared from the sulphonamide of intermediate 29 (100 mg, 0.25 mmol), 2-(1-piperazinyl)pyridine-4-boronic acid pinacol ester (80 mg, 0.28 mmol), tribasic potassium phosphate (60 mg, 0.28 mmol), and Pd(PPh$_3$)$_4$ (30 mg, 0.026 mmol) in DMF (1.6 ml) and water (0.6 ml), according to the method of intermediate 11, to give the title compound as a white solid (14 mg, 0.03 mmol, 12%). δH (D-6 DMSO, 300K) 8.16 (1H, d J 5.2 Hz), 7.97 (2H, s), 7.41 (1H, s), 7.12 (1H, s), 7.00 (1H, d J 5.2 Hz), 3.60 (3H, s), 3.50 (4H, m), 2.77 (4H, m), 1.84 (3H, s). m/z (ES$^+$, 70V) 481.1 (MH$^+$).

EXAMPLE DDD86478

2,6-Dichloro-N-(1-methyl-1H-pyrazol-4-yl)-4-(2-piperazin-1-yl-pyridin-4-yl)-benzenesulfonamide Prepared from the sulphonamide of intermediate 31 (96 mg, 0.25 mmol), 2-(1-piperazinyl)pyridine-4-boronic acid pinacol ester (80 mg, 0.28 mmol), tribasic potassium phosphate (60 mg, 0.28 mmol), and Pd(PPh$_3$)$_4$ (30 mg, 0.026 mmol) in DMF (1.6 ml) and water (0.6 ml), according to the method of intermediate 11, to give the title compound as a yellow solid (87 mg, 0.19 mmol, 74%). δH (D-6 DMSO, 300K) 8.19 (1H, d J 5.2 Hz), 7.99 (2H, s), 7.49 (1H, s), 7.14 (1H, s), 7.13 (1H, s), 7.02 (1H, d J 5.2 Hz), 3.70 (3H, s), 3.54 (4H, m), 2.83 (4H, m). m/z (ES$^+$, 70V) 467.1 (MH$^+$).

EXAMPLE DDD86479

3,5-Dichloro-3'-piperazin-1-yl-biphenyl-4-sulfonic acid (1,3,5-trimethyl-1H-pyrazol-4-yl)-amide Prepared from the boronic ester of intermediate 35 (115 mg, 0.25 mmol), 1-(3-bromophenyl)piperazine (72 mg, 0.48 mmol), tribasic potassium phosphate (72 mg, 0.34 mmol), and Pd(PPh$_3$)$_4$ (30 mg, 0.026 mmol) in DMF (1.6 ml) and water (0.4 ml), according to the method of intermediate 11, to give the title compound as a yellow solid (21 mg, 0.042 mmol, 17%). δH (CDCl$_3$, 300K) 7.67 (2H, s), 7.39 (1H, t J 7.8 Hz), 7.04 (3H, m), 3.70 (3H, s), 3.25 (4H, m), 3.09 (4H, m), 2.19 (3H, s), 1.81 (3H, s). m/z (ES$^+$, 70V) 494.1 (MH$^+$).

EXAMPLE DDD86480

2,6-Dichloro-N-(2-methyl-pyridin-3-yl)-4-(2-piperazin-1-yl-pyridin-4-yl)-benzenesulfonamide Prepared from the sulphonamide of intermediate 9 (100 mg, 0.25 mmol), 2-(1-piperazinyl)pyridine-4-boronic acid pinacol ester (87 mg, 0.30 mmol), tribasic potassium phosphate (180 mg, 0.85 mmol), and Pd(PPh$_3$)$_4$ (30 mg, 0.026 mmol) in DMF (1.6 ml) and water (0.6 ml), according to the method of intermediate 11, to give the title compound as a tan coloured solid (37 mg, 0.077 mmol, 31%). δH (D-6 DMSO, 300K) 8.18 (1H, d J 5.3 Hz), 7.78 (2H, s), 7.64 (1H, d J 4.5 Hz), 7.31 (1H, d J 7.7 Hz), 7.15 (1H, s), 7.13 (1H, s), 7.02 (1H, d J 4.7 Hz), 6.79 (1H, dd J 8.1 Hz 4.6 Hz), 3.70 (4H, m), 3.05 (4H, m), 2.29 (3H, s). m/z (ES$^+$, 70V) 478.1 (MH$^+$).

EXAMPLE DDD86481

2,6-Dichloro-N-(3-isobutyl-1,5-dimethyl-1H-pyrazol-4-yl)-4-(2-piperazin-1-yl-pyridin-4-yl)-benzenesulfonamide Prepared from the sulphonamide of intermediate 23A (115 mg, 0.25 mmol), 2-(1-piperazinyl)pyridine-4-boronic acid pinacol ester (80 mg, 0.28 mmol), tribasic potassium phosphate (60 mg, 0.28 mmol), and Pd(PPh$_3$)$_4$ (30 mg, 0.026 mmol) in DMF (1.6 ml) and water (0.4 ml), according to the method of intermediate 11, to give the title compound as a yellow solid (73 mg, 0.14 mmol, 54%). δH (D-6 DMSO, 300K) 8.20, (1H, d J 5.2 Hz), 8.06 (2H, s), 7.15 (1H, s), 7.02 (1H, d J 5.2 Hz), 3.60 (3H, s), 3.52 (4H, m), 2.80 (4H, m), 1.98 (3H, s), 1.92 (2H, d J 7.3 Hz), 1.70 (1H, m), 0.70 (6H, d J 6.6 Hz). m/z (ES$^+$, 70V) 537.2 (MH$^+$).

EXAMPLE DDD87748

(34-[2-(3-Methyl-piperazin-1-yl)-pyridin-4-yl]-N-(1,3,5-trimethyl-1H-pyrazol-4-yl)-benzenesulfonamide Prepared from the compound of intermediate 11 (250 mg, 0.66 mmol) and 2-methyl piperazine (500 mg, 5.0 mmol) in EtOH (0.75 ml) according to the method of DDD86213 to give the title compound as a white powder (157 mg, 0.36 mmol, 55%). δH (D-6 DMSO, 300K) 9.21 (1H, s), 8.23 (1H, d J 5.2 Hz), 8.01 (2H, d J 8.4 Hz), 7.74 (2H, d J 8.4 Hz), 7.13 (1H, s), 7.00 (1H, d J 5.2 Hz), 4.28 (2H, t J 13.3 Hz), 3.60 (3H, s), 3.00 (1H, d J 9.6 Hz), 2.80-2.68 (3H, m), 2.39 (1H, t J 11.3 Hz), 1.88 (3H, s), 1.63 (3H, s), 1.08 (3H, d J 6.2 Hz). m/z (ES+, 70V) 441.2 (MH+).

EXAMPLE DDD87749

4-(3,4,5,6-Tetrahydro-2H-[1,2']bipyridinyl-4'-yl)-N-(1,3,5-trimethyl-1H-pyrazol-4-yl)-benzenesulfonamide Prepared from the compound of intermediate 11 (250 mg, 0.66 mmol) and piperidine (500 mg, 5.7 mmol) in EtOH (0.75 ml) according to the method of DDD86213 to give the title compound as a white powder (189 mg, 0.44 mmol, 67%). δH (D-6 DMSO, 300K) 9.20 (1H, s), 8.19 (1H, d J 5.2 Hz), 7.96 (2H, d J 8.4 Hz), 7.74 (2H, d J 8.4 Hz), 7.13 (1H, s), 6.96 (1H, d J 5.2 Hz), 3.68-3.62 (4H, m), 3.61 (3H, s), 1.87 (3H, s), 1-70-1.55 (6H, M), 1.63 (3H, s). m/z (ES+, 70V) 426.2 (MH+).

EXAMPLE DDD87751

3'-(2-Hydroxy-ethyl)-biphenyl-4-sulfonic acid (1,3,5-trimethyl-1H-pyrazol-4-yl)-amide Prepared from the sulphonamide of Intermediate 1 (1.0 g, 2.91 mmol), 3-hydroxyethylphenyl boronic acid (579 mg, 3.49 mmol), tribasic potassium phosphate (740 mg, 3.49 mmol), Pd(dppf)Cl$_2$.DCM (119 mg, 0.146 mmol) and water (2.0 ml) in oxygen-free DMF (10.0 ml) at 130° C. for 1 h according to the method of intermediate 11, to give the title compound as a colourless solid (500 mg, 1.30 mmol, 45%). δH (CDCl$_3$, 300K) 7.78 (2H, d J 8.3 Hz), 7.68 (2H, d J 8.4 Hz), 7.49-7.47 (2H, m), 7.43 (1H, t J 8.4 Hz), 7.30 (1H, d J 7.4 Hz), 5.79 (1H, s br), 3.93 (2H, q J 6.3 Hz), 3.68 (3H, s), 2.96 (3H, t J 6.5 Hz), 2.09 (3H, s), 1.61 (3H, s), 1.44 (1H, t J 5.8 Hz). m/z (ES+, 70V) 386.2 (MH+).

EXAMPLE DDD87753

3'-[2-(4-Methyl-piperazin-1-yl)-ethyl]-biphenyl-4-sulfonic acid (1,3,5-trimethyl-1H-pyrazol-4-yl)-amide The compound of example DDD87751 (400 mg, 1.04 mmol) and triethylamine (218 μl, 158 mg, 1.56 mmol) in DCM (3.0 ml) at rt was treated dropwise with methanesulfonylchloride (97 μl, 143 mg, 1.25 mmol) and the reaction stirred for 21 h. The mixture was then diluted with DCM (40.0 ml) and the organic layer washed with H$_2$O (2×10 ml), dried over MgSO$_4$ and concentrated in vacuo to yield the crude methanesulfonate intermediate as an off-white solid (460 mg, 0.99 mmol, 95%). δH (CDCl$_3$, 300K) 7.81 (2H, d J 8.6 Hz), 7.67 (2H, d J 8.6 Hz), 7.52-7.42 (3H, m), 7.33-7.26 (1H, m), 5.76 (1H, s br), 4.48 (2H, t J 6.9 Hz), 3.69 (3H, s), 3.15 (2H, t J 6.5 Hz), 2.92 (3H, s), 2.10 (3H, s), 1.55 (3H, s). m/z (ES+, 70V) 464.1 (MH+).

A mixture of the above methanesulfonate (150 mg, 0.32 mmol), sodium carbonate (102 mg, 0.96 mmol) and N-methyl piperazine (106 μl, 96 mg, 0.96 mmol) in CH$_3$CN (2.0 ml) was heated in a microwave at 120° C. for 30 min. The crude mixture was then filtered through an SCX-2 column which was washed with DCM:MeOH (10:1, 20.0 ml), followed by elution with 7M NH$_3$ in MeOH (20.0 ml). The eluted fraction was concentrated in vacuo and subjected to chromatography (4-10% MeOH:DCM) to give the title compound as a colourless solid (90 mg, 0.21 mmol, 50%). δH (CDCl$_3$, 300K) 7.78 (2H, d J 8.5 Hz), 7.67 (2H, d J 8.5 Hz), 7.49-7.47 (2H, m), 7.45-7.43 (2H, m), 7.40 (1H, t J 7.40 Hz), 7.28 (1H, s br), 5.79 (1H, s br), 3.68 (3H, s), 2.89 (2H, t J 7.7 Hz), 2.66 (2H, t J 8.4 Hz), 2.65-2.32 (4H, m), 2.33 (3H, s br), 2.09 (3H, s), 1.60 (7H, s br). m/z (ES+, 70V) 468.2 (MH+).

EXAMPLE DDD87754

3'-(3-Phenyl-piperazin-1-ylmethyl)-biphenyl-4-sulfonic acid (1,3,5-trimethyl-1H-pyrazol-4-yl)-amide Prepared from the aldehyde of intermediate 14 (200 mg, 0.54 mmol), 2-phenylpiperazine (262 mg, 1.62 mmol) and sodium triacetoxyborohydride (343 mg, 1.62 mmol) in CHCl$_3$ (12.0 ml) at 50° C. for 24 h according to the method of example DDD86212 to give the title compound as a white solid (200 mg, 0.39 mmol, 72%). δH (CDCl$_3$, 300K) 7.78 (2H, d J 8.5 Hz), 7.69 (2H, d J 8.5 Hz), 7.58 (1H, s br), 7.49 (1H, d J 7.4 Hz), 7.42 (2H, t J 7.5 Hz), 7.38 (2H, dd J 1.5 Hz 7.3 Hz), 7.31 (2H, t J 7.1 Hz) 7.27 (1H, t J 1.3 Hz), 5.80 (1H, s br), 3.93 (1H, dd J 2.3 Hz 10.0 Hz), 3.69 (3H, s), 3.63 (2H, s), 3.14-3.08 (2H, m), 2.94 (1H, d J 10.6 Hz), 2.89 (1H, d J 11.1 Hz), 2.42 (1H, s br), 2.28 (1H, dt 3.5 Hz 7.4 Hz), 2.16 (1H, t J 10.7 Hz), 2.09 (3H, s), 1.61 (3H, s). m/z (ES+, 70V) 515.2 (MH+).

EXAMPLE DDD87755

N-(3-Hydroxy-propyl)-4-(2-piperazin-1-yl-pyridin-4-yl)-N-(1,3,5-trimethyl-1H-pyrazol-4-yl)-benzenesulfonamide Prepared from the sulphonamide of intermediate 21 (300 mg, 0.7 mmol), 2-(1-piperazinyl)pyridine-4-boronic acid pinacol ester (216 mg, 0.7 mmol), tribasic potassium phosphate (158 mg, 0.7 mmol), Pd(PPh$_3$)$_4$ (50 mg, 0.04 mmol) and water (1.0 ml) in oxygen-free DMF (5.0 ml) at 130° C. for 1 h, according to the method of intermediate 11 except with the use of Pd(PPh$_3$)$_4$ as reaction catalyst, to give the title compound as a white solid (100 mg, 0.2 mmol, 26%). δH (D-6 DMSO, 300K) 9.36 (2H, s br), 8.26 (1H, d J 5.6 Hz), 8.08 (2H, d J 8.4 Hz), 7.81 (2H, d J 8.4 Hz), 7.43 (1H, s), 7.23 (1H, d J 5.6 Hz), 3.99-3.92 (4H, m), 3.68-3.63 (1H, m), 3.63 (3H, s), 3.46-3.41 (3H, m), 3.27-3.21 (4H, m), 1.89 (3H, s), 1.57 (3H, s), 1.58-1.52 (2H, m). m/z (ES+, 70V) 485.2 (MH+).

EXAMPLE DDD87756

4-[2-(3-Phenyl-piperazin-1-yl)-pyridin-4-yl]-N-(1,3,5-trimethyl-1H-pyrazol-4-yl)-benzenesulfonamide Prepared from the compound of intermediate 11 (250 mg, 0.66 mmol) and 2-phenyl piperazine (500 mg, 3.1 mmol) in EtOH (0.75 ml) according to the method of DDD86213 to give the title compound as a white powder (182 mg, 0.36 mmol, 55%). δH (D-6 DMSO, 300K) 9.24 (1H, s br), 8.25 (1H, d J 5.2 Hz), 8.01 (2H, d J 8.4 Hz), 7.73 (2H, d J 8.4 Hz), 7.54 (2H, d J 7.4 Hz), 7.41 (2H, t J 7.35 Hz), 7.34 (1H, t J 7.35 Hz), 7.18 (1H, s), 7.03 (1H, d J 5.3 Hz), 4.42-4.39 (31-1, m), 3.81-3.78 1H, m), 3.60 (3H, s), 3.14 (1H, d J 8.8

Hz), 2.93-2.89 (3H, m), 2.70 (1H, t J 11.8 Hz), 1.87 (3H, s), 1.63 (3H, s). m/z (ES+, 70V) 503.1 (MH+).

EXAMPLE DDD87758

2'-Diethylaminomethyl-biphenyl-4-sulfonic acid (1,3,5-trimethyl-1H-pyrazol-4-yl)-amide Prepared from the aldehyde of intermediate 17 (150 mg, 0.41 mmol), diethylamine (127 μl, 90 mg, 1.23 mmol) and sodium triacetoxyborohydride (261 mg, 1.23 mmol) in CHCl$_3$ (10.0 ml) at 50° C. for 24 h according to the method of example DDD86212 to give the title compound as a white solid (106 mg, 0.25 mmol, 62%). δH (CDCl$_3$, 300K) 7.76 (2H, d J 8.2 Hz), 7.63 (1H, s br), 7.47 (2H, d J 8.4 Hz), 7.38 (1H, t J 7.0 Hz), 7.31 (1H, t J 7.1 Hz), 7.15 (1H, d J 7.7 Hz), 5.79 (1H, s br), 3.69 (3H, s), 3.41 (2H, m), 2.40 (4H, d J 5.6 Hz), 2.13 (3H, s), 1.63 (3H, s), 0.90 (6H, t J 6.5 Hz). m/z (ES+, 70V) 427.2 (MH+).

EXAMPLE DDD87759

2'-Pyrrolidin-1-ylmethyl-biphenyl-4-sulfonic acid (1,3,5-trimethyl-1H-pyrazol-4-yl)-amide Prepared from the aldehyde of intermediate 17 (150 mg, 0.41 mmol), pyrrolidine (101 μl, 87 mg, 1.23 mmol) and sodium triacetoxyborohydride (261 mg, 1.23 mmol) in CHCl$_3$ (10.0 ml) at 50° C. for 24 h according to the method of example DDD86212 to give the title compound as a white solid (166 mg, 0.39 mmol, 95%). δH (CDCl$_3$, 300K) 7.78 (2H, d J 8.2 Hz), 7.54 (3H, d J 7.3 Hz), 7.41 (1H, d J 5.9 Hz), 7.35 (1H, m), 7.21 (1H, d J 7.5 Hz), 5.81 (111, s br), 3.69 (3H, s), 3.55 (2H, s br), 2.45 (4H, s br), 2.13 (3H, s br), 1.76 (4H, s br), 1.62 (3H, s). m/z (ES+, 70V) 454.1 (MH+).

EXAMPLE DDD87761

4-[2-(3,5-Dimethyl-piperazin-1-yl)-pyridin-4-yl]-N-(1,3,5-trimethyl-1H-pyrazol-4-yl)-benzenesulfonamide Prepared from the compound of intermediate 11 (250 mg, 0.66 mmol) and 2,6-dimethylpiperazine (>95% syn isomer, 500 mg, 4.38 mmol) in EtOH (0.75 ml) according to the method of DDD86213 to give the title compound as a white powder (211 mg, 0.46 mmol, 70%). δH (D-6 DMSO, 300K) 9.22 (1H, s), 8.18 (1H, d J 4.0 Hz), 7.97 (2H, d J 7.7 Hz), 7.70 (2H, d J 7.7 Hz), 7.10 (1H, s), 6.95 (1H, s), 4.30 (2H, d J 11.8 Hz), 3.56 (3H, s), 2.76 (2H, s br), 2.26 (2H, t J 11.3 Hz), 1.84 (3H, s), 1.59 (3H, s), 1.04 (6H, d J 4.8 Hz). m/z (ES+, 70V) 455.2 (MH+).

EXAMPLE DDD87763

N-Methyl-4-(2-piperazin-1-yl-pyridin-4-yl)-N-(1,3,5-trimethyl-1H-pyrazol-4-yl)-benzenesulfonamide Prepared from the sulphonamide of Intermediate 18 (250 mg, 0.7 mmol), 2-(1-piperazinyl)pyridine-4-boronic acid pinacol ester (202 mg, 0.7 mmol), tribasic potassium phosphate (148 mg, 0.7 mmol), Pd(PPh$_3$)$_4$ (50 mg, 0.04 mmol) and water (1.0 ml) in oxygen-free DMF (5.0 ml) at 130° C. for 1 h, according to the method of intermediate 11 except with the use of Pd(PPh$_3$)$_4$ as reaction catalyst, to give the title compound as a white solid (148 mg, 0.3 mmol, 48%). δH (CDCl$_3$, 300K) 8.28 (1H, d, J 3.8 Hz), 7.79 (2H, d, J 7.2 Hz), 7.71 (2H, d, J 7.2 Hz), 6.82 (1H, d, J 3.8 Hz), 6.79 (1H, s), 3.69 (3H, s), 3.57-3.61 (4H, m), 3.21 (3H, s), 2.99-3.04 (4H, m), 2.13 (3H, s), 1.55 (3H, s). m/z (ES+, 70V) 441.2 (MH+).

EXAMPLE DDD87764

2'-(4-Methyl-piperazin-1-ylmethyl)-biphenyl-4-sulfonic acid (1,3,5-trimethyl-1H-pyrazol-4-yl)-amide Prepared from the aldehyde of intermediate 17 (150 mg, 0.41 mmol), N-methylpiperazine (136 μl, 123 mg, 1.23 mmol) and sodium triacetoxyborohydride (261 mg, 1.23 mmol) in CHCl$_3$ (10.0 ml) at 50° C. for 24 h according to the method of example DDD86212 to give the title compound as a colourless solid (150 mg, 0.33 mmol, 81%). δH (CDCl$_3$, 300K) 7.75 (2H, d J 8.4 Hz), 7.58 (2H, d J 8.3 Hz), 7.45 (1H, d J 5.9 Hz), 7.39-7.33 (2H, m), 7.22 (1H, dd J 1.6 Hz 7.3 Hz), 5.79 (1H, s br), 3.69 (3H, s), 3.33 (2H, s), 2.42 (4H, s br), 2.31 (3H, s br), 2.11 (3H, s), 1.98 (4H, s br), 1.64 (3H, s). m/z (ES+, 70V) 454.1 (MH+).

EXAMPLE DDD87765

3'-(Benzylamino-methyl)-biphenyl-4-sulfonic acid (1,3,5-trimethyl-1H-pyrazol-4-yl)-amide Prepared from the aldehyde of intermediate 14 (200 mg, 0.54 mmol), benzylamine (176 μl, 173 mg, 1.62 mmol) and sodium triacetoxyborohydride (343 mg, 1.62 mmol) in CHCl$_3$ (12.0 ml) at 50° C. for 24 h according to the method of example DDD86212 to give the title compound as a white solid (105 mg, 0.23 mmol, 42%). δH (CDCl$_3$, 300K) 7.78 (2H, d J 8.4 Hz), 7.69 (2H, d J 8.4 Hz), 7.60 (1H, s br), 7.50 (1H, d J 7.5 Hz), 7.44 (1H, t J 7.5 Hz), 7.40 (1H, d J 7.6 Hz), 7.35 (4H, d J 4.8 Hz), 7.29-7.28 (1H, m), 5.85 (1H, s br), 3.90 (2H, s br), 3.86 (2H, s br), 3.68 (3H, s), 2.08 (3H, s), 1.62 (3H, s). m/z (ES+, 70V) 461.1 (MH+).

EXAMPLE DDD87767

4-(2-[1,4]Diazepan-1-yl-pyridin-4-yl)-N-(1,3,5-trimethyl-1H-pyrazol-4-yl)-benzenesulfonamide Prepared by heating the compound of intermediate 11 (250 mg, 0.66 mmol) and homopiperazine (500 mg, 5.0 mmol) in EtOH (1.0 ml) at 155° C. for 2 h, according to the method of DDD86213 to give the title compound as a white powder (207 mg, 0.47 mmol, 71%). δH (D-6 DMSO, 300K) 8.20 (1H, d J 5.8 Hz), 7.99 (2H, d J 8.5 Hz), 7.75 (2H, d J 8.5 Hz), 6.90 (1H, s), 6.89 (1H, d J 5.8 Hz), 3.80 (2H, t J 6.1 Hz), 3.75 (2H, t J 5.8 Hz), 2.92 (2H, t J 5.2 Hz), 2.72 (2H, t J 5.6 Hz), 1.88 (3H, s), 1.83 (2H, p J 5.6 Hz), 1.63 (3H, s). m/z (ES+, 70V) 441.2 (MH+).

EXAMPLE DDD87768

3'-Piperidin-4-yl-biphenyl-4-sulfonic acid (1,3,5-trimethyl-1H-pyrazol-4-yl)-amide Prepared from the sulphonamide of intermediate 32 (500 mg, 1.28 mmol), 4-(3-bromophenyl)piperidine hydrochloride (425 mg, 1.54 mmol), tribasic potassium phosphate (652 mg, 3.0 mmol), and Pd(dppf)Cl$_2$.DCM (100 mg, 0.12 mmol) in DMF (3.0 ml) and water (0.75 ml), according to the method of intermediate 11, to give the title compound as an off-white powder (350 mg, 0.82 mmol, 64%). δH (D-6

DMSO, 300K) 7.90 (2H, d J 8.4 Hz), 7.71 (2H, d 8.4 Hz), 7.61 (1H, s), 7.58 (1H, d J 7.9 Hz), 7.46 (1H, t J 7.7 Hz), 7.33 (1H, d J 7.7 Hz), 3.58 (3H, s), 3.10-3.07 (2H, m br), 2.70 (1H, tt J 12.1 Hz 3.3 Hz), 2.63 (2H, td 10.8 Hz 1.8 Hz), 1.85 (3H, s), 1.79-1.73 (2H, m br), 1.63 (3H, s), 1.62 (qd J 12.2 Hz 3.8 Hz). m/z (ES$^+$, 70V) 425.2 (MH$^+$).

EXAMPLE DDD87769

2,6-Dichloro-4-[3-(4-methyl-piperazin-1-yl)-propyl] N-(1,3,5-trimethyl-1H-pyrazol-4-yl)-benzenesulfonamide The alkyne of example DDD86469 (65 mg, 0.14 mmol) and 10% w/w palladium on charcoal (13 mg, 20 wt %) in MeOH (7.0 ml) was stirred at rt under for 1.5 h. The mixture was filtered through a celite pad, the filter cake washed with DCM:MeOH (1:1, 2×10 ml), the combined filtrates concentrated in vacuo and subjected to chromatography (4-10% MeOH/DCM) to give the title compound as a white solid (28 mg, 0.059 mmol, 42%). δH (CDCl$_3$, 300K) 7.29 (2H, s), 6.58 (1H, s), 3.66 (3H, s), 2.63 (2H, s br), 2.47 (6H, s), 2.31 (3H, s), 2.16 (3H, s) 1.79 (2H, s br), 1.72 (3H, s), 1.59 (4H, s br). m/z (ES$^+$, 70V) 474.1 (MH$^+$).

EXAMPLE DDD87993

2,6-Dichloro-N-(1,5-dimethyl-1H-pyrazol-4-yl)-4-(2-piperazin-1-yl-pyridin-4-yl)-benzenesulfonamide Prepared from the sulphonamide of intermediate 27 (100 mg, 0.25 mmol), 2-(1-piperazinyl)pyridine-4-boronic acid pinacol ester (80 mg, 0.28 mmol), tribasic potassium phosphate (60 mg, 0.28 mmol), and Pd(PPh$_3$)$_4$ (30 mg, 0.026 mmol) in DMF (1.6 ml) and water (0.6 ml), according to the method of intermediate 11, to give the title compound as a yellow solid (32 mg, 0.07 mmol, 27%). δH (D-6 DMSO, 300K) 8.20 (1H, d J 5.2 Hz), 8.02 (2H, s), 7.20 (1H, s), 7.04 (1H, d J 5.2 Hz), 7.02 (1H, s), 3.64 (3H, s), 3.54 (4H, m), 2.82 (4H, m), 2.06 (3H, s). m/z (ES$^+$, 70V) 481.1 (MH$^+$).

EXAMPLE DDD87994

N-(2-Methyl-pyridin-3-yl)-4-(2-piperazin-1-yl-pyridin-4-yl)-benzenesulfonamide

Prepared from the sulphonamide of intermediate 8 (82 mg, 0.25 mmol), 2-(1-piperazinyl)pyridine-4-boronic acid pinacol ester (80 mg, 0.28 mmol), tribasic potassium phosphate (60 mg, 0.28 mmol), and Pd(PPh$_3$)$_4$ (30 mg, 0.026 mmol) in DMF (1.6 ml) and water (0.6 ml), according to the method of intermediate 11, to give the title compound as a yellow solid (13 mg, 0.03 mmol, 13%). δH (D-6 DMSO, 300K) 8.20 (1H, d J 5.3 Hz), 8.01 (1H, d J 4.2 Hz), 7.90 (2H, d J 8.3 Hz), 7.75 (2H, d J 8.3 Hz), 7.36 (1H, dd J 8.1 Hz 1.1 Hz), 7.11 (1H, s), 7.03 (1H, dd J 8.0 Hz 4.8 Hz), 6.99 (1H, d J 5.2 Hz), 3.62 (4H, m), 2.96 (4H, m), 2.21 (3H, s). m/z (ES$^+$, 70V) 410.2 (MH$^+$).

EXAMPLE DDD87995

N-(1,5-Dimethyl-1H-pyrazol-4-yl)-4-(2-piperazin-1-yl-pyridin-4-yl)-benzenesulfonamide Prepared from the sulphonamide of intermediate 27 (83 mg, 0.25 mmol), 2-(1-piperazinyl)pyridine-4-boronic acid pinacol ester (80 mg, 0.28 mmol), tribasic potassium phosphate (60 mg, 0.28 mmol), and Pd(PPh$_3$)$_4$ (30 mg, 0.026 mmol) in DMF (1.6 ml) and water (0.6 ml), according to the method of intermediate 11, to give the title compound as a yellow solid (22 mg, 0.05 mmol, 21%). δH (D-6 DMSO, 300K) 8.21 (1H, d J 5.2 Hz), 7.96 (2H, d J 8.4 Hz), 7.75 (2H, d 8.4 Hz), 7.09 (1H, s), 6.98 (1H, d J 5.2 Hz), 6.91 (1H, s), 4.13 (1H, s br), 3.63 (3H, s), 3.52 (4H, m), 2.82 (4H, m), 1.92 (3H, s). m/z (ES$^+$, 70V) 413.2 (MH$^+$).

EXAMPLE DDD87997

2,5-Difluoro-4-(2-piperazin-1-yl-pyridin-4-yl)-N-(1,3,5-trimethyl-1H-pyrazol-4-yl)-benzenesulfonamide Prepared from Intermediate 4 (200 mg, 0.5 mmol), 2-(1-piperazinyl)pyridine-4-boronic acid pinacol ester (152 mg, 0.5 mmol), tribasic potassium phosphate (112 mg, 0.5 mmol), Pd(PPh$_3$)$_4$ (45 mg, 0.04 mmol) and water (0.8 ml) in oxygen-free DMF (4.0 ml) at 130° C. for 1 h, according to the method of intermediate 11 except with the use of Pd(PPh$_3$)$_4$ as reaction catalyst, to give the title compound as a white solid (93 mg, 0.2 mmol, 38%). δH (CDCl$_3$, 300K) 8.28 (1H, d J 5.1 Hz), 7.52 (1H, dd J 5.7 Hz 9.1 Hz), 7.34 (1H, dd J 5.6 Hz 9.8 Hz), 6.74-6.70 (2H, m), 3.68 (3H, s), 3.59-3.54 (4H, m), 3.03-2.99 (4H, m), 2.18 (3H, s), 1.81 (3H, s). m/z (ES$^+$, 70V) 463.2 (MH$^+$).

EXAMPLE DDD87999

4-[3-(4-Methyl-piperazin-1-yl)-prop-1-ynyl]-N-(1,3,5-trimethyl-1H-pyrazol-4-yl)-benzenesulfonamide Prepared from the sulphonamide of intermediate 1 (526 mg, 1.53 mmol), 1-methyl-4-prop-2-ynyl-piperazine (253 mg, 1.83 mmol), CuI (15 mg, 0.077 mmol) and Pd(PPh$_3$)$_4$ (89 mg, 0.077 mmol), in DMF (3.0 ml) and NEt$_3$ (2.0 ml) according to the method of intermediate 36, to give the title compound as an off-white solid (390 mg, 0.97 mmol, 64%). δH (CDCl$_3$, 300K) 7.66 (2H, d J 7.2 Hz), 7.47 (2H, d J 7.6 Hz), 5.85 (1H, s br), 3.67 (3H, s), 3.67 (3H, s), 3.58 (2H, s), 2.84 (4H, s br), 2.48 (4H, s br), 2.03 (3H, s br), 1.64 (3H, s br), 1.52 (3H, s). m/z (ES$^+$, 70V) 402.1 (MH$^+$).

EXAMPLE DDD88000

6-[2-(1-Methyl-piperidin-4-yl)-ethylamino]-pyridine-3-sulfonic acid (1,3,5-trimethyl-1H-pyrazol-4-yl)-amide Prepared from the sulphonamide of intermediate 5 (528 mg, 1.8 mmol) and 2-(1-methylpiperidin-4-yl)ethanamine (500 mg, 3.5 mmol) according to method 1 of EXAMPLE 86213, to give the title compound as a white solid (190 mg, 0.5 mmol, 27%). δH (CDCl$_3$, 300K) 8.38 (1H, d, J 2.3 Hz), 7.60 (1H, dd J 2.3 Hz 9.0 Hz), 6.31 (1H, d J 9.0 Hz), 5.80 (1H, s), 4.97 (1H, bs), 3.68 (3H, s), 3.38-3.32 (2H, m), 2.87-2.81 (2H, m), 2.26 (3H, s), 2.12 (3H, s), 1.93-1.85 (2H, m), 1.73 (3H, s), 1.74-1.68 (2H, m), 1.63-1.54 (3H, m), 1.31-1.37 (2H, m). m/z (ES$^+$, 70V) 407.2 (MH$^+$)

EXAMPLE DDD88002

N-(3,5-Dimethyl-isoxazol-4-yl)-4-(2-piperazin-1-yl-pyridin-4-yl)-benzenesulfonamide Prepared from the sulphonamide of intermediate 6 (83 mg, 0.25 mmol), 2-(1-piperazinyl)pyridine-4-boronic acid pinacol ester (80 mg, 0.28 mmol), tribasic potassium phosphate (60 mg, 0.28 mmol), and Pd(PPh$_3$)$_4$ (30 mg, 0.026 mmol) in DMF (1.6 ml) and water (0.4 ml), according to the method of intermediate 11, to give the title compound as a tan coloured solid (11 mg, 0.03 mmol, 11%). δH (D-6 DMSO, 300K) 8.20, (1H, d J 5.3 Hz), 7.99 (2H, d J 8.4 Hz), 7.75 (2H, d J 8.4 Hz), 7.10 (1H, s), 6.98 (1H, dd J 5.2 Hz 1.1 Hz), 3.53 (4H, m), 2.83 (4H, m), 1.93 (3H, m), 1.80 (3H, s). m/z (ES$^+$, 70V) 482.1 (MH$^+$).

EXAMPLE DDD88003

3'-Piperidin-4-yl-biphenyl-4-sulfonic acid (2-methyl-pyridin-3-yl)-amide

Prepared from the sulphonamide of intermediate 33 (230 mg, 0.62 mmol), 4-(3-bromophenyl)piperidine hydrochloride (204 mg, 0.74 mmol), tribasic potassium phosphate (313 mg, 1.48 mmol), and Pd(dppf)Cl$_2$.DCM (50 mg, 0.06 mmol) in DMF (3.0 ml) and water (1.0 ml), according to the method of intermediate 11, to give the title compound as an off-white powder (67 mg, 0.16 mmol, 26%). δH (CDCl$_3$, 300K) 8.35 (1H, dd J 1.3 Hz 4.7 Hz), 7.76 (2H, d J 8.5 Hz), 7.75 (1H, m), 7.43-7.38 (3H, m), 7.28 (1H, m), 7.15 (1H, dd J 4.7 Hz 8.0 Hz), 3.23-3.18 (2H, m), 2.76 (2H, td J 2.1 Hz 12.1 Hz), 2.68 (1H, tt J 3.6 Hz 12.1 Hz), 2.22 (3H, s), 1.89-1.83 (2H, m br), 1.69 (2H, qd J 12.1 Hz 3.9 Hz). m/z (ES$^+$, 70V) 408.2 (MH$^+$).

EXAMPLE DDD88005

3'-Dimethylaminomethyl-biphenyl-4-sulfonic acid (1,3,5-trimethyl-1H-pyrazol-4-yl)-amide Prepared from the aldehyde of intermediate 14 (150 mg, 0.41 mmol), 2M dimethylamine solution in THF (615 ml, 1.23 mmol) and sodium triacetoxyborohydride (261 mg, 1.23 mmol) in CHCl$_3$ (10.0 ml) at 50° C. for 24 h according to the method of example DDD86212 to give the title compound as a white solid (146 mg, 0.37 mmol, 90%). δH (CDCl$_3$, 300K) 7.78 (2H, d J 6.9 Hz), 7.70 (2H, d J 7.5 Hz), 7.60 (1H, s br), 7.49 (1H, d J 6.8 Hz), 7.42 (1H, t J 7.8 Hz), 7.36 (1H, d J 6.7 Hz), 5.81 (1H, s br), 3.68 (3H, s), 3.59 (2H, s), 2.33 (6H, s), 2.08 (3H, s), 1.62 (3H, s). m/z (ES$^+$, 70V) 399.3 (MH$^+$).

EXAMPLE DDD88006

3'-imidazol-1-ylmethyl-biphenyl-4-sulfonic acid (1,3,6-trimethyl-1H-pyrazol-4-yl)-amide Prepared from the boronic ester of intermediate 32 (157 mg, 0.38 mmol), 1-(3-bromobenzyl)-1H-imidazole (114 mg, 0.48 mmol), tribasic potassium phosphate (144 mg, 0.68 mmol), and Pd(PPh$_3$)$_4$ (48 mg, 0.042 mmol) in DMF (1.6 ml) and water (0.4 ml), according to the method of intermediate 11, to give the title compound as a white solid (157 mg, 0.37 mmol, 93%). δH (D-6 DMSO, 300K) 7.84 (3H, m), 7.73-7.60 (4H, m), 7.59 (1H, m), 7.50 (1H, t J 7.7 Hz), 7.30 (1H, d J 7.7 Hz), 7.27 (1H, s), 6.92 (1H, s), 5.28 (2H, s), 3.56 (3H, s), 1.82 (3H, s), 1.59 (3H, s). m/z (ES$^+$, 70V) 422.2 (MH$^+$).

EXAMPLE DDD88007

3,5-Dichloro-3'-diethylaminomethyl-biphenyl-4-sulfonic acid (1,3,5-trimethyl-1H-pyrazol-4-yl)-amide Prepared from the sulphonamide of intermediate 15 (210 mg, 0.52 mmol), diethylamine (0.25 ml), sodium triacetoxyborohydride (220 mg, 1.04 mmol) in chloroform (3.0 ml), according to the method of example DDD85612, to give the title compound as an off-white powder (39 mg, 0.08 mmol, 15%). δH (CDCl$_3$, 300K) 7.65 (2H, s), 7.53 (1H, s), 7.43-7.37 (3H, m), 6.62 (1H, s), 3.64 (3H, s), 3.60 (2H, s), 2.52 (4H, q J 6.8 Hz), 2.14 (3H, s), 1.77 (3H, s), 1.03 (6H, t J 6.8 Hz). m/z (ES$^+$, 70V) 495.1 (MH$^+$).

EXAMPLE DDD88009

3,5-Dichloro-3'-pyrrolidin-1-ylmethyl-biphenyl-4-sulfonic acid (1,3,5-trimethyl-1H-pyrazol-4-yl)-amide Prepared from the sulphonamide of intermediate 15 (210 mg, 0.52 mmol), pyrolidine (0.25 ml) and sodium triacetoxyborohydride (220 mg, 1.04 mmol) in chloroform (3.0 ml), according to the method of example DDD85612, to give the title compound as an off-white powder (172 mg, 0.35 mmol, 67%). δH (CDCl$_3$, 300K) 7.65 (2H, s), 7.52 (1H, s), 7.45-7.37 (3H, m), 6.72 (1H, s br), 3.67 (2H, s), 3.64 (3H, s), 2.50 (4H, s br), 2.12 (3H, s), 1.77 (4H, s br), 1.73 (3H, s). m/z (ES$^+$, 70V) 493.1 (MH$^+$).

EXAMPLE DDD88186

2-Methyl-4-(2-piperazin-1-yl-pyridin-4-yl)-N-(1,3,5-trimethyl-1H-pyrazol-4-yl)-benzenesulfonamide Prepared from the sulphonamide of intermediate 20 (90 mg, 0.25 mmol), 2-(1-piperazinyl)pyridine-4-boronic acid pinacol ester (80 mg, 0.28 mmol), tribasic potassium phosphate (60 mg, 0.28 mmol), and Pd(PPh$_3$)$_4$ (30 mg, 0.026 mmol) in DMF (1.6 ml) and water (0.6 ml), according to the method of intermediate 11, to give the title compound as a yellow solid (47 mg, 0.11 mmol, 43%). δH (D-6 DMSO, 300K) 8.20 (1H, d J 5.1 Hz), 7.84 (1H, s), 7.70 (1H, dd J 8.3 Hz 1.5 Hz), 7.64 (1H, d J 8.3 Hz), 7.10 (1H, s), 6.99 (1H, dd J 5.2 Hz 1.2 Hz), 3.55 (7H, m), 2.87 (4H, m), 2.65 (3H, s), 1.84 (3H, s), 1.58 (3H, s). m/z (ES$^+$, 70V) 441.2 (MH$^+$).

EXAMPLE DDD88187

5'-(4-Methyl-piperazin-1-ylmethyl)-3'-propoxy-biphenyl-4-sulfonic acid (1,3,5-trimethyl-1H-pyrazol-4-yl)-amide Prepared from the aldehyde of intermediate 24 (150 mg, 0.35 mmol), N-methylpiperazine (0.116 ml, 105 mg, 1.05 mmol) and sodium triacetoxyborohydride (223 mg, 1.05 mmol) in CHCl$_3$ (10.0 ml) at 50° C. for 24 h according to the method of example DDD86212 to give the title compound as a white solid (143 mg, 0.28 mmol, 80%). δH (CDCl$_3$, 300K) 7.76 (2H, d J 8.4 Hz), 7.67 (2H, d J 8.4 Hz), 7.13 (1H, s br), 7.00 (1H, s br), 6.95 (1H, s br), 5.74 (1H, s br), 3.98 (2H, t J 6.6 Hz), 3.68 (3H, s), 3.54 (2H, s), 2.49 (4H, s br), 2.30 (3H, s), 2.09 (3H, s), 1.84 (2H, m), 1.60 (7H, s), 1.07 (3H, t J 7.4 Hz). m/z (ES$^+$, 70V) 512.2 (MH$^+$).

EXAMPLE DDD88188

2-Fluoro-4-(2-piperazin-1-yl-pyridin-4-yl)-N-(1,3,5-trimethyl-1H-pyrazol-4-yl)-benzenesulfonamide Prepared from the sulphonamide of intermediate 10 (91 mg, 0.25 mmol), 2-(1-piperazinyl)pyridine-4-boronic acid pinacol ester (80 mg, 0.28 mmol), tribasic potassium phosphate (60 mg, 0.28 mmol), and Pd(PPh$_3$)$_4$ (30 mg, 0.026 mmol) in DMF (1.6 ml) and water (0.6 ml), according to the method of intermediate 11, to give the title compound as a pale yellow solid (25 mg, 0.056 mmol, 22%). δH (D-6 DMSO, 300K) 8.03 (1H, m), 7.57 (2H, m), 7.46 (1H, d J 7.7 Hz), 6.90 (1H, s), 6.81 (1H, m), 3.46 (3H, s), 3.43 (4H, m), 2.78 (4H, m), 1.86 (3H, s), 1.65 (3H, s). m/z (ES$^+$, 70V) 445.2 (MH$^+$)

EXAMPLE DDD88189

3'-Piperidin-4-yl-biphenyl-4-sulfonic acid (3,5-dimethyl-isoxazol-4-yl)-amide Prepared from the sulphonamide of intermediate 34 (151 mg, 0.4 mmol), 4-(3-bromophenyl)piperidine hydrochloride (133 mg, 0.48 mmol), tribasic potassium phosphate (144 mg, 0.68 mmol), and Pd(PPh$_3$)$_4$ (48 mg, 0.042 mmol) in DMF (3.2 ml) and water (0.8 ml), according to the method of intermediate 11, to give the title compound as a white solid (19 mg, 0.046 mmol, 12%). δH (D-6 DMSO, 300K) 7.00, (4H, s), 6.76 (1H, s), 6.74 (1H, d J 7.7 Hz), 6.64 (1H, t J 6.6 Hz), 6.53 (1H, d J 6.9 Hz), 2.46 (2H, d 12.0 Hz), 2.05 (3H, m), 1.25 (1H, s), 1.19 (3H, s), 1.15 (2H, m), 1.10 (3H, s), 0.99 (2H, q, J 12.2 Hz). m/z (ES$^+$, 70V) 412.2 (MH$^+$).

EXAMPLE DDD88191

4-[3-(4-Methyl-piperazin-1-yl)-propyl]N-(1,3,5-trimethyl-1H-pyrazol-4-yl)-benzenesulfonamide Prepared from the alkyne of example DDD87999 (345 mg, 0.86 mmol) and 10% w/w palladium on charcoal (70 mg, 20 wt %) in MeOH (40 mL) for 2 h according to the method of example DDD00087769 to give the title compound as a pale yellow solid (170 mg, 0.42 mmol, 49%). δH (CDCl$_3$, 300K) 7.63 (2H, d J 8.3 Hz), 7.27-7.26 (2H, m), 5.72 (1H, s br), 3.67 (3H, s), 2.71 (6H, t J 7.4 Hz), 2.44 (6H, m), 2.08 (3H, s), 1.85 (2H, s br), 1.53 (6H, s), m/z (ES$^+$, 70V) 406.2 (MH$^+$).

EXAMPLE DDD00088193

2,6-Dichloro-N-methyl-4-(2-piperazin-1-yl-pyridin-4-yl)-N-(1,3,5-trimethyl-1H-pyrazol-4-yl)-benzenesulfonamide Prepared from the sulphonamide of Intermediate 19 (225 mg, 0.5 mmol), 2-(1-piperazinyl)pyridine-4-boronic acid pinacol ester (153 mg, 0.5 mmol), tribasic potassium phosphate (112 mg, 0.5 mmol), Pd(PPh$_3$)$_4$ (30 mg, 0.03 mmol) and water (0.5 ml) in oxygen-free DMF (3.0 ml) at 120° C. for 20 min, according to the method of intermediate 11, to give the title compound as a white solid (173 mg, 0.3 mmol, 64%). δH (D-6 DMSO, 300K) 9.23 (2H, s br), 8.27 (1H, d J 5.3 Hz), 8.15 (2H, s), 7.42 (1H, s), 7.27 (1H, d J 5.3 Hz), 3.95-3.89 (4H, m br), 3.60 (3H, s), 3.36 (3H, s), 3.25-3.19 (4H, m br), 1.97 (3H, s), 1.76 (3H, s). m/z (ES$^+$, 70V) 509.1 (MH$^+$).

EXAMPLE DDD88194

3'-Isopropoxy-5'-(4-methyl-piperazin-1-ylmethyl)-biphenyl-4-sulfonic acid (1,3,5-trimethyl-1H-pyrazol-4-yl)-amide Prepared from the aldehyde of intermediate 25 (150 mg, 0.35 mmol), N-methylpiperazine (0.116 ml, 105 mg, 1.05 mmol) and sodium triacetoxyborohydride (223 mg, 1.05 mmol) in CHCl$_3$ (10.0 ml) at 50° C. for 24 h according to the method of example DDD86212 to give the title compound as a colourless solid (120 mg, 0.23 mmol, 67%). δH (CDCl$_3$, 300K) 7.76 (2H, d J 6.9 Hz), 7.66 (2H, d J 7.5 Hz), 7.11 (1H, s br), 6.99 (1H, s br), 6.94 (1H, s br), 5.75 (1H, s br), 4.64 (1H, s br), 3.68 (3H, s), 3.54 (2H, s), 2.49 (4H, s), 2.31 (3H, s), 2.09 (3H, s), 1.66 (4H, m), 1.61 (3H, s), 1.37 (6H, d J 5.0 Hz). m/z (ES$^+$, 70V) 512.2 (MH$^+$).

EXAMPLE DDD88195

3'-Diethylaminomethyl-biphenyl-4-sulfonic acid methyl-(1,3,5-trimethyl-1H-pyrazol-4-yl)-amide Prepared from the sulphonamide of intermediate 22 (85 mg, 0.2 mmol), diethylamine (49 mg, 0.7 mmol) and sodium triacetoxyborohydride (141 mg, 0.7 mmol) in CHCl$_3$ (4 ml), according to the method of Example DDD86212 to give the title compound as a white powder (19 mg, 0.043 mmol, 22%). δH (D-6 DMSO, 300K) 9.91 (1H, s br), 8.06 (1H, s), 8.00 (2H, d J 8.5 Hz), 7.89-7.86 (1H, m), 7.81 (2H, d J 8.5 Hz), 7.66-7.61 (2H, m), 4.41 (2H, d J 5.6 Hz), 3.62 (3H, s), 3.16 (3H, s), 3.17-3.08 (3H, m), 1.92 (3H, s), 1.59 (3H, s), 1.28 (6H, t J 7.3 Hz). m/z (ES$^+$, 70V) 441.2 (MH$^+$).

EXAMPLE DDD88196

3'-(4-Methyl-piperazin-1-ylmethyl)-biphenyl-4-sulfonic acid methyl-(1,3,5-trimethyl-1H-pyrazol-4-yl)-amide Prepared from the sulphonamide of intermediate 22 (85 mg, 0.2 mmol), N-methylpiperazine (67 mg, 0.7 mmol) and sodium triacetoxyborohydride (141 mg, 0.7 mmol) in CHCl$_3$ (4 ml), according to the method of Example DDD86212 to give the title compound as a white powder (65 mg, 0.14 mmol, 69%). δH (D-6 DMSO, 300K) 8.13 (1H, s br), 8.02 (2H, d J 7.4 Hz), 7.89-7.84 (1H, m br), 7.79 (2H, d J 7.4 Hz), 7.69 (1H, s br), 7.62 (1H, s br), 4.57-4.34 (2H, m br), 3.62 (3H, s), 3.74-3.56 (4H, m br), 3.52-3.27 (4H, m br), 3.16 (3H, s), 2.83 (3H, s br), 1.91 (3H, s), 1.60 (3H, s). m/z (ES$^+$, 70V) 468.2 (MH$^+$).

EXAMPLE DDD86469

2,6-Dichloro-4-[3-(4-methyl-piperazin-1-yl)-prop-1-ynyl]-N-(1,3,5-trimethyl-1H-pyrazol-4-yl)-benzenesulfonamide Prepared from the sulphonamide of intermediate 19 (1.3 g, 3.06 mmol), 4-(propyn-3-yl)-1-methyl piperazine (1.05 g, 7.61 mmol), CuI (50 mg, 0.26 mmol) and Pd(PPh$_3$)$_4$ (100 mg, 0.08 mmol), in DMF (15 ml) and NEt$_3$ (8 ml) according to the method of intermediate 36, to give the title compound as a white solid (1.25 g, 2.66 mmol, 87%). δH (CDCl3, 300K) 7.43 (2H, s), 3.67 (3H, s), 3.54 (2H, s), 3.40 (3H, s), 2.73-2.60 (4H, s br), 2.59-2.42 (4H, s br), 2.32 (3H, s), 2.06 (3H, s), 1.83 (3H, s). m/z (ES$^+$, 70V) 470.2 (MH$^+$).

EXAMPLE DDD99837

N-(3-isobutyl-1,5-dimethyl-1H-pyrazol-4-yl)-4-(3-(1-methylpiperidin-4-yl)propyl)benzenesulfonamide Prepared from 4-allyl-1-methylpiperidine (2.18 g, 15.6 mmol) and the compound of intermediate 41 (2.0 g, 5.2 mmol) according to the method of compound DDD100096 to give the title compound as a white powder (1.84 g, 4.12 mmol, 79%). δH (CDCl₃, 300K), 7.55 (2H, d J 7.9 Hz), 7.19 (2H, d J 7.9 Hz), 5.80 (1H, br s), 3.61 (3H, s), 2.76 (2H, m), 2.58 (2H, t J 7.7 Hz), 2.19 (3H, s), 2.01 (3H, s), 1.80 (3H, m), 1.62-1.51 (m, 4H), 1.22-1.11 (4H, m), 0.64 (6H, d J 6.25 Hz). m/z (ES⁺, 70V) 446.2 (MH⁺).

EXAMPLE DDD100096

2,6-Dichloro-N-(difluoromethyl)-4-(3-(piperidin-4-yl)propyl)-N-(1,3,5-trimethyl-1H-pyrazol-4-yl)benzenesulfonamide hydrochloride salt Prototypical Procedure for Coupling of an Aryl Bromide with a 9BBN-Derived Trialkylborane Under Suzuki-Miyaura Conditions;

A solution of tert-butyl 4-allylpiperidine-1-carboxylate (293 mg, 1.29 mmol, prepared according to the methods cited by Billote, S. *Synlett.*, 1998, 4, 379-380) in 1.0 ml of THF, under argon at rt, was treated dropwise with 9-BBN (0.5M in THF; 2.6 ml, 1.3 mmol). The reaction was then heated in a microwave for 30 min at 90° C. The resulting solution was then transferred via cannula into a stirred mixture of the compound of intermediate 40 (300 mg, 0.645 mmol) and potassium phosphate (272 mg, 1.28 mmol) in DMF (2.5 ml) and water (0.75 ml) under argon. After bubbling argon through the reaction for 5 min at rt Pd(PPh₃)₄ (20 mg) was added, the reaction vessel sealed and then heated in a microwave at 60° C. for 30 min. The reaction mixture was then concentrated in vacuo, diluted with DCM (50 ml) and aqueous ammonia solution (50 ml), the organic phase separated, washed with brine (2×25 ml), dried (MgSO₄) and concentrated in vacuo. Chromatography (SiO₂, 4:6 EtOAc:hexanes) gave tert-butyl 4-(3-(3,5-dichloro-4-(N-(difluoromethyl)-N-(1,3,5-trimethyl-1H-pyrazol-4-yl)sulfamoyl)phenyl)propyl)piperidine-1-carboxylate as a colourless gum. The above named compound in DCM (10 ml) was treated with trifluoroacetic acid (1 ml), stirred at rt for 1 h then concentrated in vacuo. The residual gum was diluted with DCM (25 ml) and aqueous ammonia (25 ml), the organic phase separated, dried (MgSO4) and concentrated. Dilution with DCM (10 ml), treatment with HCl (1M in diethyl ether, 2 ml) followed by filtration under a stream of argon gave the title compound as a white hygroscopic powder (210 mg, 0.385 mmol, 60%). δH (D₂O, 300K) 7.29 (1H, t J 60.0 Hz), 7.22 (2H, s), 3.40 (3H, s), 3.13 (2H, d J 13.2 Hz), 2.68 (2H, t J 11.7 Hz), 2.36 (2H, s br), 1.66 (3H, s), 1.61-0.95 (9H, complex), 1.46 (3H, s). m/z (ES⁺, 70V) 509.2 (MH⁺).

EXAMPLE DDD100097

2,6-dichloro-N-(difluoromethyl)-4-(3-(1-methylpiperidin-4-yl)propyl)-N-(1,3,5-trimethyl-1H-pyrazol-4-yl)benzenesulfonamide Prepared from 4-allyl-1-methylpiperidine (776 mg, 5.54 mmol) and the compound of intermediate 40 (2.5 g, 5.4 mmol) according to the method of compound DDD100096 to give the title compound as a white powder (2.41 g, 4.6 mmol, 85%), δH (D-6 DMSO 300K) 7.36 (1H, t J 59.6 Hz), 7.58 (2H, s), 3.64 (3H, s), 3.35 (2H, dm), 3.2-3.0 (1H, m br), 2.86 (2H, m), 2.69 (2H, m), 2.66 (2H, t J 7.5 Hz), 1.88 (3H, s), 1.83 (3H, m), 1.66 (3H, s), 1.65-1.57 (2H, m), 1.50-1.39 (2H, m), 1.24-1.17 (2H, m). m/z (ES⁺, 70V) 523.2 (MH⁺).

EXAMPLE DDD100144

2,6-dichloro-N-(difluoromethyl)-4-(4-(1-methylpiperidin-4-yl)butyl)-N-(1,3,5-trimethyl-1H-pyrazol-4-yl)benzenesulfonamide Prepared from 4-(but-3-enyl)-1-methylpiperidine (320 mg, 2.14 mmol) and the compound of intermediate 40 (500 mg, 1.08 mmol) according to the method of compound DDD100096 to give the title compound as a white powder (197 mg, 34%), δH (D-6 DMSO 500K) 10.06 (1H, bs); 7.69 (1H, t, J 60 Hz); 7.61 (2H, s); 3.64 (3H, s); 3.36 (2H, m); 2.80 (5H, m); 2.65 (2H, m); 1.88 (3H, s); 1.79 (2H, m); 1.59 (3H, s); 1.57 (2H, m); 1.32 (7H, m). m/z (ES⁺, 70V) 537.2 (MH⁺).

EXAMPLE DDD100153

2,6-dichloro-4-(3-(1-methylpiperidin-4-yl)propyl)-N-(2,2,2-trifluoroethyl)-N-(1,3,5-trimethyl-1H-pyrazol-4-yl)benzenesulfonamide Prepared from 4-allyl-1-methylpiperidine (448 mg, 3.2 mmol) and the compound of intermediate 47 (790 mg, 1.6 mmol) according to the method of DDD100096 to give the title compound as a colourless oil (784 mg, 1.41 mmol, 88%). δH (CDCl₃, 300K) 7.20 (2H, s), 4.87-4.73 (1H, m), 3.94-3.67 (1H, m), 3.67 (3H, s), 3.29 (2H, brd, J=7.3 Hz), 2.63-2.52 (5H, m), 2.40 (2H, brs), 2.18 (3H, s), 1.79 (4H, brd, J=13.5 Hz), 1.61 (3H, s), 1.56 (1H, brs), 1.34-1.29 (4H, m). m/z (ES⁺, 70V) 555.1 (MH⁺).

EXAMPLE DDD100798

N-(3-isobutyl-1,5-dimethyl-1H-pyrazol-4-yl)-4-(2,3,4,5-tetrahydro-1H-benzo[c]azepin-8-yl)benzenesulfonamide Hydrochloride Prepared from the boronic ester of intermediate 42 (321 mg, 0.71 mmol), 8-Bromo-2,3,4,5-tetrahydro-1H-2-benzazepine (160 mg, 0.71 mmol, prepared according to the methods cited by H. Stark et al, Chem Bio Chem, 2004, 5, 508-518 and G. L. Grunewald et al, Bioorg. Med. Chem., 9, 2001, 1957-1965), tribasic potassium phosphate (150 mg, 0.71 mmol), and Pd(PPh₃)₄ (30 mg, 0.026 mmol) in DMF (5 ml) and water (1.5 ml), according to the method of intermediate 11, Dilution with DCM (10 ml), treatment with HCl (1M in diethyl ether, 2 ml) followed by evaporation, trituration with ether and filtration under a stream of argon gave the title compound as a white hygroscopic powder (300 mg, 0.61 mmol, 87%). δH (D-6 DMSO, 500K) 9.15 (1H, s), 9.04 (1H, bs), 7.87 (2H, d J 8.6 Hz), 7.85 (1H, d J 1.9 Hz), 7.72 (2H, d J 8.6 Hz), 7.68 (1H, dd J 7.9 Hz 1.9 Hz), 7.41 (1H, d J 7.9 Hz), 4.41 (2H, m), 3.56 (3H, s), 3.37 (2H, m), 3.04 (2H, m), 1.90 (4H, m), 1.77 (3H, s), 1.72 (1H, m), 1.70 (6H, d J 6.6 Hz). m/z (ES⁺, 70V) 453.3 (MH⁺).

EXAMPLE 100868

N-(3-isobutyl-1,5-dimethyl-1H-pyrazol-4-yl)-4-(2-methyl-2,3,4,5-tetrahydro-1H-benzo[c]azepin-8-yl)benzenesulfonamide Hydrochloride The amine of Example DDD100798 (150 mg, 0.31 mmol) was taken up in formic acid (10 ml) and paraformaldehyde (92 mg, 3.10 mmol) added. The reaction mixture was heated at 85° C. for 18 h then allowed to cool and concentrated to dryness. The residue was basified with aqueous ammonia solution (20 ml), extracted with DCM (20 ml) and the organics concentrated in vacuo to give a gum which was subjected to chromatography (SiO$_2$, 94:5:1 DCM:MeOH: saturated aqueous ammonia solution). Dilution with DCM (10 ml), treatment with HCl (1M in diethyl ether, 2 ml) followed by evaporation, trituration with ether and filtration under a stream of argon gave the title compound as a white hygroscopic powder (60 mg, 0.12 mmol, 39%). δH (D$_2$O, 500K) 7.81 (2H, m), 7.77 (2H, m), 7.68 (2H, m), 7.42 (1H, m), 4.56 (1H, m), 3.71 (1H, m), 3.69 (3H, s), 3.51 (1H, m), 3.08 (2H, m), 2.88 (3H, bs), 2.15 (1H, m), 1.98 (3H, s), 1.95 (1H, m), 1.89 (2H, m), 1.64 (1H, m), 0.67 (6H, d J 6.7 Hz). m/z (ES$^+$, 70V) 467.3 (MH$^+$).

Biological Data

TABLE 1

Enzyme and Cellular Activity of N-Myristoyltransferase Inhibitors

Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activities are for inhibition of *T. brucei brucei* (blood stream form, variant 221).

| Reference Number | STRUCTURE | IC$_{50}$ (μM) NMT Enzyme | ED$_{50}$ (μM) T. brucei | MH+ |
|---|---|---|---|---|
| DDD16771 | 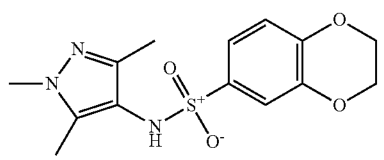 [SMILES: Cc1nn(C)c(C)c1N[S+](=O)([O-])c1ccc2c(c1)OCCO2] | 4.0 | >1 | 324.1 |
| DDD22988 | 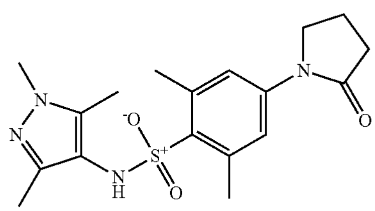 | 8.3 | >1 | 377.2 |
| DDD48025 | 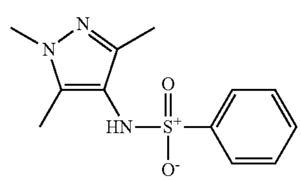 [SMILES: Cc1nn(C)c(C)c1N[S+](=O)([O-])c1ccccc1] | 11.8 | >1 | 266.1 |
| DDD60006 | 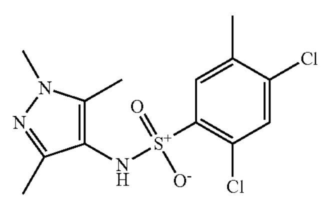 [SMILES: Cc1cc([S+](=O)([O-])Nc2c(C)nn(C)c2C)c(Cl)cc1Cl] | 16.4 | >1 | 349.1 |
| DDD61393 | 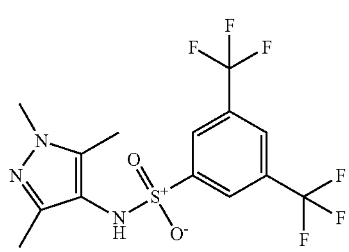 [SMILES: Cc1nn(C)c(C)c1N[S+](=O)([O-])c1cc(C(F)(F)F)cc(C(F)(F)F)c1] | 15.0 | >1 | 401.2 |
| DDD61495 | 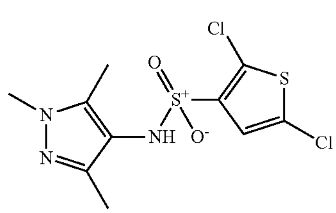 [SMILES: Cc1nn(C)c(C)c1N[S+](=O)([O-])c1cc(Cl)sc1Cl] | 6.4 | >1 | 340.1 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD64558 | 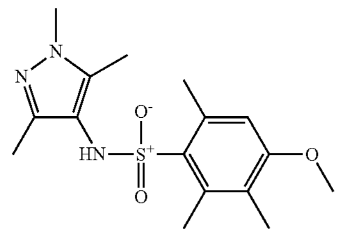 | 2.1<br>20.0 (HuNMT-1) | 21.1 | 338.1 |
| DDD64750 | 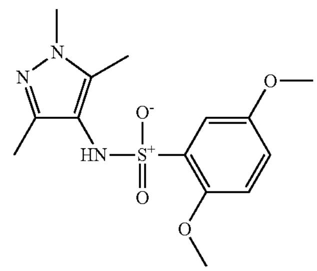 | 30.0 | >1 | 326.1 |
| DDD64780 | 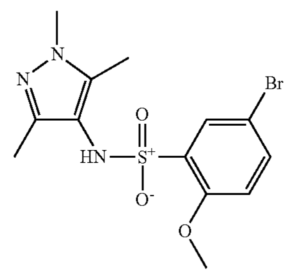 [SMILES: COc1ccc(Br)cc1[S+](=O)([O-])Nc1c(C)nn(C)c1C] | 30.0 | >1 | 338.2 |
| DDD71230 | 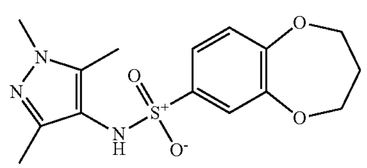 [SMILES: Cc1nn(C)c(C)c1N[S+](=O)([O-])c1ccc2c(c1)OCCCO2] | 3.5 | >1 | 338.2 |
| DDD71231 | 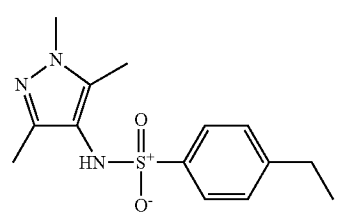 | 4.6 | >1 | 293.1 |
| DDD71232 | 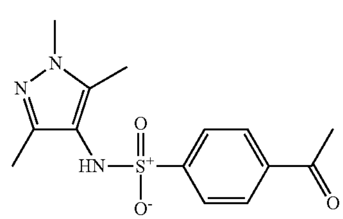 [SMILES: CC(=O)c1ccc([S+](=O)([O-])Nc2c(C)nn(C)c2C)cc1] | 42.0 | >1 | 308.1 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD71233 | 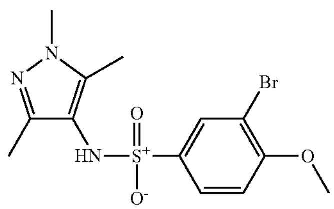 | 2.6 | >1 | 374.2 |
| DDD71234 | 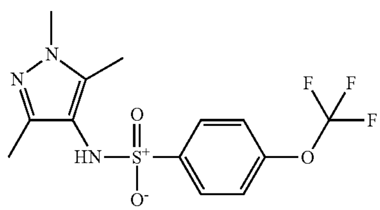 [SMILES: Cc1nn(C)c(C)c1N[S+](=O)([O-])c1ccc(OC(F)(F)F)cc1] | 2.7 | >1 | 350.1 |
| DDD71235 | 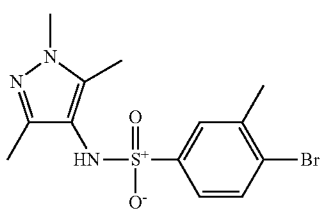 [SMILES: Cc1cc([S+](=O)([O-])Nc2c(C)nn(C)c2C)ccc1Br] | 5.4 | >1 | 359.1 |
| DDD71237 | 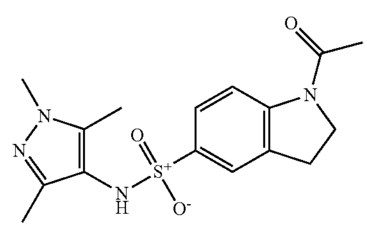 [SMILES: CC(=O)N1CCc2cc([S+](=O)([O-])Nc3c(C)nn(C)c3C)ccc21] | 8.8 | >1 | 349.2 |
| DDD71238 | 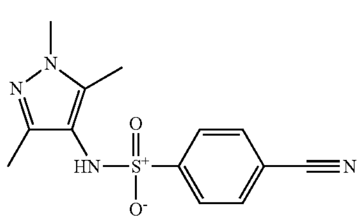 [SMILES: Cc1nn(C)c(C)c1N[S+](=O)([O-])c1ccc(C#N)cc1] | 32.6 | >1 | 291.2 |
| DDD71239 | 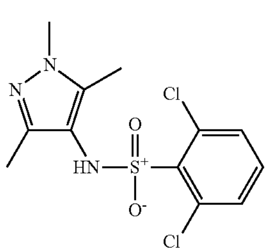 [SMILES: Cc1nn(C)c(C)c1N[S+](=O)([O-])c1c(Cl)cccc1Cl] | 1.0 | 23.2 | 335.1 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT)
enzyme inhibition data are given in parentheses. Cellular activitites are for inhibition of *T. brucei brucei* (blood stream form, variant 221).

| Reference Number | STRUCTURE | IC$_{50}$ (µM) NMT Enzyme | ED$_{50}$ (µM) *T. brucei* | MH+ |
|---|---|---|---|---|
| DDD71240 | 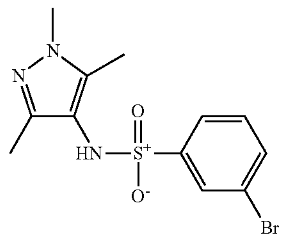 [SMILES: Cc1nn(C)c(C)c1N[S+](=O)([O-])c1cccc(Br)c1] | 8.0 | >1 | 344.1 |
| DDD71241 | 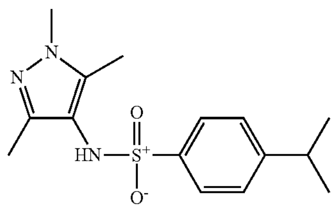 [SMILES: Cc1nn(C)c(C)c1N[S+](=O)([O-])c1ccc(C(C)C)cc1] | 1.5 | >1 | 308.2 |
| DDD71242 | 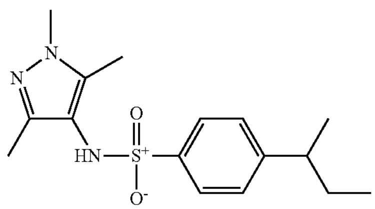 [SMILES: CCC(C)c1ccc([S+](=O)([O-])Nc2c(C)nn(C)c2C)cc1] | 4.3 | >1 | 322.2 |
| DDD71243 | 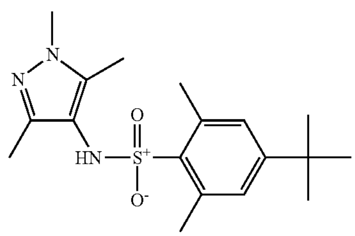 [SMILES: Cc1cc(C(C)(C)C)cc(C)c1[S+](=O)([O-])Nc1c(C)nn(C)c1C] | 0.50 | 5.8 | 350.2 |
| DDD71244 | 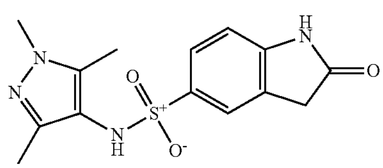 [SMILES: Cc1nn(C)c(C)c1N[S+](=O)([O-])c1ccc2c(c1)CC(=O)N2] | 15.9 | >1 | 321.2 |
| DDD71245 | 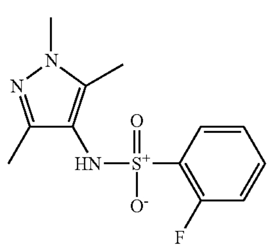 [SMILES: Cc1nn(C)c(C)c1N[S+](=O)([O-])c1ccccc1F] | 5.6 | >1 | 284.1 |
| DDD71246 | 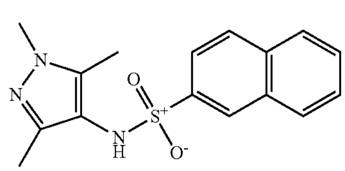 [SMILES: Cc1nn(C)c(C)c1N[S+](=O)([O-])c1ccc2ccccc2c1] | 8.4 | >1 | 316.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD71247 | 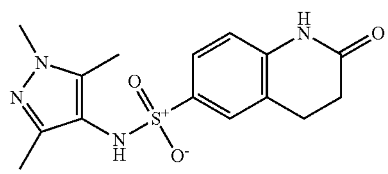 [SMILES: Cc1nn(C)c(C)c1N[S+](=O)([O-])c1ccc2c(c1)CCC(=O)N2] | 3.4 | >1 | 335.1 |
| DDD71248 | 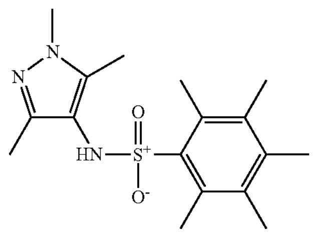 | 62.5 | >1 | 336.2 |
| DDD71250 | 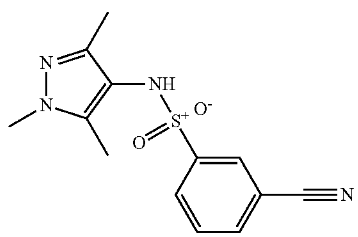 | 28.1 | >1 | 291.2 |
| DDD71251 | 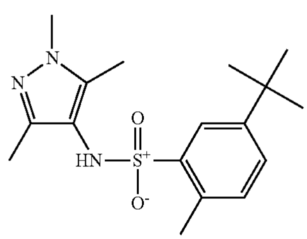 [SMILES: Cc1ccc(C(C)(C)C)cc1[S+](=O)([O-])Nc1c(C)nn(C)c1C] | >100 | >1 | 336.1 |
| DDD71252 | 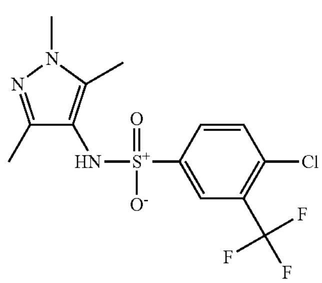 [SMILES: Cc1nn(C)c(C)c1N[S+](=O)([O-])c1ccc(Cl)c(C(F)(F)F)c1] | 17.4 | >1 | 368.2 |
| DDD71253 | 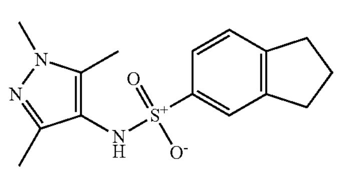 [SMILES: Cc1nn(C)c(C)c1N[S+](=O)([O-])c1ccc2c(c1)CCC2] | 5.6 | >1 | 306.1 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (µM) NMT Enzyme | $ED_{50}$ (µM) *T. brucei* | MH+ |
|---|---|---|---|---|
| DDD71274 | 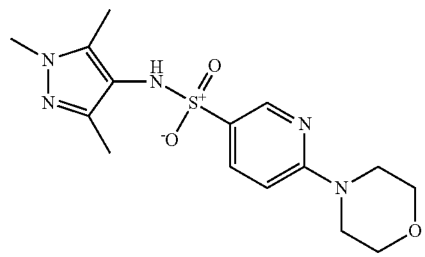 | 2.0 | >1 | 352.2 |
| DDD71275 | 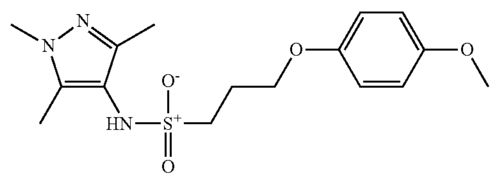 | 62.0 | >1 | 354.2 |
| DDD71276 | 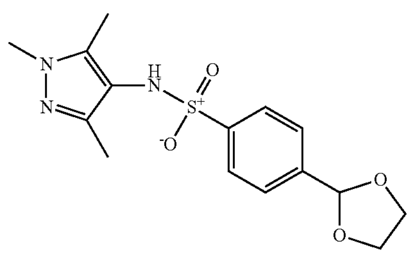 | 9.5 | >1 | 338.2 |
| DDD71277 | 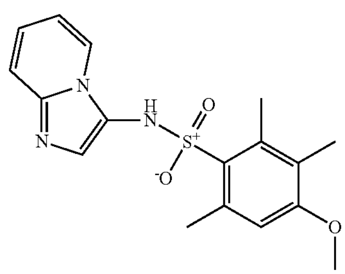 | 95.0 | >1 | 346.1 |
| DDD71278 | 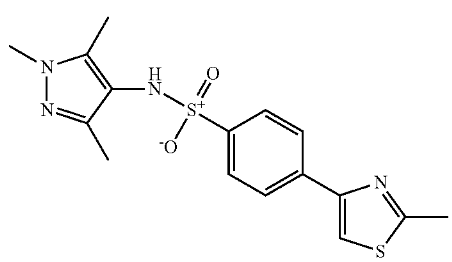 | 12.1 | >1 | 363.2 |
| DDD71279 | 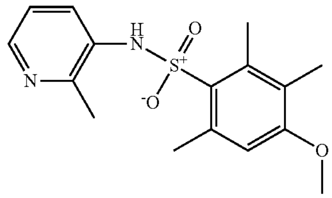 | 10.0<br>70.0 (HuNMT-1) | >1 | 321.1 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | IC$_{50}$ (μM) NMT Enzyme | ED$_{50}$ (μM) *T. brucei* | MH+ |
|---|---|---|---|---|
| DDD71280 | 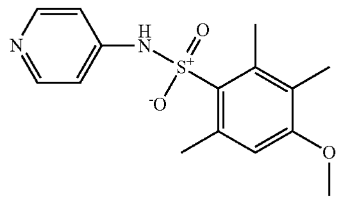 | >100 | >1 | 307.1 |
| DDD71281 | 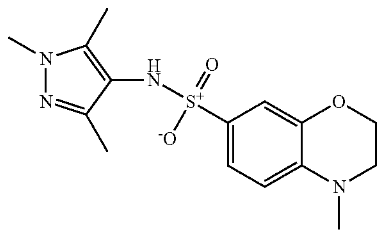 | 16.1 | >1 | 337.2 |
| DDD71282 | 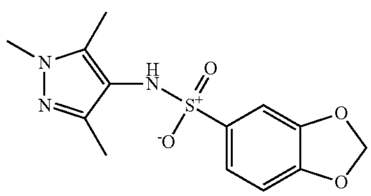 | 4.0 | >1 | 310.2 |
| DDD71283 | 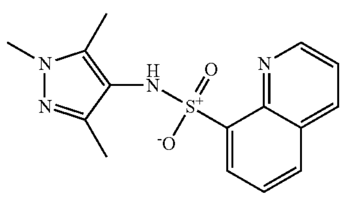 | 7.4 | >1 | 317.1 |
| DDD71284 | 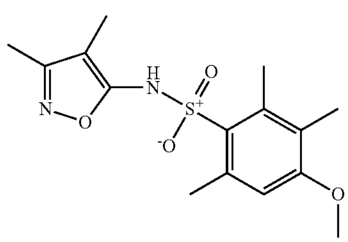 | >100 | >1 | 325.2 |
| DDD71285 | 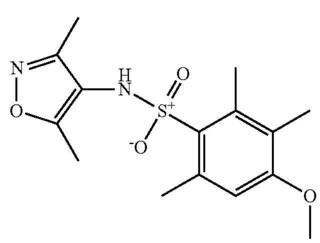 | 19.3 | >1 | 325.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (µM) NMT Enzyme | $ED_{50}$ (µM) *T. brucei* | MH+ |
|---|---|---|---|---|
| DDD71286 | 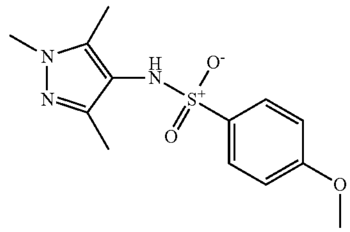 | 9.8 | >1 | 296.1 |
| DDD71287 | 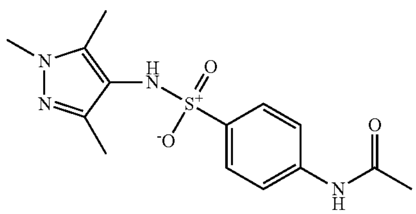 | 2.8 | >1 | 323.1 |
| DDD71288 | 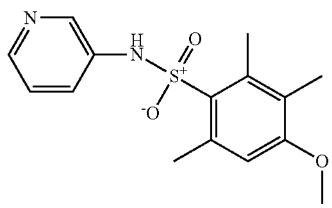 | >100 | >1 | 307.2 |
| DDD71290 | 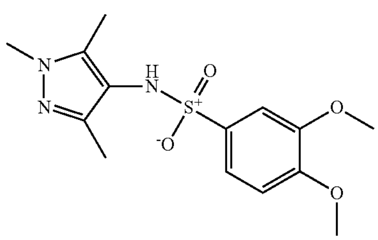 | 41.0 | >1 | 326.1 |
| DDD71291 | 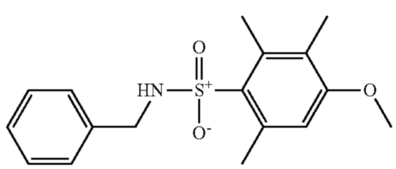 [SMILES: COc1cc(C)c([S+](=O)([O-])NCc2ccccc2)c(C)c1C] | >100 | >1 | 320.2 |
| DDD71292 | 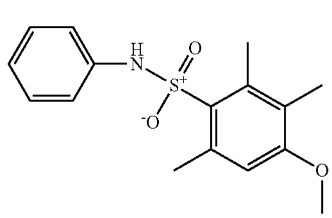 | >100 | >1 | 306.1 |
| DDD71293 | 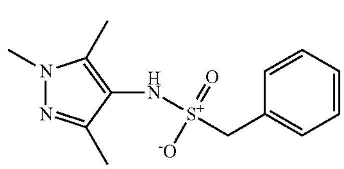 | >100 | >1 | 280.1 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD71294 | 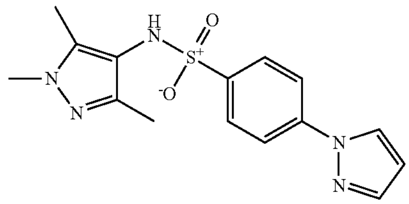 | 4.8 | >1 | 332.1 |
| DDD71295 | 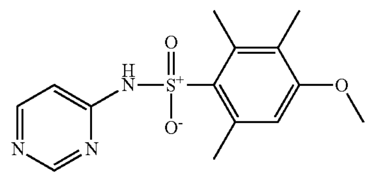 [SMILES: COc1cc(C)c([S+](=O)([O-])Nc2ccncn2)c(C)c1C] | 30.0 | >1 | 308.1 |
| DDD71296 | 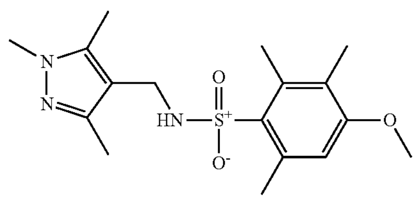 | >100 | >1 | 352.2 |
| DDD71297 | 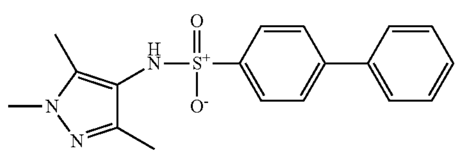 [SMILES: Cc1nn(C)c(C)c1N[S+](=O)([O-])c1ccc(-c2ccccc2)cc1] | 10.5 | >1 | 342.1 |
| DDD71590 | 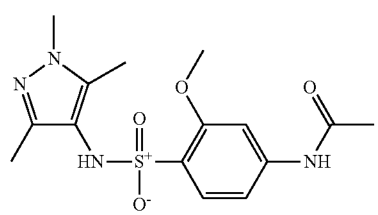 [SMILES: COc1cc(NC(C)=O)ccc1[S+](=O)([O-])Nc1c(C)nn(C)c1C] | 62.0 | >1 | 352.1 |
| DDD71593 | 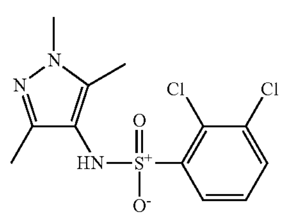 [SMILES: Cc1nn(C)c(C)c1N[S+](=O)([O-])c1cccc(Cl)c1Cl] | 3.2 | >1 | 335.1 |
| DDD00071594 | 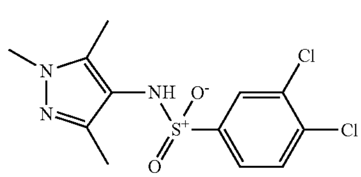 [SMILES: Cc1nn(C)c(C)c1N[S+](=O)([O-])c1ccc(Cl)c(Cl)c1] | 9.9 | >1 | 334.1 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activities are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD71600 | 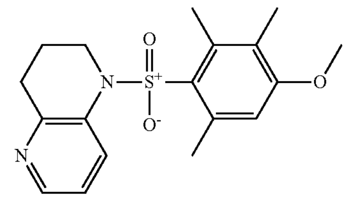 [SMILES: COc1cc(C)c([S+](=O)([O-])N2CCCc3ncccc32)c(C)c1C] | 51.0 | >1 | 347.2 |
| DDD71601 | 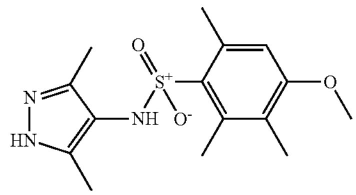 [SMILES: COc1cc(C)c([S+](=O)([O-])Nc2c(C)n[nH]c2C)c(C)c1C] | >100 | >1 | 324.2 |
| DDD71607 | 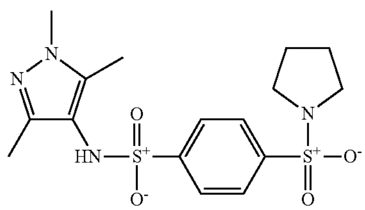 [SMILES: Cc1nn(C)c(C)c1N[S+](=O)([O-])c1ccc([S+](=O)([O-])N2CCCC2)cc1] | >100 | >1 | 399.2 |
| DDD71608 | 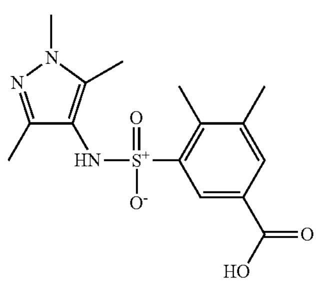 [SMILES: Cc1cc(C(=O)O)cc([S+](=O)([O-])Nc2c(C)nn(C)c2C)c1C] | >100 | >1 | 338.1 |
| DDD71622 | 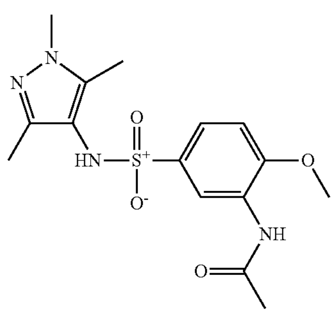 | 41.0 | >1 | 353.1 |
| DDD71623 | 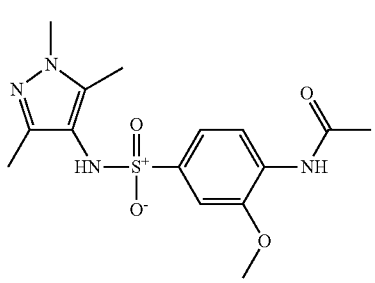 [SMILES: COc1cc([S+](=O)([O-])Nc2c(C)nn(C)c2C)ccc1NC(C)=O] | 42.0 | >1 | 353.1 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD71630 | 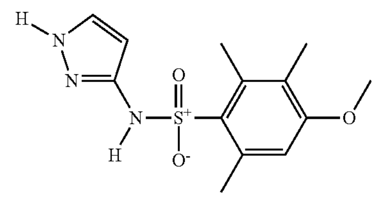 [SMILES: COc1cc(C)c([S+](=O)([O-])Nc2cc[nH]n2)c(C)c1C] | >100 | >1 | 296.1 |
| DDD71637 | 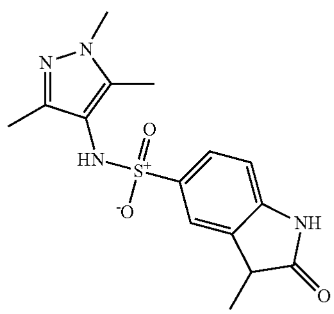 | 11.7 | >1 | 335.2 |
| DDD71644 | 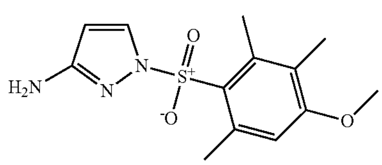 | >100 | >1 | 296.1 |
| DDD71645 | 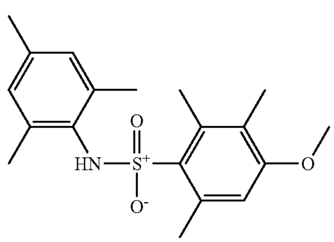 | >100 | >1 | 348.5 |
| DDD73219 | 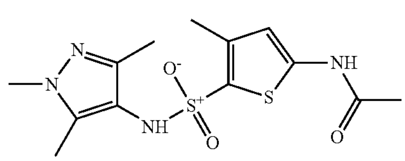 [SMILES: CC(=O)Nc1cc(C)c([S+](=O)([O-])Nc2c(C)nn(C)c2C)s1] | 69.0 | >1 | 343.2 |
| DDD73220 | 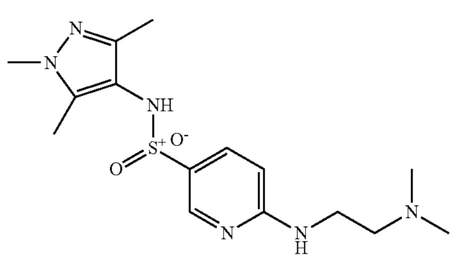 | 2.4 | >1 | 353.1 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | IC$_{50}$ (μM) NMT Enzyme | ED$_{50}$ (μM) T. brucei | MH+ |
|---|---|---|---|---|
| DDD73221 | 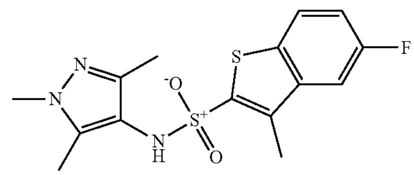 | 6.6 | >1 | 354.2 |
| DDD73222 | 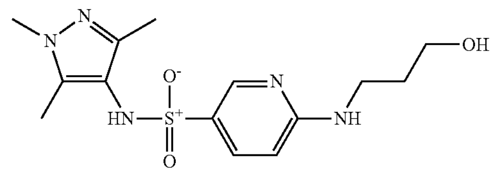 [SMILES: Cc1nn(C)c(C)c1N[S+](=O)([O-])c1ccc(NCCCO)nc1] | 1.0 | >1 | 340.1 |
| DDD73223 | 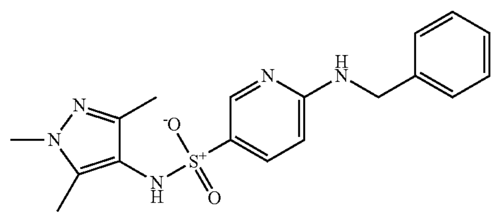 | 1.4 | >1 | 371.1 |
| DDD73224 | 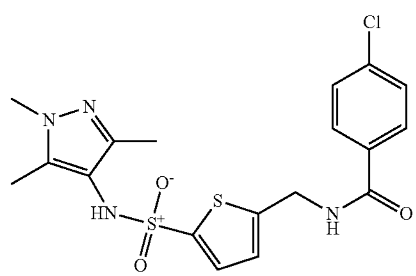 [SMILES: Cc1nn(C)c(C)c1N[S+](=O)([O-])c1ccc(CNC(=O)c2ccc(Cl)cc2)s1] | 1.5 | >1 | 438.2 |
| DDD73225 | 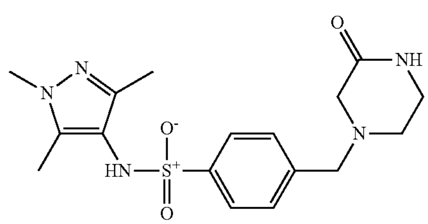 [SMILES: Cc1nn(C)c(C)c1N[S+](=O)([O-])c1ccc(CN2CCNC(=O)C2)cc1] | >100 | >1 | 378.1 |
| DDD73226 | 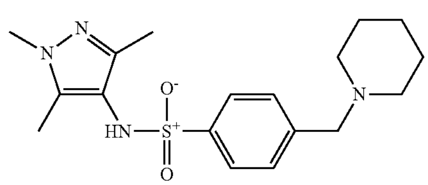 [SMILES: Cc1nn(C)c(C)c1N[S+](=O)([O-])c1ccc(CN2CCCCC2)cc1] | >100 | >1 | 363.1 |
| DDD73227 | 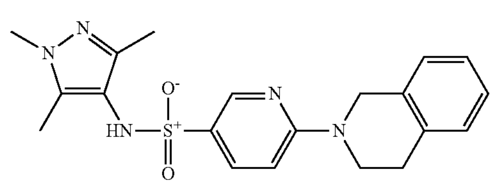 [SMILES: Cc1nn(C)c(C)c1N[S+](=O)([O-])c1ccc(N2CCc3ccccc3C2)nc1] | 0.9 | 8.1 | 398.1 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activities are for inhibition of *T. brucei brucei* (blood stream form, variant 221).

| Reference Number | STRUCTURE | $IC_{50}$ (μM) NMT Enzyme | $ED_{50}$ (μM) T. brucei | MH+ |
|---|---|---|---|---|
| DDD73228 | 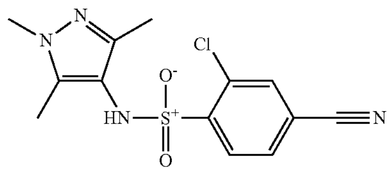 [SMILES: Cc1nn(C)c(C)c1N[S+](=O)([O-])c1ccc(C#N)cc1Cl] | 13.5 | >1 | 324.2 |
| DDD73229 | 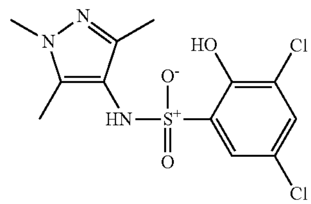 [SMILES: Cc1nn(C)c(C)c1N[S+](=O)([O-])c1cc(Cl)cc(Cl)c1O] | >100 | >1 | 351.1 |
| DDD73230 | 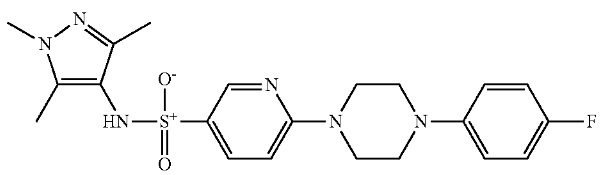 [SMILES: Cc1nn(C)c(C)c1N[S+](=O)([O-])c1ccc(N2CCN(c3ccc(F)cc3)CC2)nc1] | 10.7 | >1 | 445.1 |
| DDD73231 | 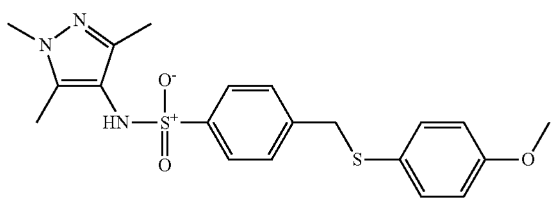 | 0.76 | 6.7 | 418.2 |
| DDD73232 | 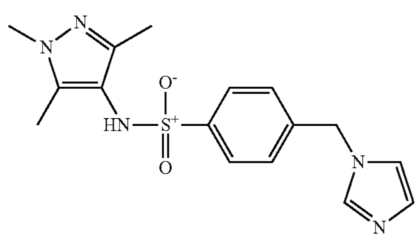 [SMILES: Cc1nn(C)c(C)c1N[S+](=O)([O-])c1ccc(Cn2ccnc2)cc1] | 1.9 | 18.6 | 346.2 |
| DDD73233 | 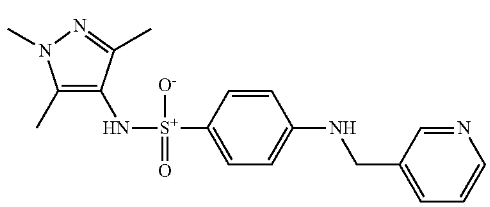 [SMILES: Cc1nn(C)c(C)c1N[S+](=O)([O-])c1ccc(NCc2cccnc2)cc1] | 2.7 | >1 | 373.1 |
| DDD73234 | 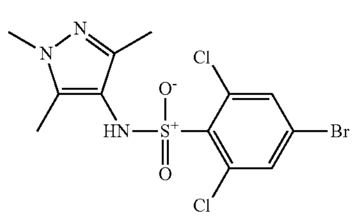 [SMILES: Cc1nn(C)c(C)c1N[S+](=O)([O-])c1c(Cl)cc(Br)cc1Cl] | 0.55 | 14.3 | 413.9 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD73235 | 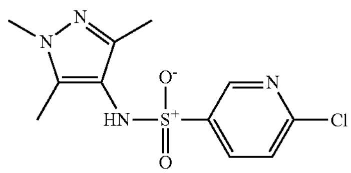 [SMILES: Cc1nn(C)c(C)c1N[S+](=O)([O-])c1ccc(Cl)nc1] | 17.0 | >1 | 301.1 |
| DDD73236 | 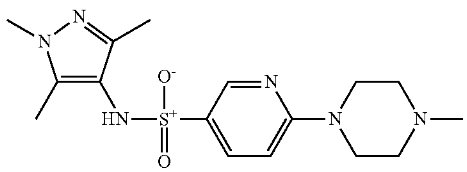 | 11.9 | >1 | 365.1 |
| DDD73237 | 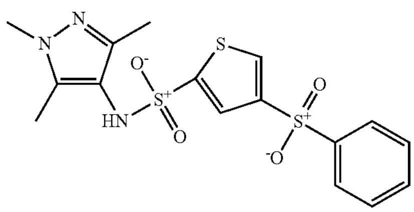 | 10.4 | >1 | 412.2 |
| DDD73238 | 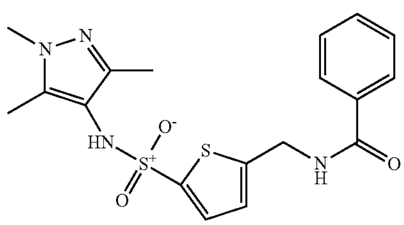 [SMILES: Cc1nn(C)c(C)c1N[S+](=O)([O-])c1ccc(CNC(=O)c2ccccc2)s1] | 0.63 | 6.9 | 405.2 |
| DDD73239 | 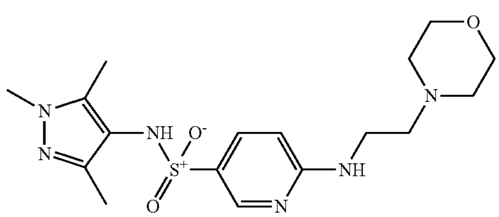 [SMILES: Cc1nn(C)c(C)c1N[S+](=O)([O-])c1ccc(NCCN2CCOCC2)nc1] | 38.7 | >50 | 395.1 |
| DDD73240 | 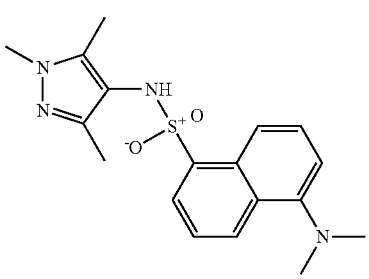 | 1.6 | >1 | 359.1 |
| DDD73241 | 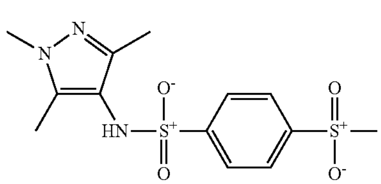 | 4.2 | >1 | 344.1 |

TABLE 1-continued

Enzyme and Cellular Activity of N-Myristoyltransferase Inhibitors

Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD73242 | 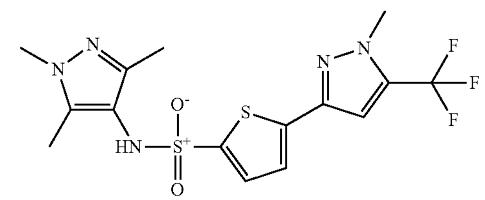 [SMILES: Cc1nn(C)c(C)c1N[S+](=O)([O-])c1ccc(-c2cc(C(F)(F)F)n(C)n2)s1] | 32.0 | >1 | 420.2 |
| DDD73243 | 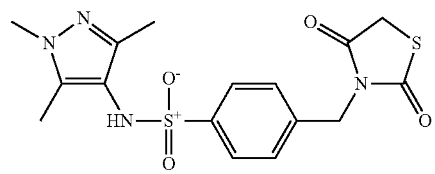 [SMILES: Cc1nn(C)c(C)c1N[S+](=O)([O-])c1ccc(CN2C(=O)CSC2=O)cc1] | 5.8 | >1 | 395.2 |
| DDD73262 | 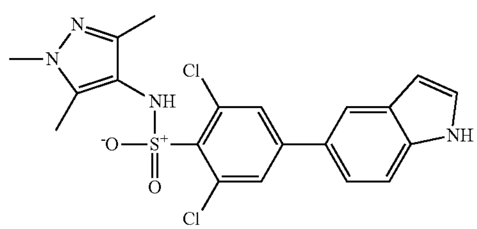 | 6.9 | >1 | 450.1 |
| DDD73263 | 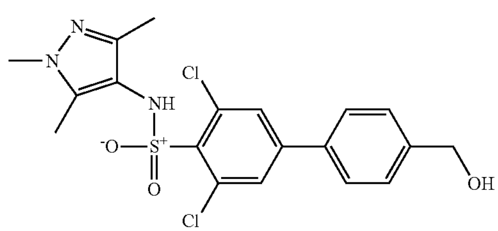 | 0.92 | 3.4 | 441.2 |
| DDD73264 | 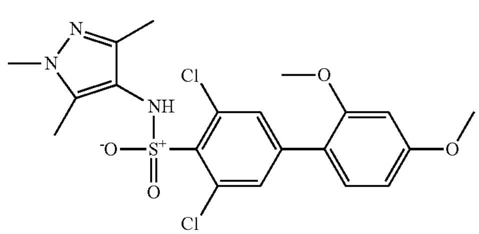 | 7.0 | >1 | 471.2 |
| DDD73265 | 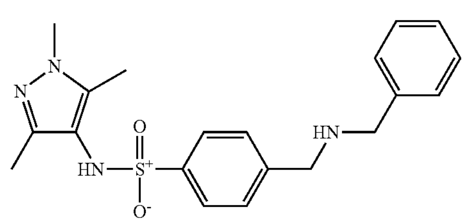 [SMILES: Cc1nn(C)c(C)c1N[S+](=O)([O-])c1ccc(CNCc2ccccc2)cc1] | 22.5 | >1 | 385.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | IC$_{50}$ (µM) NMT Enzyme | ED$_{50}$ (µM) *T. brucei* | MH+ |
|---|---|---|---|---|
| DDD73266 | 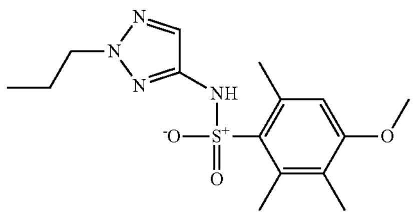 | >100 | >1 | 339.1 |
| DDD73267 | 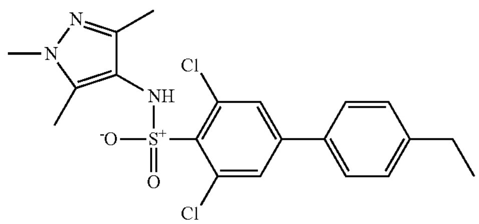 | 44.5 | >1 | 438.2 |
| DDD73268 | 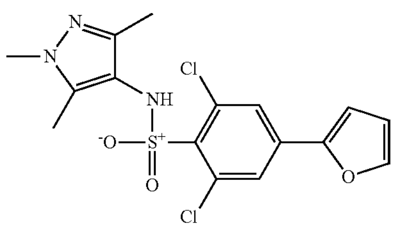 | 3.6 | >1 | 400.1 |
| DDD73269 | 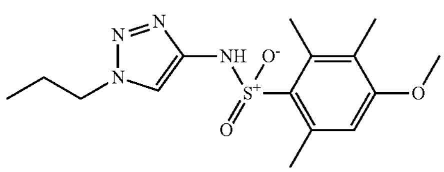 [SMILES: CCCn1cc(N[S+](=O)([O-])c2c(C)cc(OC)c(C)c2C)nn1] | >100 | >1 | 339.1 |
| DDD73271 | 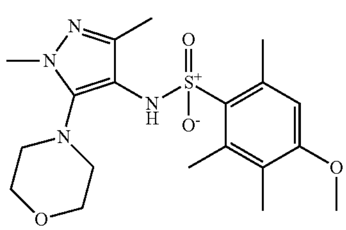 | >100 | >1 | 409.1 |
| DDD73272 | 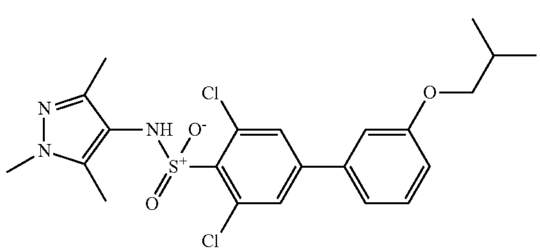 [SMILES: Cc1nn(C)c(C)c1N[S+](=O)([O-])c1c(Cl)cc(-c2cccc(OCC(C)C)c2)cc1Cl] | 35.0 | >1 | 482.1 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (µM) NMT Enzyme | $ED_{50}$ (µM) *T. brucei* | MH+ |
|---|---|---|---|---|
| DDD73273 | 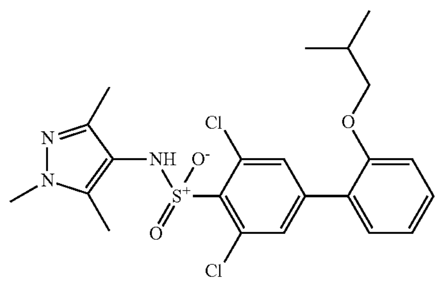 [SMILES: Cc1nn(C)c(C)c1N[S+](=O)([O-])c1c(Cl)cc(-c2ccccc2OCC(C)C)cc1Cl] | 25.5 | >1 | 483.1 |
| DDD73274 | 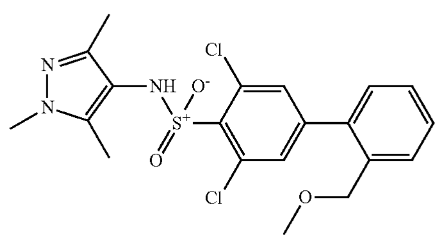 [SMILES: COCc1ccccc1-c1cc(Cl)c([S+](=O)([O-])Nc2c(C)nn(C)c2C)c(Cl)c1] | 32.2 | >1 | 455.2 |
| DDD73277 | 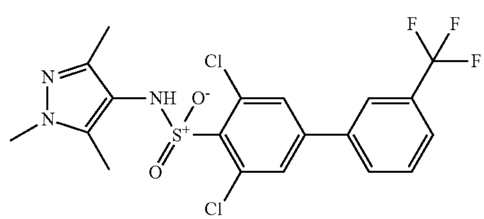 [SMILES: Cc1nn(C)c(C)c1N[S+](=O)([O-])c1c(Cl)cc(-c2cccc(C(F)(F)F)c2)cc1Cl] | 40.0 | >1 | 478.1 |
| DDD73278 | 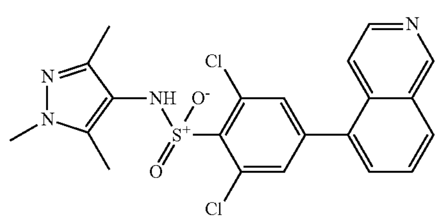 [SMILES: Cc1nn(C)c(C)c1N[S+](=O)([O-])c1c(Cl)cc(-c2cccc3cnccc23)cc1Cl] | 26.9 | >1 | 461.1 |
| DDD73279 | 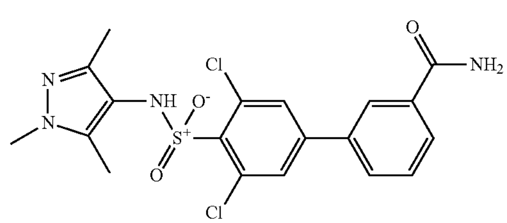 [SMILES: Cc1nn(C)c(C)c1N[S+](=O)([O-])c1c(Cl)cc(-c2cccc(C(N)=O)c2)cc1Cl] | 1.1 | 2.1 | 453.2 |
| DDD73280 | 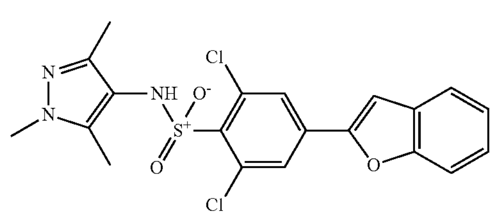 [SMILES: Cc1nn(C)c(C)c1N[S+](=O)([O-])c1c(Cl)cc(-c2cc3ccccc3o2)cc1Cl] | 20.7 | >1 | 450.1 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (µM) NMT Enzyme | $ED_{50}$ (µM) *T. brucei* | MH+ |
|---|---|---|---|---|
| DDD73319 | 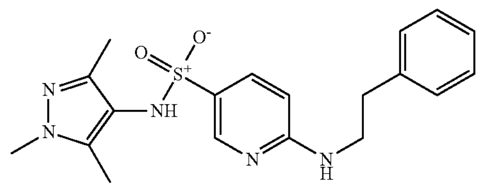 [SMILES: Cc1nn(C)c(C)c1N[S+](=O)([O-])c1ccc(NCCc2ccccc2)nc1] | 1.1 | 8.4 | 385.1 |
| DDD73320 | 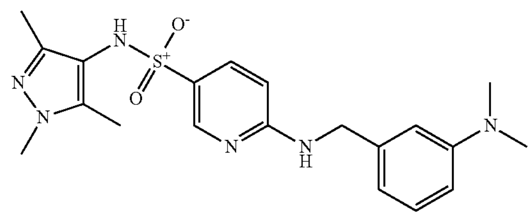 [SMILES: Cc1nn(C)c(C)c1N[S+](=O)([O-])c1ccc(NCc2cccc(N(C)C)c2)nc1] | 2.6 | 16.3 | 415.1 |
| DDD73321 | 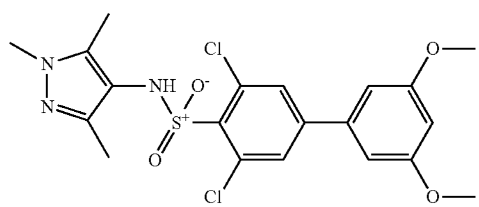 | 4.3 | >1 | 470.1 |
| DDD73322 | 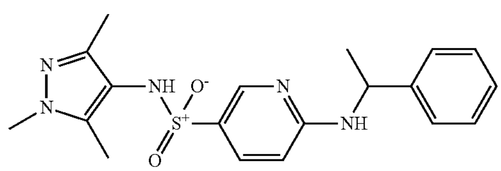 [SMILES: Cc1nn(C)c(C)c1N[S+](=O)([O-])c1ccc(NC(C)c2ccccc2)nc1] | 0.86 | 5.4 | 386.1 |
| DDD73323 | 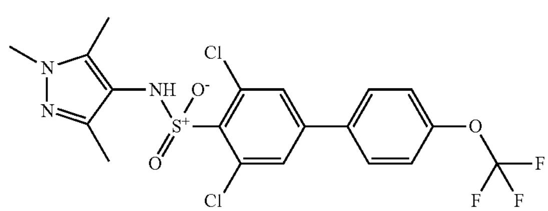 [SMILES: Cc1nn(C)c(C)c1N[S+](=O)([O-])c1c(Cl)cc(-c2ccc(OC(F)(F)F)cc2)cc1Cl] | 89.0 | >1 | 495.1 |
| DDD73324 | 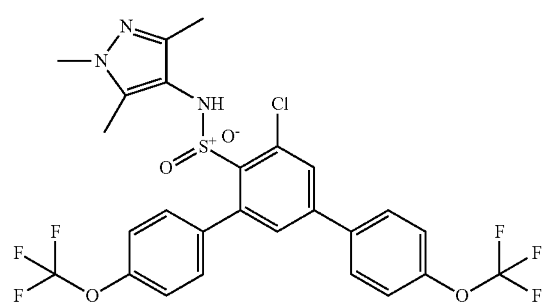 | >100 | >1 | 620.1 |
| DDD73325 | 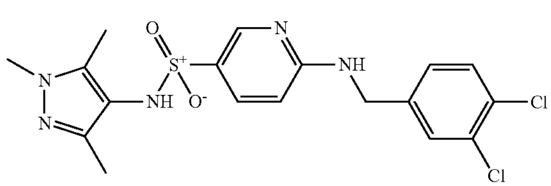 [SMILES: Cc1nn(C)c(C)c1N[S+](=O)([O-])c1ccc(NCc2ccc(Cl)c(Cl)c2)nc1] | 12.8 | >1 | 440.1 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD73326 | 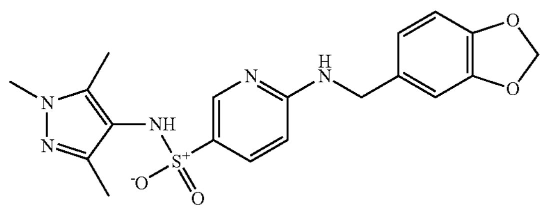 | 1.4 | >1 | 416.2 |
| DDD73327 | 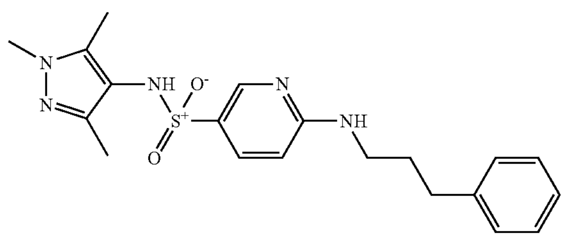 [SMILES: Cc1nn(C)c(C)c1N[S+](=O)([O-])c1ccc(NCCCc2ccccc2)nc1] | 2.8 | >1 | 400.2 |
| DDD73328 | 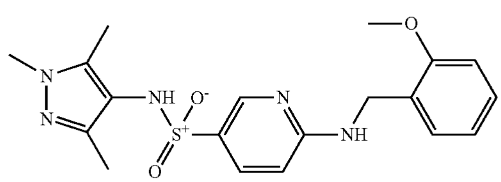 [SMILES: COc1ccccc1CNc1ccc([S+](=O)([O-])Nc2c(C)nn(C)c2C)cn1] | 2.4 | 19.1 | 402.2 |
| DDD73329 | 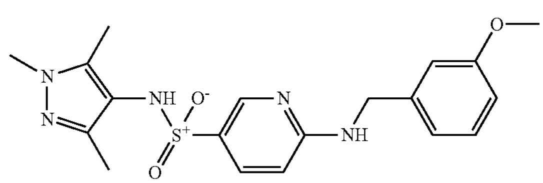 | 1.6 | >1 | 402.1 |
| DDD73330 | 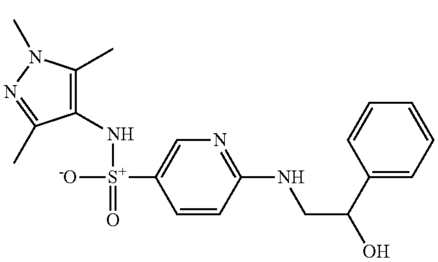 | 2.3 | >1 | 402.1 |
| DDD73331 | 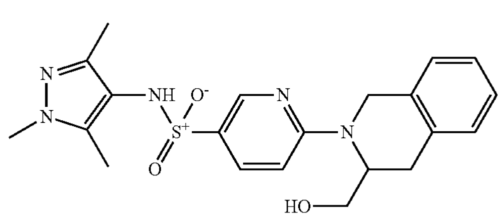 [SMILES: Cc1nn(C)c(C)c1N[S+](=O)([O-])c1ccc(N2Cc3ccccc3CC2CO)nc1] | 6.0 | >1 | 428.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD73332 | 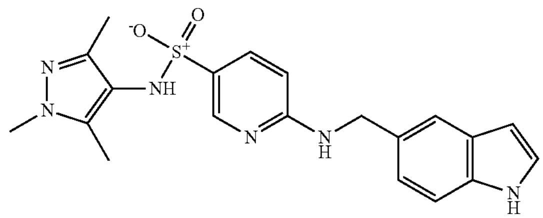 | 0.34 | 3.2 | 411.1 |
| DDD73333 | 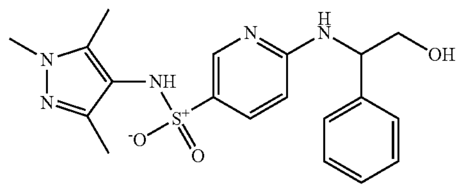 | >100 | >1 | 402.1 |
| DDD73475 | 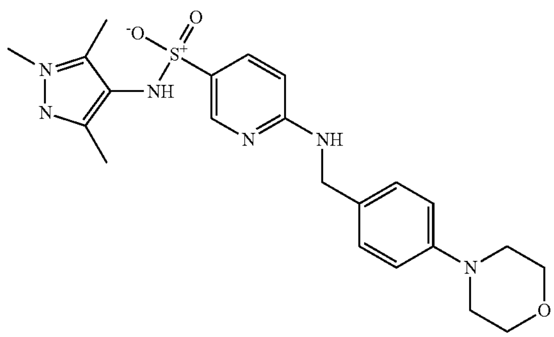 | 0.88 | 10.5 | 457.2 |
| DDD73476 | 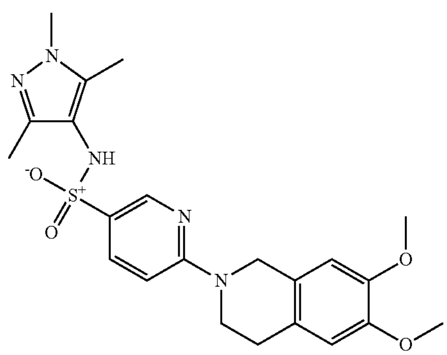 | 0.32<br>2.3 (HuNMT-1)<br>4.8 (AfNMT) | 1.8 | 458.1 |
| DDD73477 | 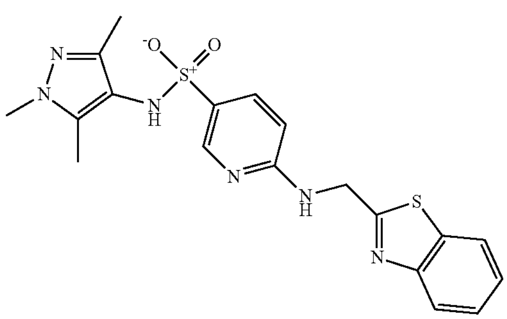 | 0.46 | 6.0 | 429.2 |

TABLE 1-continued

Enzyme and Cellular Activity of N-Myristoyltransferase Inhibitors

Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | IC$_{50}$ (µM) NMT Enzyme | ED$_{50}$ (µM) *T. brucei* | MH+ |
|---|---|---|---|---|
| DDD73478 | 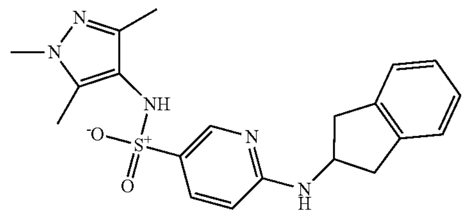 | 0.36 | 4.5 | 398.1 |
| DDD73479 | 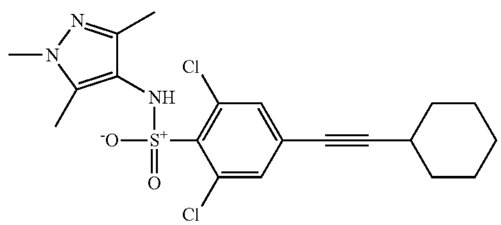 | >100 | >1 | 440.1 |
| DDD73480 | 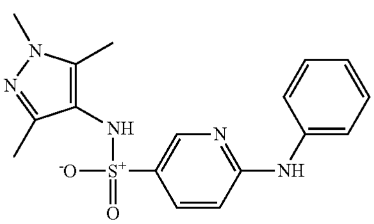 | 4.5 | 22.1 | 358.2 |
| DDD73481 | 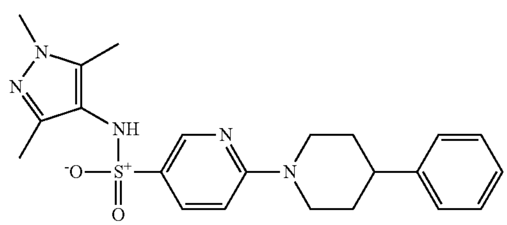 | 6.9 | >1 | 426.1 |
| DDD73482 | 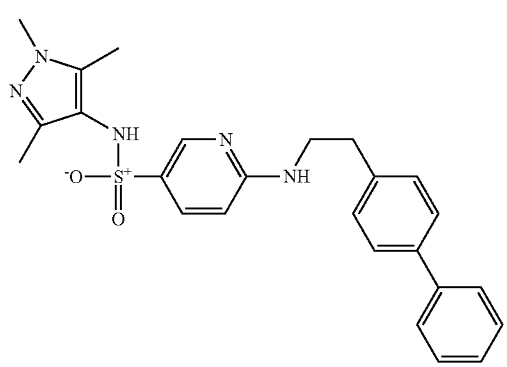 | 60.0 | >1 | 462.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD73483 | 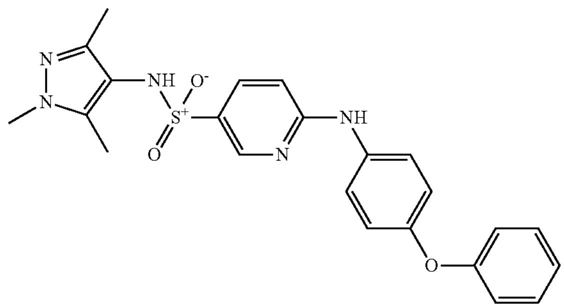 [SMILES: Cc1nn(C)c(C)c1N[S+](=O)([O-])c1ccc(Nc2ccc(Oc3ccccc3)cc2)nc1] | >100 | >1 | 450.1 |
| DDD73484 | 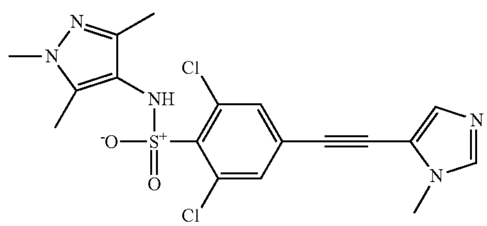 | 0.67 | 3.1 | 438.1 |
| DDD73485 | 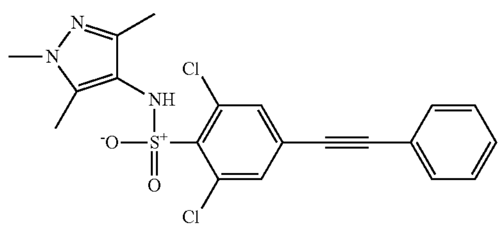 | 34.3 | >1 | 434.1 |
| DDD73486 | 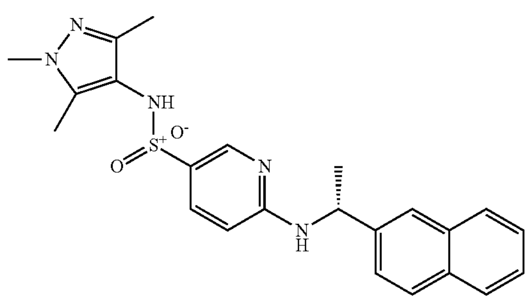 | 2.8 | >1 | 436.2 |
| DDD73487 | 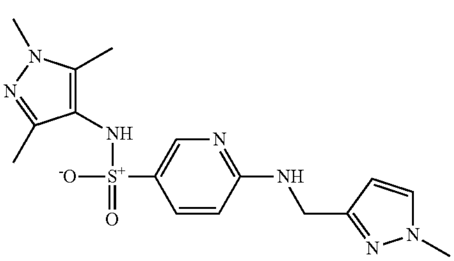 | 1.2 | 14.2 | 376.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (µM) NMT Enzyme | $ED_{50}$ (µM) *T. brucei* | MH+ |
|---|---|---|---|---|
| DDD73488 | 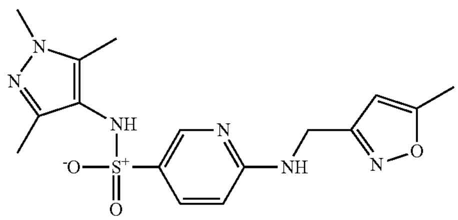 | 0.83 | 7.9 | 375.1 |
| DDD73489 | 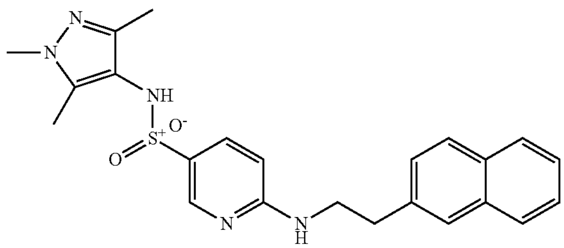 | 12.4 | >1 | 436.2 |
| DDD73490 | 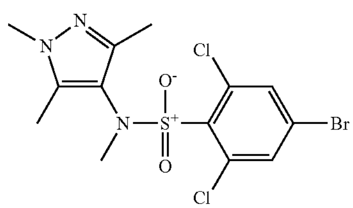 [SMILES: Cc1nn(C)c(C)c1N(C)[S+](=O)([O-])c1c(Cl)cc(Br)cc1Cl] | 0.36<br>4.0 (HuNMT-1)<br>3.9 (AfNMT) | 2.8 | 427.9 |
| DDD73491 | 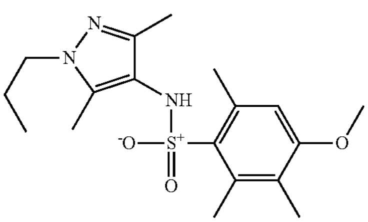 | 28.4 | >1 | 366.2 |
| DDD73492 | 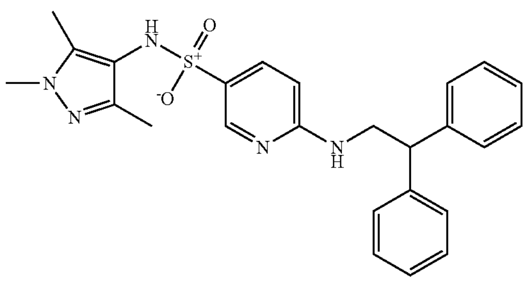 | 13.6 | >1 | 462.1 |
| DDD73493 | 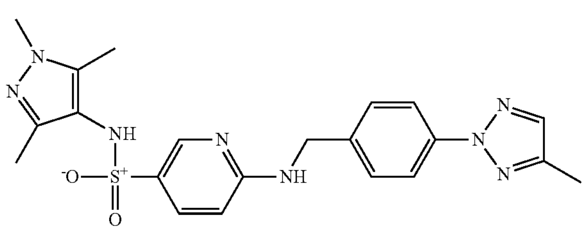 | 4.4 | >1 | 453.1 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (µM) NMT Enzyme | $ED_{50}$ (µM) T. brucei | MH+ |
|---|---|---|---|---|
| DDD73494 | 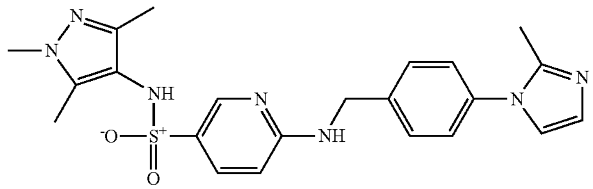 | 0.71 | 8.8 | 452.2 |
| DDD73495 | 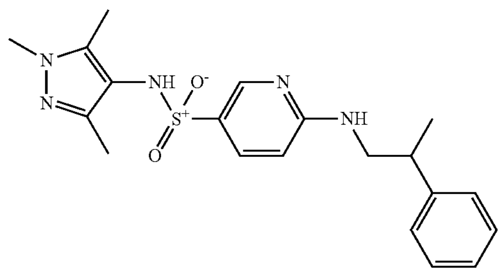 [SMILES: Cc1nn(C)c(C)c1N[S+](=O)([O-])c1ccc(NCC(C)c2ccccc2)nc1] | 0.96 | 7.8 | 400.2 |
| DDD73496 | 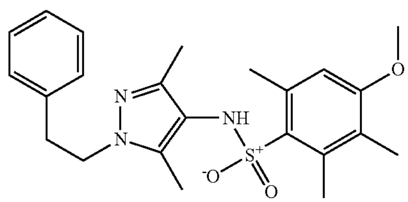 | >100 | >1 | 428.1 |
| DDD73497 | 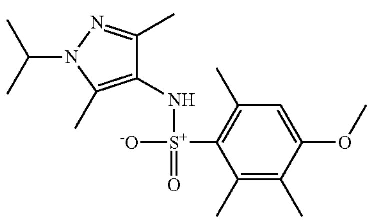 | >100 | >1 | 366.1 |
| DDD73498 | 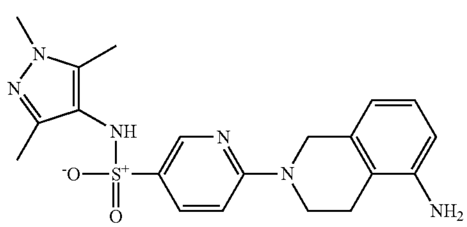 | 0.32<br>4.3 (HuNMT-1)<br>14.7 (AfNMT) | 2.6 | 413.2 |
| DDD73499 | 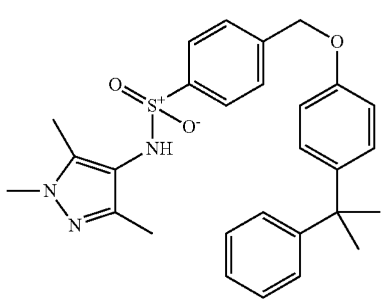 [SMILES: Cc1nn(C)c(C)c1N[S+](=O)([O-])c1ccc(COc2ccc(C(C)(C)c3ccccc3)cc2)cc1] | >100 | >1 | 490.2 |

TABLE 1-continued

Enzyme and Cellular Activity of N-Myristoyltransferase Inhibitors

Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD73500 | 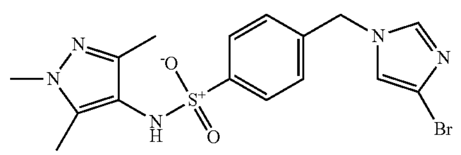 | 2.5 | >1 | 425.1 |
| DDD73501 | 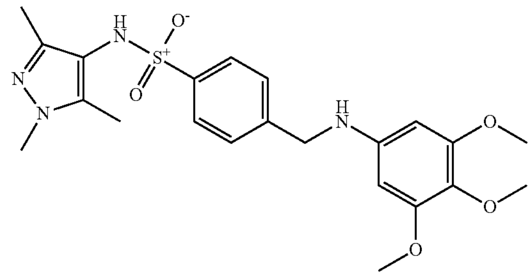 [SMILES: COc1cc(NCc2ccc([S+](=O)([O-])Nc3c(C)nn(C)c3C)cc2)cc(OC)c1OC] | 19.0 | >1 | 461.2 |
| DDD73502 | 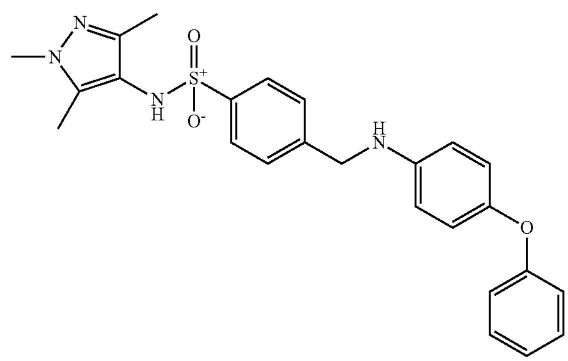 [SMILES: Cc1nn(C)c(C)c1N[S+](=O)([O-])c1ccc(CNc2ccc(Oc3ccccc3)cc2)cc1] | 4.8 | >1 | 463.2 |
| DDD73503 | 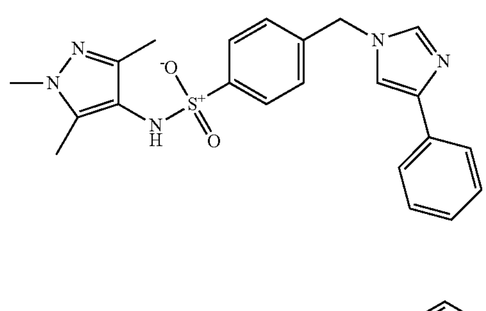 | 2.5 | 10.5 | 422.1 |
| DDD73504 | 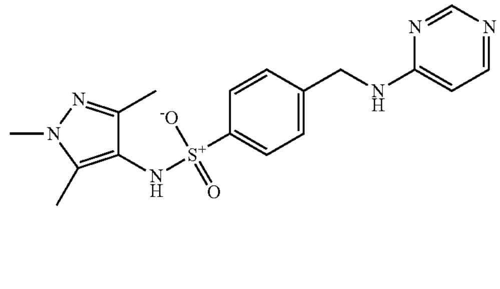 | 4.2 | >1 | 373.1 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD73505 | 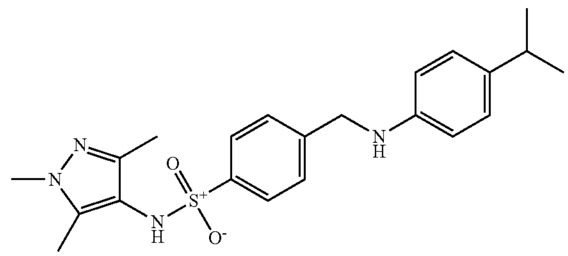 [SMILES: Cc1nn(C)c(C)c1N[S+](=O)([O-])c1ccc(CNc2ccc(C(C)C)cc2)cc1] | 9.7 | >1 | 413.1 |
| DDD73506 | 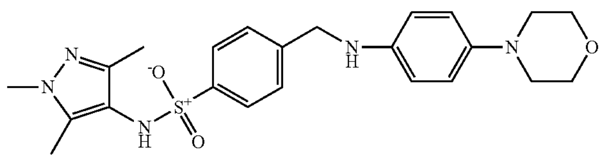 | 10.0 | >1 | 456.1 |
| DDD73507 | 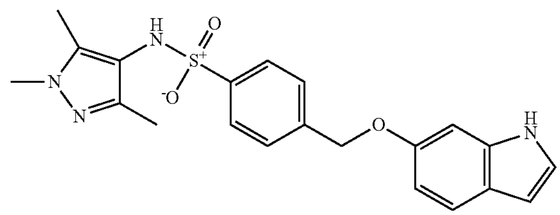 | 4.5 | >1 | 411.2 |
| DDD73508 | 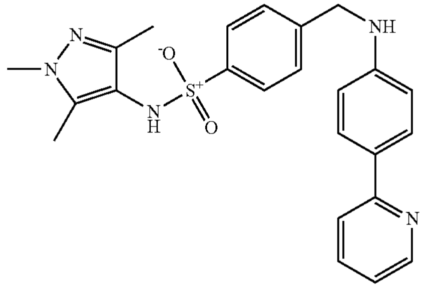 | 5.2 | >1 | 448.1 |
| DDD73509 | 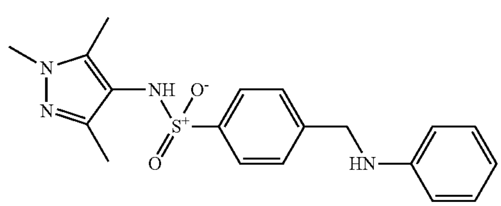 [SMILES: Cc1nn(C)c(C)c1N[S+](=O)([O-])c1ccc(CNc2ccccc2)cc1] | 3.8 | >1 | 371.2 |
| DDD73510 | 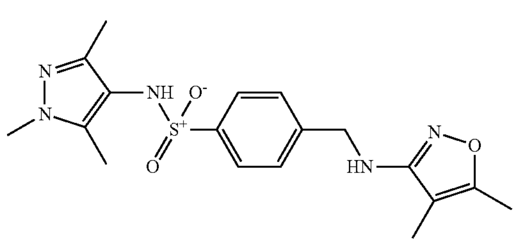 | 26.9 | >1 | 390.1 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD73511 | 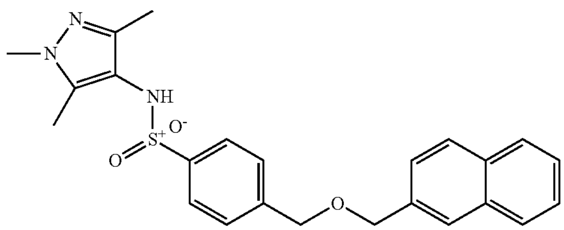 | >100 | >1 | 436.2 |
| DDD73512 | 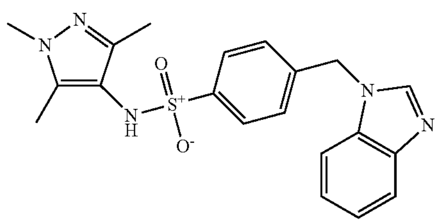 [SMILES: Cc1nn(C)c(C)c1N[S+](=O)([O-])c1ccc(Cn2cnc3ccccc32)cc1] | 6.1 | >1 | 396.1 |
| DDD73513 | 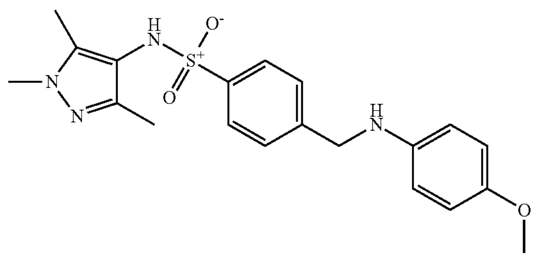 | 5.7 | >1 | 401.2 |
| DDD73514 | 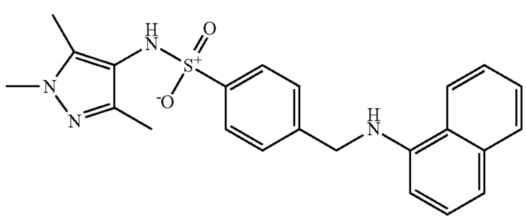 | 4.7 | >1 | 420.1 |
| DDD73515 | 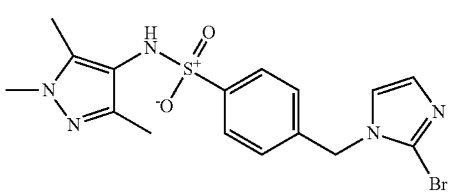 | 1.9 | >1 | 425.2 |
| DDD73516 | 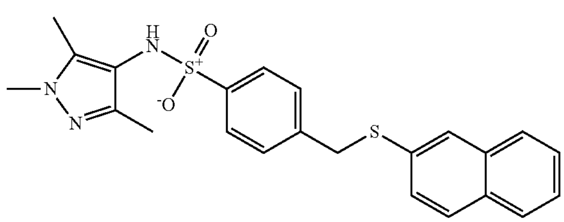 | 47.6 | >1 | 438.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | IC$_{50}$ (μM) NMT Enzyme | ED$_{50}$ (μM) *T. brucei* | MH+ |
|---|---|---|---|---|
| DDD85591 | 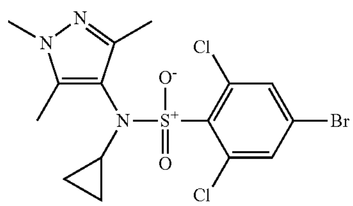 [SMILES: Cc1nn(C)c(C)c1N(C1CC1)[S+](=O)([O-])c1c(Cl)cc(Br)cc1Cl] | 0.59 | 5.3 | 452.2 |
| DDD85592 | 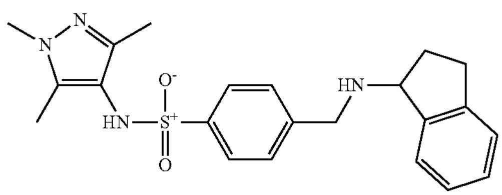 [SMILES: Cc1nn(C)c(C)c1N[S+](=O)([O-])c1ccc(CNC2CCc3ccccc32)cc1] | 44.0 | >1 | 411.2 |
| DDD85593 | 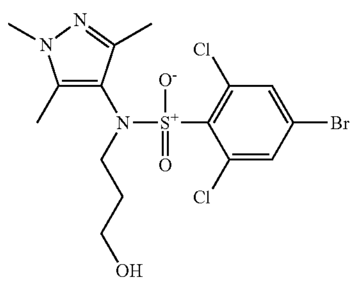 [SMILES: Cc1nn(C)c(C)c1N(CCCO)[S+](=O)([O-])c1c(Cl)cc(Br)cc1Cl] | 0.36 | 3.5 | 472.1 |
| DDD85594 | 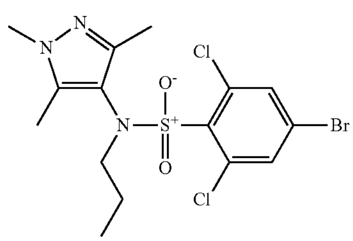 [SMILES: CCCN(c1c(C)nn(C)c1C)[S+](=O)([O-])c1c(Cl)cc(Br)cc1Cl] | 3.2 | 21.0 | 456.1 |
| DDD85595 | 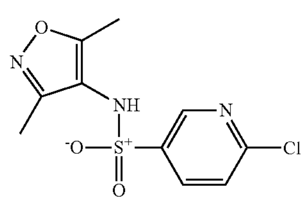 | 66.7 | >1 | 286.2 |
| DDD85596 | 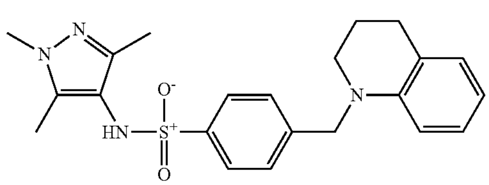 [SMILES: Cc1nn(C)c(C)c1N[S+](=O)([O-])c1ccc(CN2CCCc3ccccc32)cc1] | 41.7 | >1 | 411.1 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD85597 | 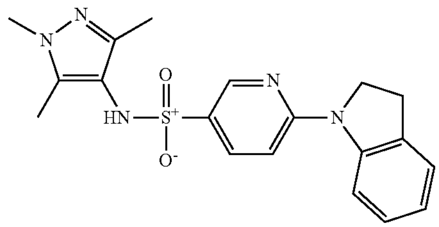 [SMILES: Cc1nn(C)c(C)c1N[S+](=O)([O-])c1ccc(N2CCc3ccccc32)nc1] | 8.0 | >1 | 384.1 |
| DDD85598 | 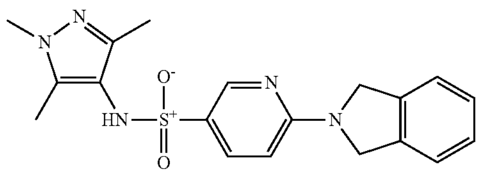 [SMILES: Cc1nn(C)c(C)c1N[S+](=O)([O-])c1ccc(N2Cc3ccccc3C2)nc1] | 18.2 | >1 | 384.1 |
| DDD85599 | 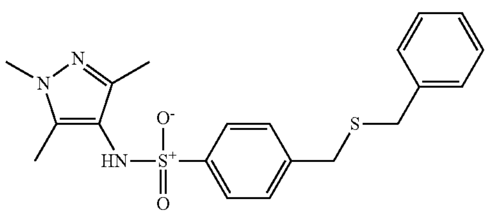 [SMILES: Cc1nn(C)c(C)c1N[S+](=O)([O-])c1ccc(CSCc2ccccc2)cc1] | 2.4 | >1 | 402.1 |
| DDD85600 | 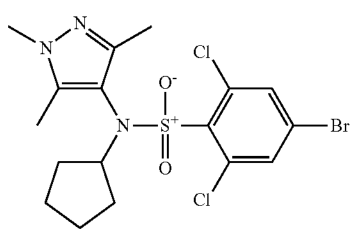 [SMILES: Cc1nn(C)c(C)c1N(C1CCCC1)[S+](=O)([O-])c1c(Cl)cc(Br)cc1Cl] | 1.9 | 5.9 | 482.2 |
| DDD85601 | 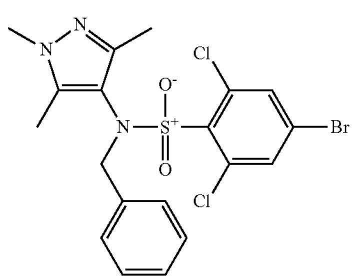 [SMILES: Cc1nn(C)c(C)c1N(Cc1ccccc1)[S+](=O)([O-])c1c(Cl)cc(Br)cc1Cl] | 23.3 | >1 | 503.1 |
| DDD85602 | 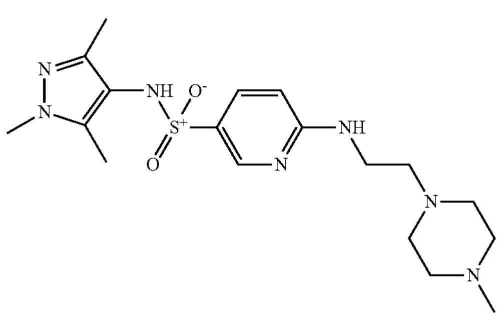 | 0.14<br>9.5 (HuNMT-1)<br>2.9 (AfNMT) | 0.63 | 408.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) T. brucei | MH+ |
|---|---|---|---|---|
| DDD85603 | 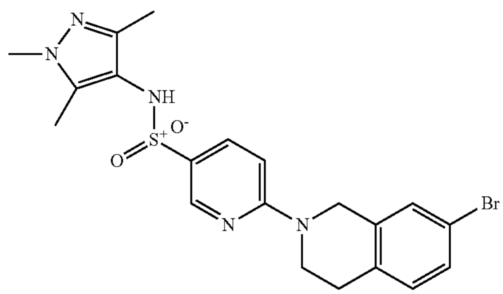 | 2.4 | >1 | 477.1 |
| DDD85604 | 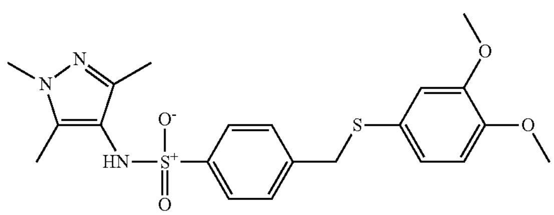 | 3.3 | >1 | 448.2 |
| DDD85605 | 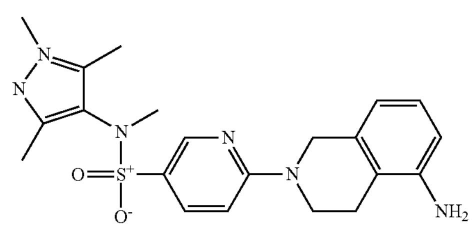 | 0.57 | 2.4 | 427.2 |
| DDD85606 | 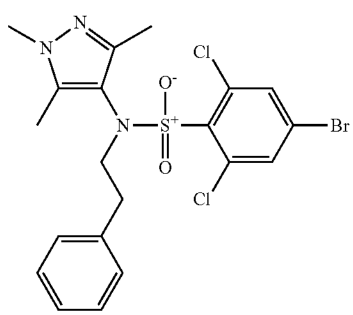 [SMILES: Cc1nn(C)c(C)c1N(CCc1ccccc1)[S+](=O)([O-])c1c(Cl)cc(Br)cc1Cl] | 4.9 | 3.6 | 518.2 |
| DDD85607 | 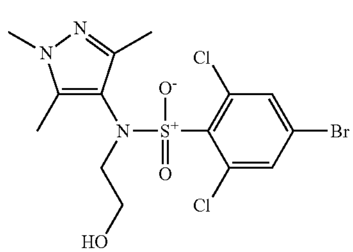 [SMILES: Cc1nn(C)c(C)c1N(CCO)[S+](=O)([O-])c1c(Cl)cc(Br)cc1Cl] | 1.1 | 7.1 | 458.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activities are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD85608 | 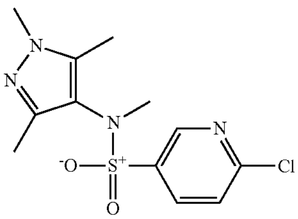 | 18.5 | >1 | 314.2 |
| DDD85609 | 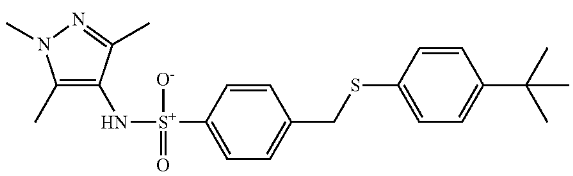 [SMILES: Cc1nn(C)c(C)c1N[S+](=O)([O-])c1ccc(CSc2ccc(C(C)(C)C)cc2)cc1] | 69.5 | >1 | 444.2 |
| DDD85610 | 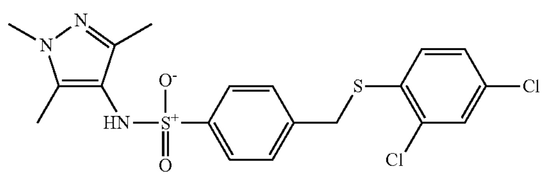 [SMILES: Cc1nn(C)c(C)c1N[S+](=O)([O-])c1ccc(CSc2ccc(Cl)cc2Cl)cc1] | 61.6 | >1 | 456.1 |
| DDD85611 | 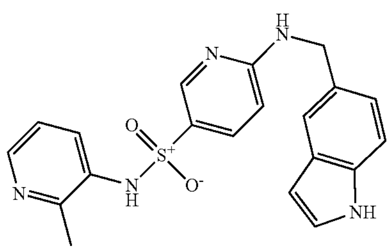 [SMILES: Cc1ncccc1N[S+](=O)([O-])c1ccc(NCc2ccc3[nH]ccc3c2)nc1] | 7.2 | >1 | 394.2 |
| DDD85612 | 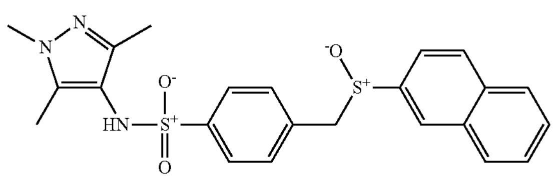 | 9.3 | >1 | 454.6 |
| DDD85613 | 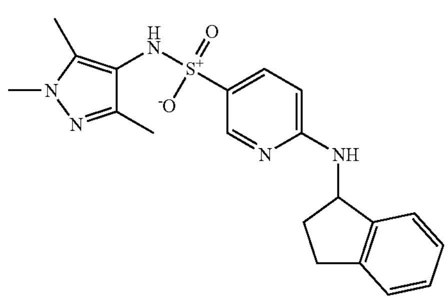 | 6.6 | >1 | 398.2 |
| DDD85624 | 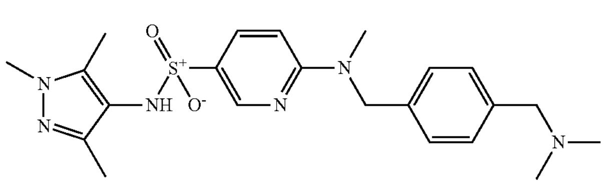 | 0.36 | 1.5 | 443.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (µM) NMT Enzyme | $ED_{50}$ (µM) *T. brucei* | MH+ |
|---|---|---|---|---|
| DDD85625 | 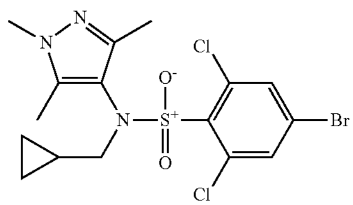 [SMILES: Cc1nn(C)c(C)c1N(CC1CC1)[S+](=O)([O-])c1c(Cl)cc(Br)cc1Cl] | 0.67 | 4.6 | 466.1 |
| DDD85626 | 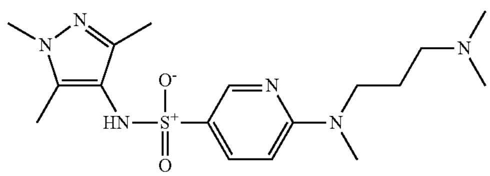 | 0.61 | 1.9 | 381.1 |
| DDD85627 | 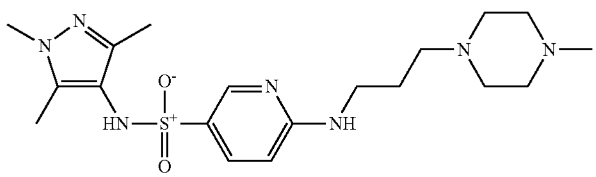 | 0.12 | 0.62 | 422.2 |
| DDD85628 | 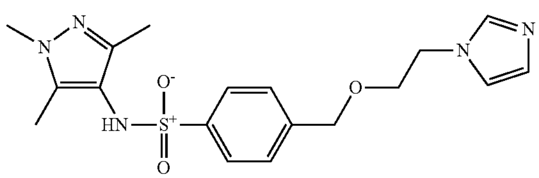 [SMILES: Cc1nn(C)c(C)c1N[S+](=O)([O-])c1ccc(COCCn2ccnc2)cc1] | 11.1 | >1 | 390.1 |
| DDD85629 | 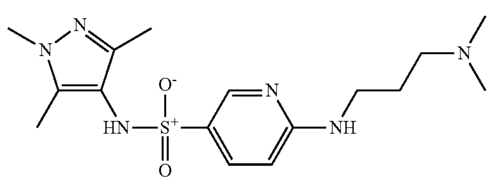 | 2.4 | 38.0 | 367.2 |
| DDD85630 | 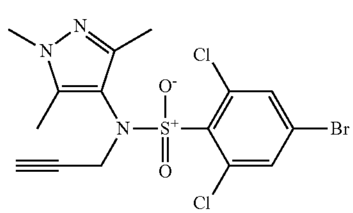 [SMILES: C#CCN(c1c(C)nn(C)c1C)[S+](=O)([O-])c1c(Cl)cc(Br)cc1Cl] | 1.7 | >1 | 451.1 |
| DDD85631 | 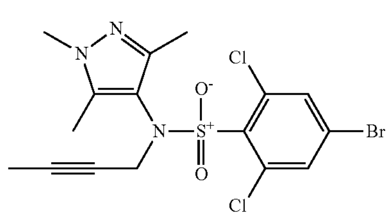 [SMILES: CC#CCN(c1c(C)nn(C)c1C)[S+](=O)([O-])c1c(Cl)cc(Br)cc1Cl] | 9.3 | >1 | 465.1 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | IC$_{50}$ (μM) NMT Enzyme | ED$_{50}$ (μM) *T. brucei* | MH+ |
|---|---|---|---|---|
| DDD85632 | 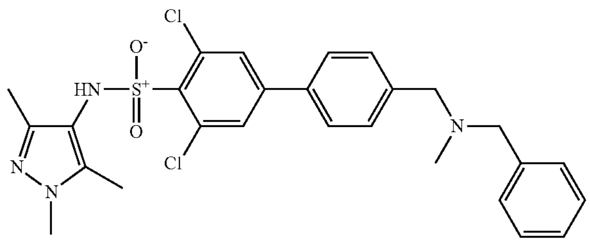 [SMILES: Cc1nn(C)c(C)c1N[S+](=O)([O-])c1c(Cl)cc(-c2ccc(CN(C)Cc3ccccc3)cc2)cc1Cl] | 57.5 | >1 | 544.2 |
| DDD85633 | 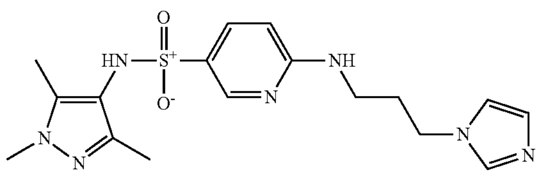 [SMILES: Cc1nn(C)c(C)c1N[S+](=O)([O-])c1ccc(NCCCn2ccnc2)nc1] | 2.0 | >50 | 390.1 |
| DDD85634 | 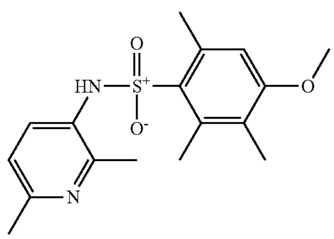 [SMILES: COc1cc(C)c([S+](=O)([O-])Nc2ccc(C)nc2C)c(C)c1C] | 27.9 | >1 | 335.1 |
| DDD85635 | 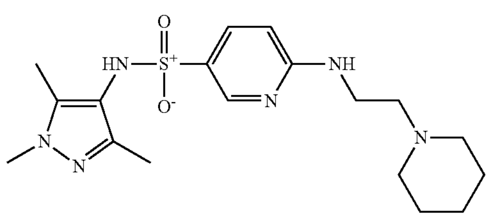 [SMILES: Cc1nn(C)c(C)c1N[S+](=O)([O-])c1ccc(NCCN2CCCCC2)nc1] | 11.2 | 48.1 | 393.1 |
| DDD85636 | 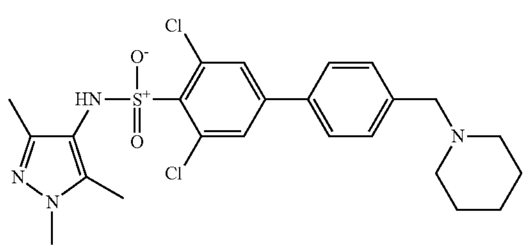 [SMILES: Cc1nn(C)c(C)c1N[S+](=O)([O-])c1c(Cl)cc(-c2ccc(CN3CCCCC3)cc2)cc1Cl] | 75.5 | >1 | 508.1 |
| DDD85637 | 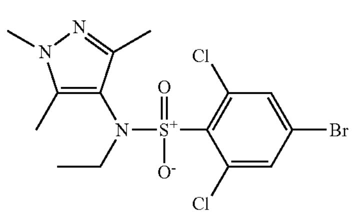 [SMILES: CCN(c1c(C)nn(C)c1C)[S+](=O)([O-])c1c(Cl)cc(Br)cc1Cl] | 0.50 | 3.2 | 441.1 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activities are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD85638 | 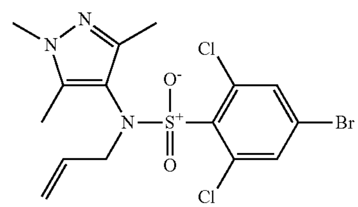 [SMILES: C=CCN(c1c(C)nn(C)c1C)[S+](=O)([O-])c1c(Cl)cc(Br)cc1Cl] | 0.90 | >1 | 453.2 |
| DDD85639 | 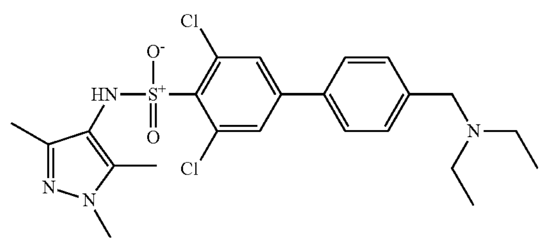 [SMILES: CCN(CC)Cc1ccc(-c2cc(Cl)c([S+](=O)([O-])Nc3c(C)nn(C)c3C)c(Cl)c2)cc1] | 11.7 | >1 | 496.1 |
| DDD85640 | 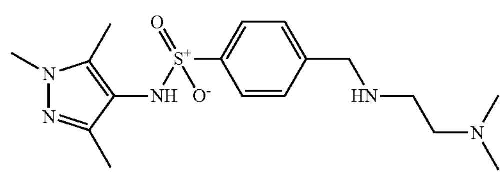 | 3.3 | >50 | 366.1 |
| DDD85641 | 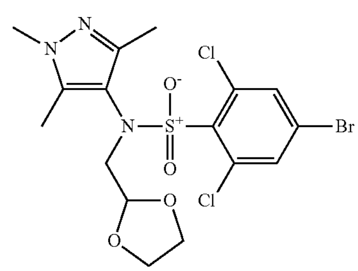 [SMILES: Cc1nn(C)c(C)c1N(CC1OCCO1)[S+](=O)([O-])c1c(Cl)cc(Br)cc1Cl] | 1.7 | 16.3 | 499.1 |
| DDD85642 | 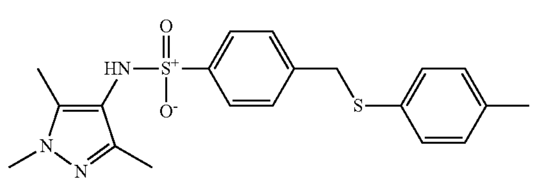 | 5.2 | >1 | 401.2 |
| DDD85643 | 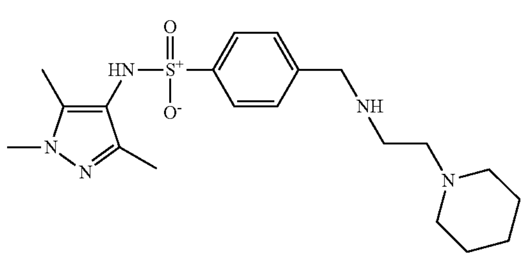 [SMILES: Cc1nn(C)c(C)c1N[S+](=O)([O-])c1ccc(CNCCN2CCCCC2)cc1] | 8.0 | >1 | 406.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activities are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD85644 | 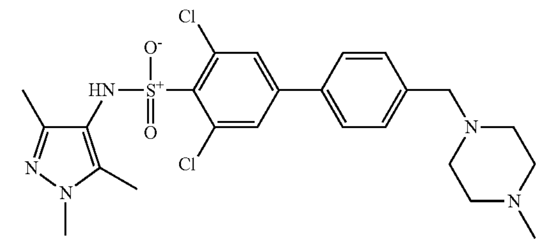 | 1.3 | 2.1 | 521.2 |
| DDD85645 | 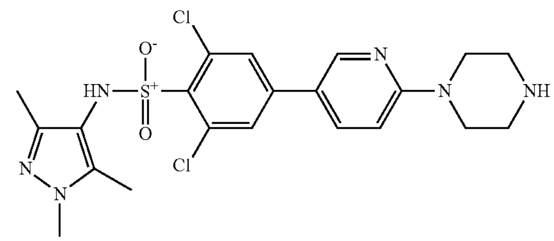 [SMILES: Cc1nn(C)c(C)c1N[S+](=O)([O-])c1c(Cl)cc(-c2ccc(N3CCNCC3)nc2)cc1Cl] | 0.36 | 0.23 | 495.2 |
| DDD85646 | 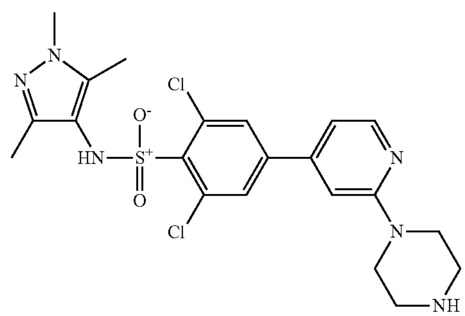 [SMILES: Cc1nn(C)c(C)c1N[S+](=O)([O-])c1c(Cl)cc(-c2ccnc(N3CCNCC3)c2)cc1Cl] | 0.001<br>0.003 (HuNMT-1)<br>0.009 (NWT) | 0.001 | 496.1 |
| DDD85647 | 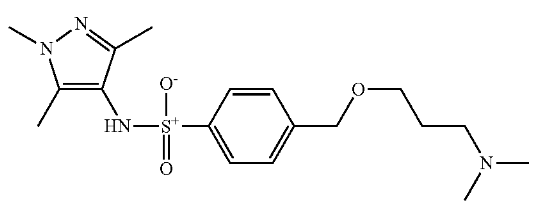 | 66.1 | >1 | 381.1 |
| DDD85648 | 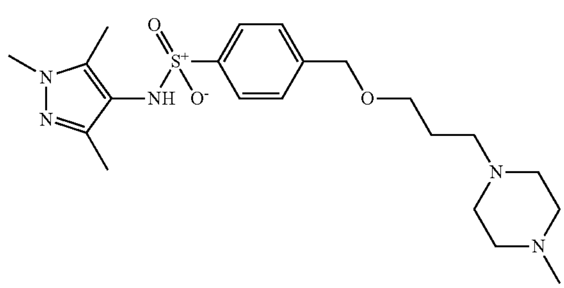 | 47.7 | >1 | 436.2 |
| DDD85649 | 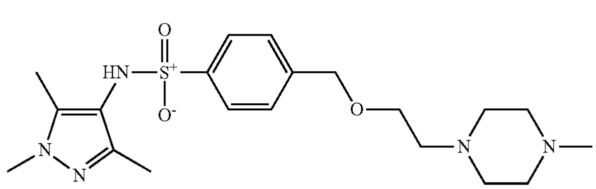 | 40.0 | >1 | 422.1 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD85650 | 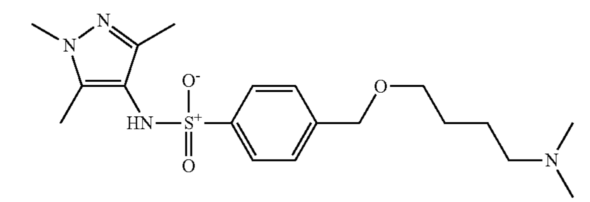 | 52.6 | >1 | 395.1 |
| DDD85651 | 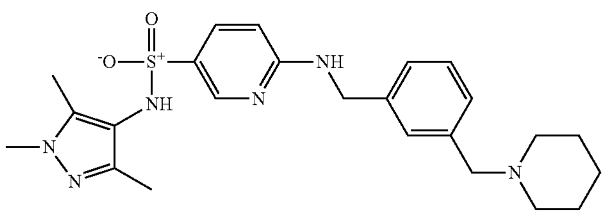 | 1.8 | 9.8 | 469.2 |
| DDD86206 | 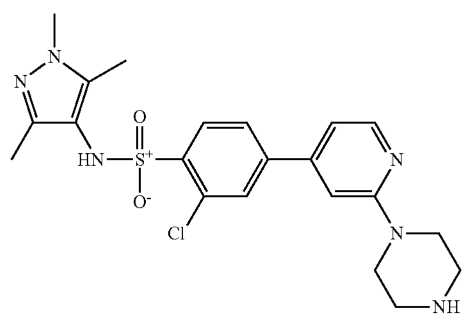 [SMILES: Cc1nn(C)c(C)c1N[S+](=O)([O-])c1ccc(-c2ccnc(N3CCNCC3)c2)cc1Cl] | 0.001<br>0.003 (HuNMT-1) | 0.001 | 461.2 |
| DDD86208 | 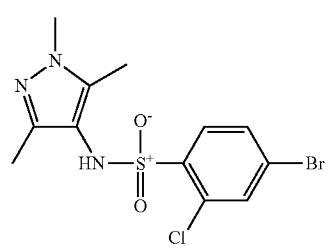 [SMILES: Cc1nn(C)c(C)c1N[S+](=O)([O-])c1ccc(Br)cc1Cl] | 3.5 | >1 | 379.9 |
| DDD86209 | 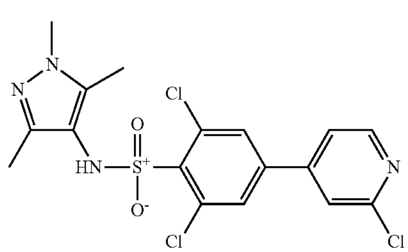 [SMILES: Cc1nn(C)c(C)c1N[S+](=O)([O-])c1c(Cl)cc(-c2ccnc(Cl)c2)cc1Cl] | 1.0 | >1 | 447.0 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | IC$_{50}$ (μM) NMT Enzyme | ED$_{50}$ (μM) *T. brucei* | MH+ |
|---|---|---|---|---|
| DDD86210 | 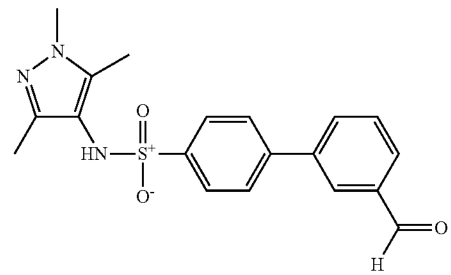 [SMILES: Cc1nn(C)c(C)c1N[S+](=O)([O-])c1ccc(-c2cccc(C=O)c2)cc1] | 6.0 | >1 | 370.2 |
| DDD86211 | 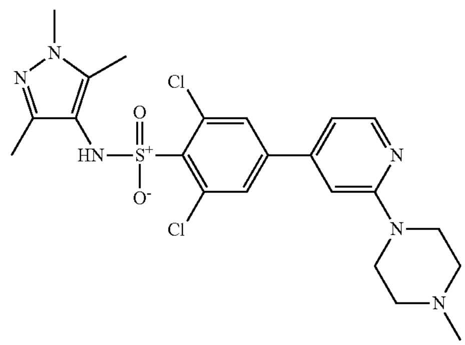 | 0.69 | 0.19 | 509.1 |
| DDD86212 | 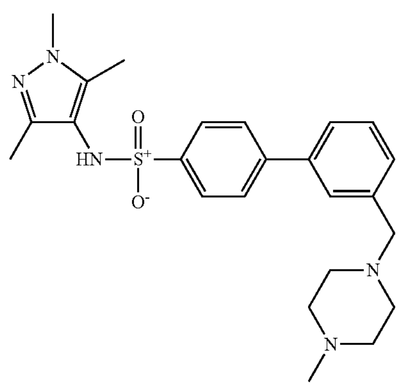 [SMILES: Cc1nn(C)c(C)c1N[S+](=O)([O-])c1ccc(-c2cccc(CN3CCN(C)CC3)c2)cc1] | 0.011<br>0.008 (HuNMT-1)<br>0.015 (AfNMT) | 0.03 | 453.1 |
| DDD86213 | 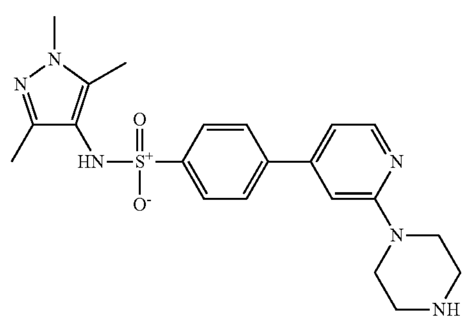 [SMILES: Cc1nn(C)c(C)c1N[S+](=O)([O-])c1ccc(-c2ccnc(N3CCNCC3)c2)cc1] | 0.001<br>0.007 (HuNMT-1)<br>0.01 (AfNMT) | 0.003 | 426.1 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | IC$_{50}$ (µM) NMT Enzyme | ED$_{50}$ (µM) T. brucei | MH+ |
|---|---|---|---|---|
| DDD86291 | 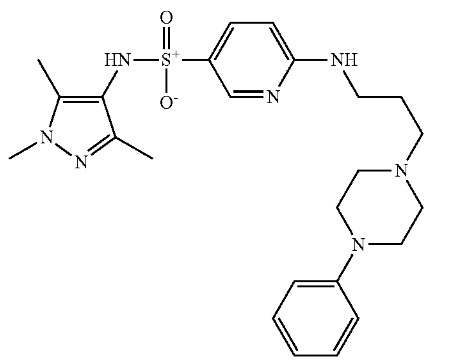 [SMILES: Cc1nn(C)c(C)c1N[S+](=O)([O-])c1ccc(NCCCN2CCN(c3ccccc3)CC2)nc1] | 1.0 | >1 | 484.9 |
| DDD86292 | 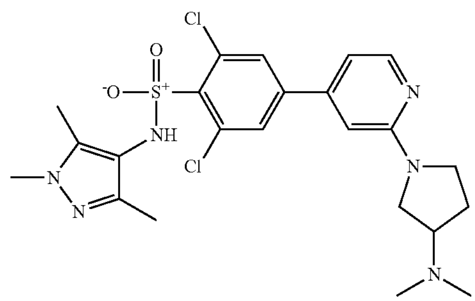 | 1.0 | >1 | 523.2 |
| DDD86293 | 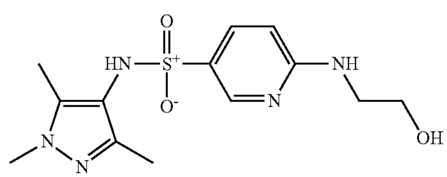 [SMILES: Cc1nn(C)c(C)c1N[S+](=O)([O-])c1ccc(NCCO)nc1] | 1.0 | >1 | 326.2 |
| DDD86294 | 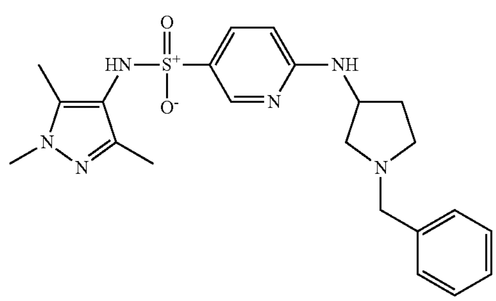 [SMILES: Cc1nn(C)c(C)c1N[S+](=O)([O-])c1ccc(NC2CCN(Cc3ccccc3)C2)nc1] | 1.0 | >1 | 441.9 |
| DDD86295 | 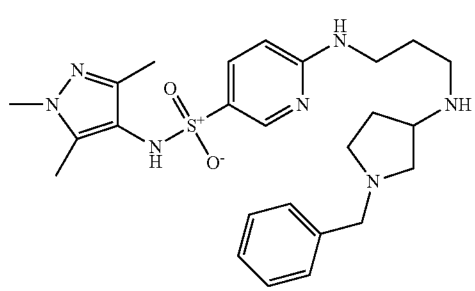 [SMILES: Cc1nn(C)c(C)c1N[S+](=O)([O-])c1ccc(NCCCNC2CCN(Cc3ccccc3)C2)nc1] | 1.0 | >1 | 498.1 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (µM) NMT Enzyme | $ED_{50}$ (µM) *T. brucei* | MH+ |
|---|---|---|---|---|
| DDD86296 | 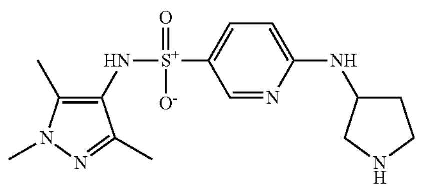 [SMILES: Cc1nn(C)c(C)c1N[S+](=O)([O-])c1ccc(NC2CCNC2)nc1] | 1.2 | >1 | 350.1 |
| DDD86297 | 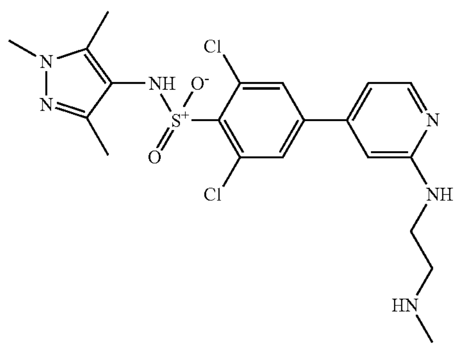 | 1.0 | >1 | 483.1 |
| DDD86298 | 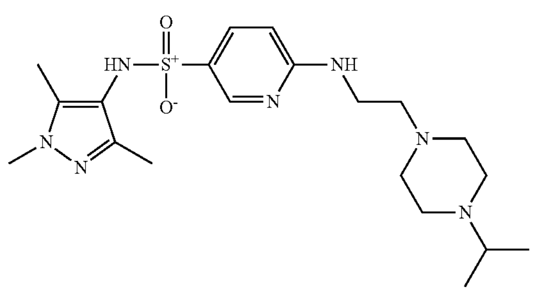 [SMILES: Cc1nn(C)c(C)c1N[S+](=O)([O-])c1ccc(NCCN2CCN(C(C)C)CC2)nc1] | 1.0 | >1 | 436.1 |
| DD86299 | 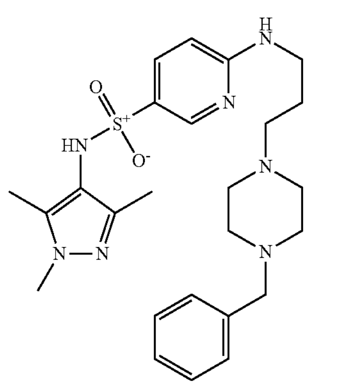 [SMILES: Cc1nn(C)c(C)c1N[S+](=O)([O-])c1ccc(NCCCN2CCN(Cc3ccccc3)CC2)nc1] | 1.0 | >1 | 498.2 |
| DDD86300 | 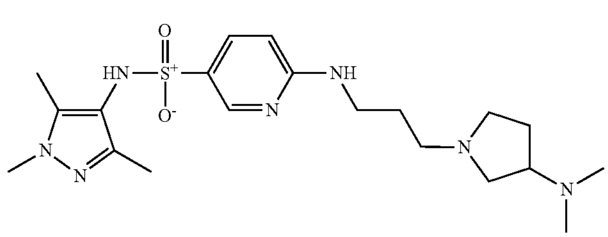 | 0.07 | 1.73 | 435.1 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activities are for inhibition of *T. brucei brucei* (blood stream form, variant 221).

| Reference Number | STRUCTURE | IC$_{50}$ (µM) NMT Enzyme | ED$_{50}$ (µM) T. brucei | MH+ |
|---|---|---|---|---|
| DDD86301 | 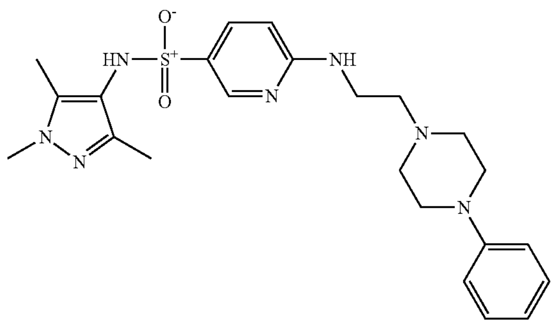 [SMILES: Cc1nn(C)c(C)c1N[S+](=O)([O-])c1ccc(NCCN2CCN(c3ccccc3)CC2)nc1] | 1.0 | >1 | 469.1 |
| DDD86302 | 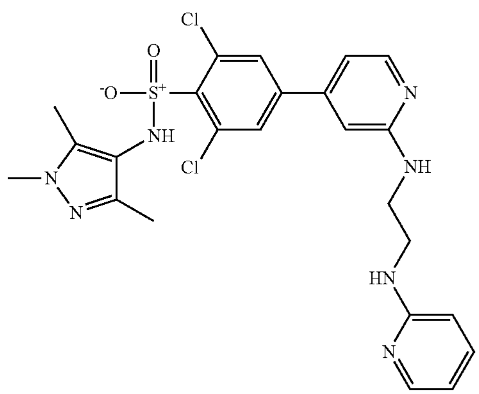 | 1.0 | >1 | 546.1 |
| DDD86303 | 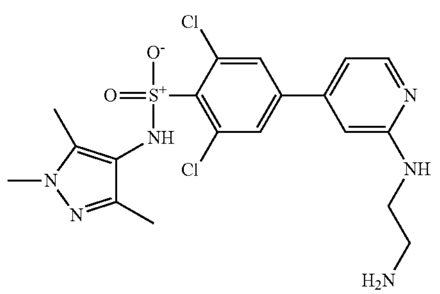 [SMILES: Cc1nn(C)c(C)c1N[S+](=O)([O-])c1c(Cl)cc(-c2ccnc(NCCN)c2)cc1Cl] | 1.0 | >1 | 469.2 |
| DDD86304 | 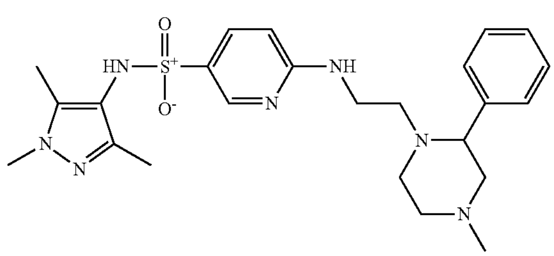 [SMILES: Cc1nn(C)c(C)c1N[S+](=O)([O-])c1ccc(NCCN2CCN(C)CC2c2ccccc2)nc1] | 1.0 | >1 | 484.1 |
| DDD86305 | 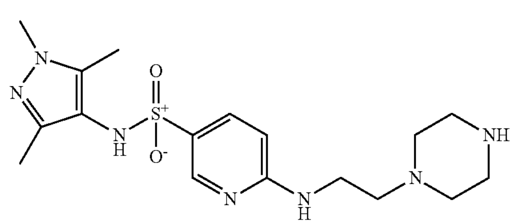 [SMILES: Cc1nn(C)c(C)c1N[S+](=O)([O-])c1ccc(NCCN2CCNCC2)nc1] | 0.87 | >1 | 393.1 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD86306 | 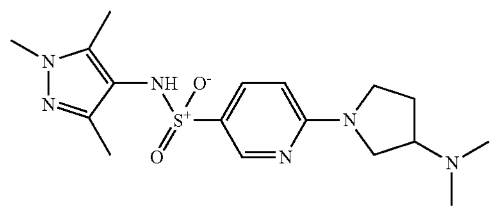 | 1.0 | >1 | 378.2 |
| DDD86307 | 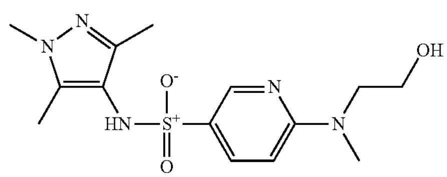 [SMILES: Cc1nn(C)c(C)c1N[S+](=O)([O-])c1ccc(N(C)CCO)nc1] | 1.0 | >1 | 339.1 |
| DDD86308 | 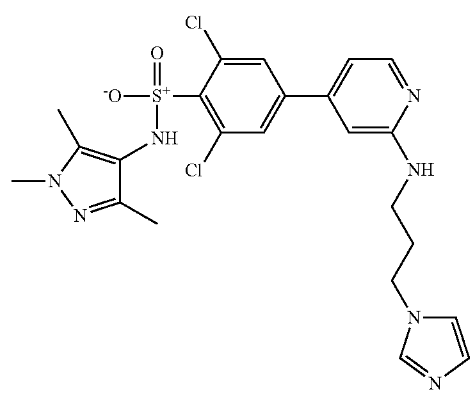 | 1.0 | >1 | 534.1 |
| DDD86309 | 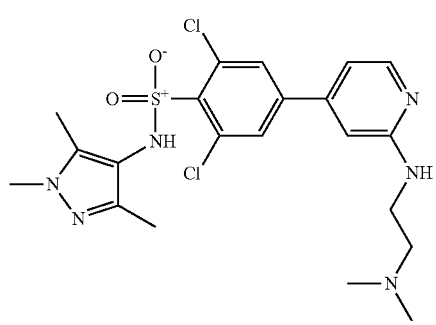 | 1.0 | >1 | 497.1 |
| DDD86310 | 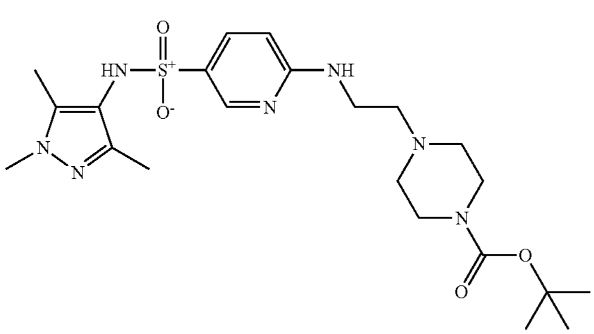 [SMILES: Cc1nn(C)c(C)c1N[S+](=O)([O-])c1ccc(NCCN2CCN(C(=O)OC(C)(C)C)CC2)nc1] | 1.0 | >1 | 494.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | IC$_{50}$ (µM) NMT Enzyme | ED$_{50}$ (µM) *T. brucei* | MH+ |
|---|---|---|---|---|
| DDD86311 | 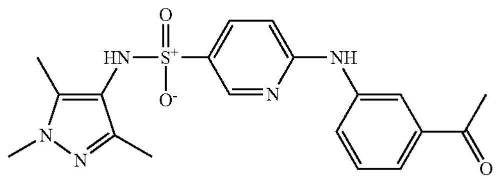 [SMILES: CC(=O)c1cccc(Nc2ccc([S+](=O)([O-])Nc3c(C)nn(C)c3C)cn2)c1] | 1.0 | >1 | 400.2 |
| DDD86312 | 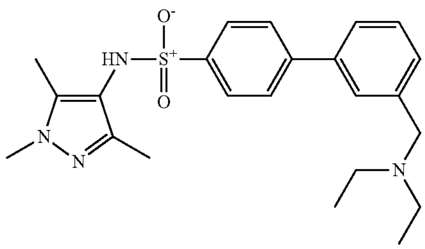 [SMILES: CCN(CC)Cc1cccc(-c2ccc([S+](=O)([O-])Nc3c(C)nn(C)c3C)cc2)c1] | 0.03 | 0.07 | 427.2 |
| DDD86314 | 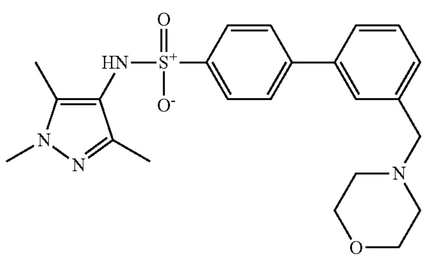 [SMILES: Cc1nn(C)c(C)c1N[S+](=O)([O-])c1ccc(-c2cccc(CN3CCOCC3)c2)cc1] | 1.0 | >1 | 441.1 |
| DDD86315 | 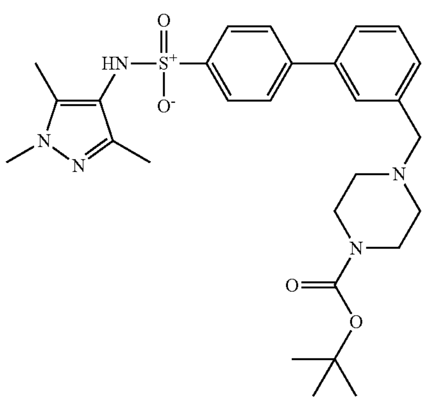 [SMILES: Cc1nn(C)c(C)c1N[S+](=O)([O-])c1ccc(-c2cccc(CN3CCN(C(=O)OC(C)(C)C)CC3)c2)cc1] | 1.0 | >1 | 540.1 |
| DDD86316 | 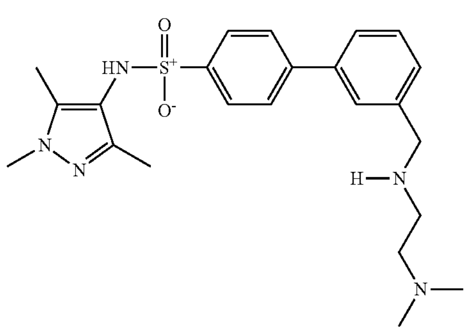 | 0.61 | 5.0 | 442.1 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD86317 | 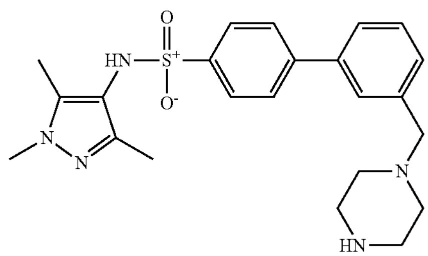 [SMILES: Cc1nn(C)c(C)c1N[S+](=O)([O-])c1ccc(-c2cccc(CN3CCNCC3)c2)cc1] | 0.01 | 0.02 | 440.1 |
| DDD86318 | 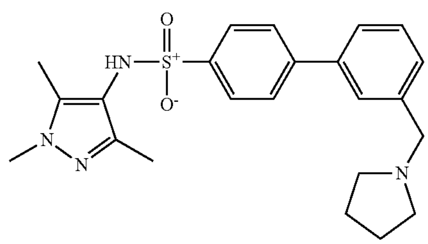 [SMILES: Cc1nn(C)c(C)c1N[S+](=O)([O-])c1ccc(-c2cccc(CN3CCCC3)c2)cc1] | 0.08 | 0.21 | 425.1 |
| DDD86467 | 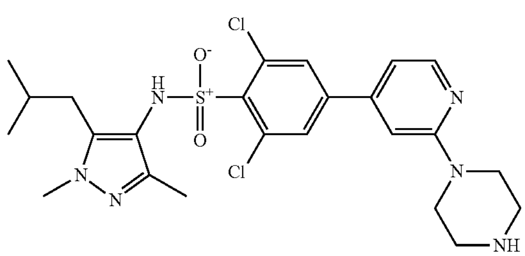 [SMILES: Cc1nn(C)c(CC(C)C)c1N[S+](=O)([O-])c1c(Cl)cc(-c2ccnc(N3CCNCC3)c2)cc1Cl] | 0.01 | 0.003 | 537.2 |
| DDD86468 | 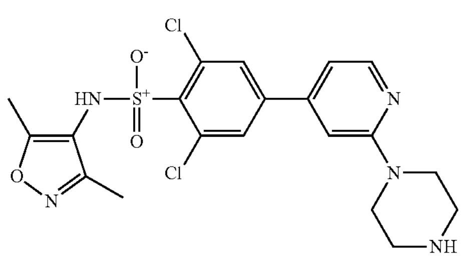 [SMILES: Cc1noc(C)c1N[S+](=O)([O-])c1c(Cl)cc(-c2ccnc(N3CCNCC3)c2)cc1Cl] | 0.01 | 0.20 | 482.1 |
| DDD86469 | 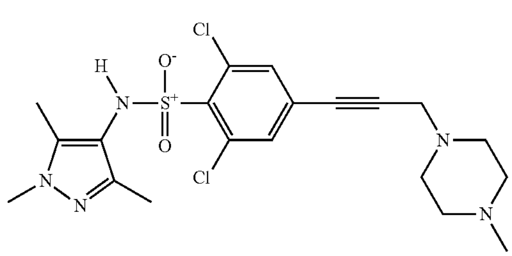 | 0.17 | 0.55 | 470.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activities are for inhibition of *T. brucei brucei* (blood stream form, variant 221).

| Reference Number | STRUCTURE | IC$_{50}$ (μM) NMT Enzyme | ED$_{50}$ (μM) T. brucei | MH+ |
|---|---|---|---|---|
| DDD86470 | 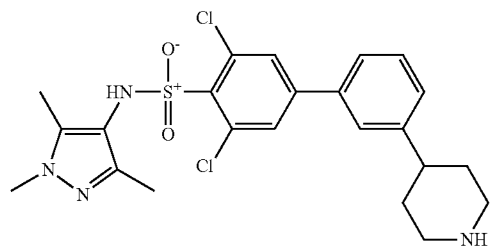 [SMILES: Cc1nn(C)c(C)c1N[S+](=O)([O-])c1c(Cl)cc(-c2cccc(C3CCNCC3)c2)cc1Cl] | 0.01<br>0.02 (HuNMT-1)<br>0.007 (AfNMT) | 0.02 | 493.1 |
| DDD86471 | 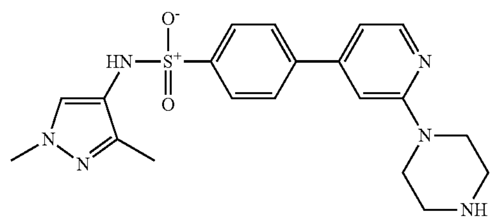 [SMILES: Cc1nn(C)cc1N[S+](=O)([O-])c1ccc(-c2ccnc(N3CCNCC3)c2)cc1] | 0.01 | 0.009 | 413.2 |
| DDD86472 | 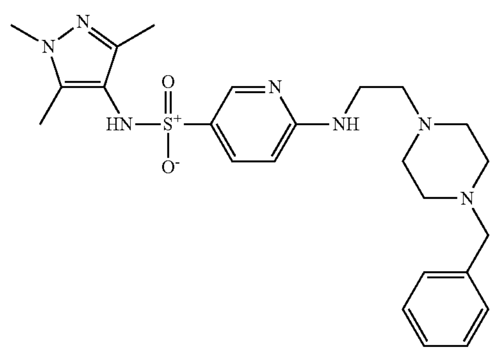 [SMILES: Cc1nn(C)c(C)c1N[S+](=O)([O-])c1ccc(NCCN2CCN(Cc3ccccc3)CC2)nc1] | 10.0 | >1 | 483.2 |
| DDD86473 | 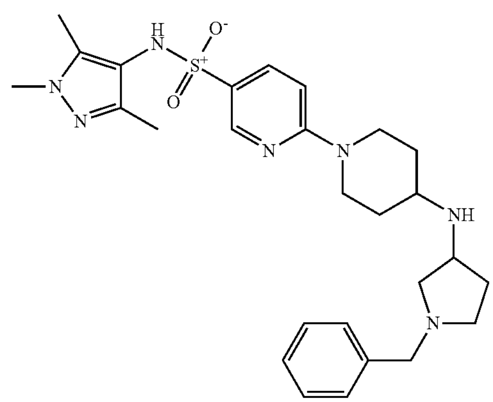 [SMILES: Cc1nn(C)c(C)c1N[S+](=O)([O-])c1ccc(N2CCC(NC3CCN(Cc4ccccc4)C3)CC2)nc1] | 10.0 | >1 | 523.2 |
| DDD86474 | 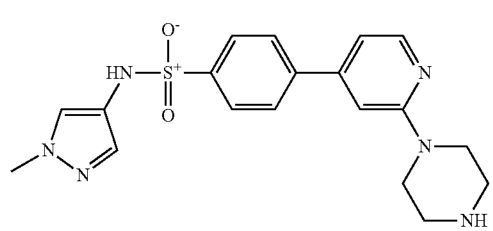 [SMILES: Cn1cc(N[S+](=O)([O-])c2ccc(-c3ccnc(N4CCNCC4)c3)cc2)cn1] | 0.07 | 0.65 | 399.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (µM) NMT Enzyme | $ED_{50}$ (µM) *T. brucei* | MH+ |
|---|---|---|---|---|
| DDD86475 | 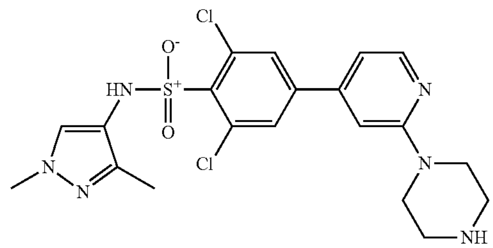 [SMILES: Cc1nn(C)cc1N[S+](=O)([O-])c1c(Cl)cc(-c2ccnc(N3CCNCC3)c2)cc1Cl] | 0.001<br>0.01 (HuNMT-1) | 0.003 | 481.1 |
| DDD86476 | 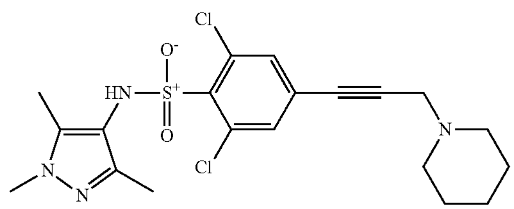 [SMILES: Cc1nn(C)c(C)c1N[S+](=O)([O-])c1c(Cl)cc(C#CCN2CCCCC2)cc1Cl] | 5.9 | >1 | 455.2 |
| DDD86477 | 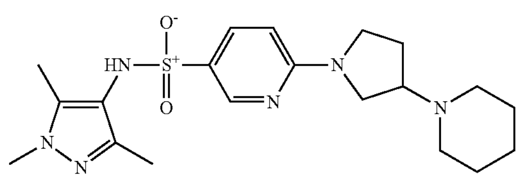 [SMILES: Cc1nn(C)c(C)c1N[S+](=O)([O-])c1ccc(N2CCC(N3CCCCC3)C2)nc1] | 7.2 | >1 | 418.2 |
| DDD86478 | 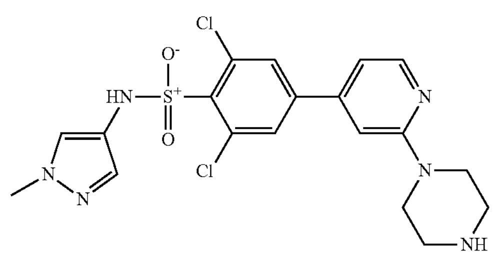 | 0.04<br>0.06 (HuNMT-1) | 0.24 | 467.1 |
| DDD86479 | 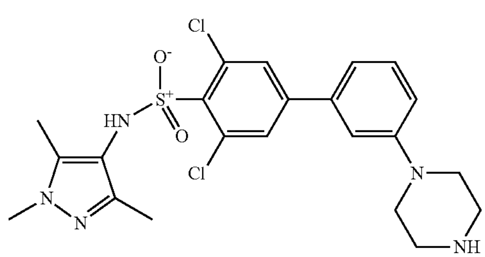 [SMILES: Cc1nn(C)c(C)c1N[S+](=O)([O-])c1c(Cl)cc(-c2cccc(N3CCNCC3)c2)cc1Cl] | 0.01<br>0.016 (HuNMT-1) | 0.005 | 494.1 |
| DDD86480 | 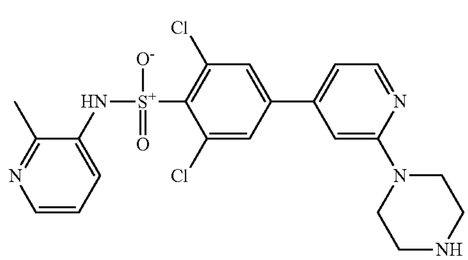 [SMILES: Cc1ncccc1N[S+](=O)([O-])c1c(Cl)cc(-c2ccnc(N3CCNCC3)c2)cc1Cl] | 0.02<br>0.08 (HuNMT-1) | 0.33 | 478.1 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | IC$_{50}$ (μM) NMT Enzyme | ED$_{50}$ (μM) *T. brucei* | MH+ |
|---|---|---|---|---|
| DDD86481 | 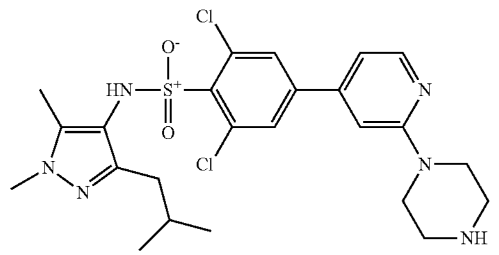 [SMILES: Cc1c(N[S+](=O)([O-])c2c(Cl)cc(-c3ccnc(N4CCNCC4)c3)cc2Cl)c(CC(C)C)nn1C] | 0.001<br>0.003 (HuNMT-1) | 0.002 | 537.2 |
| DDD87748 | 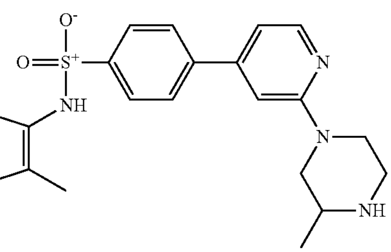 | 0.001<br>0.008 (HuNMT-1) | 0.001 | 441.2 |
| DDD87749 | 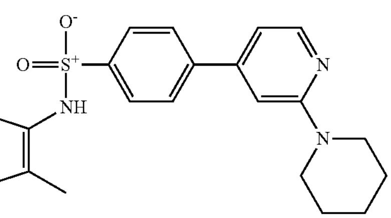 | 0.79<br>9.3 (HuNMT-1)<br>9.3 (AfNMT) | 1.28 | 426.2 |
| DDD87751 | 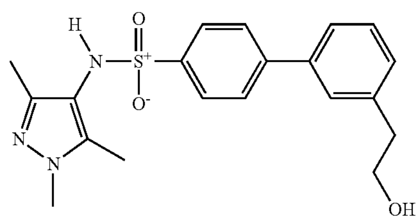 [SMILES: Cc1nn(C)c(C)c1N[S+](=O)([O-])c1ccc(-c2cccc(CCO)c2)cc1] | 5.0 | >1 | 386.2 |
| DDD87753 | 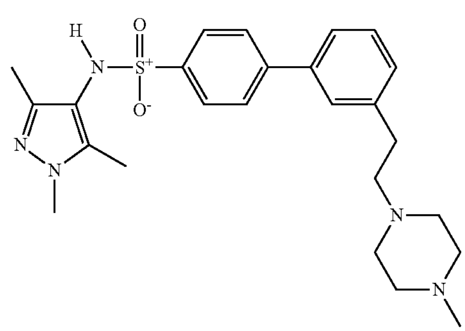 | 0.23<br>0.18 (HuNMT-1)<br>0.80 (AfNMT) | >1 | 464.1 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD87754 | 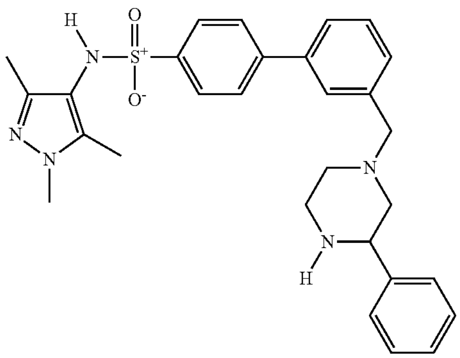 [SMILES: Cc1nn(C)c(C)c1N[S+](=O)([O-])c1ccc(-c2cccc(CN3CCNC(c4ccccc4)C3)c2)cc1] | 0.34 | 1.6 | 515.2 |
| DDD87755 | 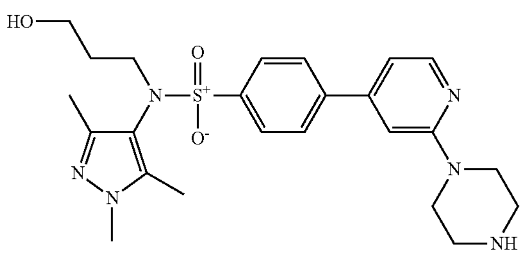 [SMILES: Cc1nn(C)c(C)c1N(CCCO)[S+](=O)([O-])c1ccc(-c2ccnc(N3CCNCC3)c2)cc1] | 0.05 | 0.98 | 485.2 |
| DDD87756 | 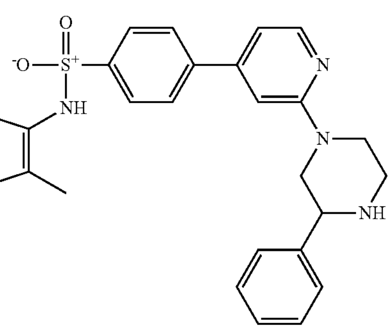 | 0.76 | >1 | 503.1 |
| DDD87757 | 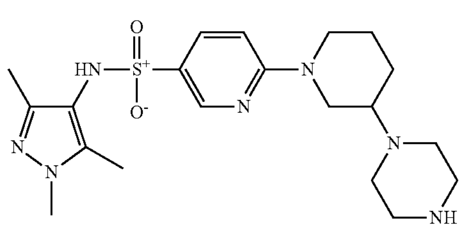 [SMILES: Cc1nn(C)c(C)c1N[S+](=O)([O-])c1ccc(N2CCCC(N3CCNCC3)C2)nc1] | 0.003<br>0.01 (HuNMT-1)<br>0.09 (AfNMT) | 0.003 | 434.2 |
| DDD87758 | 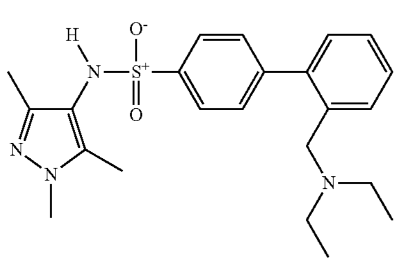 [SMILES: CCN(CC)Cc1ccccc1-c1ccc([S+](=O)([O-])Nc2c(C)nn(C)c2C)cc1] | 40.1 | >1 | 427.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
| --- | --- | --- | --- | --- |
| DDD87759 | 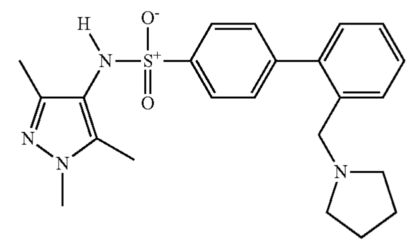 [SMILES: Cc1nn(C)c(C)c1N[S+](=O)([O-])c1ccc(-c2ccccc2CN2CCCC2)cc1] | 0.91 | >1 | 454.1 |
| DDD87760 | 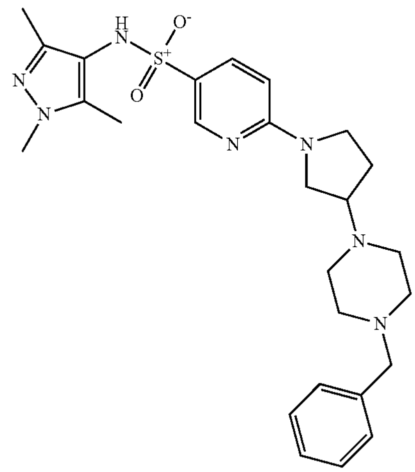 [SMILES: Cc1nn(C)c(C)c1N[S+](=O)([O-])c1ccc(N2CCC(N3CCN(Cc4ccccc4)CC3)C2)nc1] | 34.4 | >1 | 510.2 |
| DDD87761 | 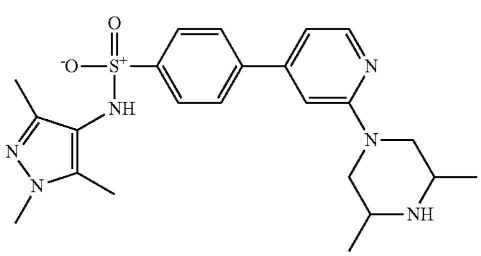 | 0.01 0.04 (HuNMT-1) 0.11 (AfNMT) | 0.02 | 455.2 |
| DDD87762 | 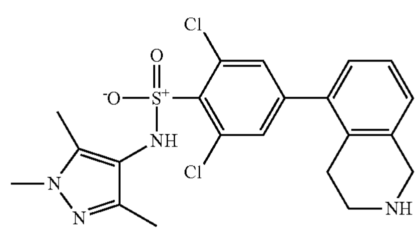 | 2.6 | >1 | 465.1 |
| DDD87763 | 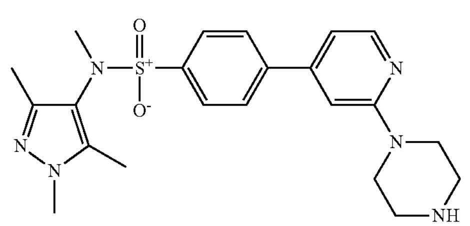 [SMILES: Cc1nn(C)c(C)c1N(C)[S+](=O)([O-])c1ccc(-c2ccnc(N3CCNCC3)c2)cc1] | 0.003 0.02 (HuNMT-1) | 0.003 | 441.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | IC$_{50}$ (µM) NMT Enzyme | ED$_{50}$ (µM) *T. brucei* | MH+ |
|---|---|---|---|---|
| DDD87764 | 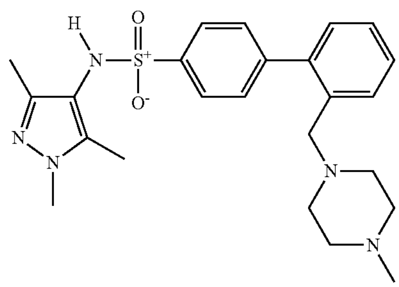 | 0.97 | >1 | 454.1 |
| DDD87765 | 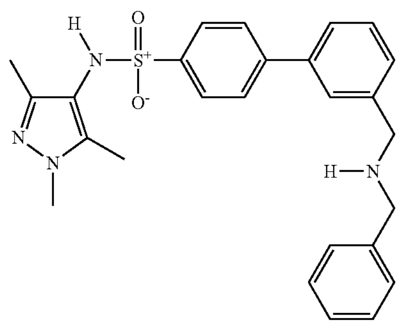 [SMILES: Cc1nn(C)c(C)c1N[S+](=O)([O-])c1ccc(-c2cccc(CNCc3ccccc3)c2)cc1] | 2.8 | >1 | 461.1 |
| DDD87766 | 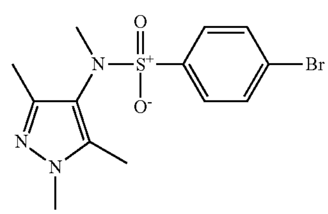 [SMILES: Cc1nn(C)c(C)c1N(C)[S+](=O)([O-])c1ccc(Br)cc1] | 10.0 | >1 | 404.1 |
| DDD87767 | 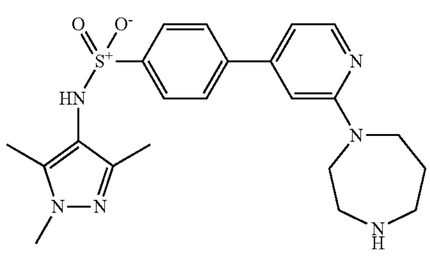 [SMILES: Cc1nn(C)c(C)c1N[S+](=O)([O-])c1ccc(-c2ccnc(N3CCCNCC3)c2)cc1] | 0.002<br>0.008 (HuNMT-1)<br>0.008 (AfNMT) | 0.003 | 441.2 |
| DDD87768 | 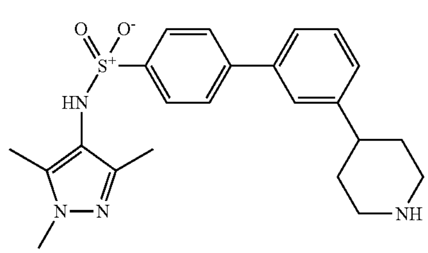 [SMILES: Cc1nn(C)c(C)c1N[S+](=O)([O-])c1ccc(-c2cccc(C3CCNCC3)c2)cc1] | 0.01 | 0.06 | 425.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (µM) NMT Enzyme | $ED_{50}$ (µM) *T. brucei* | MH+ |
|---|---|---|---|---|
| DDD87769 | 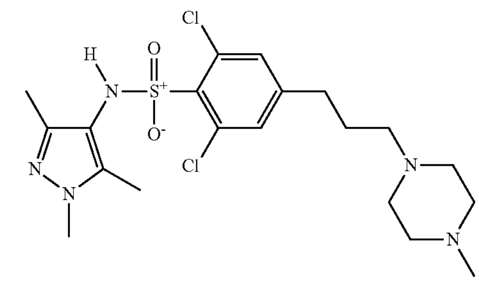 | 0.003<br>0.27 (AfNMT) | 0.008 | 474.1 |
| DDD87993 | 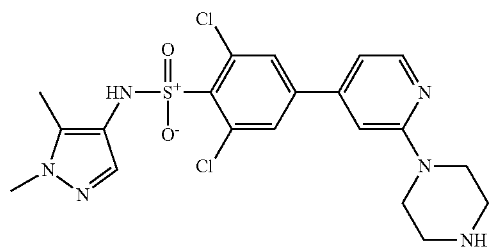 [SMILES: Cc1c(N[S+](=O)([O-])c2c(Cl)cc(-c3ccnc(N4CCNCC4)c3)cc2Cl)cnn1C] | 0.005<br>0.009 (HuNMT-1) | 0.01 | 481.1 |
| DDD87994 | 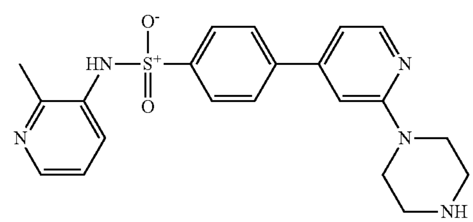 | 0.01<br>0.23 (AfNMT) | 0.11 | 410.2 |
| DDD87995 | 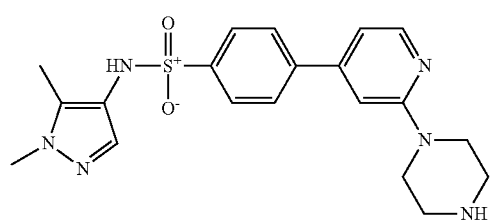 | 0.06 | 0.02 | 413.2 |
| DDD87997 | 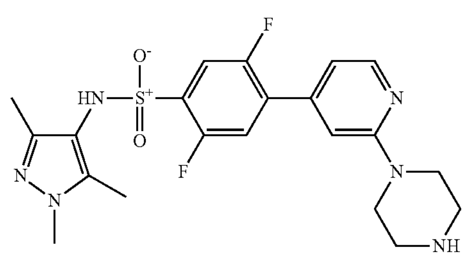 [SMILES: Cc1nn(C)c(C)c1N[S+](=O)([O-])c1cc(F)c(-c2ccnc(N3CCNCC3)c2)cc1F] | 0.03<br>0.013 (HuNMT-1)<br>0.02 (AfNMT) | 0.003 | 463.2 |
| DDD87999 | 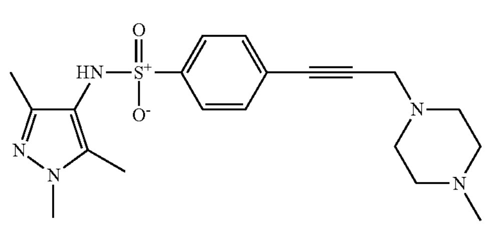 | 0.21 | >1 | 402.1 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (µM) NMT Enzyme | $ED_{50}$ (µM) *T. brucei* | MH+ |
|---|---|---|---|---|
| DDD88000 | 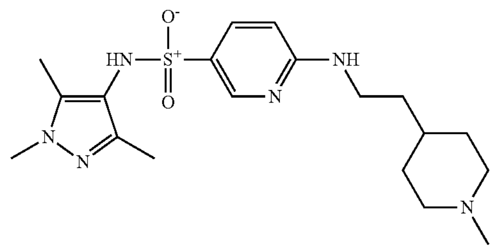 | 0.03<br>1.5 (AfNMT) | 0.77 | 407.2 |
| DDD88002 | 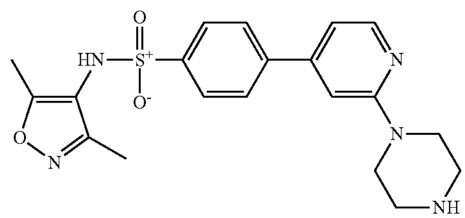 [SMILES: Cc1noc(C)c1N[S+](=O)([O-])c1ccc(-c2ccnc(N3CCNCC3)c2)cc1] | 0.02<br>0.65 (HuNMT-1)<br>0.79 (AfNMT) | 0.14 | 482.1 |
| DDD88003 | 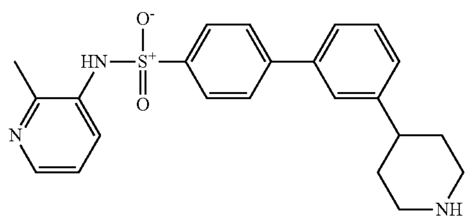 [SMILES: Cc1ncccc1N[S+](=O)([O-])c1ccc(-c2cccc(C3CCNCC3)c2)cc1] | 0.16 | 1.9 | 408.2 |
| DDD88004 | 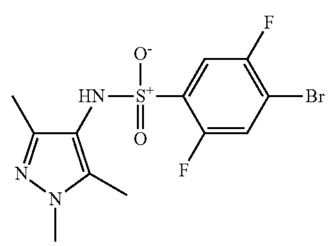 [SMILES: Cc1nn(C)c(C)c1N[S+](=O)([O-])c1cc(F)c(Br)cc1F] | 6.2 | >1 | 380.0 |
| DDD88005 | 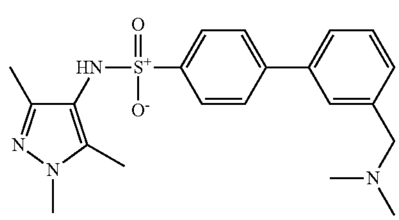 | 0.23 | 0.1 | 399.3 |
| DDD88006 | 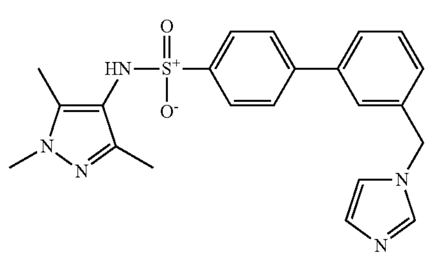 [SMILES: Cc1nn(C)c(C)c1N[S+](=O)([O-])c1ccc(-c2cccc(Cn3ccnc3)c2)cc1] | 0.35<br>4.2 (AfNMT) | 3.9 | 422.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | IC$_{50}$ (μM) NMT Enzyme | ED$_{50}$ (μM) T. brucei | MH+ |
|---|---|---|---|---|
| DDD88007 | 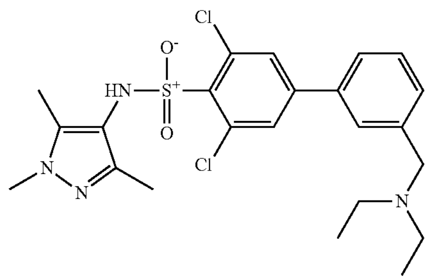 [SMILES: CCN(CC)Cc1cccc(-c2cc(Cl)c([S+](=O)([O-])Nc3c(C)nn(C)c3C)c(Cl)c2)c1] | 0.02<br>0.13 (HuNMT-1)<br>0.14 (AfNMT) | 0.08 | 495.1 |
| DDD88008 | 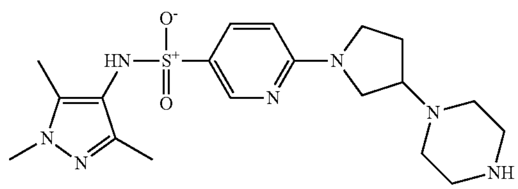 [SMILES: Cc1nn(C)c(C)c1N[S+](=O)([O-])c1ccc(N2CCC(N3CCNCC3)C2)nc1] | 0.11 | 18.0 | 420.2 |
| DDD88009 | 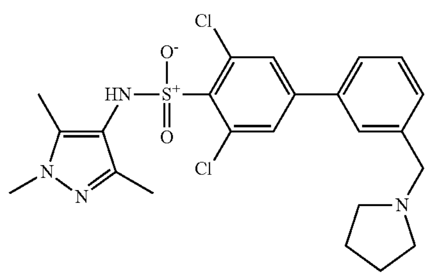 [SMILES: Cc1nn(C)c(C)c1N[S+](=O)([O-])c1c(Cl)cc(-c2cccc(CN3CCCC3)c2)cc1Cl] | 0.02 | 0.10 | 493.1 |
| DDD88186 | 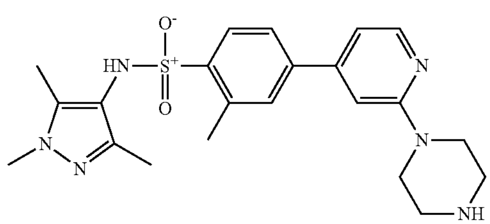 [SMILES: Cc1cc(-c2ccnc(N3CCNCC3)c2)ccc1[S+](=O)([O-])Nc1c(C)nn(C)c1C] | 0.003<br>0.006 (HuNMT-1) | 0.003 | 441.2 |
| DDD88187 | 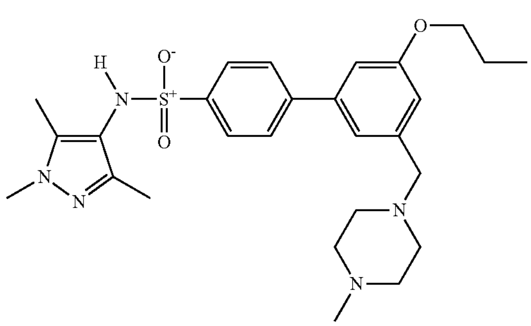 [SMILES: CCCOc1cc(CN2CCN(C)CC2)cc(-c2ccc([S+](=O)([O-])Nc3c(C)nn(C)c3C)cc2)c1] | 0.37 | 2.15 | 512.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (µM) NMT Enzyme | $ED_{50}$ (µM) *T. brucei* | MH+ |
|---|---|---|---|---|
| DDD88188 | 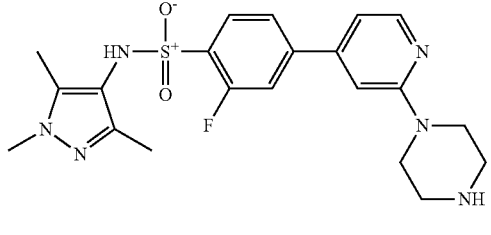 | 0.003<br>0.009 (HuNMT-1) | 0.005 | 445.2 |
| DDD88189 | 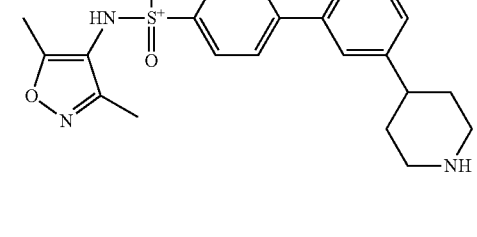 | 0.43 | >1 | 412.2 |
| DDD88190 | 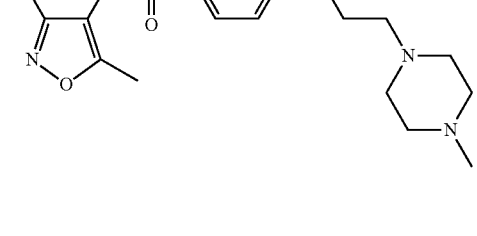 | 1.1 | 31.0 | 393.1 |
| DDD88191 | 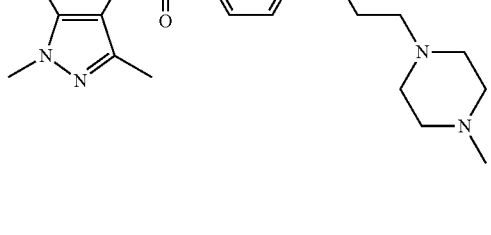 | 0.12<br>10.0 (AfNMT) | 0.67 | 406.2 |
| DDD88193 | 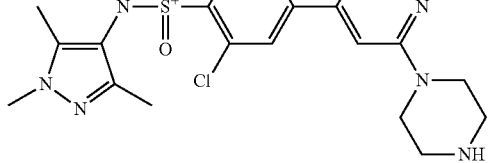 | 0.003<br>0.005 (HuNMT-1)<br>0.007 (AfNMT) | 0.005 | 509.1 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT)
enzyme inhibition data are given in parentheses. Cellular activitites are for inhibition of *T. brucei brucei* (blood stream form, variant 221).

| Reference Number | STRUCTURE | $IC_{50}$ (µM) NMT Enzyme | $ED_{50}$ (µM) *T. brucei* | MH+ |
|---|---|---|---|---|
| DDD88194 | 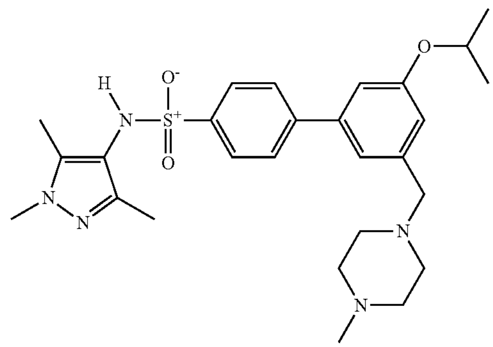 [SMILES: Cc1nn(C)c(C)c1N[S+](=O)([O-])c1ccc(-c2cc(CN3CCN(C)CC3)cc(OC(C)C)c2)cc1] | 0.48 | 2.0 | 512.2 |
| DDD88195 | 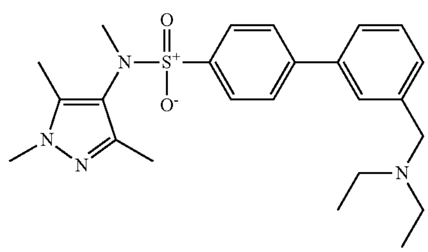 [SMILES: CCN(CC)Cc1cccc(-c2ccc([S+](=O)([O-])N(C)c3c(C)nn(C)c3C)cc2)c1] | 0.05 | 0.51 | 441.2 |
| DDD88196 | 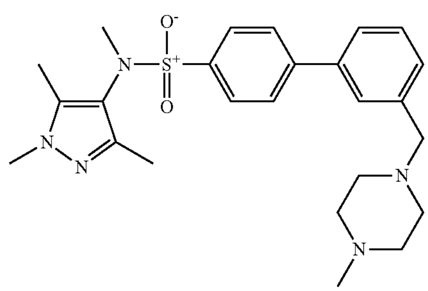 [SMILES: Cc1nn(C)c(C)c1N(C)[S+](=O)([O-])c1ccc(-c2cccc(CN3CCN(C)CC3)c2)cc1] | 0.02<br>0.017 (HuNMT-1)<br>0.035 (AfNMT) | 0.05 | 468.2 |
| DDD88197 | 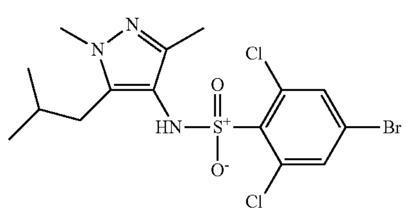 [SMILES: Cc1nn(C)c(CC(C)C)c1N[S+](=O)([O-])c1c(Cl)cc(Br)cc1Cl] | 13.8 | 45.9 | 456.0 |
| DDD88198 | 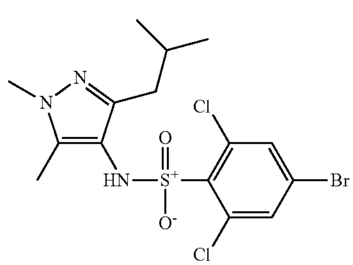 [SMILES: Cc1c(N[S+](=O)([O-])c2c(Cl)cc(Br)cc2Cl)c(CC(C)C)nn1C] | 0.71 | 2.3 | 456.0 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (µM) NMT Enzyme | $ED_{50}$ (µM) *T. brucei* | MH+ |
|---|---|---|---|---|
| DDD88315 | 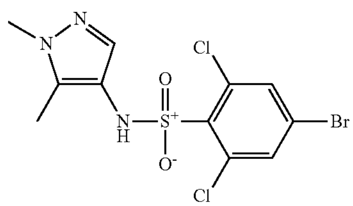 [SMILES: Cc1c(N[S+](=O)([O-])c2c(Cl)cc(Br)cc2Cl)cnn1C] | 20.0<br>70.8 (HuNMT-1) | >10 | 399.9 |
| DDD88316 | 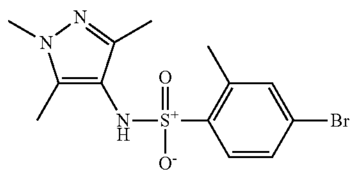 | 12.7<br>107 (HuNMT-1) | >10 | 358.0 |
| DDD88317 | 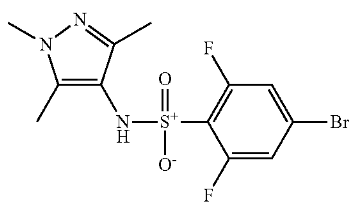 | 10.0<br>>100 (HuNMT-1) | >10 | 379.0 |
| DDD88318 | 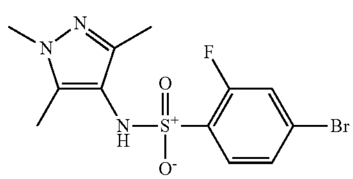 [SMILES: Cc1cc(Br)ccc1[S+](=O)([O-])Nc1c(C)nn(C)c1C] | 10.0<br>87.0 (HuNMT-1) | >10 | 362.0 |
| DDD88319 | 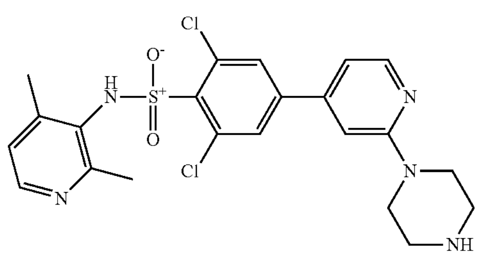 [SMILES: Cc1ccnc(C)c1N[S+](=O)([O-])c1c(Cl)cc(-c2ccnc(N3CCNCC3)c2)cc1Cl] | 0.045<br>0.77 (HuNMT-1) | 0.69 | 492.1 |
| DDD88320 | 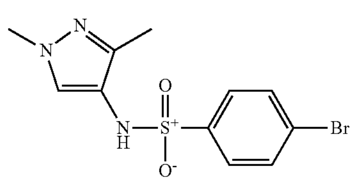 [SMILES: Cc1nn(C)cc1N[S+](=O)([O-])c1ccc(Br)cc1] | 44.1<br>>100 (HuNMT-1) | >10 | 330.0 |
| DDD88321 | 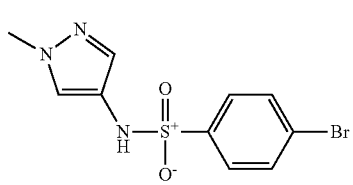 [SMILES: Cn1cc(N[S+](=O)([O-])c2ccc(Br)cc2)cn1] | >100<br>>100 (HuNMT-1) | >10 | 316.0 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD88322 | 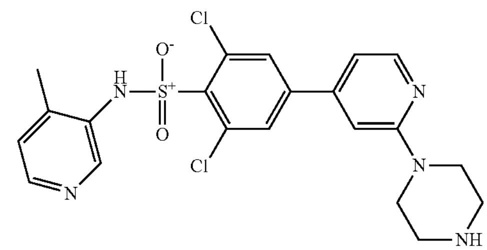 [SMILES: Cc1ccncc1N[S+](=O)([O-])c1c(Cl)cc(-c2ccnc(N3CCNCC3)c2)cc1Cl] | 0.182<br>1.5 (HuNMT-1) | 1.93 | 478.1 |
| DDD88323 | 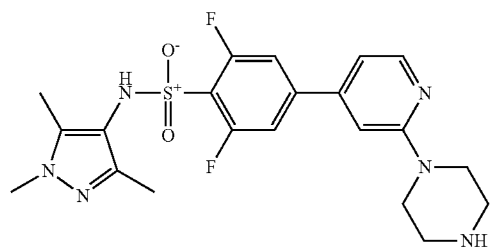 [SMILES: Cc1nn(C)c(C)c1N[S+](=O)([O-])c1c(F)cc(-c2ccnc(N3CCNCC3)c2)cc1F] | 0.004<br>0.29 (HuNMT-1) | 0.005 | 463.2 |
| DDD88324 | 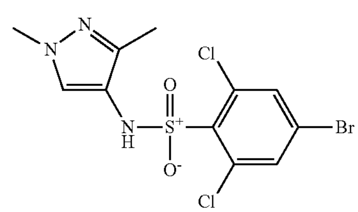 [SMILES: Cc1nn(C)cc1N[S+](=O)([O-])c1c(Cl)cc(Br)cc1Cl] | 75.4<br>3.36 (HuNMT-1) | >10 | 399.9 |
| DDD88325 | 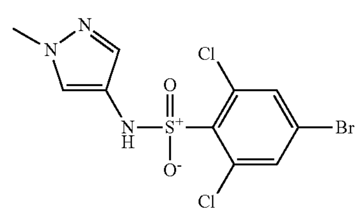 [SMILES: Cn1cc(N[S+](=O)([O-])c2c(Cl)cc(Br)cc2Cl)cn1] | >100<br>>100 (HuNMT-1) | >10 | 385.9 |
| DDD88326 | 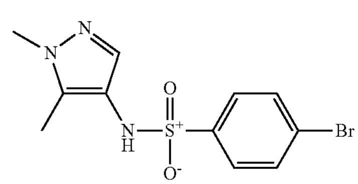 [SMILES: Cc1c(N[S+](=O)([O-])c2ccc(Br)cc2)cnn1C] | >100<br>>100 (HuNMT-1) | >10 | 330.0 |
| DDD88523 | 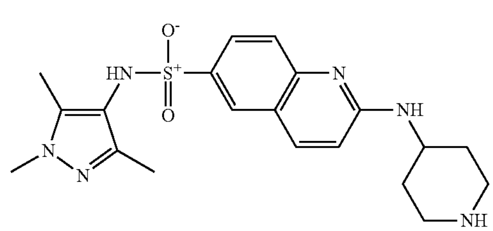 [SMILES: Cc1nn(C)c(C)c1N[S+](=O)([O-])c1ccc2nc(NC3CCNCC3)ccc2c1] | 0.61<br>6.3 (HuNMT-1) | >1 | 415.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD88533 | 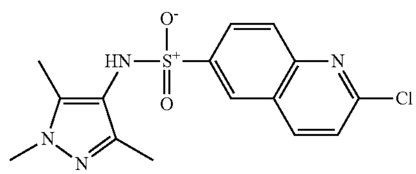 [SMILES: Cc1nn(C)c(C)c1N[S+](=O)([O-])c1ccc2nc(Cl)ccc2c1] | 5.98<br>17.7 (HuNMT-1) | >10 | 351.1 |
| DDD88549 | 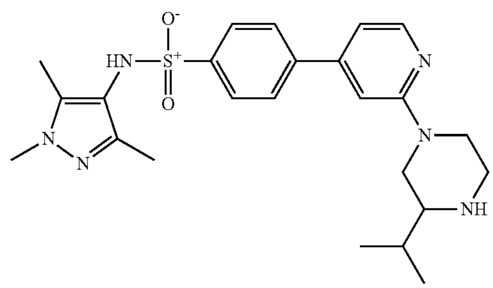 [SMILES: Cc1nn(C)c(C)c1N[S+](=O)([O-])c1ccc(-c2ccnc(N3CCNC(C(C)C)C3)c2)cc1] | 0.025<br>0.24 (HuNMT-1) | 0.11 | 468.2 |
| DDD88557 | 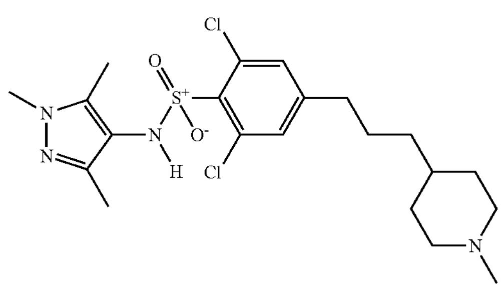 | 0.002<br>0.301 (HuNMT-1)<br>0.001 (LmNMT) | 0.002 | 472.2 |
| DDD88558 | 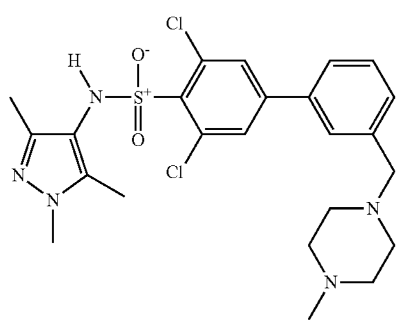 [SMILES: Cc1nn(C)c(C)c1N[S+](=O)([O-])c1c(Cl)cc(-c2cccc(CN3CCN(C)CC3)c2)cc1Cl] | 0.006<br>0.007 (HuNMT-1) | 0.009 | 522.1 |
| DDD88559 | 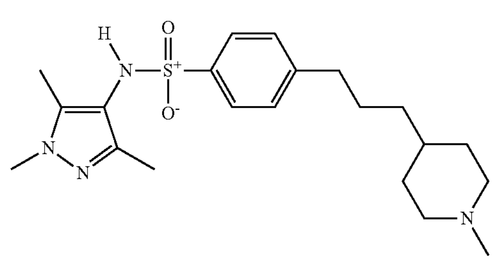 | 0.008<br>0.175 (HuNMT-1) | 0.038 | 405.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activities are for inhibition of *T. brucei brucei* (blood stream form, variant 221).

| Reference Number | STRUCTURE | $IC_{50}$ (µM) NMT Enzyme | $ED_{50}$ (µM) *T. brucei* | MH+ |
|---|---|---|---|---|
| DDD88560 | 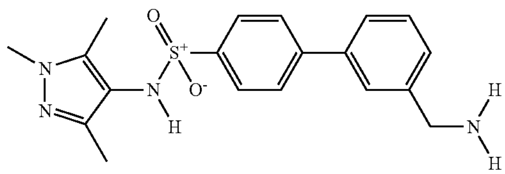 [SMILES: Cc1nn(C)c(C)c1N[S+](=O)([O-])c1ccc(-c2cccc(CN)c2)cc1] | 0.054<br>0.272 (HuNMT-1) | 2.15 | 371.1 |
| DDD88580 | 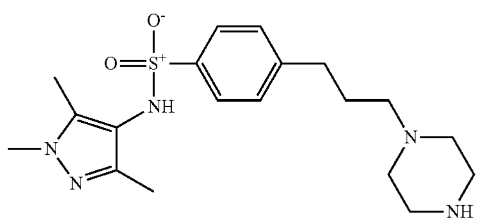 [SMILES: Cc1nn(C)c(C)c1N[S+](=O)([O-])c1ccc(CCCN2CCNCC2)cc1] | 0.077<br>1.0 (HuNMT-1) | 1.13 | 391.2 |
| DDD88636 | 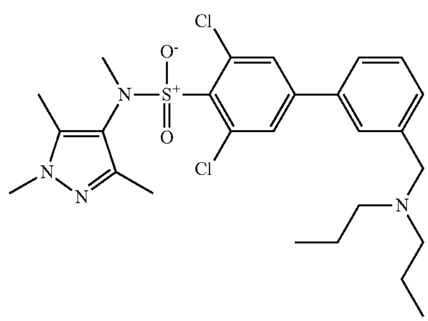 [SMILES: CCCN(CCC)Cc1cccc(-c2cc(Cl)c([S+](=O)([O-])N(C)c3c(C)nn(C)c3C)c(Cl)c2)c1] | 0.92<br>3.7 (HuNMT-1) | 1.89 | 537.2 |
| DDD88638 | 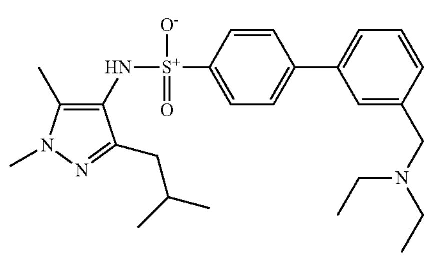 [SMILES: CCN(CC)Cc1cccc(-c2ccc([S+](=O)([O-])Nc3c(CC(C)C)nn(C)c3C)cc2)c1] | 0.009<br>0.047 (HuNMT-1) | 0.084 | 469.3 |
| DDD88640 | 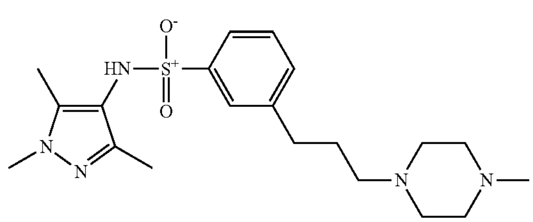 | >1<br>>1 (HuNMT-1) | 18.7 | 406.2 |
| DDD88641 | 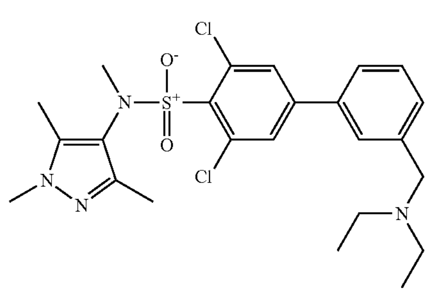 [SMILES: CCN(CC)Cc1cccc(-c2cc(Cl)c([S+](=O)([O-])N(C)c3c(C)nn(C)c3C)c(Cl)c2)c1] | 0.029<br>0.31 (HuNMT-1) | 0.31 | 509.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) T. brucei | MH+ |
|---|---|---|---|---|
| DDD88642 | 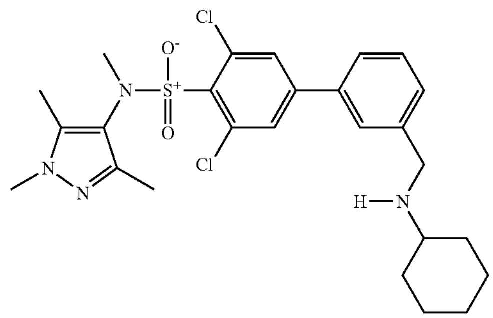 [SMILES: Cc1nn(C)c(C)c1N(C)[S+](=O)([O-])c1c(Cl)cc(-c2cccc(CNC3CCCCC3)c2)cc1Cl] | 0.39<br>4.48 (HuNMT-1) | 0.89 | 535.2 |
| DDD88643 | 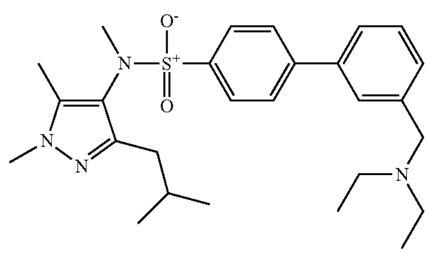 [SMILES: CCN(CC)Cc1cccc(-c2ccc([S+](=O)([O-])N(C)c3c(CC(C)C)nn(C)c3C)cc2)c1] | 0.063<br>0.144 (HuNMT-1) | 0.49 | 483.3 |
| DDD88644 | 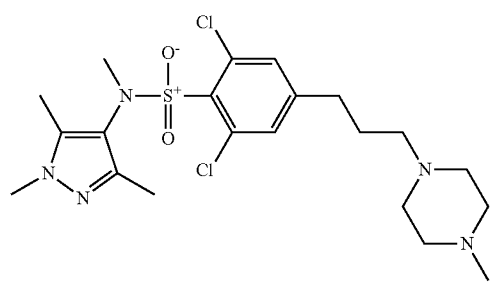 | 0.003<br>0.188 (HuNMT-1) | 0.012 | 488.2 |
| DDD88645 | 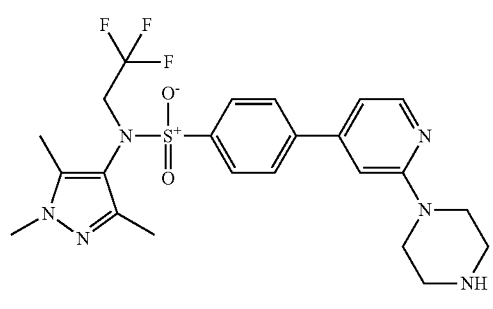 [SMILES: Cc1nn(C)c(C)c1N(CC(F)(F)F)[S+](=O)([O-])c1ccc(-c2ccnc(N3CCNCC3)c2)cc1] | 0.003<br>0.021 (HuNMT-1) | 0.021 | 509.2 |
| DDD88646 | 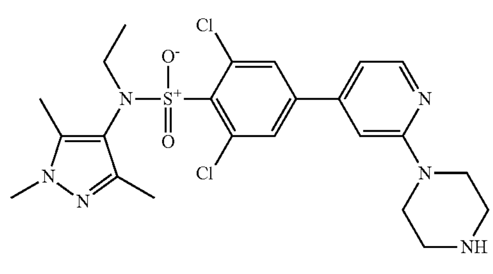 [SMILES: CCN(c1c(C)nn(C)c1C)[S+](=O)([O-])c1c(Cl)cc(-c2ccnc(N3CCNCC3)c2)cc1Cl] | 0.002<br>0.003 (HuNMT-1) | 0.002 | 523.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD90022 | 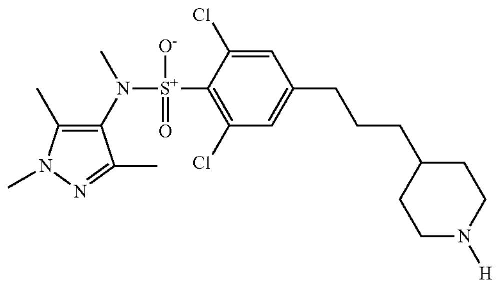 [SMILES: Cc1nn(C)c(C)c1N(C)[S+](=O)([O-])c1c(Cl)cc(CCCC2CCNCC2)cc1Cl] | 0.002 0.004 (HuNMT-1) | 0.002 | 473.2 |
| DDD90023 | 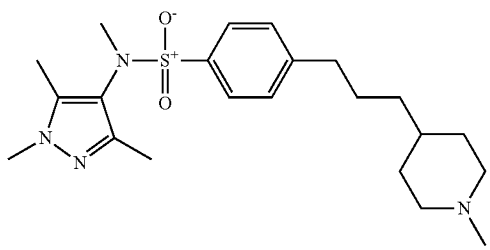 | 0.016 0.397 (HuNMT-1) | 0.20 | 419.2 |
| DDD90057 | 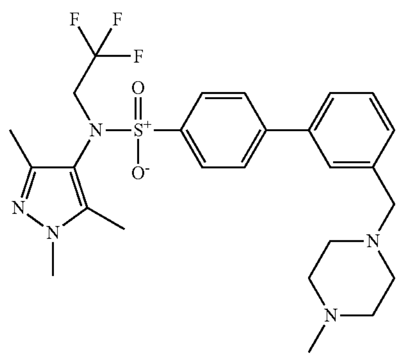 [SMILES: Cc1nn(C)c(C)c1N(CC(F)(F)F)[S+](=O)([O-])c1ccc(-c2cccc(CN3CCN(C)CC3)c2)cc1] | 0.085 0.075 (HuNMT-1) | 0.73 | 536.2 |
| DDD90058 | 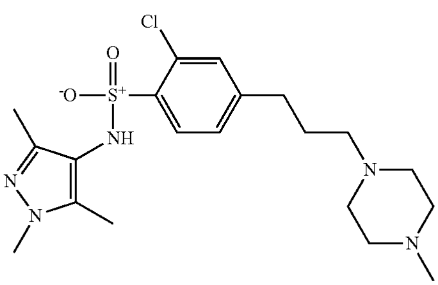 | 0.027 0.740 (HuNMT-1) | 0.20 | 440.2 |
| DDD90059 | 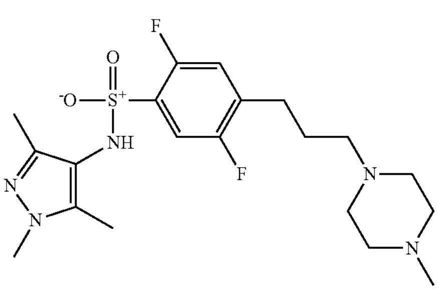 | 0.054 0.548 (HuNMT-1) | 0.48 | 442.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (µM) NMT Enzyme | $ED_{50}$ (µM) *T. brucei* | MH+ |
|---|---|---|---|---|
| DDD90060 | 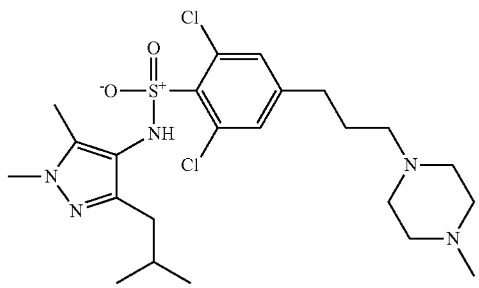 | 0.006 0.180 (HuNMT-1) | 0.02 | 516.2 |
| DDD90086 | 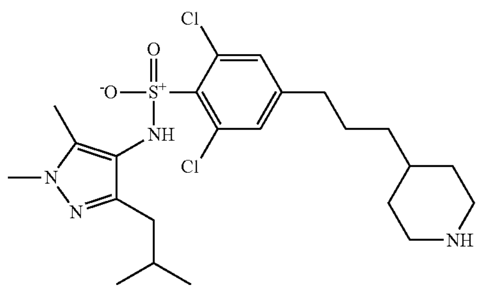 | 0.004 0.01 (HuNMT-1) | 0.006 | 501.2 |
| DDD90091 | 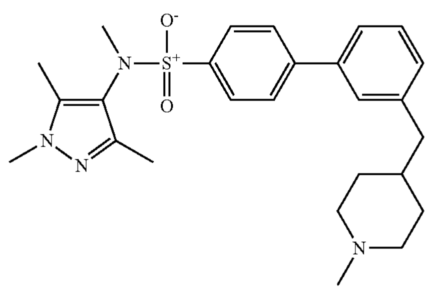 [SMILES: Cc1nn(C)c(C)c1N(C)[S+](=O)([O-])c1ccc(-c2cccc(CC3CCN(C)CC3)c2)cc1] | 0.009 0.009 (HuNMT-1) | 0.063 | 467.2 |
| DDD90098 | 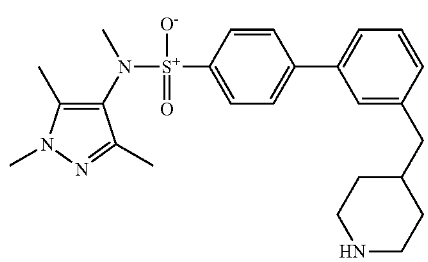 [SMILES: Cc1nn(C)c(C)c1N(C)[S+](=O)([O-])c1ccc(-c2cccc(CC3CCNCC3)c2)cc1] | 0.008 0.047 (HuNMT-1) | 0.060 | 453.2 |
| DDD90106 | 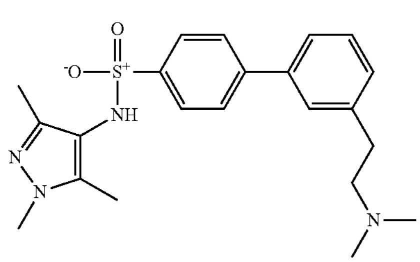 | 0.024 0.064 (HuNMT-1) | 0.251 | 413.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD90107 | 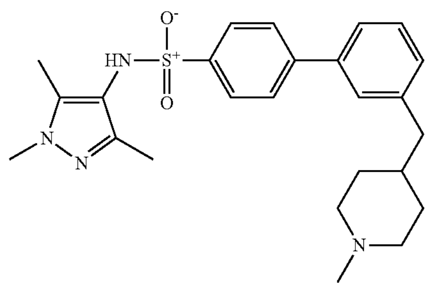 [SMILES: Cc1nn(C)c(C)c1N[S+](=O)([O-])c1ccc(-c2cccc(CC3CCN(C)CC3)c2)cc1] | 0.004<br>0.005 (HuNMT-1) | 0.040 | 453.2 |
| DDD90111 | 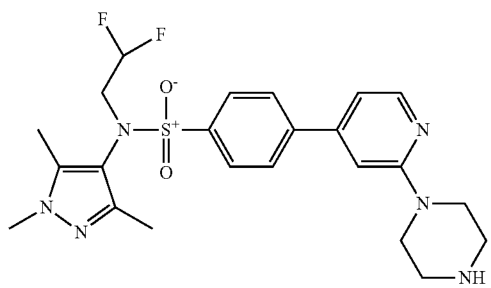 [SMILES: Cc1nn(C)c(C)c1N(CC(F)F)[S+](=O)([O-])c1ccc(-c2ccnc(N3CCNCC3)c2)cc1] | 0.003<br>0.019 (HuNMT-1) | 0.005 | 491.2 |
| DDD90112 | 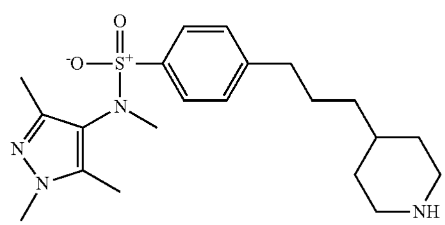 | 0.017<br>0.164 (HuNMT-1) | 0.270 | 405.2 |
| DDD90115 | 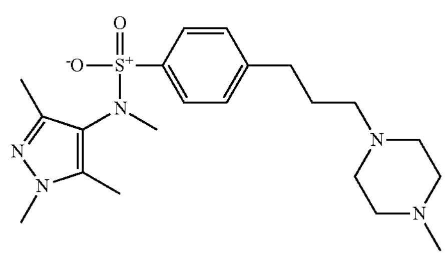 | 0.260<br>6.1 (HuNMT-1) | 2.21 | 420.1 |
| DDD90118 | 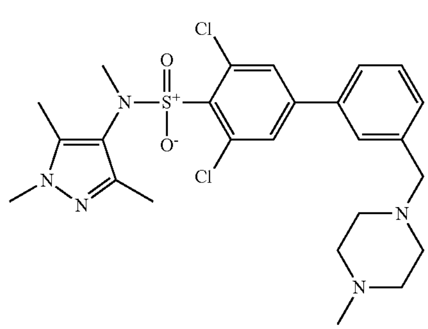 [SMILES: Cc1nn(C)c(C)c1N(C)[S+](=O)([O-])c1c(Cl)cc(-c2cccc(CN3CCN(C)CC3)c2)cc1Cl] | 0.004<br>0.005 (HuNMT-1) | 0.015 | 536.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activities are for inhibition of *T. brucei brucei* (blood stream form, variant 221).

| Reference Number | STRUCTURE | $IC_{50}$ (µM) NMT Enzyme | $ED_{50}$ (µM) *T. brucei* | MH+ |
|---|---|---|---|---|
| DDD90142 | 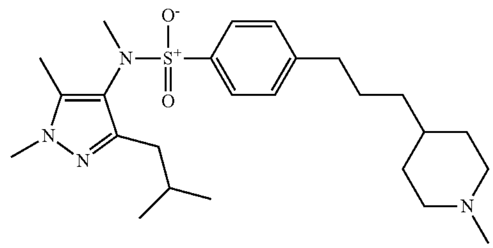 | 0.012<br>0.234 (HuNMT-1) | 0.168 | 461.3 |
| DDD90143 | 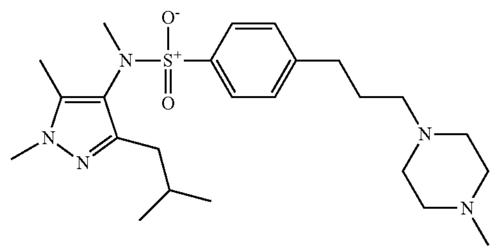 | 0.082<br>1.37 (HuNMT-1) | 0.81 | 462.3 |
| DDD90144 | 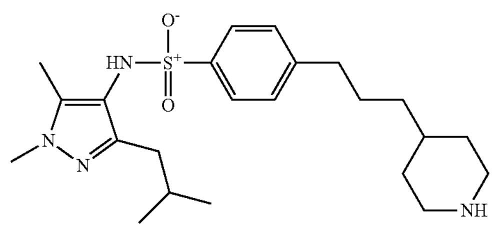 [SMILES: Cc1c(N[S+](=O)([O-])c2ccc(CCCC3CCNCC3)cc2)c(CC(C)C)nn1C] | 0.006<br>0.088 (HuNMT-1) | 0.034 | 433.3 |
| DDD90145 | 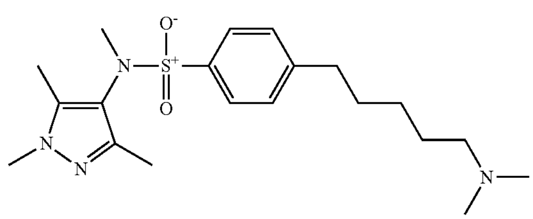 | 0.09<br>0.76 (HuNMT-1) | 1.00 | 393.2 |
| DDD90146 | 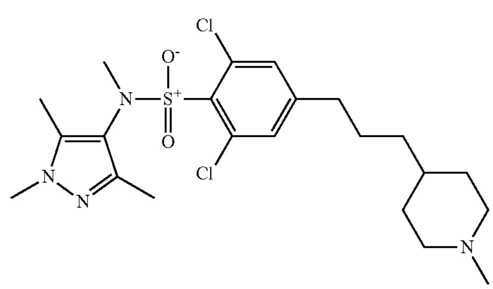 | 0.002<br>0.018 (HuNMT-1) | 0.002 | 487.2 |
| DDD90147 | 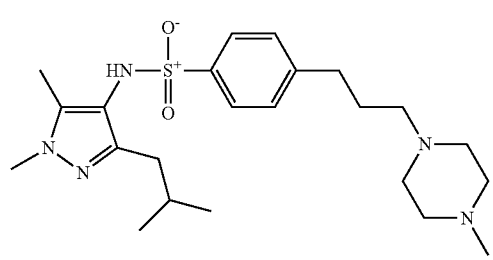 | 0.034<br>0.939 (HuNMT-1) | 0.20 | 448.3 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD90152 | 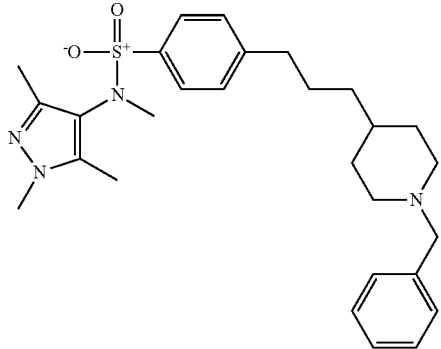 | 0.50<br>>1 (HuNMT-1) | >1 | 495.3 |
| DDD90153 | 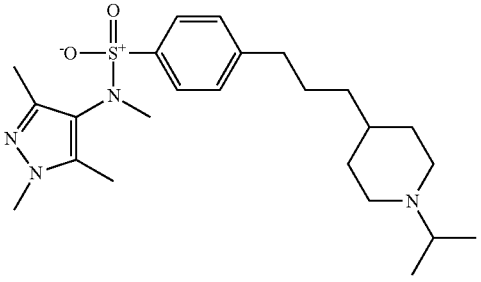 | 0.31<br>>1 (HuNMT-1) | >1 | 447.3 |
| DDD90154 | 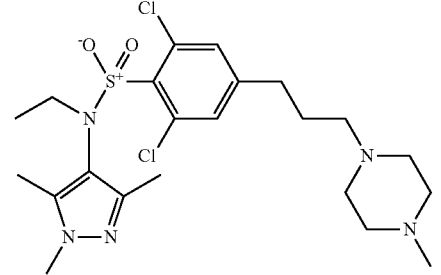 | 0.003<br>0.352 (HuNMT-1) | 0.023 | 502.5 |
| DDD90155 | 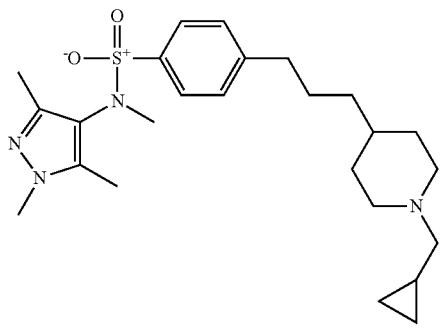 | >1<br>>1 (HuNMT-1) | 4.0 | 459.3 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | IC$_{50}$ (μM) NMT Enzyme | ED$_{50}$ (μM) *T. brucei* | MH+ |
|---|---|---|---|---|
| DDD99735 | 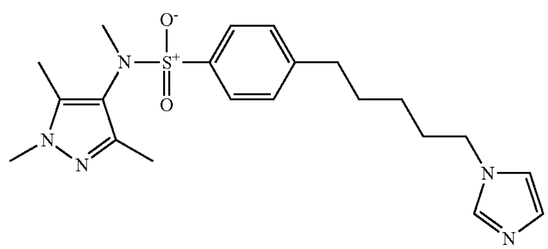 [SMILES: Cc1nn(C)c(C)c1N(C)[S+](=O)([O-])c1ccc(CCCCCn2ccnc2)cc1] | 0.83<br>2.9 (HuNMT-1) | >1 | 416.2 |
| DDD99736 | 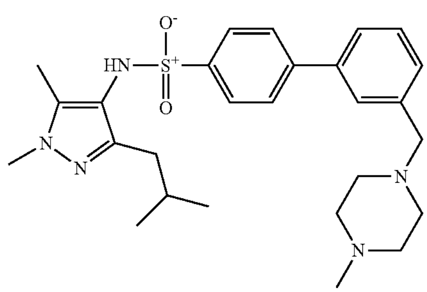 [SMILES: Cc1c(N[S+](=O)([O-])c2ccc(-c3cccc(CN4CCN(C)CC4)c3)cc2)c(CC(C)C)nn1C] | 0.068<br>0.25 (HuNMT-1) | 0.41 | 496.3 |
| DDD99739 | 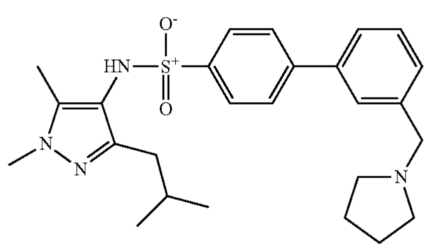 [SMILES: Cc1c(N[S+](=O)([O-])c2ccc(-c3cccc(CN4CCCC4)c3)cc2)c(CC(C)C)nn1C] | 0.005<br>0.12 (HuNMT-1) | 0.058 | 467.3 |
| DDD99741 | 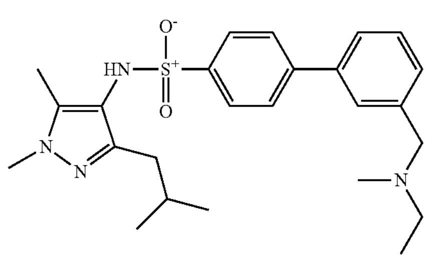 [SMILES: CCN(C)Cc1cccc(-c2ccc([S+](=O)([O-])Nc3c(CC(C)C)nn(C)c3C)cc2)c1] | 0.005<br>0.021 (HuNMT-1) | 0.047 | 455.3 |
| DDD99742 | 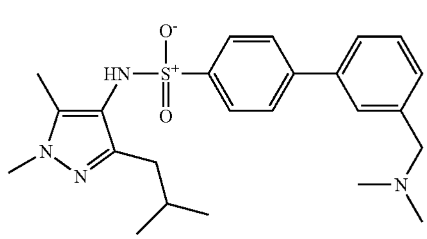 | 0.003<br>0.015 (HuNMT-1)<br>0.035 (LmNMT) | 0.019 | 441.3 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | IC$_{50}$ (µM) NMT Enzyme | ED$_{50}$ (µM) T. brucei | MH+ |
|---|---|---|---|---|
| DDD99743 | 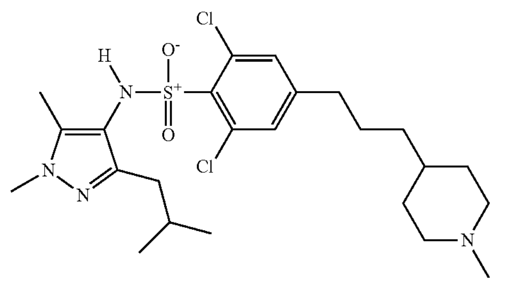 | 0.003<br>0.016 (HuNMT-1) | 0.005 | 515.3 |
| DDD99745 | 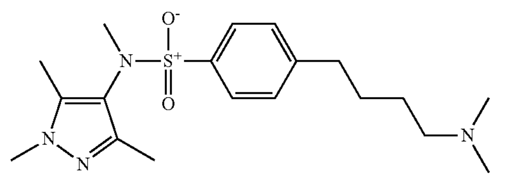 | 2.1<br>>10 (HuNMT-1) | >1 | 379.3 |
| DDD99746 | 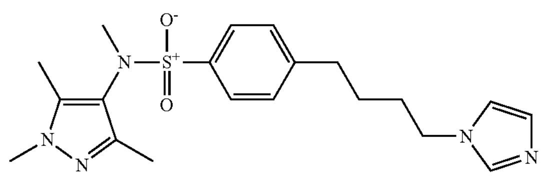 [SMILES: Cc1nn(C)c(C)c1N(C)[S+](=O)([O-])c1ccc(CCCCn2ccnc2)cc1] | 2.0<br>>10 (HuNMT-1) | >1 | 402.3 |
| DDD99747 | 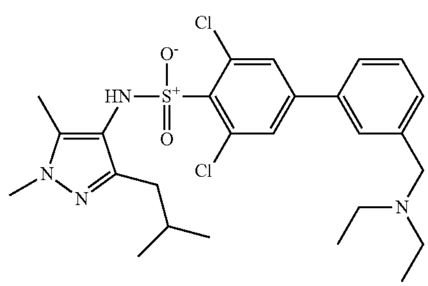 [SMILES: CCN(CC)Cc1cccc(-c2cc(Cl)c([S+](=O)([O-])Nc3c(CC(C)C)nn(C)c3C)c(Cl)c2)c1] | 0.008<br>0.81 (HuNMT-1) | 0.067 | 537.2 |
| DDD99748 | 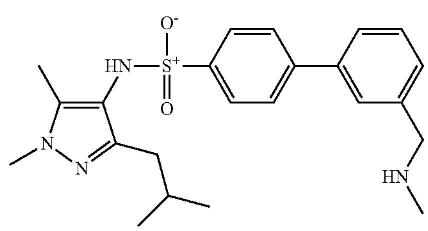 | 0.006<br>0.019 (HuNMT-1) | 0.036 | 427.2 |
| DDD99749 | 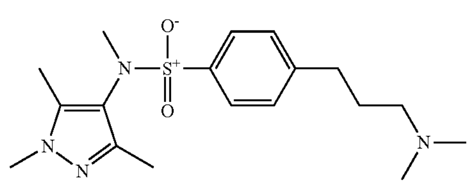 | 0.45<br>>1 (HuNMT-1) | >1 | 365.3 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | IC$_{50}$ (µM) NMT Enzyme | ED$_{50}$ (µM) *T. brucei* | MH+ |
|---|---|---|---|---|
| DDD99750 | 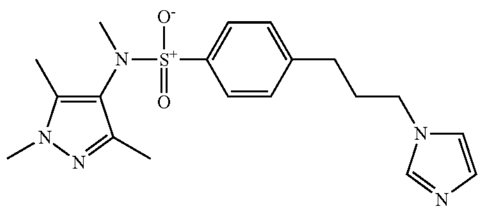 [SMILES: Cc1nn(C)c(C)c1N(C)[S+](=O)([O-])c1ccc(CCCn2ccnc2)cc1] | >1<br>>1 (HuNMT-1) | >1 | 388.3 |
| DDD99751 | 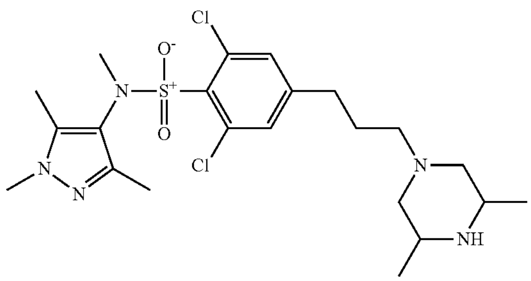 | 0.003<br>0.141 (HuNMT-1) | 0.021 | 502.2 |
| DDD99752 | 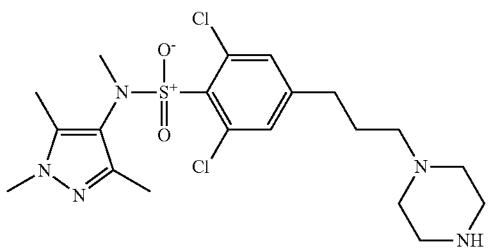 [SMILES: Cc1nn(C)c(C)c1N(C)[S+](=O)([O-])c1c(Cl)cc(CCCN2CCNCC2)cc1Cl] | 0.003<br>0.051 (HuNMT-1) | 0.019 | 474.2 |
| DDD99753 | 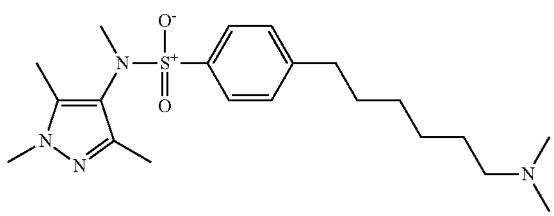 | 0.029<br>0.076 (HuNMT-1) | 0.406 | 407.3 |
| DDD99754 | 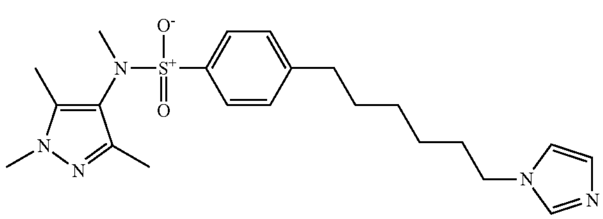 [SMILES: Cc1nn(C)c(C)c1N(C)[S+](=O)([O-])c1ccc(CCCCCCn2ccnc2)cc1] | 0.105<br>2.1 (HuNMT-1)<br>>1 (AfNMT) | >1 | 430.3 |
| DDD99755 | 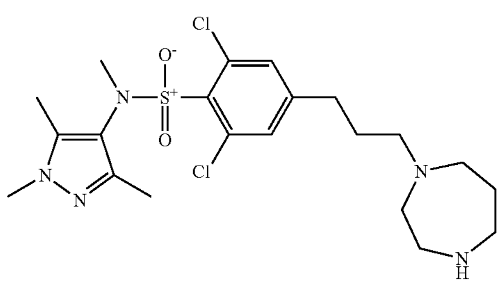 [SMILES: Cc1nn(C)c(C)c1N(C)[S+](=O)([O-])c1c(Cl)cc(CCCN2CCCNCC2)cc1Cl] | 0.003<br>0.011 (HuNMT-1) | 0.002 | 488.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (µM) NMT Enzyme | $ED_{50}$ (µM) *T. brucei* | MH+ |
|---|---|---|---|---|
| DDD99756 | 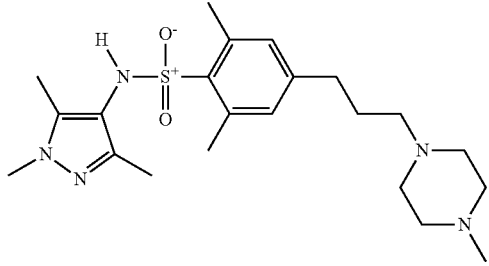 | 0.011<br>0.98 (HuNMT-1) | 0.121 | 343.3 |
| DDD099757 | 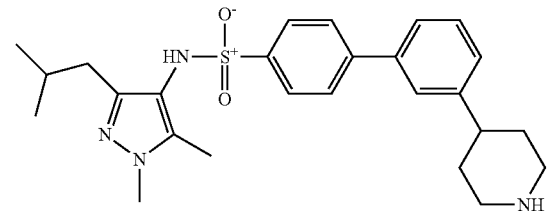 [SMILES: Cc1c(N[S+](=O)([O-])c2ccc(-c3cccc(C4CCNCC4)c3)cc2)c(CC(C)C)nn1C] | 0.006<br>0.054 (HuNMT-1) | 0.061 | 467.3 |
| DDD99758 | 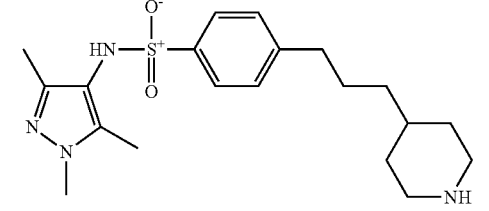 [SMILES: Cc1nn(C)c(C)c1N[S+](=O)([O-])c1ccc(CCCC2CCNCC2)cc1] | 0.009<br>0.127 (HuNMT-1) | 0.110 | 391.3 |
| DDD99759 | 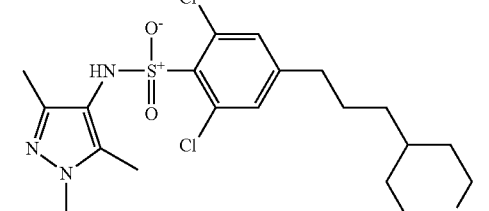 | 0.002<br>0.008 (HuNMT-1) | 0.003 | 459.0 |
| DDD99760 | 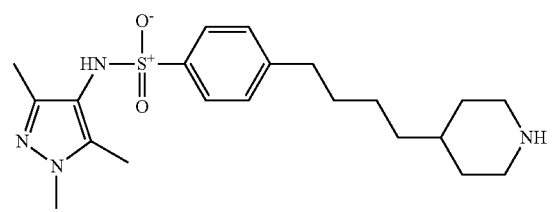 [SMILES: Cc1nn(C)c(C)c1N[S+](=O)([O-])c1ccc(CCCCC2CCNCC2)cc1] | 0.005<br>0.029 (HuNMT-1) | 0.010 | 405.3 |
| DDD99761 | 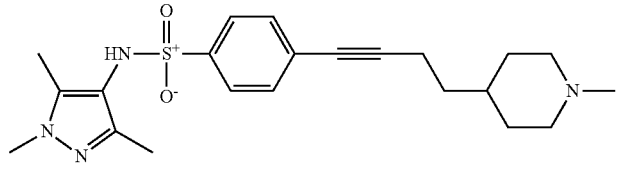 | 0.028<br>0.250 (HuNMT-1) | 0.240 | 415.3 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD99763 | 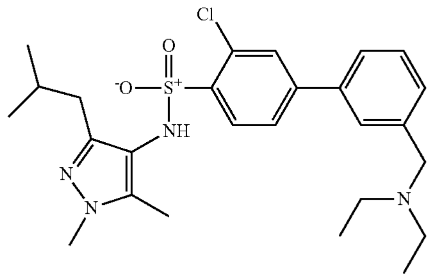 | 0.007<br>0.058 (HuNMT-1) | 0.053 | 503.3 |
| DDD99815 | 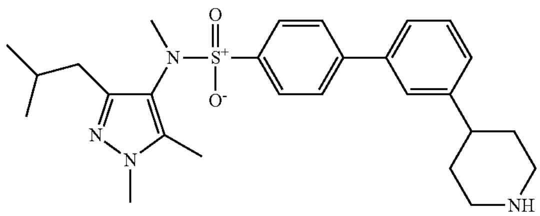 [SMILES: Cc1c(N(C)[S+](=O)([O-])c2ccc(-c3cccc(C4CCNCC4)c3)cc2)c(CC(C)C)nn1C] | 0.025<br>0.19 (HuNMT-1) | 0.123 | 481.3 |
| DDD99816 | 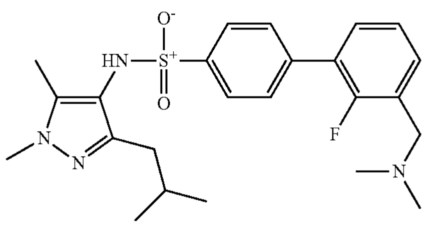 | 0.016<br>0.153 (HuNMT-1) | 0.031 | 459.2 |
| DDD99817 | 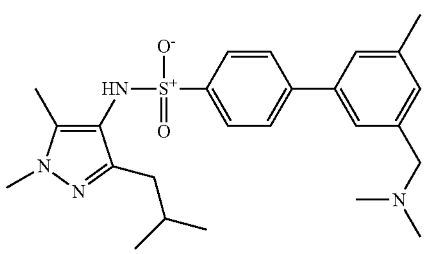 | 0.014<br>0.56 (HuNMT-1) | 0.047 | 455.2 |
| DDD99818 | 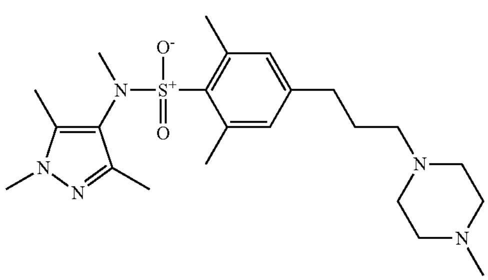 | 0.011<br>0.85 (HuNMT-1) | 0.047 | 448.3 |
| DDD99819 | 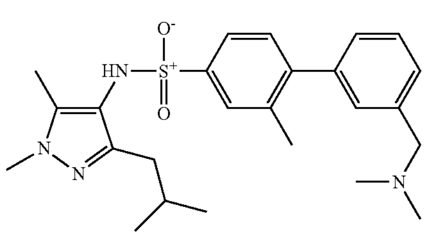 | 0.008<br>0.041 (HuNMT-1) | 0.043 | 455.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD99820 | 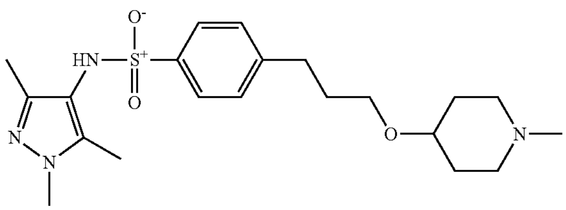 | 0.005<br>0.052 (HuNMT-1) | 0.020 | 421.2 |
| DDD99821 | 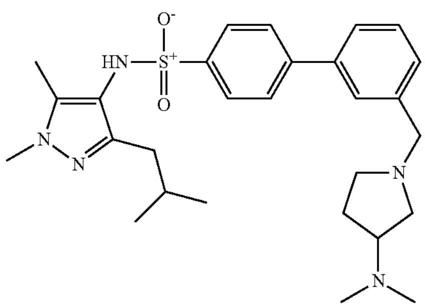 [SMILES: Cc1c(N[S+](=O)([O-])c2ccc(-c3cccc(CN4CCC(N(C)C)C4)c3)cc2)c(CC(C)C)nn1C] | 0.16<br>3.8 (HuNMT-1) | 0.59 | 510.3 |
| DDD99822 | 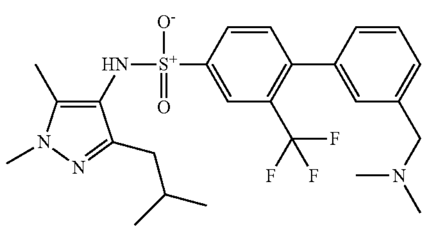 | 0.006<br>0.017 (HuNMT-1) | 0.051 | 509.3 |
| DDD99823 | 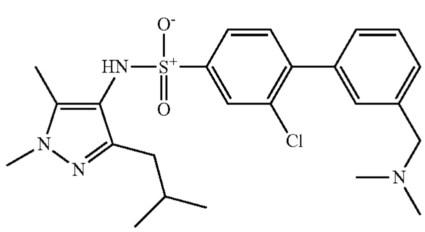 | 0.006<br>0.033 (HuNMT-1) | 0.041 | 475.3 |
| DDD99824 | 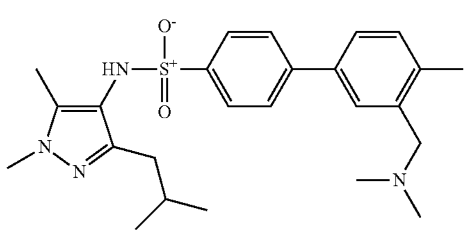 | 0.004<br>0.013 (HuNMT-1) | 0.014 | 455.2 |

TABLE 1-continued

Enzyme and Cellular Activity of N-Myristoyltransferase Inhibitors

Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (µM) NMT Enzyme | $ED_{50}$ (µM) *T. brucei* | MH+ |
|---|---|---|---|---|
| DDD99825 | 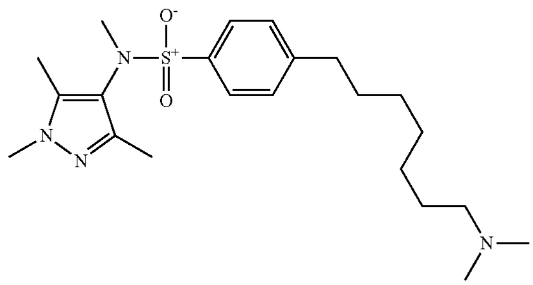 | 0.011<br>0.036 (HuNMT-1)<br>0.039 (LmNMT) | 0.054 | 421.3 |
| DDD99826 | 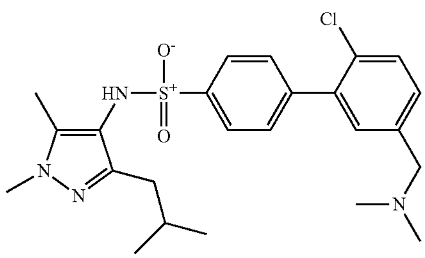 | 0.016<br>0.094 (HuNMT-1) | 0.104 | 475.2 |
| DDD99827 | 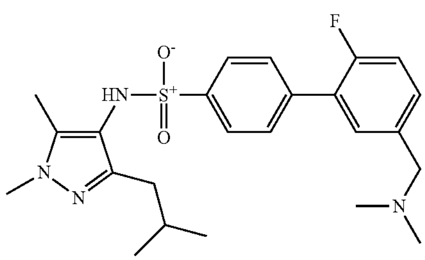 | 0.007<br>0.029 (HuNMT-1) | 0.019 | 459.2 |
| DDD99830 | 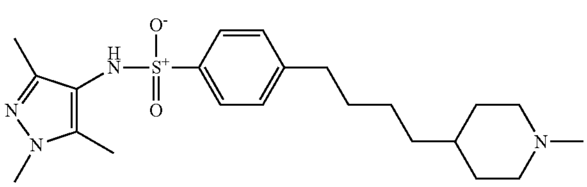 [SMILES: Cc1nn(C)c(C)c1N[S+](=O)([O-])c1ccc(CCCCC2CCN(C)CC2)cc1] | 0.003<br>0.032 (HuNMT-1)<br>0.011 (LmNMT) | 0.020 | 419.3 |
| DDD99832 | 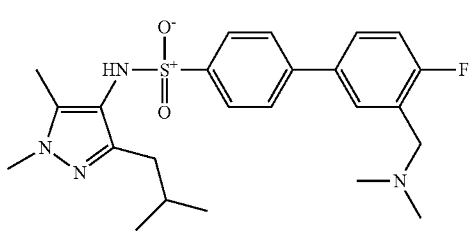 [SMILES: Cc1c(N[S+](=O)([O-])c2ccc(-c3ccc(F)c(CN(C)C)c3)cc2)c(CC(C)C)nn1C] | 0.003<br>0.011 (HuNMT-1)<br>0.044 (AfNMT) | 0.010 | 459.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) T. brucei | MH+ |
|---|---|---|---|---|
| DDD99833 | 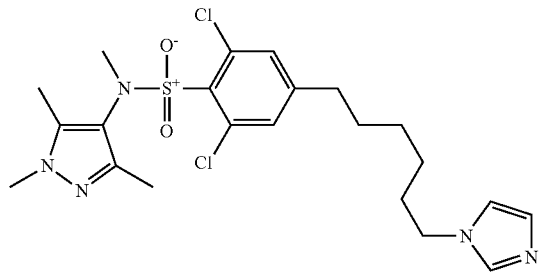 [SMILES: Cc1nn(C)c(C)c1N(C)[S+](=O)([O-])c1c(Cl)cc(CCCCCCn2ccnc2)cc1Cl] | 0.003<br>0.168 (HuNMT-1)<br>0.009 (LmNMT) | 0.018 | 498.2 |
| DDD99834 | 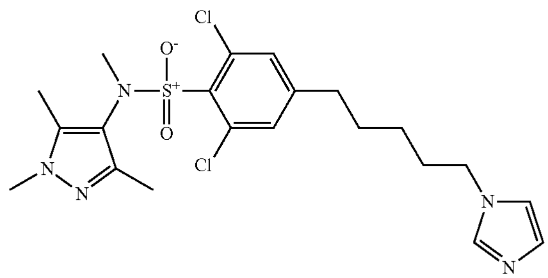 [SMILES: Cc1nn(C)c(C)c1N(C)[S+](=O)([O-])c1c(Cl)cc(CCCCCn2ccnc2)cc1Cl] | 0.019<br>0.47 (HuNMT-1) | 0.225 | 484.2 |
| DDD99835 | 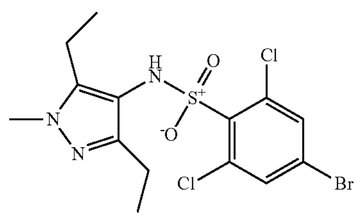 | 0.38<br>>1 (HuNMT-1) | >1 | 442.0 |
| DDD99836 | 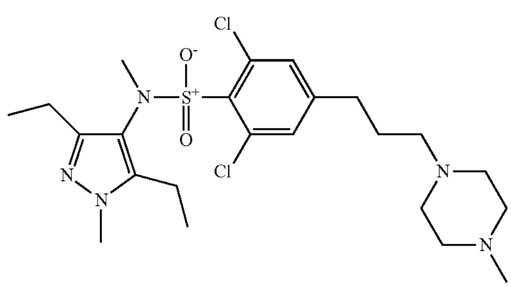 [SMILES: CCc1nn(C)c(CC)c1N(C)[S+](=O)([O-])c1c(Cl)cc(CCCN2CCN(C)CC2)cc1Cl] | 0.003<br>0.15 (HuNMT-1) | 0.013 | 516.2 |
| DDD99837 | 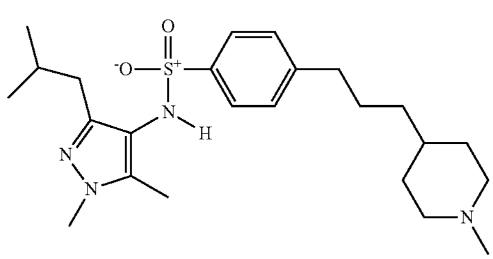 | 0.007<br>0.12 (HuNMT-1)<br>0.20 (AfNMT) | 0.036 | 447.3 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activities are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD99838 | 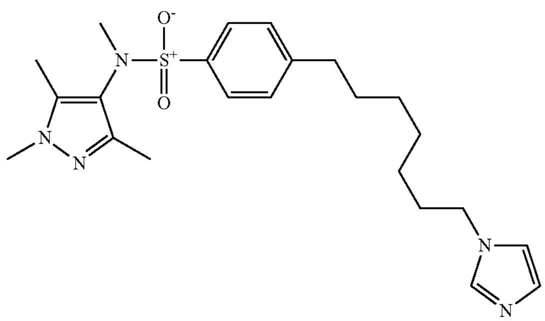 [SMILES: Cc1nn(C)c(C)c1N(C)[S+](=O)([O-])c1ccc(CCCCCCCn2ccnc2)cc1] | 0.17<br>0.37 (HuNMT-1) | >1 | 444.25 |
| DDD100086 | 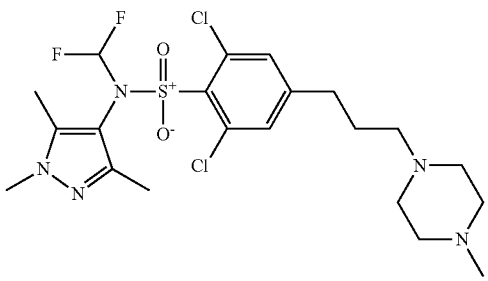 | 0.003<br>0.145 (HuNMT-1) | 0.012 | 524.2 |
| DDD100088 | 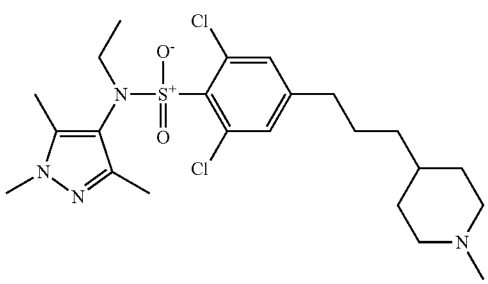 | 0.002<br>0.024 (HuNMT-1) | 0.003 | 501.2 |
| DDD100091 | 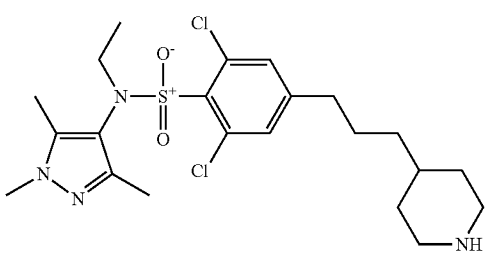 [SMILES: CCN(c1c(C)nn(C)c1C)[S+](=O)([O-])c1c(Cl)cc(CCCC2CCNCC2)cc1Cl] | 0.002<br>0.009 (HuNMT-1) | 0.004 | 487.2 |
| DDD100093 | 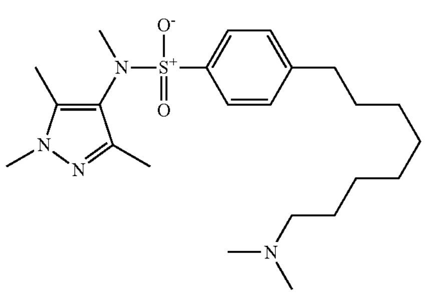 [SMILES: Cc1nn(C)c(C)c1N(C)[S+](=O)([O-])c1ccc(CCCCCCCCN(C)C)cc1] | 0.162<br>0.021 (HuNMT-1) | 0.106 | 435.3 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | IC$_{50}$ (μM) NMT Enzyme | ED$_{50}$ (μM) T. brucei | MH+ |
|---|---|---|---|---|
| DDD100094 | 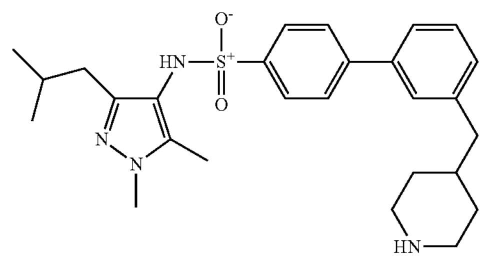 [SMILES: Cc1c(N[S+](=O)([O-])c2ccc(-c3cccc(CC4CCNCC4)c3)cc2)c(CC(C)C)nn1C] | 0.003<br>0.025 (HuNMT-1) | 0.008 | 481.3 |
| DDD100095 | 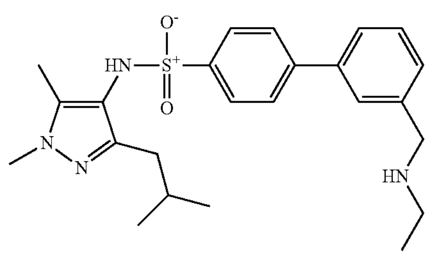 [SMILES: CCNCc1cccc(-c2ccc([S+](=O)([O-])Nc3c(CC(C)C)nn(C)c3C)cc2)c1] | 0.005<br>0.022 (HuNMT-1) | 0.055 | 441.3 |
| DDD100096 | 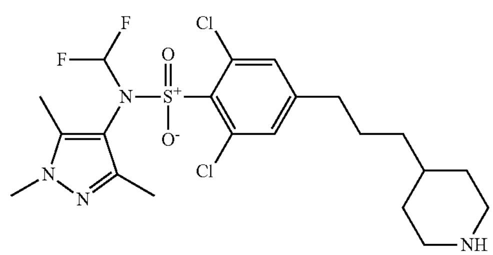 [SMILES: Cc1nn(C)c(C)c1N(C(F)F)[S+](=O)([O-])c1c(Cl)cc(CCCC2CCNCC2)cc1Cl] | 0.003<br>0.009 (HuNMT-1) | 0.003 | 509.2 |
| DDD100097 | 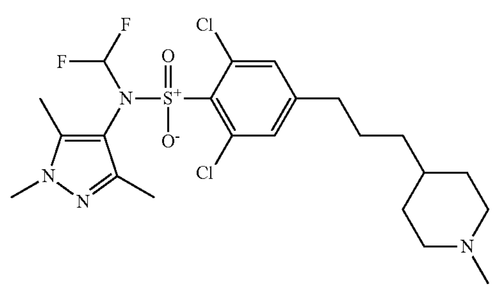 | 0.002<br>0.021 (HuNMT-1) | 0.001 | 523.2 |
| DDD100139 | 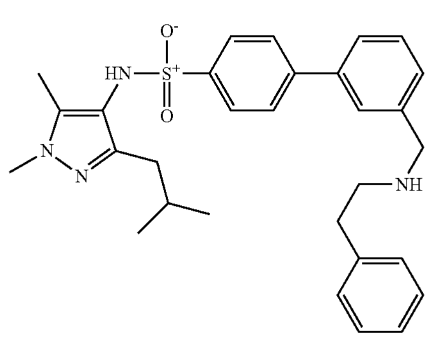 [SMILES: Cc1c(N[S+](=O)([O-])c2ccc(-c3cccc(CNCCc4ccccc4)c3)cc2)c(CC(C)C)nn1C] | 1.4<br>2.3 (HuNMT-1) | >1 | 517.3 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | IC$_{50}$ (µM) NMT Enzyme | ED$_{50}$ (µM) T. brucei | MH+ |
|---|---|---|---|---|
| DDD100140 | 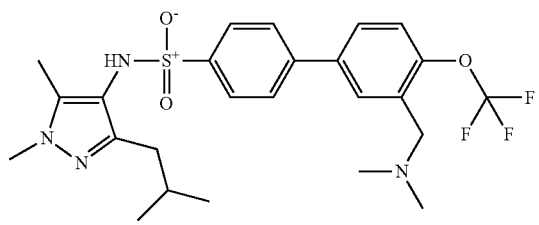 [SMILES: Cc1c(N[S+](=O)([O-])c2ccc(-c3ccc(OC(F)(F)F)c(CN(C)C)c3)cc2)c(CC(C)C)nn1C] | 0.12<br>0.74 (HuNMT-1) | >1 | 525.3 |
| DDD100141 | 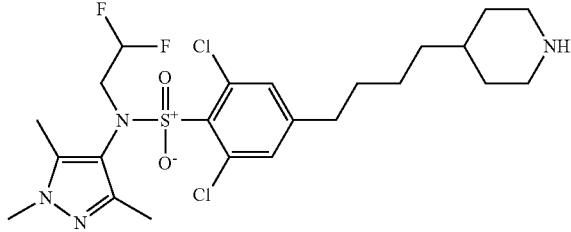 [SMILES: Cc1nn(C)c(C)c1N(CC(F)F)[S+](=O)([O-])c1c(Cl)cc(CCCCC2CCNCC2)cc1Cl] | 0.003<br>0.033 (HuNMT-1)<br>0.003 (LmNMT) | 0.003 | 537.2 |
| DDD100142 | 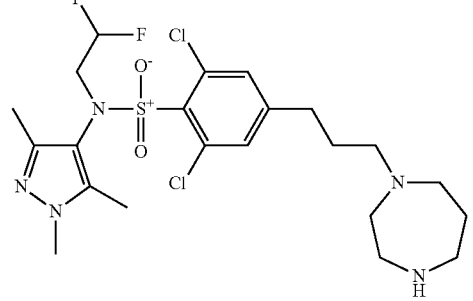 | 0.004<br>0.081 (HuNMT-1) | 0.014 | 538.0 |
| DDD100143 | 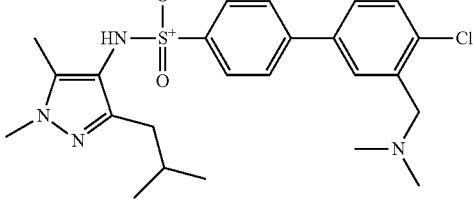 | 0.003<br>0.01 (HuNMT-1) | 0.017 | 475.2 |
| DDD100144 | 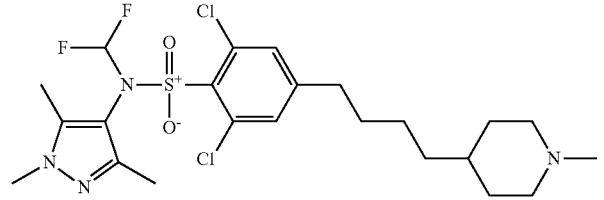 | 0.002<br>0.006 (HuNMT-1)<br>0.001 (LmNMT) | 0.001 | 537.0 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD100145 | 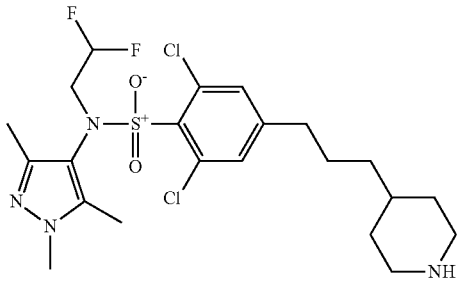 [SMILES: Cc1nn(C)c(C)c1N(CC(F)F)[S+](=O)([O-])c1c(Cl)cc(CCCC2CCNCC2)cc1Cl] | 0.011<br>0.148 (HuNMT-1)<br>0.035 (LmNMT) | 0.02 | 523.2 |
| DDD100146 | 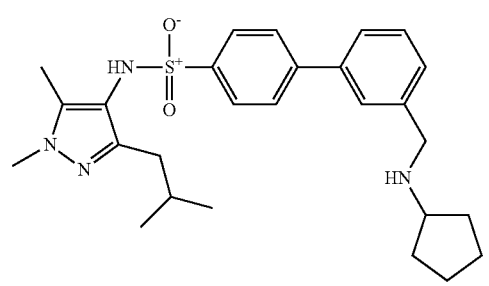 [SMILES: Cc1c(N[S+](=O)([O-])c2ccc(-c3cccc(CNC4CCCC4)c3)cc2)c(CC(C)C)nn1C] | 0.36<br>2.3 (HuNMT-1) | >1 | 481.3 |
| DDD100147 | 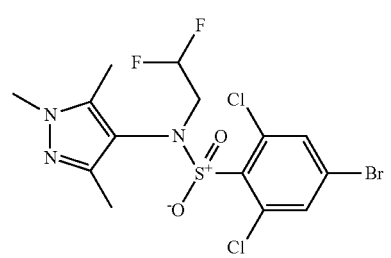 | 3.2<br>>10 (HuNMT-1) | >1 | 477.9 |
| DDD100148 | 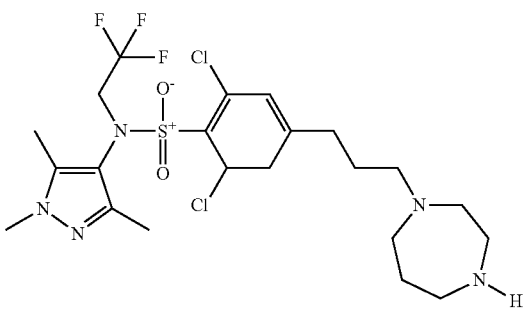 [SMILES: Cc1nn(C)c(C)c1N(CC(F)(F)F)[S+](=O)([O-])C1=C(Cl)C=C(CCCN2CCCNCC2)CC1Cl] | 0.008<br>0.21 (HuNMT-1) | 0.018 | 558.2 |
| DDD100149 | 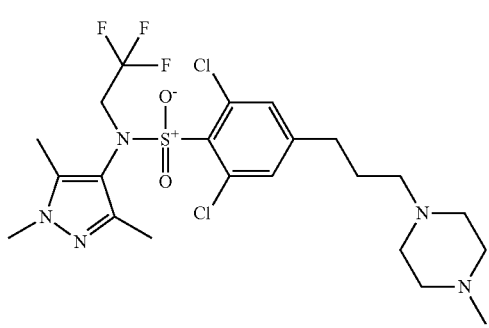 | 0.014<br>2.4 (HuNMT-1) | 0.132 | 556.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (µM) NMT Enzyme | $ED_{50}$ (µM) *T. brucei* | MH+ |
|---|---|---|---|---|
| DDD100150 | 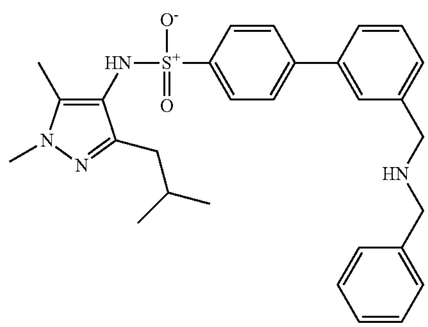 [SMILES: Cc1c(N[S+](=O)([O-])c2ccc(-c3cccc(CNCc4ccccc4)c3)cc2)c(CC(C)C)nn1C] | 1.3<br>4.0 (HuNMT-1) | >1 | 503.3 |
| DDD100151 | 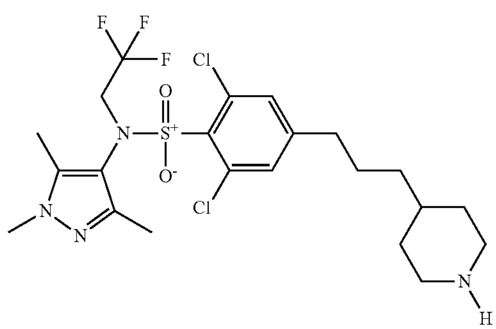 [SMILES: Cc1nn(C)c(C)c1N(CC(F)(F)F)[S+](=O)([O-])c1c(Cl)cc(CCCC2CCNCC2)cc1Cl] | 0.011<br>0.134 (HuNMT-1) | 0.034 | 541.1 |
| DDD100153 | 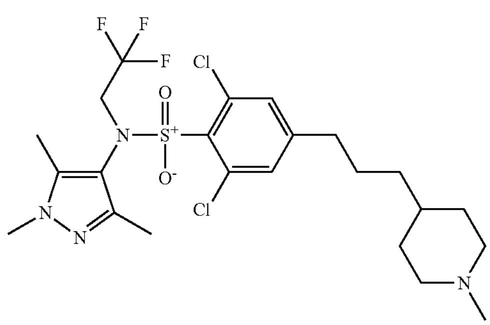 | 0.005<br>0.323 (HuNMT-1) | 0.023 | 555.2 |
| DDD100156 | 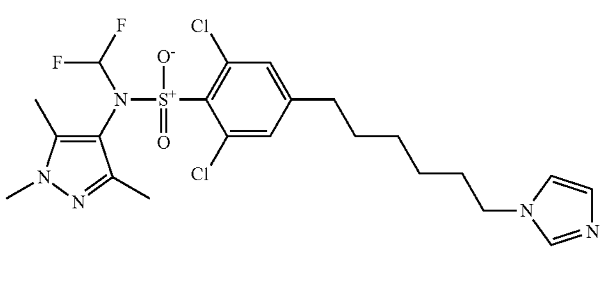 [SMILES: Cc1nn(C)c(C)c1N(C(F)F)[S+](=O)([O-])c1c(Cl)cc(CCCCCCn2ccnc2)cc1Cl] | 0.016<br>1.1 (HuNMT-1)<br>0.048 (LmNMT) | 0.148 | 534.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD100157 | 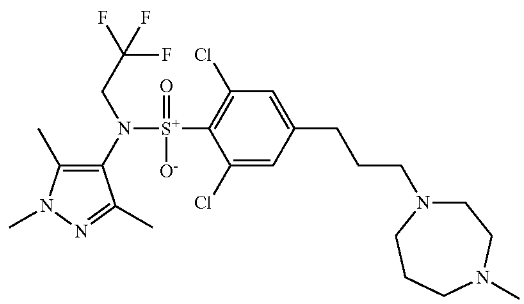 | 0.006<br>0.21 (HuNMT-1) | 0.014 | 570.2 |
| DDD100158 | 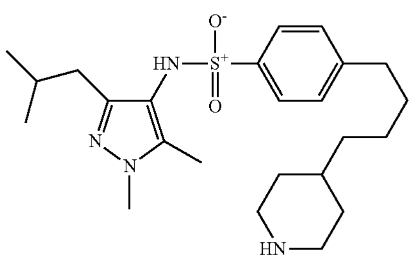 [SMILES: Cc1c(N[S+](=O)([O-])c2ccc(CCCCC3CCNCC3)cc2)c(CC(C)C)nn1C] | 0.006<br>0.056 (HuNMT-1) | 0.048 | 447.0 |
| DDD100159 | 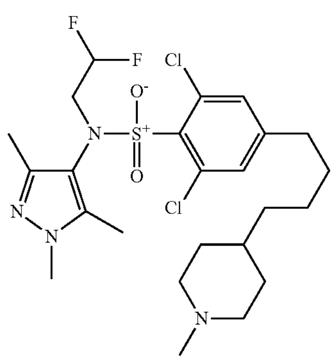 [SMILES: Cc1nn(C)c(C)c1N(CC(F)F)[S+](=O)([O-])c1c(Cl)cc(CCCCC2CCN(C)CC2)cc1Cl] | 0.004<br>0.06 (HuNMT-1) | 0.009 | 551.0 |
| DDD100160 | 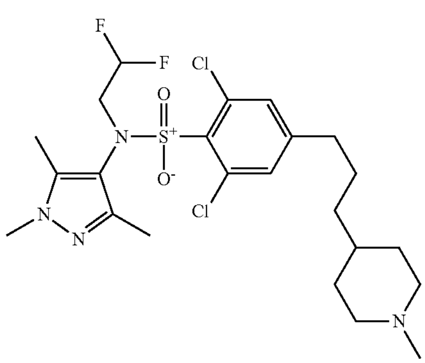 | 0.003<br>0.345 (HuNMT-1) | 0.013 | 537.0 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT)
enzyme inhibition data are given in parentheses. Cellular activitites are for inhibition of *T. brucei brucei* (blood stream form, variant 221).

| Reference Number | STRUCTURE | IC$_{50}$ (μM) NMT Enzyme | ED$_{50}$ (μM) *T. brucei* | MH+ |
|---|---|---|---|---|
| DDD100161 | 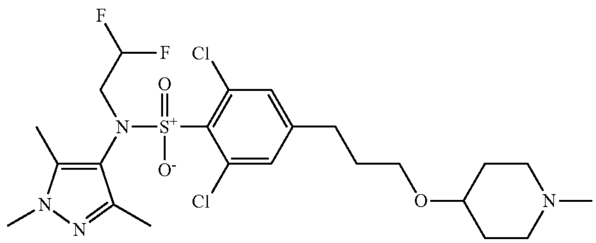 | 0.002<br>0.034 (HuNMT-1) | 0.006 | 553.0 |
| DDD100162 | 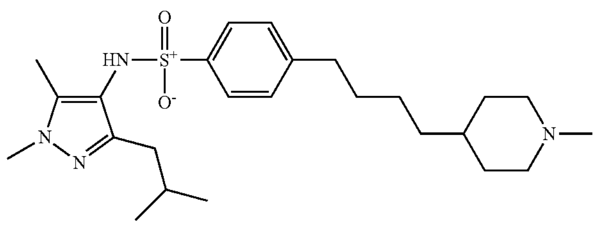 | 0.01<br>0.173 (HuNMT-1) | 0.093 | 461.4 |
| DDD100163 | 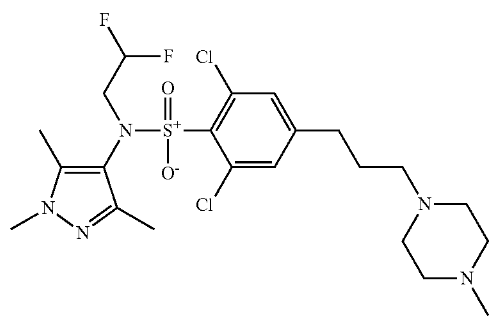 | 0.014<br>1.7 (HuNMT-1) | 0.125 | 538.2 |
| DDD100164 | 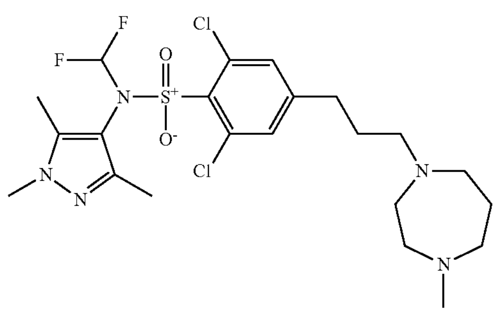 [SMILES: Cc1nn(C)c(C)c1N(C(F)F)[S+](=O)([O-])c1c(Cl)cc(CCCN2CCCN(C)CC2)cc1Cl] | 0.002<br>0.007 (HuNMT-1)<br>0.005 (LmNMT) | 0.001 | 538.2 |
| DDD100165 | 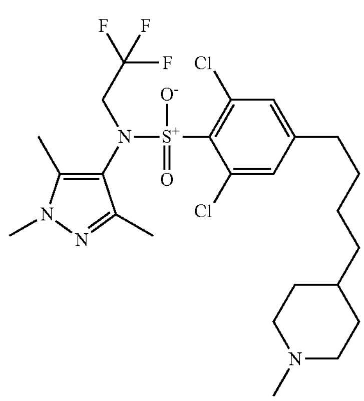 [SMILES: Cc1nn(C)c(C)c1N(CC(F)(F)F)[S+](=O)([O-])c1c(Cl)cc(CCCCC2CCN(C)CC2)cc1Cl] | 0.004<br>0.11 (HuNMT-1) | 0.020 | 569.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) T. brucei | MH+ |
|---|---|---|---|---|
| DDD100166 | 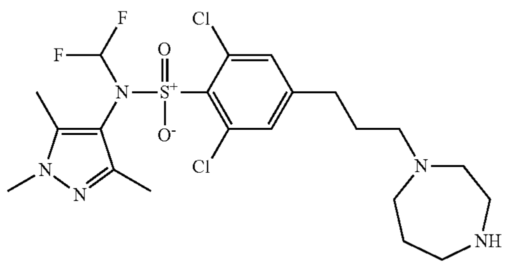 [SMILES: Cc1nn(C)c(C)c1N(C(F)F)[S+](=O)([O-])c1c(Cl)cc(CCCN2CCCNCC2)cc1Cl] | 0.005<br>0.008 (HuNMT-1) | 0.002 | 524.2 |
| DDD100167 | 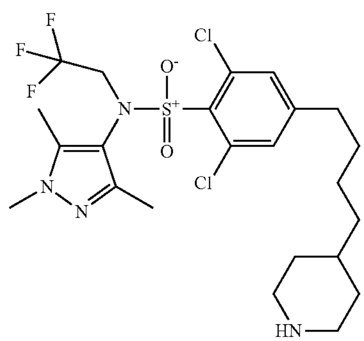 [SMILES: Cc1nn(C)c(C)c1N(CC(F)(F)F)[S+](=O)([O-])c1c(Cl)cc(CCCCC2CCNCC2)cc1Cl] | 0.004<br>0.071 (HuNMT-1) | 0.014 | 555.2 |
| DDD100168 | 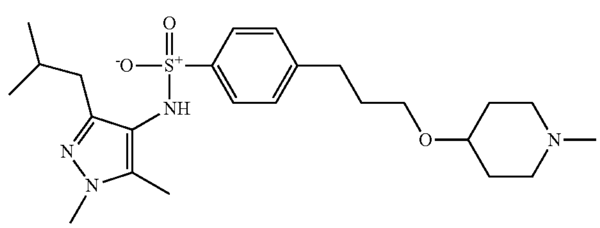 | 0.009<br>0.168 (HuNMT-1) | 0.110 | 463.2 |
| DDD100169 | 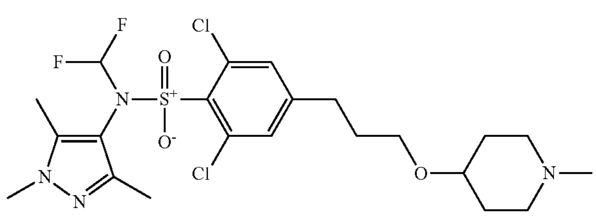 | 0.003<br>0.005 (HuNMT-1)<br>0.001 (LmNMT) | 0.001 | 539.1 |
| DDD100790 | 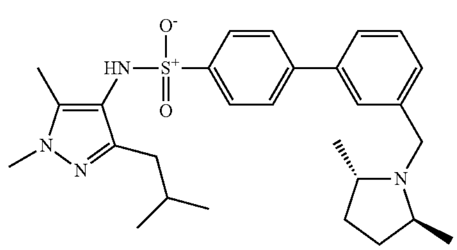 | 0.043<br>0.52 (HuNMT-1)<br>0.35 (LmNMT) | 0.269 | 495.3 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) T. brucei | MH+ |
|---|---|---|---|---|
| DDD100791 | 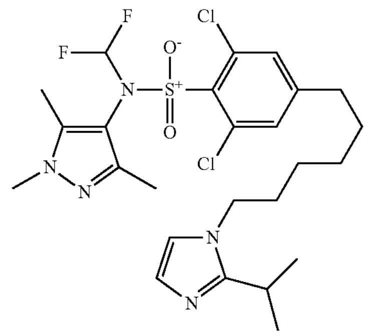 [SMILES: Cc1nn(C)c(C)c1N(C(F)F)[S+](=O)([O-])c1c(Cl)cc(CCCCCCn2ccnc2C(C)C)cc1Cl] | 0.21<br>2.1 (HuNMT-1)<br>0.044 (LmNMT) | 0.344 | 576.2 |
| DDD100792 | 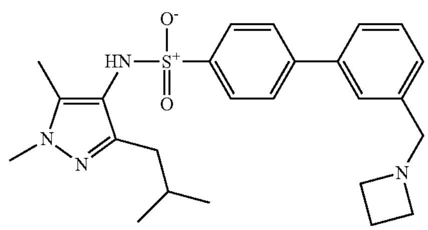 [SMILES: Cc1c(N[S+](=O)([O-])c2ccc(-c3cccc(CN4CCC4)c3)cc2)c(CC(C)C)nn1C] | 0.01<br>0.076 (HuNMT-1)<br>0.23 (LmNMT) | 0.143 | 481.3 |
| DDD100793 | 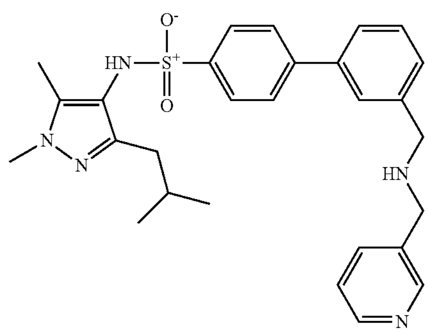 [SMILES: Cc1c(N[S+](=O)([O-])c2ccc(-c3cccc(CNCc4cccnc4)c3)cc2)c(CC(C)C)nn1C] | 0.026<br>0.33 (HuNMT-1)<br>1.4 (LmNMT) | 0.54 | 504.3 |
| DDD100794 | 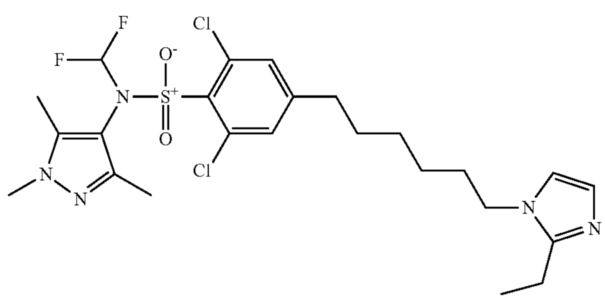 [SMILES: CCc1nccn1CCCCCCc1cc(Cl)c([S+](=O)([O-])N(c2c(C)nn(C)c2C)C(F)F)c(Cl)c1] | 0.013<br>0.49 (HuNMT-1)<br>0.024 (LmNMT) | 0.160 | 562.2 |
| DDD100795 | 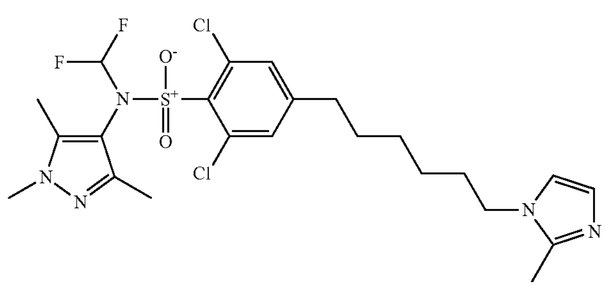 [SMILES: Cc1nn(C)c(C)c1N(C(F)F)[S+](=O)([O-])c1c(Cl)cc(CCCCCCn2ccnc2C)cc1Cl] | 0.003<br>0.042 (HuNMT-1)<br>0.002 (LmNMT) | 0.005 | 548.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (µM) NMT Enzyme | $ED_{50}$ (µM) T. brucei | MH+ |
|---|---|---|---|---|
| DDD100796 | 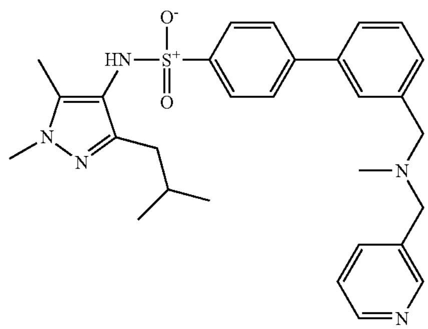 [SMILES: Cc1c(N[S+](=O)([O-])c2ccc(-c3cccc(CN(C)Cc4cccnc4)c3)cc2)c(CC(C)C)nn1C] | 0.86<br>>1 (HuNMT-1)<br>>1 (LmNMT) | >1 | 518.3 |
| DDD100797 | 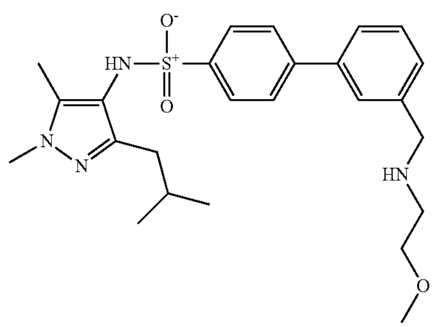 [SMILES: COCCNCc1cccc(-c2ccc([S+](=O)([O-])Nc3c(CC(C)C)nn(C)c3C)cc2)c1] | 0.023<br>0.077 (HuNMT-1)<br>0.27 (LmNMT) | 0.492 | 471.3 |
| DDD100798 | 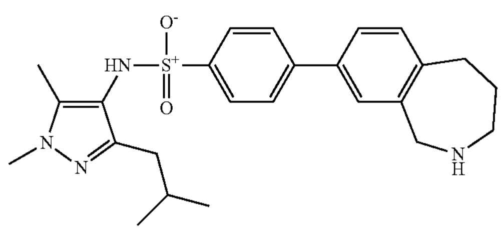 [SMILES: Cc1c(N[S+](=O)([O-])c2ccc(-c3ccc4c(c3)CNCCC4)cc2)c(CC(C)C)nn1C] | 0.003<br>0.004 (HuNMT-1)<br>0.025 (LmNMT) | 0.006 | 453.3 |
| DDD100799 | 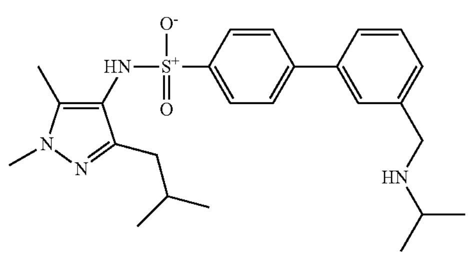 [SMILES: Cc1c(N[S+](=O)([O-])c2ccc(-c3cccc(CNC(C)C)c3)cc2)c(CC(C)C)nn1C] | 0.02<br>0.24 (HuNMT-1)<br>0.47 (LmNMT) | 0.293 | 455.3 |
| DDD100800 | 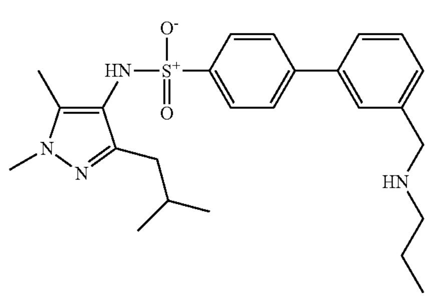 [SMILES: CCCNCc1cccc(-c2ccc([S+](=O)([O-])Nc3c(CC(C)C)nn(C)c3C)cc2)c1] | 0.006<br>0.021 (HuNMT-1)<br>0.073 (LmNMT) | 0.052 | 455.3 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (µM) NMT Enzyme | $ED_{50}$ (µM) *T. brucei* | MH+ |
|---|---|---|---|---|
| DDD100801 | 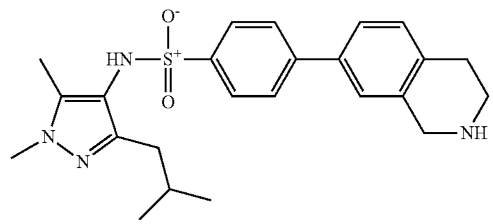 [SMILES: Cc1c(N[S+](=O)([O-])c2ccc(-c3ccc4c(c3)CNCC4)cc2)c(CC(C)C)nn1C] | 0.004<br>0.011 (HuNMT-1)<br>0.011 (LmNMT) | 0.014 | 439.2 |
| DDD100802 | 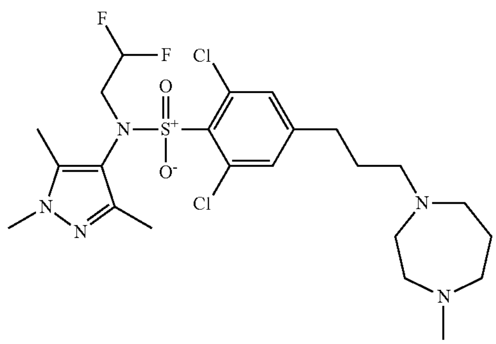 [SMILES: Cc1nn(C)c(C)c1N(CC(F)F)[S+](=O)([O-])c1c(Cl)cc(CCCN2CCCN(C)CC2)cc1Cl] | 0.003<br>0.101 (HuNMT-1)<br>0.005 (LmNMT) | 0.004 | 552.0 |
| DDD100803 | 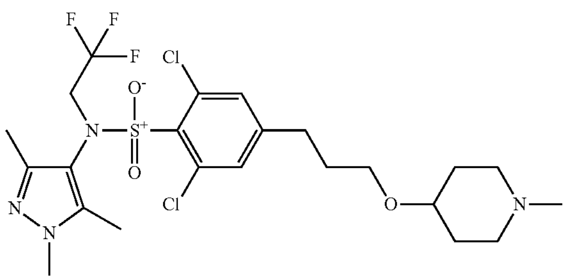 | 0.002<br>0.046 (HuNMT-1)<br>0.005 (LmNMT) | 0.008 | 571.2 |
| DDD100804 | 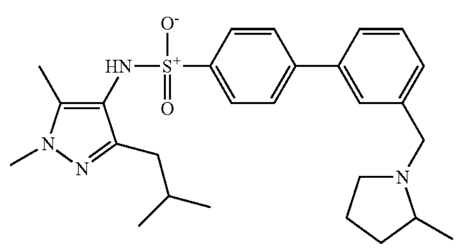 | 0.006<br>0.061 (HuNMT-1)<br>0.077 (LmNMT) | 0.035 | 481.3 |
| DDD100805 | 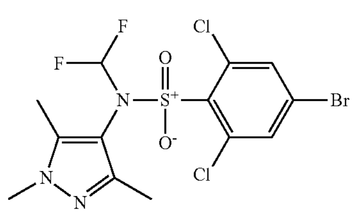 [SMILES: Cc1nn(C)c(C)c1N(C(F)F)[S+](=O)([O-])c1c(Cl)cc(Br)cc1Cl] | 0.27<br>>1 (HuNMT-1)<br>>1 (LmNMT) | >1 | 463.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) T. brucei | MH+ |
|---|---|---|---|---|
| DDD100806 | 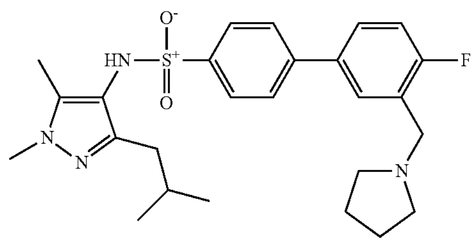 [SMILES: Cc1c(N[S+](=O)([O-])c2ccc(-c3ccc(F)c(CN4CCCC4)c3)cc2)c(CC(C)C)nn1C] | 0.004<br>0.057 (HuNMT-1)<br>0.224 (LmNMT) | 0.033 | 485.3 |
| DDD100807 | 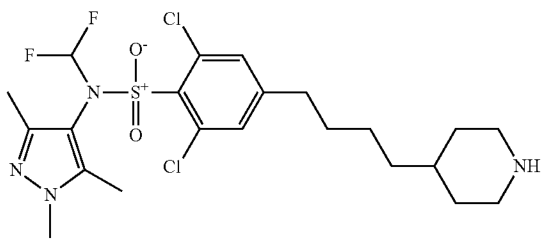 [SMILES: Cc1nn(C)c(C)c1N(C(F)F)[S+](=O)([O-])c1c(Cl)cc(CCCCC2CCNCC2)cc1Cl] | 0.002<br>0.004 (HuNMT-1)<br>0.001 (LmNMT) | 0.001 | 523.2 |
| DDD100862 | 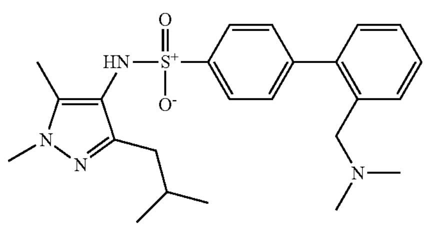 [SMILES: Cc1c(N[S+](=O)([O-])c2ccc(-c3ccccc3CN(C)C)cc2)c(CC(C)C)nn1C] | 0.358<br>0.174 (HuNMT-1)<br>>1 μM (LmNMT) | >1 μM | 441.2 |
| DDD100863 | 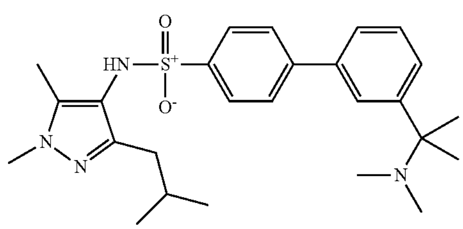 [SMILES: Cc1c(N[S+](=O)([O-])c2ccc(-c3cccc(C(C)(C)N(C)C)c3)cc2)c(CC(C)C)nn1C] | 0.006<br>0.051 (HuNMT-1)<br>0.091 (LmNMT) | 0.015 | 469.3 |
| DDD100865 | 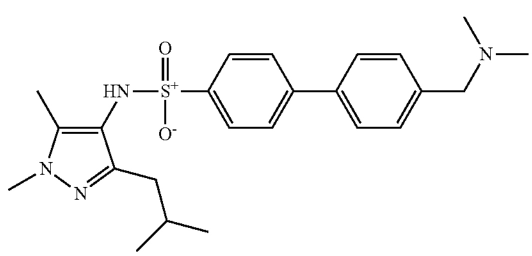 | 0.097<br>0.314 (HuNMT-1)<br>1.9 (LmNMT) | 7.3 | 441.2 |
| DDD100866 | 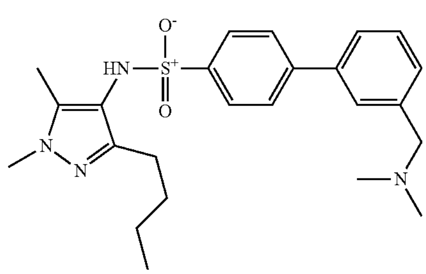 | 0.010<br>0.047 (HuNMT-1)<br>0.054 (LmNMT) | 3.2 | 441.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activities are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD100867 | 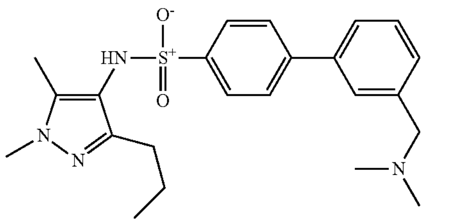 | 0.006<br>0.039 (HuNMT-1)<br>0.074 (LmNMT) | 0.048 | 427.2 |
| DDD100868 | 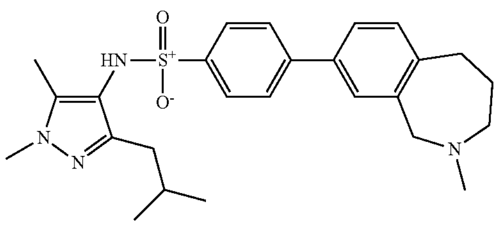 [SMILES: Cc1c(N[S+](=O)([O-])c2ccc(-c3ccc4c(c3)CN(C)CCC4)cc2)c(CC(C)C)nn1C] | 0.015<br>0.002 (HuNMT-1)<br>0.004 (LmNMT) | 0.0009 | 467.3 |
| DDD100869 | 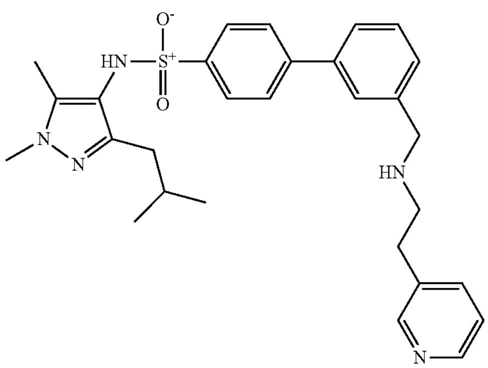 [SMILES: Cc1c(N[S+](=O)([O-])c2ccc(-c3cccc(CNCCc4cccnc4)c3)cc2)c(CC(C)C)nn1C] | 0.004<br>0.006 (HuNMT-1)<br>0.019 (LmNMT) | 5.7 | 518.3 |
| DDD100870 | 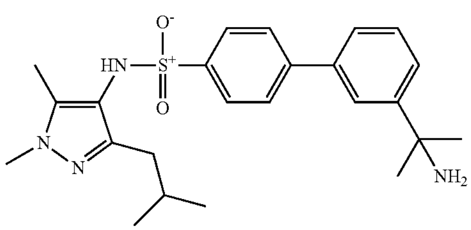 [SMILES: Cc1c(N[S+](=O)([O-])c2ccc(-c3cccc(C(C)(C)N)c3)cc2)c(CC(C)C)nn1C] | 0.005<br>0.018 (HuNMT-1)<br>0.045 (LmNMT) | 0.013 | 441.2 |
| DDD100871 | 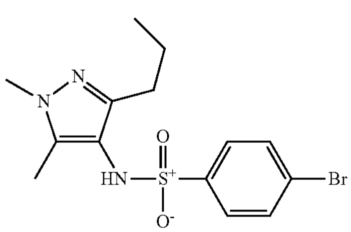 [SMILES: CCCc1nn(C)c(C)c1N[S+](=O)([O-])c1ccc(Br)cc1] | 7.95<br>>1 μM (HuNMT-1)<br>>1 μM (LmNMT) | 51.0 | 374.0 |
| DDD100872 | 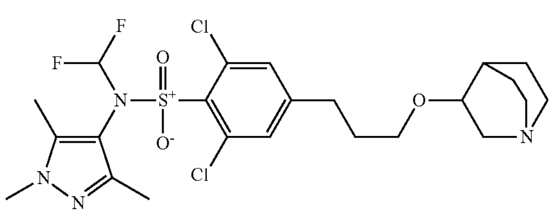 [SMILES: Cc1nn(C)c(C)c1N(C(F)F)[S+](=O)([O-])c1c(Cl)cc(CCCOC2CN3CCC2CC3)cc1Cl] | 0.003<br>0.017 (HuNMT-1)<br>0.005 (LmNMT) | 0.002 | 551.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | IC$_{50}$ (μM) NMT Enzyme | ED$_{50}$ (μM) T. brucei | MH+ |
|---|---|---|---|---|
| DDD100873 | 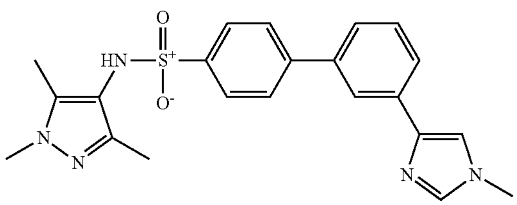 | 13.8<br>>1 μM (HuNMT-1)<br>>1 μM (LmNMT) | >1 μM | 422.2 |
| DDD100874 | 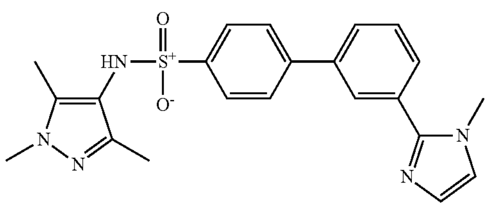 | 0.740<br>>1 μM (HuNMT-1)<br>>1 μM (LmNMT) | >1 μM | 422.2 |
| DDD100875 | 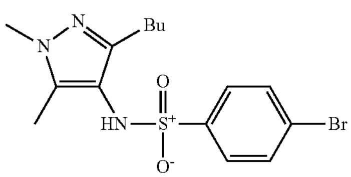 | 2.68<br>>1 μM (HuNMT-1)<br>>1 μM (LmNMT) | 20.5 | 386.1 |
| DDD100876 | 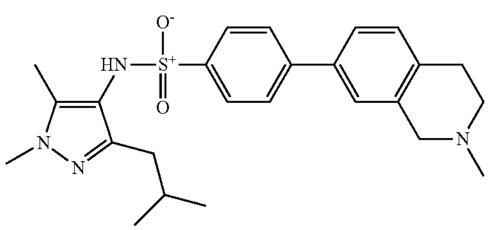 | 0.006<br>0.020 (HuNMT-1)<br>0.059 (LmNMT) | 0.014 | 453.3 |
| DDD100877 | 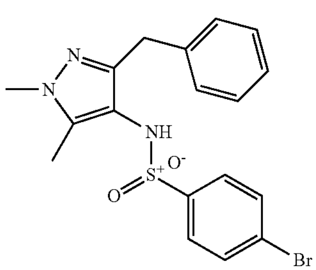 | 123.0<br>>1 μM (HuNMT-1)<br>>1 μM (LmNMT) | 33.9 | 420.0 |
| DDD100878 | 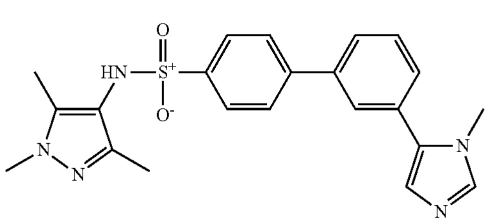 | 0.262<br>2.4 (HuNMT-1)<br>0.906 (LmNMT) | >1 μM | 422.2 |

TABLE 1-continued

Enzyme and Cellular Activity of N-Myristoyltransferase Inhibitors

Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activities are for inhibition of *T. brucei brucei* (blood stream form, variant 221).

| Reference Number | STRUCTURE | IC$_{50}$ (μM) NMT Enzyme | ED$_{50}$ (μM) *T. brucei* | MH+ |
|---|---|---|---|---|
| DDD100879 | 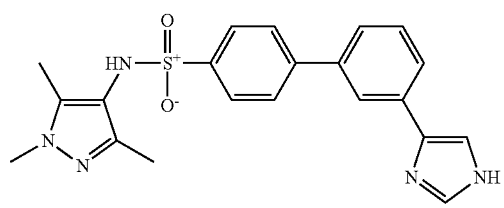 [SMILES: Cc1nn(C)c(C)c1N[S+](=O)([O-])c1ccc(-c2cccc(-c3c[nH]cn3)c2)cc1] | 0.803<br>2.6 (HuNMT-1)<br>1.59 (LmNMT) | >1 μM | 408.2 |
| DDD100880 | 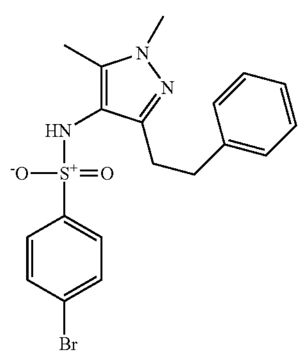 | >1 μM<br>>1 μM (HuNMT-1)<br>>1 μM (LmNMT) | 21.4 | 436.0 |
| DDD100881 | 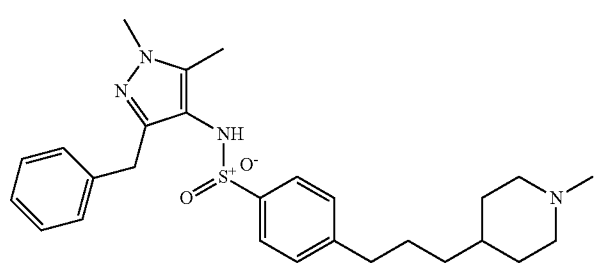 | 0.020<br>0.233 (HuNMT-1)<br>0.778 (LmNMT) | 0.234 | 481.3 |
| DDD100882 | 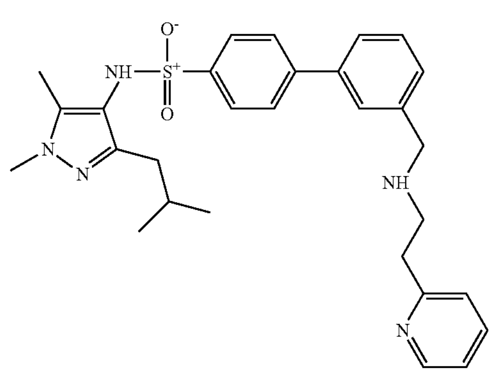 [SMILES: Cc1c(N[S+](=O)([O-])c2ccc(-c3cccc(CNCCc4ccccn4)c3)cc2)c(CC(C)C)nn1C] | 0.305<br>0.769 (HuNMT-1)<br>>1 μM (LmNMT) | 2.45 | 518.3 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activities are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD100883 | 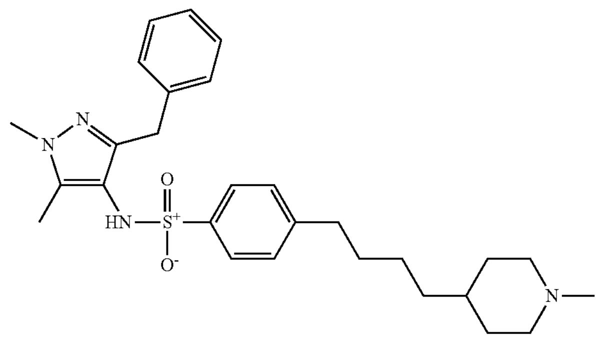 | 0.023<br>>1 μM (HuNMT-1)<br>0.672 (LmNMT) | 0.427 | 495.3 |
| DDD100884 | 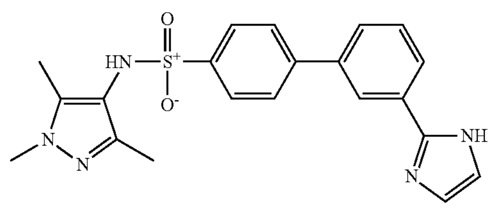 [SMILES: Cc1nn(C)c(C)c1N[S+](=O)([O-])c1ccc(-c2cccc(-c3ncc[nH]3)c2)cc1] | 1.08<br>>1 μM (HuNMT-1)<br>>1 μM (LmNMT) | >1 μM | 408.2 |
| DDD100885 | 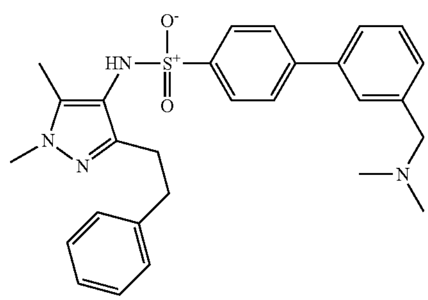 | 0.032<br>0.096 (HuNMT-1)<br>0.211 (LmNMT) | 9.72 | 489.2 |
| DDD100886 | 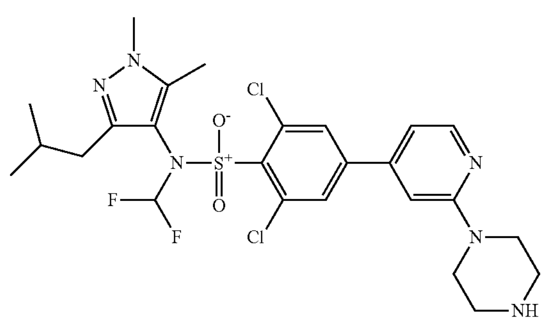 [SMILES: Cc1c(N(C(F)F)[S+](=O)([O-])c2c(Cl)cc(-c3ccnc(N4CCNCC4)c3)cc2Cl)c(CC(C)C)nn1C] | 0.016<br>0.019 (HuNMT-1)<br>0.16 (LmNMT) | 0.004 | 587.2 |
| DDD100887 | 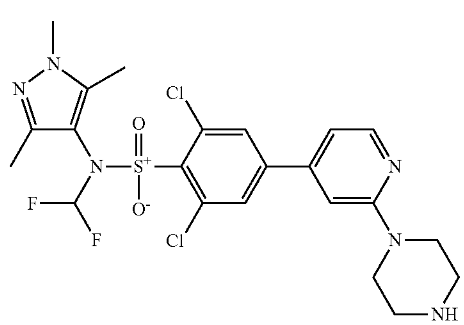 [SMILES: Cc1nn(C)c(C)c1N(C(F)F)[S+](=O)([O-])c1c(Cl)cc(-c2ccnc(N3CCNCC3)c2)cc1Cl] | 0.010<br>0.018 (HuNMT-1)<br>0.005 (LmNMT) | 0.005 | 545.1 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | IC$_{50}$ (µM) NMT Enzyme | ED$_{50}$ (µM) *T. brucei* | MH+ |
|---|---|---|---|---|
| DDD100888 | 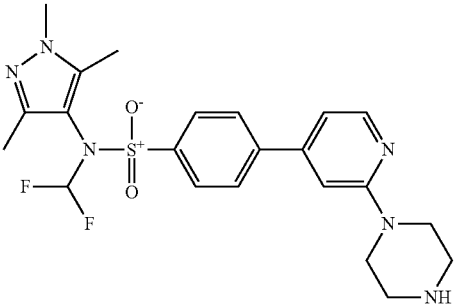 [SMILES: Cc1nn(C)c(C)c1N(C(F)F)[S+](=O)([O-])c1ccc(-c2ccnc(N3CCNCC3)c2)cc1] | 0.004<br>0.012 (HuNMT-1)<br>0.005 (LmNMT) | 0.003 | 477.2 |
| DDD100889 | 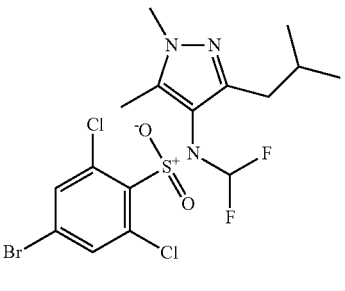 | 5.3<br>1.3 (HuNMT-1)<br>1.2 (LmNMT) | >1 µM | 506.0 |
| DDD100891 | 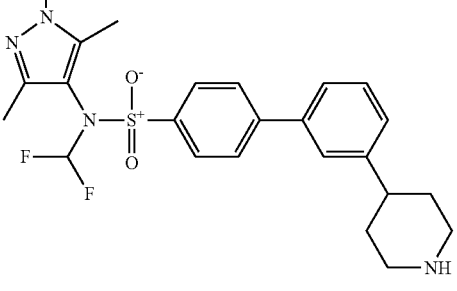 | 0.020<br>0.100 (HuNMT-1)<br>0.045 (LmNMT) | 0.129 | 474.2 |
| DDD100965 | 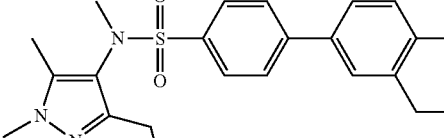 | 0.025<br>0.037 (HuNMT-1)<br>0.026 (LmNMT) | nd | 452.2 |
| DDD100966 | 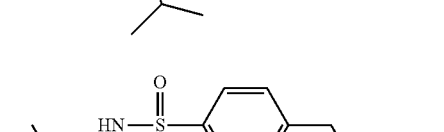 | 0.012<br>0.22 (HuNMT-1)<br>0.012 (LmNMT) | nd | 432.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (µM) NMT Enzyme | $ED_{50}$ (µM) T. brucei | MH+ |
|---|---|---|---|---|
| DDD100968 | 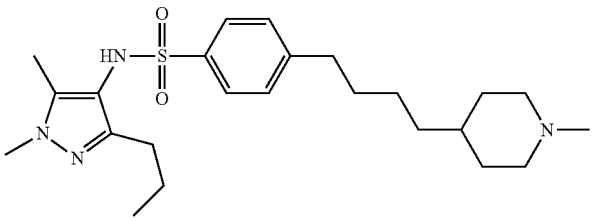 | 0.016<br>0.14 (HuNMT-1)<br>0.045 (LmNMT) | nd | 446.2 |
| DDD100969 | 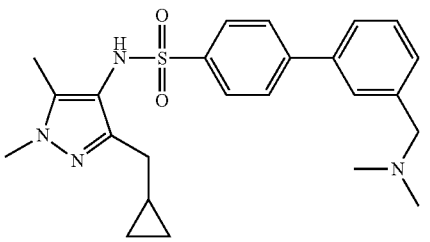 | 0.010<br>0.019 (HuNMT-1)<br>0.044 (LmNMT) | nd | 438.2 |
| DDD100971 | 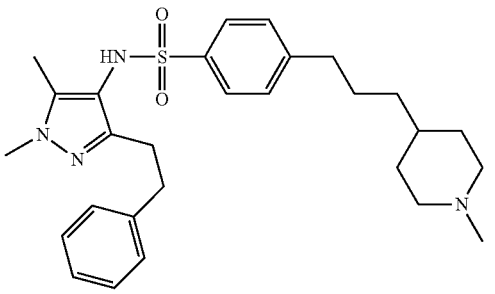 | 0.04<br>0.63 (HuNMT-1)<br>0.55 (LmNMT) | nd | 494.2 |
| DDD100972 | 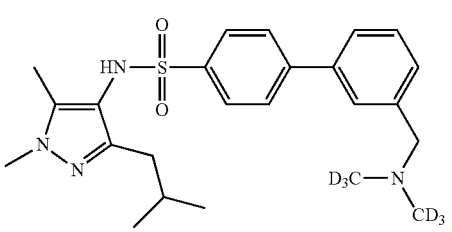 [SMILES: [2H]C([2H])([2H])N(Cc1cccc(-c2ccc(S(=O)(=O)Nc3c(CC(C)C)nn(C)c3C)cc2)c1)C([2H])([2H])[2H]] | 0.005<br>0.014 (HuNMT-1)<br>0.005 (LmNMT) | nd | 446.2 |
| DDD100974 | 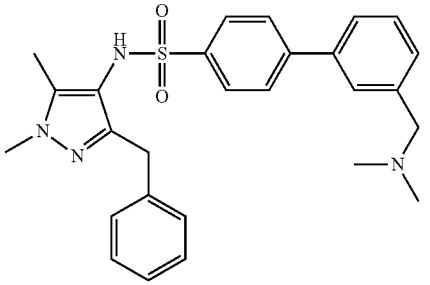 | 0.026<br>0.11 (HuNMT-1)<br>0.028 (LmNMT) | nd | 474.2 |

TABLE 1-continued

Enzyme and Cellular Activity of N-Myristoyltransferase Inhibitors
Enzyme activities are for *T. brucei* NMT. Where present, Human (HuNMT-1), *Aspergillus fumigatus* (AfNMT) and *Leishmania major* (LmNMT) enzyme inhibition data are given in parentheses. Cellular activitites are for inhibition of *T. brucei brucei* (blood stream form, variant 221).

| Reference Number | STRUCTURE | $IC_{50}$ (μM) NMT Enzyme | $ED_{50}$ (μM) *T. brucei* | MH+ |
|---|---|---|---|---|
| DDD100978 | 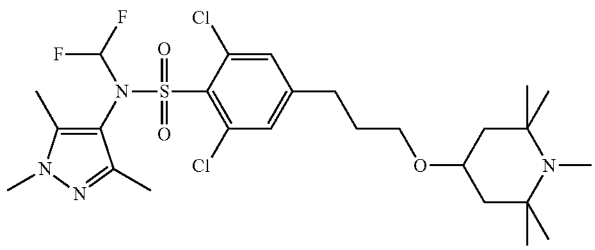 | 0.019<br>>1.0 (HuNMT-1)<br>0.04 (LmNMT) | nd | 594.2 |
| DDD100979 | 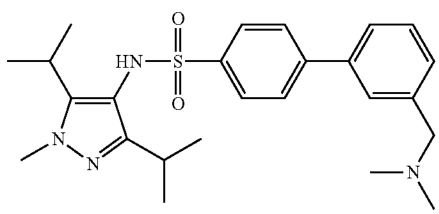 [SMILES: CC(C)c1nn(C)c(C(C)C)c1NS(=O)(=O)c1ccc(-c2cccc(CN(C)C)c2)cc1] | 0.20<br>0.20 (HuNMT-1)<br>>1.0 (LmNMT) | nd | 454.2 |
| DDD100980 | 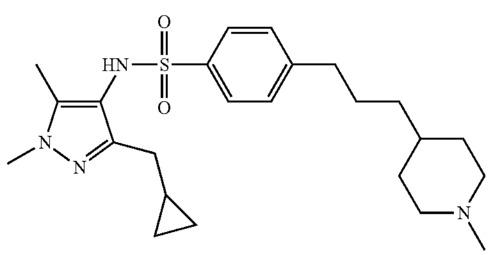 | 0.028<br>0.15 (HuNMT-1)<br>0.13 (LmNMT) | nd | 444.2 |
| DDD100985 | 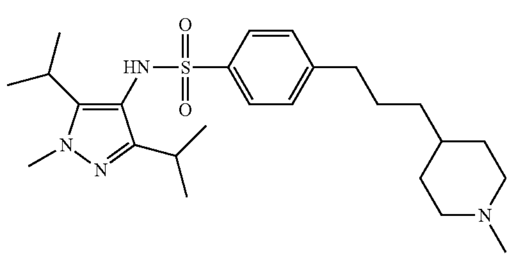 [SMILES: CC(C)c1nn(C)c(C(C)C)c1NS(=O)(=O)c1ccc(CCCC2CCN(C)CC2)cc1] | 0.10<br>0.62 (HuNMT-1)<br>0.38 (LmNMT) | nd | 460.2 |
| DDD100986 | 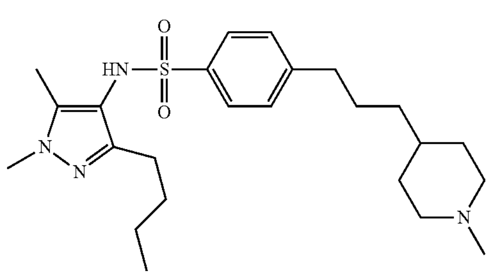 | 0.018<br>0.33 (HuNMT-1)<br>0.16 (LmNMT) | nd | 446.2 |

TABLE 1-continued

Enzyme and Cellular Activity of N-Myristoyltransferase Inhibitors
Enzyme activities are for T. brucei NMT. Where present, Human (HuNMT-1), Aspergillus fumigatus (AfNMT) and Leishmania major (LmNMT) enzyme inhibition data are given in parentheses. Cellular activitites are for inhibition of T. brucei brucei (blood stream form, variant 221).

| Reference Number | STRUCTURE | $IC_{50}$ (μM) NMT Enzyme | $ED_{50}$ (μM) T. brucei | MH+ |
|---|---|---|---|---|
| DDD100990 | 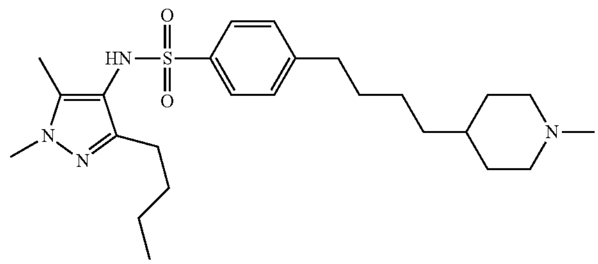 | 0.024<br>0.40 (HuNMT-1)<br>0.13 (LmNMT) | nd | 460.2 |
| DDD100991 | 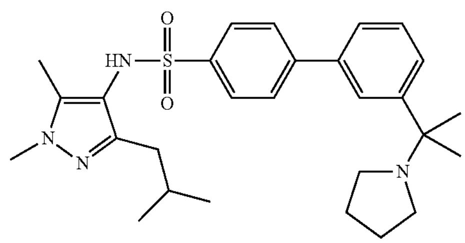 [SMILES: Cc1c(NS(=O)(=O)c2ccc(-c3cccc(C(C)(C)N4CCCC4)c3)cc2)c(CC(C)C)nn1C] | 0.005<br>0.03 (HuNMT-1)<br>0.05 (LmNMT) | nd | 494.2 |

TABLE 2

Activity of N-Myristoyltransferase Inhibitors Against Human Cancer Cell Lines

| | $IC_{50}$ (μM) | | | | | | | | |
|---|---|---|---|---|---|---|---|---|---|
| Reference | HT29 | HCT116 | SkBr3 | RT112 | C6 | H460 | MRC5 | HT1080 | A549 |
| DDD85646 | 0.112 | 0.234 | 0.108 | 0.330 | 1.16 | 1.32 | 0.123 | 0.06 | 0.157 |
| DDD86206 | 0.154 | 0.422 | 0.141 | 0.425 | 1.89 | 2.53 | 0.209 | 0.086 | 0.213 |

TABLE 3

Activity of N-Myristoyltransferase Inhibitors Against Human Cancer Cell Lines

| | $IC_{50}$(μM) | | | |
|---|---|---|---|---|
| Reference | NCI-H1299 | MDA-MB-231 | OE19 | OE21 |
| DDD85646 | 0.57 | 0.23 | 0.66 | 0.29 |
| DDD86212 | 1.08 | 0.64 | 4.37 | 1.39 |
| DDD86470 | 3.71 | 0.89 | 4.57 | 1.20 |
| DDD86481 | 0.096 | 0.047 | 0.132 | 0.057 |

TABLE 4

Activity of N-Myristoyltransferase Inhibitors Against Human Cancer Cell Lines

| | $IC_{50}$(μM) | | |
|---|---|---|---|
| Reference | MDA-MB-231 | HT-29 | HCT116 |
| DDD85646 | 0.23 | 0.112 | 0.234 |
| DDD88558 | 0.448 | 0.176 | 0.629 |
| DDD90086 | 0.537 | 0.281 | 0.921 |
| DDD90149 | 2.23 | >10 | 1.91 |
| DDD100144 | 0.218 | n.d. | 0.282 |
| DDD100169 | 0.249 | n.d. | 0.419 |

Assessment of the CNS penetration of NMT inhibitors was determined in the female NMRI mouse following i.v. dosing (n=3 per dose group, concentration measured after t=5 min).

TABLE 5

Drug concentration in blood and brain in the female NMRI mouse at t = 5 min following single i.v. dosing (average of three animals)

| Reference | Dose | Conc (ng/ml in blood) | Conc (ng/ml in brain) | Brain:Blood |
|---|---|---|---|---|
| DDD73490 | 0.33 mg/kg | 52 | 314 | 6.0 |
| DDD88195 | 1.0 mg/kg | 116 | 93 | 0.8 |
| DDD88638 | 2.0 mg/kg | 281 | 378 | 1.35 |
| DDD90154 | 2.0 mg/kg | 455 | 608 | 1.34 |
| DDD99742 | 2.0 mg/kg | 642 | 422 | 0.66 |
| DDD99837 | 3.0 mg/kg | 388 | 99 | 0.26 |
| DDD100097 | 2.0 mg/kg | 224 | 335 | 1.50 |
| DDD100144 | 2.0 mg/kg | 413 | 545 | 1.32 |
| DDD100153 | 2.0 mg/kg | 269 | 171 | 0.64 |

Assessment of the antitrypanosomal efficacy of DDD85646 in an acute model of trypanosomiasis was determined at six dose levels in the female NMRI mouse (n=3 per dose group). Compound was dosed for four days b.i.d. at the stated level, commencing three days after infection with $1\times10^4$ trypanosomes (T. brucei brucei, blood stream form, variant 221).

The invention claimed is:

1. A compound having the structure:

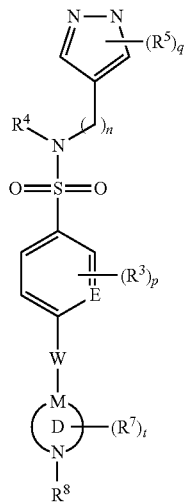

wherein
- n is 0, 1, 2, 3, 4, 5 or 6;
- E is independently selected from C and N;
- W is selected from a hydrocarbyl optionally substituted with $R^{11}$, an optionally substituted aryl or heteroaryl group and a carbocyclyl optionally substituted with one or more of halogen, cyano, amino, hydroxy, $C_{1-6}$ alkyl and $C_{1-6}$ alkoxy groups;
- where M is selected from C and N;
- $R^3$, $R^4$ and $R^5$ are independently selected from hydrogen, $R^{12}$, hydrocarbyl optionally substituted with $R^{12}$, and —$(CH_2)_l$-heterocyclyl optionally substituted with $R^{12}$; wherein $R^1$ and $R^2$ taken together with the atoms to which they are attached may form a heterocycle, optionally substituted with one or more $R^{12}$;
- l is 0, 1, 2, 3, 4, 5 or 6;
- wherein each $R^{11}$ and $R^{12}$ is independently selected from halogen, trifluoromethyl, cyano, thio, nitro, oxo, =$NR^{13}$, —$OR^{13}$, —$SR^{13}$, —$C(O)R^{13}$, —$C(O)OR^{13}$, —$OC(O)R^{13}$, —$NR^{13}COR^{14}$, —$NR^{13}CONR^{13}{}_2$, —$NR^{13}COR^{14}$, —$NR^{13}CO_2R^{14}$, —$S(O)R^{13}$, —$S(O)_2R^{13}$, —$SONR^{13}{}_2$, —$NR^{13}S(O)_2R^{14}$; —$CSR^{13}$, —$N(R^{13})R^{14}$, —$C(O)N(R^{13})R^{14}$, —$SO_2N(R^{13})R^{14}$ and $R^{15}$;
- wherein $R^{13}$ and $R^{14}$ are each independently selected from hydrogen or $R^{15}$;
- wherein $R^{15}$ is selected from hydrocarbyl, carbocyclyl and —$(CH_2)_m$-heterocyclyl, and each $R^{15}$ is optionally and independently substituted with one or more of halogen, cyano, amino, hydroxy, $C_{1-6}$ alkyl and $C_{1-6}$ alkoxy;
- ring D is an optionally substituted nitrogen containing 6 or 7 membered heterocycle, wherein each substitutable carbon or nitrogen in Ring D is optionally and independently substituted by one or more $R^7$;
- $R^7$ is independently selected from hydrogen, $R^{20}$, hydrocarbyl optionally substituted with $R^{20}$, and —$(CH_2)_v$-heterocyclyl optionally substituted with $R^{20}$;
- v is 0, 1, 2, 3, 4, 5 or 6;
- wherein each $R^{20}$ is independently selected from halogen, trifluoromethyl, cyano, thio, nitro, oxo, =$NR^{21}$, —$OR^{21}$, —$SR^{21}$, —$C(O)R^{21}$, —$C(O)OR^{21}$, —$OC(O)R^{21}$, —$NR^{21}COR^{22}$, —$NR^{21}CONR^{22}{}_2$, —$NR^{21}COR^{22}$, —$NR^{21}CO_2R^{22}$, —$S(O)R^{21}$, —$S(O)_2R^{21}$, —$SONR^{21}{}_2$, —$NR^{21}S(O)_2R^{22}$; —$CSR^{21}$, $N(R^{21})R^{22}$, —$C(O)N(R^{21})R^{22}$, —$SO_2N(R^{21})R^{22}$ and $R^{23}$;
- wherein $R^{21}$ and $R^{22}$ are each independently selected from hydrogen or $R^{23}$; wherein $R^{23}$ is selected from hydrocarbyl, carbocyclyl and —$(CH_2)_w$-heterocyclyl, and each $R^{23}$ is optionally and independently substituted with one or more of halogen, cyano, amino, hydroxy, $C_{1-6}$ alkyl and $C_{1-6}$ alkoxy;
- w is 0, 1, 2, 3, 4, 5 or 6;
- $R^8$ is selected from the list of optional substituents represented by the group $R^4$;
- m is 0, 1, 2, 3, 4, 5 or 6;
- p is 0, 1, 2, 3 or 4, wherein the values of $R^4$ may be the same or different;
- q is 0, 1, 2, 3 or 4, wherein the values of $R^5$ may be the same or different; and
- t is 0, 1, 2, 3, 4, 5 or 6, wherein the values of $R^7$ may be the same or different;

or a pharmaceutically acceptable salt thereof.

2. A compound as claimed in claim 1 wherein E is C.

3. A compound as claimed in claim 1 having the structure:

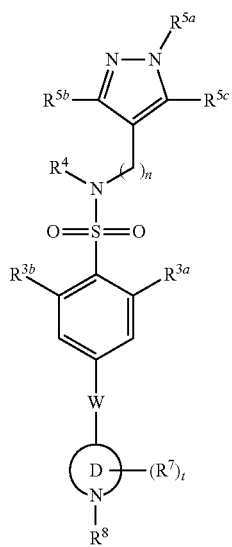

wherein $R^{5a}$, $R^{5b}$ and $R^{5c}$ are independently selected from hydrogen, $R^{12}$, hydrocarbyl optionally substituted with $R^{12}$, and —$(CH_2)_t$-heterocyclyl optionally substituted with $R^{12}$;

wherein $R^{3a}$ and $R^{3b}$ are independently selected from hydrogen, $R^{12}$, hydrocarbyl optionally substituted with $R^{12}$, and —$(CH_2)_t$-heterocyclyl optionally substituted with $R^{12}$.

4. A compound as claimed in claim 3 wherein $R^{5a}$, $R^{5b}$ and $R^{5c}$ independently represent $C_{1-6}$ alkyl.

5. A compound as claimed in claim 1 having the structure:

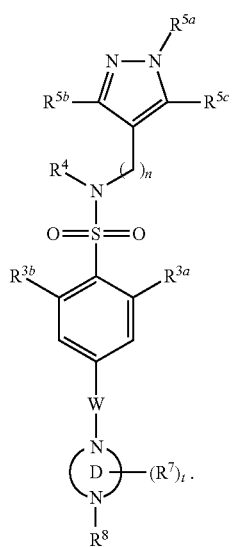

6. A compound as claimed in claim 1 wherein W is $C_{1-6}$ alkyl or cycloalkyl.

7. A compound as claimed in claim 1 wherein $R^4$ is selected from hydrogen or $C_{1-6}$ alkyl optionally substituted with halogen.

8. A compound as claimed in claim 1 selected from the group consisting of:

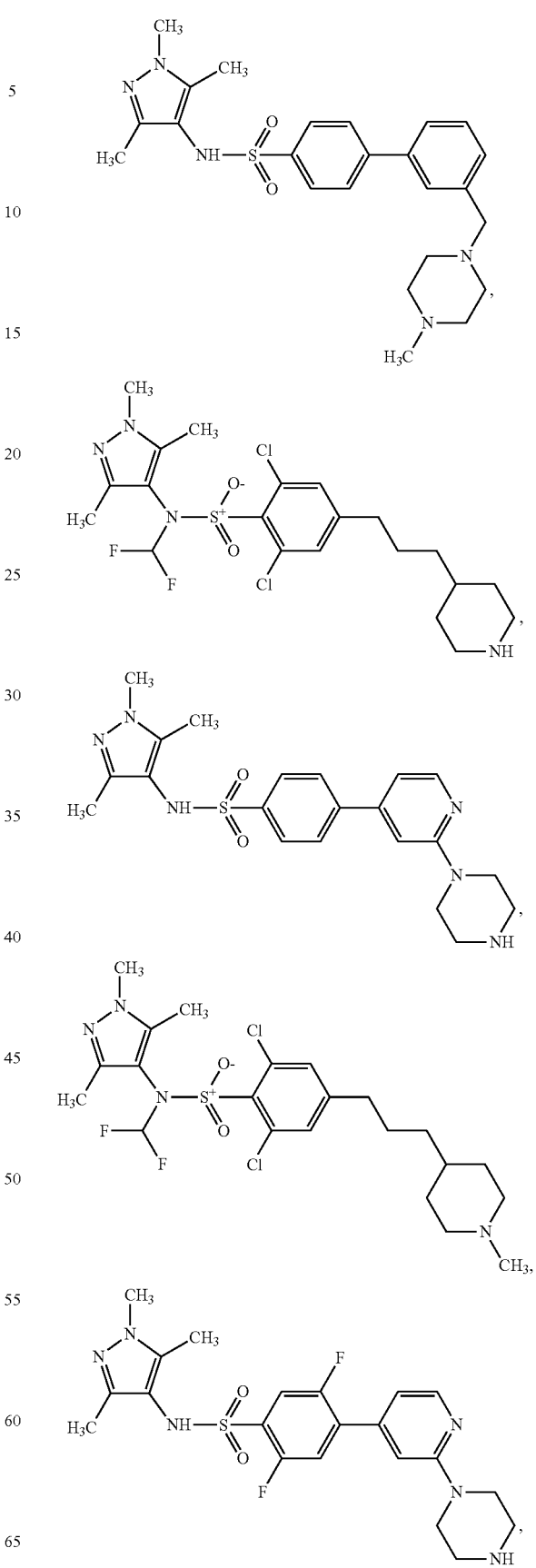

-continued

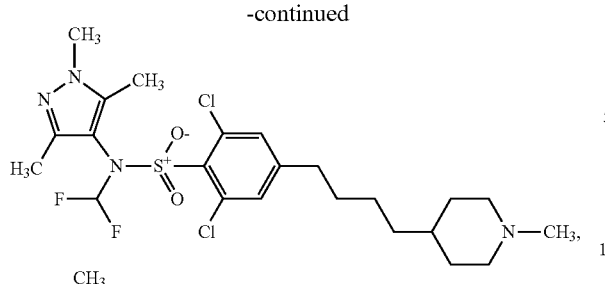

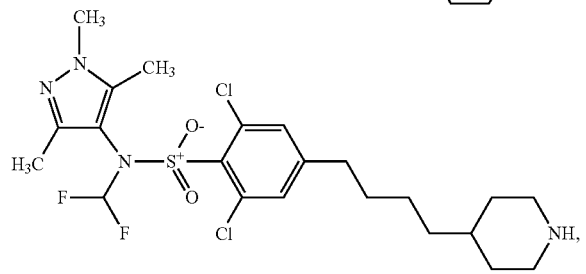

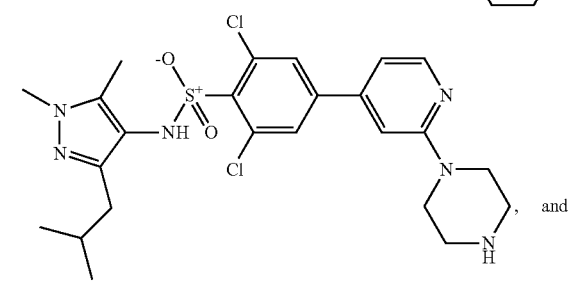

-continued

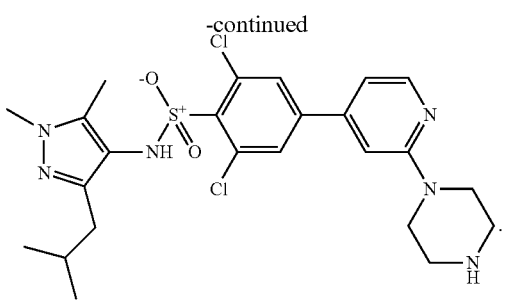

9. A compound as claimed in claim 1 wherein one or more of $R^3$ and $R^5$ taken together with the atoms to which they are attached form a carbocycle, optionally substituted with $R^{12}$.

10. A compound as claimed in claim 1 wherein $R^4$ is selected from hydrogen and $C_{1-6}$ alkyl optionally substituted with fluoro.

11. A compound as claimed in claim 3 wherein $R^{5a}$, $R^{5b}$ and $R^{5c}$ are independently selected from hydrogen, $R^{12}$, $C_{1-6}$ alkyl, alkenyl, alkynyl and haloalkyl, optionally substituted with $R^{12}$.

12. A compound as claimed in claim 3 wherein $R^{3a}$ and $R^{3b}$ are independently selected from hydrogen, $R^{12}$, $C_{1-6}$ alkyl, alkenyl, alkynyl and haloalkyl, optionally substituted with $R^{12}$.

* * * * *

SEQUENCE LISTING

<160> NUMBER OF SEQ ID NOS: 1

<210> SEQ ID NO 1
<211> LENGTH: 15
<212> TYPE: PRT
<213> ORGANISM: Homo sapiens

<400> SEQUENCE: 1

Gly Cys Gly Gly Ser Lys Val Lys Pro Gln Pro Pro Gln Ala Lys
1               5                   10                  15